United States Patent
Muraoka et al.

[11] Patent Number: 5,843,957
[45] Date of Patent: Dec. 1, 1998

[54] NAPHTHYRIDINE DERIVATIVES

[75] Inventors: Masami Muraoka, Toyonaka; Katsuhisa Ioriya, Osaka; Naohito Ohashi, Takatsuki; Hideki Yagi, Nishinomiya, all of Japan

[73] Assignee: Sumitomo Pharmaceuticals Company, Ltd., Osaka, Japan

[21] Appl. No.: 978,146

[22] Filed: Nov. 25, 1997

Related U.S. Application Data

[63] Continuation-in-part of PCT/JP96/01429 May 28, 1996.

[30] Foreign Application Priority Data

| May 19, 1995 | [JP] | Japan | ................................... | 7-158475 |
| Nov. 26, 1996 | [JP] | Japan | ................................... | 8-331523 |

[51] Int. Cl.$^6$ ........................ A61K 31/435; C07D 471/04
[52] U.S. Cl. ...................... 514/300; 514/253; 544/362; 546/122
[58] Field of Search ............... 546/122; 544/362; 514/253, 300

[56] References Cited

U.S. PATENT DOCUMENTS 3,993,656  11/1976  Rooney et al. ..................... 546/122

FOREIGN PATENT DOCUMENTS

| 0421456 | 4/1991 | European Pat. Off. . |
| 0472116 | 2/1992 | European Pat. Off. . |
| 0481243 | 4/1992 | European Pat. Off. . |
| 9109017 | 6/1991 | WIPO . |
| 9219614 | 11/1992 | WIPO . |

OTHER PUBLICATIONS

H. Tawada et al., Chem. Pharm. Bull. 43(4) 616–625 (1995).

Primary Examiner—Bernard Dentz
Attorney, Agent, or Firm—Birch, Stewart, Kolasch & Birch, LLP

[57] ABSTRACT

Naphthyridine derivative of the formula:

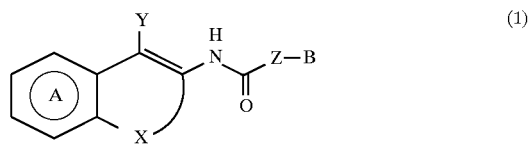

wherein Ring A is substituted or unsubstituted pyridine, X is $-N(R^2)-CO-$ ($R^2$ is H, alkyl, substituted alkyl, etc.), Z is a direct bond, $-NH-$, $C_1-C_2$ alkylene, or $-CH=CH-$, Y is alkyl, substituted alkyl, aromatic group or substituted aromatic group, etc., B is alkyl, substituted alkyl, aromatic group or substituted aromatic group, or an acid addition salt thereof, these compounds having acyl-CoA: cholesterol acyl transferase inhibitory activity, and being useful as an agent for prophylaxis or treatment of hyperlipidemia, atherosclerosis, and related diseases thereof.

22 Claims, No Drawings

NAPHTHYRIDINE DERIVATIVES

This application is a continuation-in-part of PCT international application no. PCT/JP96/01429 which has an international filing date of 28 May 1996 which designated the United States, the entire contents of which are hereby incorporated by reference.

TECHNICAL FIELD

The present invention relates to a naphthyridine derivative or an acid addition salt thereof, which shows acyl-CoA: cholesterol acyl transferase (ACAT) inhibitory activity, and is useful as an agent for treatment of hyperlipidemia and atherosclerosis, and a use thereof.

PRIOR ART

Cerebral vessel disorders such as stroke, or myocardial infarction, which rank in high causes of death in developed countries, break out with being accompanied by atherosclerosis as basal disease. From the results of epidemiology research, it is pointed out that hypercholesterolemia is one of the risk factors for atherosclerosis, and there are mainly used anti-hyperlipidemic agents which can reduce cholesterol level in blood in the prophylaxis or treatment thereof. However, there is no sufficiently effective agent in terms of the effects thereof. Recently, it is observed that cells derived from macrophage accumulate cholesterol ester droplets within the cells and become foam cells in atherosclerotic lesions, and it is clarified that these foam cells deeply participate in the development of atherosclerotic lesions (Atherosclerosis, 10, 164–177, 1990). In addition, it is reported that ACAT activity is increased and cholesterol esters are accumulated in the vascular wall of atherosclerotic lesions (Biochem. Biophys. Acta, 617, 458–471, 1980). Therefore, an inhibitor of ACAT, which catalyses cholesterol esterification, is expected to suppress the formation or the development of atherosclerotic lesions as a result of the inhibition of foam cell formation and of cholesterol accumulation in the vascular wall.

On the other hand, cholesterol in food is absorbed in the free form at intestinal epidermal cells, and then released in the form of chylomicron esterified by ACAT into the blood. Therefore, an inhibitor of ACAT is expected to reduce the cholesterol level in the blood caused by the inhibition of absorption of cholesterol in food at the intestine and reabsorption of cholesterol released into the intestine (J. Lipid. Research, 34, 279–294, 1993).

Japanese Patent Publication (Kokai) Nos. 3-181465, 3-223254 and Japanese Patent Publication (Kohyo) No. 6-501025 disclose some kinds of quinoline derivatives having ACAT inhibitory activity, and Japanese Patent Publication (Kokai) No. 5-32666 discloses some kinds of thienopyridine derivatives having an ACAT inhibitory activity, but these compounds are different in structure from the present compounds.

DISCLOSURE OF INVENTION

An object of the present invention is to provide a naphthyridine derivative having an ACAT inhibitory activity and that is useful as an agent for treatment of hyperlipidemia and atherosclerosis.

The present inventors have intensively studied in order to obtain a compound having a potent ACAT inhibitory activity, and have found that a naphthyridine derivative of the following formula (1) and an acid addition salt thereof show such an activity, and then have accomplished the present invention. The compounds of the present invention have a different structure from the above-mentioned known compounds, and they are novel compounds.

A naphthyridine derivative of the formula:

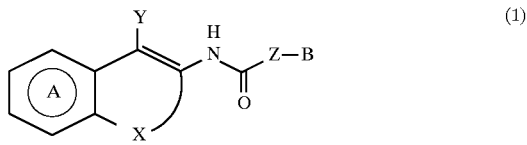

wherein Ring A is a substituted or unsubstituted pyridine ring,

X is a group of the formula:

wherein $R^2$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group, or a group of the formula:

wherein W is a hydrogen atom or a group :—$OR^1$ ($R^1$ is an alkyl group, a substituted alkyl group, an alkenyl group, a substituted alkenyl group, an alkynyl group, or a substituted alkynyl group), Z is a direct bond, —NH—, an alkylene group having 1 to 2 carbon atoms, or —CH=CH—, Y is an alkyl group, a substituted alkyl group, a cycloalkyl group, a substituted cycloalkyl group, an aromatic group, or a substituted aromatic group, B is an alkyl group, a substituted alkyl group, an alkenyl group, a substituted alkenyl group, a cycloalkyl group, a substituted cycloalkyl group, an aromatic group, or a substituted aromatic group, or an acid addition salt thereof.

Each group in the present invention is explained below.

Ring A is a substituted or unsubstituted pyridine ring, and the nitrogen atom thereof may be at any position except for the fused positions of the fused ring (that is, the nitrogen atom cannot be a bridgehead atom of the fused ring), and the preferable Ring A is a group of the following formulae (a), (b) and (c).

Besides, the substituent of the pyridine ring may be, for example, a lower alkyl group, a halogen atom, a cyano group, a trifluoromethyl group, a nitro group, an amino group, a mono-lower alkylamino group, a di-lower alkylamino group, a hydroxy group, a lower alkoxy group, a lower alkylthio group, a lower alkylsulfinyl group, a lower alkylsulfonyl group, etc.

The term "lower" in the present invention means that alkyl moiety described with "lower" is a lower alkyl group, and the lower alkyl group includes an alkyl group having 1 to 6 carbon atoms such as methyl, ethyl, propyl, 2-propyl, butyl, pentyl, hexyl, etc. The halogen atom is a fluorine atom, chlorine atom, bromine atom, and iodine atom. The substituted pyridine ring has one or more substituents which are the same or different.

The alkyl group or the alkyl moiety of the substituted alkyl group for $R^1$, $R^2$ and Y includes, for example, a straight chain or branched chain alkyl group having 1 to 15 carbon atoms, such as methyl, ethyl, propyl, 2-propyl, butyl, 2-butyl, 2-methylpropyl, 1,1-dimethylethyl, pentyl, 3-pentyl, 3-methylbutyl, hexyl, 3-hexyl, 4-methylpentyl, 4-heptyl, octyl, 4-octyl, decyl, etc.

The alkenyl group or the alkenyl moiety of the substituted alkenyl group for $R^1$ and $R^2$ includes, for example, a straight chain or branched chain alkenyl group having 2 to 15 carbon atoms, such as vinyl, allyl, 2-propenyl, 2-methyl-2-propenyl, 2-butenyl, 3-butenyl, 3-methyl-2-butenyl, 4-pentenyl, 3-hexenyl, 3-ethyl-2-pentenyl, 4-ethyl-3-hexenyl, etc.

The alkynyl group or the alkynyl moiety of the substituted alkynyl group for $R^1$ and $R^2$ includes, for example, a straight chain or branched chain alkynyl group having 3 to 15 carbon atoms, such as 2-propynyl, 3-butynyl, 4-pentynyl, 3-hexynyl, 5-methyl-2-hexynyl, 6-methyl-4-heptynyl, etc.

The alkyl group or the alkyl moiety of the substituted alkyl group for B includes, for example, a straight chain or branched chain alkyl group having 1 to 20 carbon atoms, such as methyl, ethyl, propyl, 2-propyl, butyl, 2-butyl, 2-methyl-propyl, 1,1-dimethylethyl, pentyl, 3-pentyl, hexyl, heptyl, octyl, undecyl, dodecyl, hexadecyl, 2,2-dimethyldodecyl, 2-tetradecyl, n-octadecyl, etc.

The alkenyl group or the alkenyl moiety of the substituted alkenyl group for B includes, for example, a straight chain or branched chain alkenyl group having 3 to 20 carbon atoms and having 1 to 2 double bonds, such as 2-propenyl, 2-butenyl, 3-methyl-2-butenyl, 3-pentenyl, 2-octenyl, 5-nonenyl, 4-undecenyl, 5-heptadecenyl, 3-octadecenyl, 9-octadecenyl, 2,2-dimethyl-9-octadecenyl, 9,12-octadecadienyl, etc.

The cycloalkyl group or the cycloalkyl moiety of the substituted cycloalkyl group includes, for example, a cycloalkyl group having 3 to 7 carbon atoms, such as cyclopropyl, cyclobutyl, cyclopentyl, cyclohexyl, cycloheptyl, etc.

The aromatic group includes, for example, an aryl group and a heteroaryl group.

The aryl group includes, for example, an aryl group having carbon atoms of not more than 10, such as a phenyl group, a naphthyl group, etc.

The heteroaryl group or the heteroaryl moiety of the heteroarylmethyl group includes, for example, a 5- to 6-membered heteromonocyclic group having 1 to 2 nitrogen atoms, a 5- to 6-membered heteromonocyclic group having 1 to 2 nitrogen atoms and one oxygen atom or one sulfur atom, a 5-membered heteromonocyclic group having one oxygen atom or one sulfur atom, a heterobicyclic group formed by fusing a 6-membered ring and a 5- or 6-membered ring and having 1 to 4 nitrogen atoms, such as 2-pyridyl, 3-pyridyl, 4-pyridyl, 2-thienyl, 3-thienyl, 3-oxadiazolyl, 1-imidazolyl, 2-imidazolyl, 2-thiazolyl, 3-isothiazolyl, 2-oxazolyl, 3-isoxazolyl, 2-furyl, 3-furyl, 3-pyrrolyl, 2-quinolyl, 8-quinolyl, 2-quinazolinyl, 8-purinyl, etc.

The substituted aromatic group has one or more substituents which are the same or different, and the substituents are, for example, a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, a lower alkylsulfonamido group, or a group of the formula: —$D^1$—E—F ($D^1$ is a direct bond, an oxygen atom, a sulfur atom, or a group of the formula: —$NR^3$— ($R^3$ is a hydrogen atom or a lower alkyl group), E is a divalent hydrocarbon group having 1 to 8 carbon atoms and optionally containing an unsaturated bond, or a phenylene group, F is a hydrogen atom, a hydroxy group, a carboxyl group, a lower alkoxycarbonyl group, a benzyloxycarbonyl group, a halogen atom, a cyano group, a benzyloxy group, a lower alkoxy group, a lower alkanoyloxy group, a lower alkylthio group, a lower alkylsulfinyl group, a lower alkylsulfonyl group, a benzenesulfonyloxy group being optionally substituted by an alkyl group (e.g., p-toluenesulfonyloxy group), a lower alkanoylamino group, a lower alkoxycarbonylamino group, a lower alkylsulfonamido group, a phthalimido group, a cycloalkyl group, an aryl group, a substituted aryl group, a heteroaryl group, a substituted heteroaryl group, a group of the formula: —$NR^4R^5$ ($R^4$ and $R^5$ are independently a hydrogen atom, a lower alkyl group, a di-lower alkylamino-substituted lower alkyl group, a lower alkoxy-substituted lower alkyl group, a cycloalkyl group, a lower alkoxycarbonyl group, a heteroarylmethyl group, or an aralkyl group, or $R^4$ and $R^5$ may combine each other, and with the adjacent nitrogen atom to which they bond, form a cyclic amino group having 4 to 8 carbon atoms as ones forming the said ring, and having one —$NR^8$— ($R^8$ is a hydrogen atom, a lower alkyl group, a phenyl group, a lower alkoxycarbonyl group, or a benzyl group) or one oxygen atom in the cycle thereof), or a group of the formula: —C(=O)$NR^4R^5$ ($R^4$ and $R^5$ are the same as defined above)), or an acid addition salt thereof.

The divalent hydrocarbon group having 1 to 6, or 1 to 8 carbon atoms and optionally having an unsaturated bond includes, for example, an alkylene chain such as methylene, ethylene, trimethylene, tetramethylene, pentamethylene, hexamethylene, etc., an alkenylene chain such as propenylene, butenylene, etc., an alkynylene chain such as ethynylene, propynylene, butynylene, or an alkynylene of the following formula:

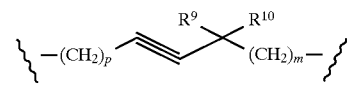

($R^9$ and $R^{10}$ are independently a hydrogen atom, a methyl group, an ethyl group or a propyl group, or $R^9$ and $R^{10}$ may combine each other to form a cycloalkane ring having 3 to 7 carbon atoms, m is an integer of 0 to 6, and p is an integer of 0 to 6), such as the following formulae:

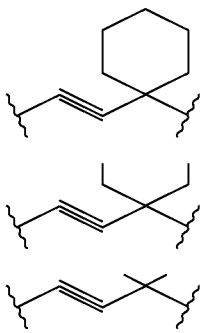

The substituted heteroaryl group for F has one or more substituents which are the same or different, and the substituents are, for example, a halogen atom, a cyano group, a trifluoromethyl group, a nitro group, a hydroxy group, a methylenedioxy group, a lower alkyl group, a lower alkoxy group, a benzyloxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, or a lower alkylsulfonamido group.

The heteroaryl group for F includes, for example, a 5- to 6-membered cyclic group having 1 to 3 nitrogen atoms, a 5-membered cyclic group having one oxygen atom or one sulfur atom, or a bicyclic group formed by fusing a 6-membered ring and a 5- or 6-membered ring, and having 1 to 4 nitrogen atoms, such as 2-pyridyl, 3-pyridyl, 4-pyridyl, 1-pyrrolyl, 1-imidazolyl, 1-(1,2,4-triazolyl), 2-thienyl, 3-thienyl, 2-furyl, 3-furyl, 2-quinolyl, etc. The substituted heteroaryl group for F has one or more substituents which are the same or different, and the substituents are, for example, a lower alkyl group, a lower alkoxy group, a halogen atom, etc.

The cyclic amino group formed by $NR^4R^5$ includes, for example, a group represented by the formula:

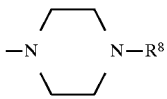

(wherein $R^8$ is the same as defined above) such as 4-lower alkyl-1-piperazinyl, 4-phenyl-1-piperazinyl, 4-benzyl-1-piperazinyl, etc., or a monocyclic group such as 1-pyrrolidinyl, 1-piperidinyl, 1-homopiperidinyl, 4-morpholinyl, etc., or a bicyclic group such as 3-azabicyclo-[3.2.2]nonane, etc.

The substituted alkyl group, the substituted cycloalkyl group, the substituted alkenyl group, and the substituted alkynyl group have one or more substituents which are the same or different, and the substituents are, for example, a halogen atom, a cyano group, a phenoxy group, a benzyloxy group, a trifluoromethyl group, a hydroxy group, a lower alkoxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a lower alkoxycarbonylamino group, a carboxyl group, a lower alkoxycarbonyl group, a lower alkylthio group, a lower alkylsulfinyl group, a lower alkylsulfonyl group, a lower alkanoylamino group, a lower alkylsulfonamido group, a tri-lower alkylsilyl group, a phthalimido group, a heteroaryl group, a saturated heterocyclic group, or a group of the formula: —$D^2$—E—F ($D^2$ is an oxygen atom, a sulfur atom, or a group of the formula: —$NR^3$ ($R^3$ is the same as defined above), E and F are the same as defined above). The heteroaryl group is the same heteroaryl groups for the above-mentioned F. The saturated heterocyclic group includes, for example, a 5- to 8-membered cyclic group having one nitrogen atom, a 6- to 8-membered cyclic group having two nitrogen atoms, and a 6- to 8-membered cyclic group having one nitrogen atom and one oxygen atom, such as 1-piperidinyl, 1-pyrrolidinyl, etc.

The substituted alkyl group includes an alkyl group having 1 to 6 carbon atoms which is substituted by a cycloalkyl group or a substituted cycloalkyl group, or an aralkyl group or a substituted aralkyl group.

The aralkyl group or the substituted aralkyl group includes an alkyl group having 1 to 6 carbon atoms which is substituted by the above-mentioned aryl group or substituted aryl group, for example, benzyl, 1-phenylethyl, 2-phenylethyl, 2-naphthylmethyl, etc.

The preferable groups for Y are, for example, a phenyl group or pyridyl group which may optionally be substituted. The substituted phenyl and the substituted pyridyl group have one or more substituents which are the same or different, and the preferable substituents are, for example, a halogen atom such as fluorine atom, chlorine atom, etc., a cyano group, a trifluoromethyl group, a nitro group, a hydroxy group, methylenedioxy group, a lower alkyl group, a lower alkoxy group, a lower alkanoyloxy group, an amino group, a mono-lower alkylamino group, a di-lower alkylamino group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, a lower alkanoylamino group, a lower alkylsulfonamido group, or a group of the formula: —$D^1$—E—F ($D^1$, E and F are the same as defined above). The preferable groups for E are, for example, a straight alkylene, alkenylene or alkynylene chain having 1 to 6 carbon atoms, and the more preferable ones are a straight alkylene or alkynylene having 1 to 3 carbon atoms. The preferable groups for F are, for example, a hydroxy group, a halogen atom, a cyano group, a lower alkoxy group, a lower alkanoyloxy group, a lower alkylthio group, a lower alkylsulfinyl group, a lower alkylsulfonyl group, a lower alkanoylamino group, a lower alkylsulfonamido group, a heteroaryl group, or a group of the formula: —$NR^4R^5$ ($R^4$ and $R^5$ are the same as defined above), and the more preferable one are a substituted or unsubstituted heteroaryl group (e.g., 2-pyridyl, 3-pyridyl, 2-methyl-3-pyridyl, 4-pyridyl, 1-imidazolyl, 1-(1,2,4-triazolyl), etc.), or a group of the formula: —$NR^4R^5$ ($R^4$ and $R^5$ are the same as defined above). The preferable group of the formula: —$NR^4R^5$ ($R^4$ and $R^5$ are the same as defined above) includes, for example, dimethylamino, diethylamino, diisopropylamino, pyrrolidinyl, piperidinyl, morpholinyl, 4-methylpiperazinyl, etc.

The preferable groups for B are a phenyl group or heteroaryl group which may optionally be substituted, and the more preferable groups for B are a phenyl group or pyridyl group which is substituted by 1 to 3 groups selected from a halogen atom such as a fluorine atom, chlorine atom, etc., a lower alkyl group, a lower alkoxy group and a lower alkylthio group, for example, 2,6-diisopropylphenyl, 2,4,6-trimethylphenyl, 2,4,6-trimethoxyphenyl, 2,4-difluorophenyl, 2,4,6-trifluorophenyl, 2,4-bis(methylthio) pyridin-3-yl, 2,4-bis(methylthio)-6-methylpyridin-3-yl, etc.

The preferable groups for X are groups of the following formulae:

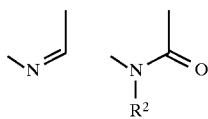

wherein $R^2$ is the same as defined above.

The preferable groups for $R^2$ are, for example, a hydrogen atom, an alkyl group, a substituted alkyl group, an alkenyl group, or a substituted alkenyl group. The substituted alkyl group and the substituted alkenyl group have one or more substituents which are the same or different, and the preferable substituents are, for example, a halogen atom such as fluorine atom, chlorine atom, etc., a cyano group, a benzyloxy group, a hydroxy group, a lower alkoxy group, a lower alkanoyloxy group, a carbamoyl group, a lower alkylaminocarbonyl group, a di-lower alkylaminocarbonyl group, a carboxyl group, a lower alkoxycarbonyl group, a lower alkylthio group, a lower alkylsulfinyl group, a lower alkylsulfonyl group, an aryl group, a lower alkanoylamino group, a lower alkylsulfonamido group, a phthalimido group, a heteroaryl group, a saturated heterocyclic group, etc. The more preferable substituents are, for example, a fluorine atom, a chlorine atom, a cyano group, a hydroxy group, a carbamoyl group, a 2-pyridyl group, a 3-pyridyl group, a 4-pyridyl group, etc.

The acid for forming an acid addition salt includes, for example, inorganic acids such as hydrochloric acid, hydrobromic acid, hydroiodic acid, sulfuric acid, nitric acid, etc., or organic acids such as acetic acid, oxalic acid, citric acid, malic acid, tartaric acid, fumaric acid, maleic acid, methanesulfonic acid, etc.

The compounds of the present invention may have a stereoisomer due to an asymmetric carbon atom thereof. In such cases, the present compounds also include each isomer or a mixture thereof.

The present compounds and an acid addition salt may be in the form of an anhydrous crystal thereof, or in the form of a solvate thereof such as hydrate.

The compounds of the above-mentioned formula (1) or an acid addition salt thereof can be administered either parenterally or orally when used as the above-mentioned drug. The present compounds can be formulated into liquid preparations such as solutions, emulsions, suspensions, etc., and can be administered in the form of an injection, and if necessary, buffering agents, solubilizers and isotonic agents may be added thereto. The present compounds can also be administered rectally in the form of a suppository. The present compounds can also be administered orally in the form of a conventional administration form such as tablets, capsules, syrups, and suspension. These pharmaceutical preparations can be formulated by mixing an active ingredient with conventional carriers or diluents, binding agents or stabilizers by a conventional manner.

The dosage, the frequency of administration of the present compounds may vary according to the conditions, ages, weights of the patients and the administration form, etc., but the present compounds can be administered in a dosage of 1 to about 500 mg per an adult per day, once a day, or divided into 2–4 dosage units.

The naphthyridine derivative which is an active ingredient of the present invention may be prepared by the following processes.

The compound (1) wherein Z is —NH— may be prepared by the following process.

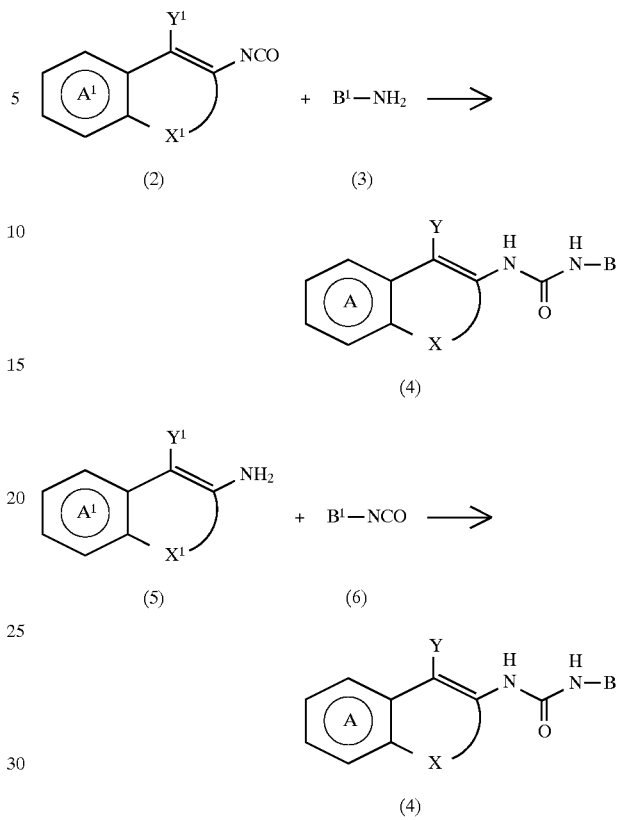

wherein Ring A, X, Y and B are the same as defined above, Ring $A^1$ is the same groups for Ring A but when these groups contain a reactive group as a substituent such as an amino group, an alkylamino group, a hydroxy group, etc. then these reactive groups should be protected, $X^1$ is the same groups for X, but when these groups contain a reactive group as a substituent such as an amino group, an alkylamino group, a hydroxy group, a carboxyl group, etc., then these reactive groups should be protected, $Y^1$ is the same groups for Y, but when these groups contain a reactive group as a substituent such as an amino group, an alkylamino group, a hydroxy group, a carboxyl group, etc., then these reactive groups should be protected, and $B^1$ is the same groups for B but when these groups contain a reactive group as a substituent such as an amino group, an alkylamino group, a hydroxy group, carboxyl group, etc., then these reactive groups should be protected.

The isocyanate derivative (2) and the amine derivative (3) or an acid addition salt thereof are usually reacted in a solvent at a temperature of from 0° C. to a boiling point of the solvent, preferably at a temperature of from room temperature to 120° C., and if necessary, the protecting groups of the product are removed to give the urea derivative (4). The solvent may be any solvent which does not disturb the reaction, but preferably ethers (e.g., ethyl ether, isopropyl ether, tetrahydrofuran, dioxane, etc), aromatic hydrocarbons (e.g., benzene, toluene, etc.), esters (e.g., methyl acetate, ethyl acetate, etc.), N,N-dimethylformamide, dimethylsulfoxide, and the like.

When the amine derivative (3) is used in the form of an acid addition salt thereof, the reaction may preferably proceed by converting the compound (3) into a free form, if necessary. In this case, an agent for converting the compound (2) into a free form is preferably a tertiary amine such as triethylamine, etc., or an aromatic amine such as pyridine, etc. On the other hand, the amine derivative (5) or an acid addition salt thereof and the isocyanate derivative (6) are reacted to give the urea derivative (4), as well.

The protecting groups for amino group, alkylamino group, hydroxy group, carboxyl group, etc., may be conventional protecting groups which are used in the field of the organic chemistry, for example, the protecting group for hydroxy group may be benzyl group, acetyl group, etc., and the protecting group for amino group may be benzyl group, etc., and these protecting groups may be introduced and removed by a conventional method, such as by a method disclosed in PROTECTIVE GROUPS IN ORGANIC SYNTHESIS, 2nd ed., John Wiley & Sons, Inc.; New York.

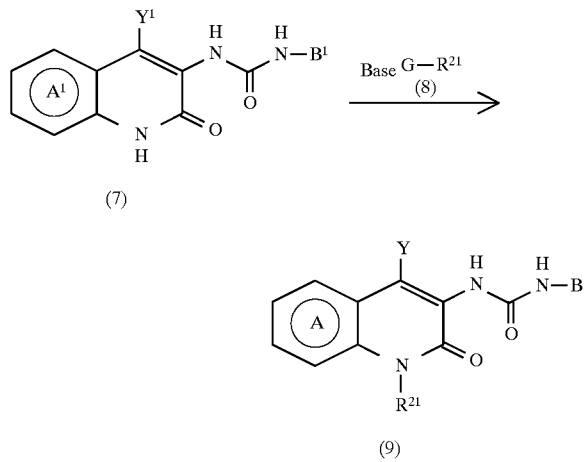

wherein Ring A, Y, B, Ring $A^1$, $Y^1$, and $B^1$ are the same as defined above, $R^{21}$ is the same groups as for $R^2$ but when these groups contain a reactive group as a substituent such as an amino group, an alkylamino group, a hydroxy group, carboxyl group, etc., then these reactive groups should be protected, and G is a leaving group.

Among the urea derivatives (4), the compound of the formula (7) is reacted with an alkylating agent of the formula (8), and if necessary, the protecting groups of the product are removed to give the urea derivative of the formula (9). The alkylation reaction is carried out in a solvent at a temperature of from 0° C. to 100° C., preferably at a temperature of from room temperature to 70° C. in the presence of a base. The solvent includes, for example, ethers (e.g., tetrahydrofuran, dioxane), ketones (e.g., acetone, 2-butanone), aromatic hydrocarbons (e.g., benzene, toluene), N,N-dimethylformamide, etc. The base includes, for example, sodium hydride, potassium carbonate, sodium carbonate, triethylamine, etc. The leaving group represented by G is usually a halogen atom such as chlorine atom, bromine atom, iodine atom, etc., or an aromatic sulfonyloxyoxy group such as p-toluenesulfonyloxy group.

The compound (1) wherein Z is a direct bond, an alkylene group having 1 to 2 carbon atoms, or —CH═CH— can be prepared by the following process.

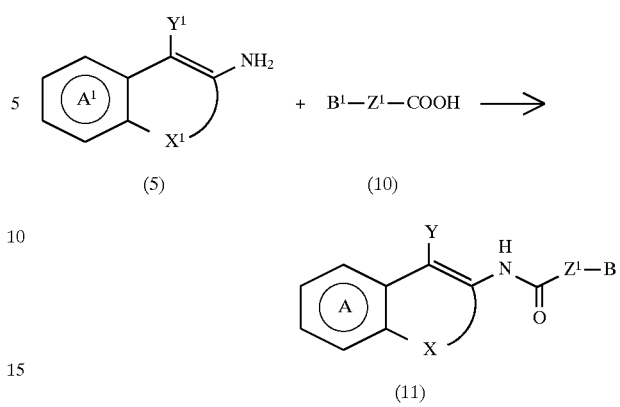

wherein Ring A, Y, B, X, Ring $A^1$, $Y^1$, $B^1$ and $X^1$ are the same as defined above, $Z^1$ is a direct bond, an alkylene group having 1 to 2 carbon atoms, or —CH═CH—.

The amine derivative of the formula (5) or an acid addition salt thereof is condensed with the carboxylic acid derivative of the formula (10) in a solvent at a temperature of from 0° C. to 100° C., preferably at a temperature of from 0° C. to 60° C. with using a condensation agent, and the protecting groups of the product are removed, if necessary, to give the amide derivative of the formula (11). The condensation agent includes, for example, dicyclohexylcarbodiimide (DCC), diethyl cyanophosphate (DEPC), 1-ethyl-3-(3'-dimethylaminopropyl)-carbodiimide hydrochloride (WSC), etc. The reaction may preferably be carried out by addition of a base in an amount of 1 to 5 mole equivalents, preferably in an amount of 1 to 3 mole equivalents, to the amount of the amine derivative (5) or acid addition salts thereof. The base is preferably selected from tertiary amines such as triethylamine, etc., or aromatic amines such as pyridine, etc. The solvent may be, for example, ethers (e.g., tetrahydrofuran, dioxane, etc.), aromatic hydrocarbons (e.g., benzene, toluene, etc.), esters (e.g., ethyl acetate, etc.), N,N-dimethylformamide, dimethylsulfoxide, etc.

The carboxylic acid derivative (10) may be converted into a reactive derivative thereof, and then reacted with the amine derivative (5) in a solvent at a temperature of from −10° C. to 120° C., preferably at a temperature of from 0° C. to 60° C. to give the amide derivative (11). The reactive derivative of the compound (10) includes, for example, an acid chloride, an acid bromide, an acid anhydride, or a mixed acid anhydride with methyl carbonate, ethyl carbonate. The reaction may preferably be carried out by addition of a base in an amount of 1 to 5 mole equivalents, preferably in an amount of 1 to 3 mole equivalents. The base includes, for example, tertiary amines such as triethylamine, etc., aromatic amines such as pyridine, alkali metal carbonates such as sodium carbonate, potassium carbonate, alkali metal hydrogen carbonates such as sodium hydrogen carbonate, etc. The solvent may be, for example, halogenated solvents (e.g., chloroform, dichloromethane, etc.), ethers (e.g., tetrahydrofuran, dimethoxyethane, etc.), aromatic hydrocarbons (e.g., benzene, toluene, etc.), esters (e.g., ethyl acetate, etc.), pyridine or N,N-dimethylformamide.

The amide derivative (11) wherein $Z^1$ is —CH$_2$CH$_2$— can also be prepared by reduction of the amide derivative (10) wherein $Z^1$ is —CH═CH—. The reduction is carried out in a solvent by using a reducing agent (e.g., lithium aluminum hydride, sodium borohydride, lithium borohydride, etc.) in an amount of 0.5 to 5 mole equivalents, preferably in an amount of 0.5 to 2 mole equivalents, at a temperature of from −5° C. to 120° C., preferably at a temperature of from 0° C. to 80° C. The solvent includes, for example, alcohols (e.g., methanol, ethanol, etc.) and ethers (e.g., ethyl ether, tetrahydrofuran, dioxane, etc.). The reduction is also carried by catalytic reduction. For example, the reduction is carried out by using as a catalyst palladium carbon, platinum oxide, Raney-nickel, etc. in a solvent under atmospheric pressure to a pressure of 5 atms of hydrogen gas, at a temperature of from 0° C. to 100° C., preferably at a temperature of from room temperature to 60° C. The solvent may be selected from alcohols (e.g., methanol, ethanol, etc.), formic acid, acetic acid, etc.

The substituents of Ring A, Y, X or B in the urea derivative (4) and the amide derivative (11) thus obtained can be converted into others, if necessary. For example, a lower alkylthio group can be converted into a lower alkylsulfonyl group by oxidization. A nitro group is converted into an amino group by reduction. An amino group can be alkylated to a mono- or di-alkylamino group, or an amino group can also be acylated. A 3-chloropropoxy group is converted into a 3-(1-imidazolyl)propoxy group. A halogen atom such as bromine atom or iodine atom can be converted into a 1-propargyl group having a hydroxy group, an amino group, etc. at 3-position thereof, by using a palladium catalyst. Moreover, such propargyl group can be converted into a propyl group by a hydrogenation reaction. Such conversion reactions can be carried out by using a well-known technique which is usually applied in the organic chemistry field. As one of the conversion reactions of the substituents, the alkylation reaction can be carried out as follows.

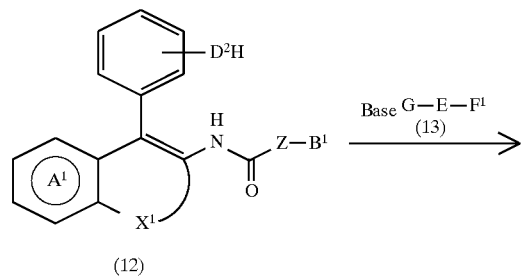

(12)

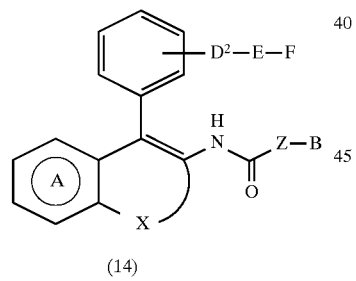

(14)

wherein Ring A, B, X, Z, E, F, G, $D^2$, Ring $A^1$, $B^1$, and $X^1$ are the same as defined above, $F^1$ is the same groups as for F but when these groups contain a reactive group as a substituent such as an amino group, an alkylamino group, a hydroxy group, a carboxyl group, etc., then these reactive groups should be protected.

The compound (12) is reacted with the alkylating agent (13) in a solvent, and if necessary, the protecting groups of the product are removed, to give the compound (14). The reaction is usually carried out at a temperature of from 0° C. to 100° C., preferably at a temperature of from room temperature to 70° C., in the presence of a base. The solvent may be, for example, ethers (e.g., tetrahydrofuran, dioxane, etc.), aromatic hydrocarbons (e.g., benzene, toluene, etc.), ketones (e.g., acetone, 2-butanone, etc.), dimethylformamide, etc. The base may be, for example, sodium hydride, potassium carbonate, sodium carbonate, triethylamine, etc. When potassium carbonate or sodium carbonate is used, the efficiency of the reaction is optionally increased by addition of sodium iodide or potassium iodide. The leaving group represented by G is usually halogen atoms such as chlorine atom, bromine atom, iodine atom, etc., or an aromatic sulfonyloxy group such as p-toluenesulfonyloxy group, etc.

The starting compound (2) or (5) for preparing the compound (1) of the present invention or an acid addition salt thereof can be prepared by the following process or by a modified process thereof.

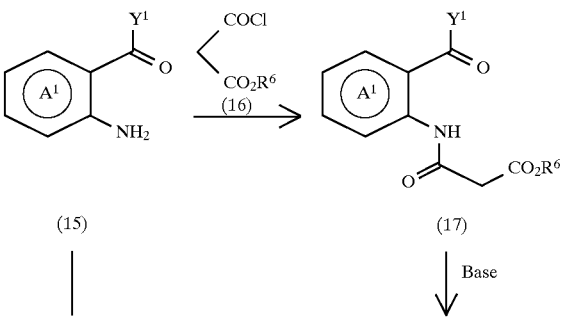

(15)  (17)

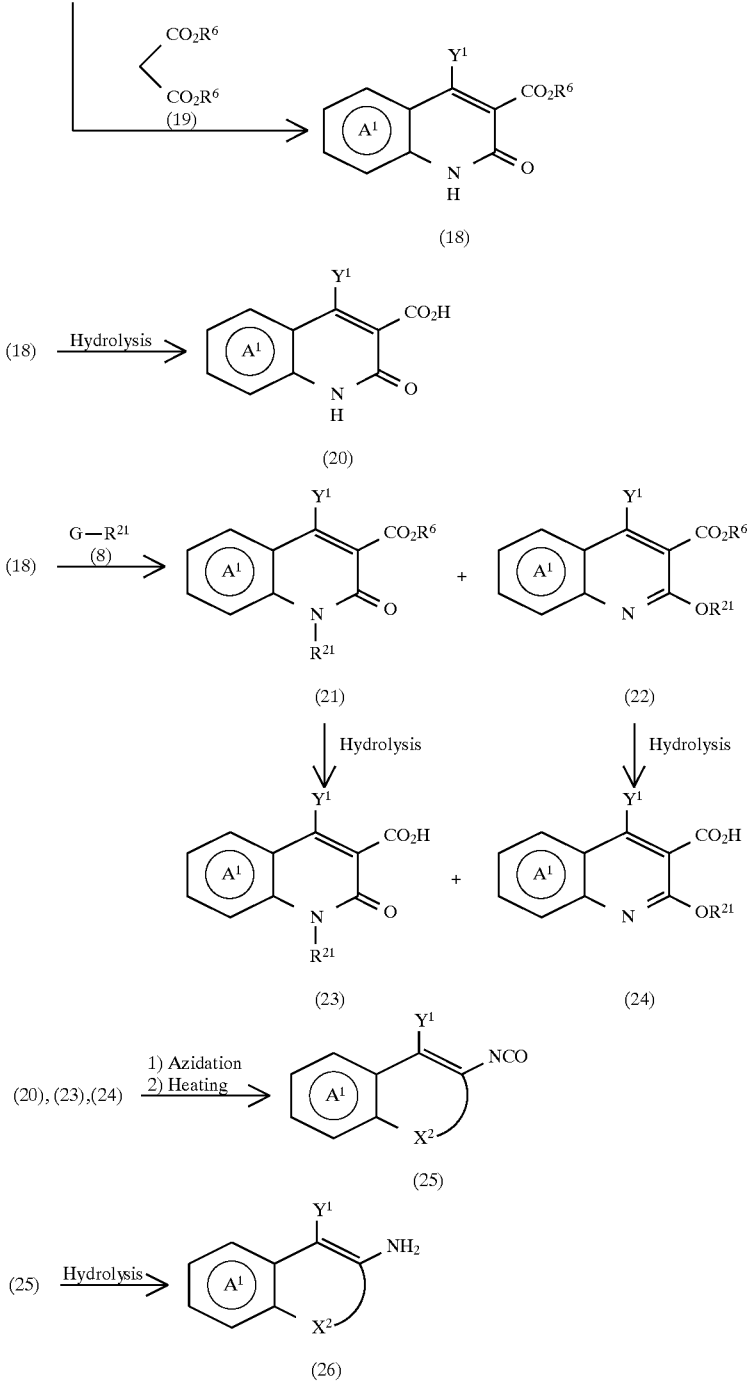

wherein Ring $A^1$, $Y^1$, $R^{21}$, and G are the same as defined above, $R^6$ is a lower alkyl group, and $X^2$ is —NH—CO—, —NR$^{21}$—CO— or —N=C(OR$^{21}$)—.

The starting compound (15) is prepared by the method disclosed in the literature, for example, J. Heterocyclic Chem., 26, 105–112, 1989, or a modified method thereof. The lower alkyl group represented by $R^6$ is preferably one having 1 to 4 carbon atoms, such as methyl, ethyl, propyl, isopropyl, butyl, etc.

The aminoketone derivative (15) is reacted with the acid chloride (16) in the presence of a base in a solvent at a temperature of from -20° C. to 150° C., preferably at a temperature of from 0° C. to 120° C., to give the amide derivative (17). The solvent may be, for example, ethers (e.g., ethyl ether, tetrahydrofuran, dioxane, etc.), aromatic hydrocarbons (e.g., benzene, toluene, etc.), halogenated solvents (e.g., dichloromethane, chloroform, etc.), pyridine, N,N- dimethylformamide, etc. The base includes, for example, triethylamine, pyridine, potassium carbonate, sodium carbonate, sodium hydrogen carbonate, etc. The amide derivative (17) thus obtained is subjected to cyclization reaction in a solvent such as benzene, toluene, tetrahydrofuran, dimethoxyethane, etc., at a temperature of from 0° C. to 200° C., preferably at a temperature of from room temperature to 170° C., in the presence of a base in an amount of 0.1 to 3 mole equivalents, preferably in an amount of 0.1 to 2 mole equivalents to give the compound (18). The base includes, for example, potassium t-butoxide, sodium methoxide, sodium ethoxide, piperidine, triethylamine, 1,5-diazabicyclo[4.3.0]-non-5-ene (DBN), 1,8-diazabicyclo[5.4.0]-7-undecene (DBU), and 1,4-diaza-bicyclo[2.2.2]octane (DABCO). The compound (18) can also be prepared by heating the compound (15) with the malonic acid diester derivative (19) in the presence of an amine (e.g., piperidine, pyrrolidine, triethylamine, pyridine, DBN, DBU, DABCO, etc.), or potassium fluoride, tetrabutylammonium fluoride, at a temperature of from 60° C. to 200° C., without a solvent.

On the other hand, the compound (18) is reacted with the alkylating agent (8) in the presence of a base at a temperature of from 0° C. to 150° C., preferably at a temperature of from room temperature to 100° C., in a solvent, to give the N-alkyl compound (21) and/or the O-alkyl compound (22). The solvent includes, for example, alcohols (e.g., methanol, ethanol, etc.), ethers (e.g., tetrahydrofuran, dioxane, etc.), ketones (e.g., acetone, 2-butanone, etc.), and dimethylformamide. The base includes, for example, sodium hydroxide, potassium hydroxide, sodium methoxide, sodium ethoxide, potassium t-butoxide, sodium hydride, potassium carbonate, sodium carbonate, triethylamine, etc. The leaving group represented by G is usually a halogen atom such as chlorine atom, bromine atom, iodine atom, etc., or an aromatic sulfonyloxy group such as p-toluenesulfonyloxy group. In this reaction, there is obtained a mixture of the compound (21) and the compound (22), but both compounds can be separated by recrystallization or chromatography. On the other hand, the compound (21) can be preferentially obtained by selecting the kinds of the compound (18), the kinds of the solvents, the kinds of the base, or reaction temperature.

The hydrolysis of the compound (18), the compound (21) and the compound (22) is carried out by a conventional method, for example, in a solvent such as methanol, ethanol, isopropanol, tetrahydrofuran, dioxane, dimethoxyethane, etc., at a temperature of from 0° C. to 150° C., preferably at a temperature of from 0° C. to 100° C., by using a hydroxide of an alkali metal or an alkaline earth metal such as sodium hydroxide, potassium hydroxide, barium hydroxide, etc. The carboxylic acid derivative of the formulae (20), (23) or (24) can be converted into the isocyanate derivative (25) by a conventional method, and if necessary, the compound (25) is further converted into the amine derivative (26). For example, the carboxylic acid derivative of the formulae (20), (23) or (24) is converted into an acid azide compound by using an azidation agent (e.g., diphenylphosphoryl azide (DPPA), etc.) in an amount of 1 to 3 mole equivalents, in the presence of a base (e.g., triethylamine, N-methylmorpholine, etc.), at a temperature of from 0° C. to 150° C., preferably at a temperature of from room temperature to 120° C. in a solvent such as aromatic hydrocarbons (e.g., benzene, toluene), N,N-dimethylformamide, etc., and the acid azide compound thus obtained is heated at a temperature of from 20° C. to 200° C., preferably at a temperature of from 30° C. to 150° C. without isolating from the reaction mixture, to give the compound (25). Moreover, the compound (25) is hydrolyzed in the same manner as in the hydrolysis of the compound (18), (21) or (22), to give the compound (26).

Some of the compounds (5) can be prepared by the following process, or by a modified process thereof.

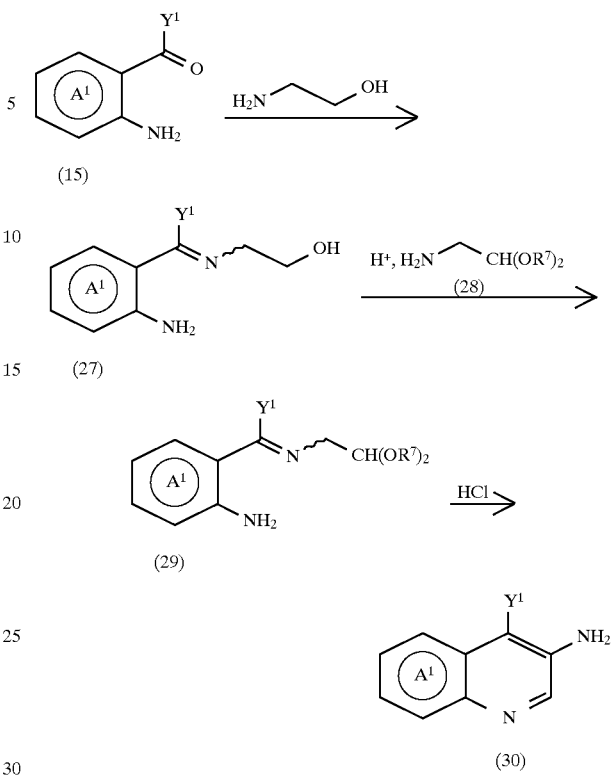

wherein Ring $A^1$ and $Y^1$ are the same as defined above, and $R^7$ is an alkyl group.

The alkyl group for $R^7$ is preferably ones having 1 to 4 carbon atoms such as methyl, ethyl, propyl, isopropyl, butyl, etc.

The aminoketone derivative (15) is treated in the same manner as disclosed in Yakugaku Zasshi, vol. 93, p. 1263 (1973), or a modified method thereof, to give the aminonaphthyridine derivative (30).

The present compounds obtained by the present process, and the intermediates thereof may be purified by a conventional method, for example, column chromatography, recrystallization, etc. The solvent for recrystallization may be, for example, alcohols (e.g., methanol, ethanol, 2-propanol, etc.), ethers (e.g., diethyl ether, etc.), esters (e.g., ethyl acetate, etc.), aromatic solvents (e.g., toluene, etc.), ketones (e.g., acetone, etc.), hydrocarbons (e.g., hexane, etc.), or a mixture of these solvents, which is selected according to the kinds of the compound to be recrystallized.

The representatives of the present compound obtained by the above process are as follows:

N-[4-(3-methoxyphenyl)-1,2-dihydro-2-oxo-1,8-naphthyridin-3-yl]-N'-(2,6-diisopropylphenyl)urea N-(1-methyl-4-phenyl-1,2-dihydro-2-oxo-1,8-naphthyridin-3-yl)-N'-(2,6-diisopropylphenyl)urea N-[1-methyl-4-(2-chlorophenyl)-1,2-dihydro-2-oxo-1,8-naphthyridin-3-yl]-N'-(2,6-diisopropylphenyl)urea N-[1-methyl-4-(2-methoxyphenyl)-1,2-dihydro-2-oxo-1,8-naphthyridin-3-yl]-N'-(2,6-diisopropylphenyl)urea N-[1-methyl-4-(3-methoxyphenyl)-1,2-dihydro-2-oxo-1,8-naphthyridin-3-yl]-N'-(2,6-diisopropylphenyl)urea N-[1-methyl-4-(4-methoxyphenyl)-1,2-dihydro-2-oxo-1,8-naphthyridin-3-yl]-N'-(2,6-diisopropylphenyl)urea N-[1-methyl-4-(2-hydroxyphenyl)-1,2-dihydro-2-oxo-1,8-naphthyridin-3-yl]-N'-(2,6-diisopropylphenyl)urea N-[1-methyl-4-(3-hydroxyphenyl)-1,2-dihydro-2-oxo-1,8-naphthyridin-3-yl]-N'-(2,6-diisopropylphenyl)urea N-[1-methyl-4-(4-hydroxyphenyl)-1,2-dihydro-2-oxo-1,8-naphthyridin-3-yl]-N'-(2,6-diisopropylphenyl)urea N-[1-methyl-4-(2-aminophenyl)-1,2-dihydro-2-oxo-1,8-naphthyridin-3-yl]-N'-(2,6-diisopropylphenyl)urea N-[1-methyl-4-(3-aminophenyl)-1,2-dihydro-2-oxo-1,8-naphthyridin-3-yl]-N'-(2,6-diisopropylphenyl)urea N-[1-methyl-4-(4-aminophenyl)-1,2-dihydro-2-oxo-1,8-naphthyridin-3-yl]-N'-(2,6-diisopropylphenyl)urea N-[1-methyl-4-{3-(2-hydroxyethoxy)phenyl}-1,2-dihydro-2-oxo-1,8-naphthyridin-3-yl]-N'-(2,6-diisopropylphenyl)urea N-[1-methyl-4-{3-(2-acetoxyethoxy)phenyl}-1,2-dihydro-2-oxo-1,8-naphthyridin-3-yl]-N'-(2,6-diisopropylphenyl)urea N-[1-methyl-4-{3-(2-diethylaminoethoxy)phenyl}-1,2-dihydro-2-oxo-1,8-naphthyridin-3-yl]-N'-(2,6-diisopropylphenyl)urea N-[1-methyl-4-{3-(2-diethylaminoethoxy)phenyl}-1,2-dihydro-2-oxo-1,8-naphthyridin-3-yl]-N'-(2,6-diisopropylphenyl)urea N-[1-methyl-4-{3-(4-pyridylmethoxy)phenyl}-1,2-dihydro-2-oxo-1,8-naphthyridin-3-yl]-N'-(2,6-diisopropylphenyl)urea N-[1-methyl-4-{3-(3-hydroxypropoxy)phenyl}-1,2-dihydro-2-oxo-1,8-naphthyridin-3-yl]-N'-(2,6-diisopropylphenyl)urea N-[1-methyl-4-{3-(3-acetoxypropoxy)phenyl}-1,2-dihydro-2-oxo-1,8-naphthyridin-3-yl]-N'-(2,6-diisopropylphenyl)urea N-[1-methyl-4-{3-(3-dimethylaminopropoxy)phenyl}-1,2-dihydro-2-oxo-1,8-naphthyridin-3-yl]-N'-(2,6-diisopropylphenyl)urea N-[1-methyl-4-[3-{3-(4-phenyl-1-piperazinyl)propoxy}phenyl]-1,2-dihydro-2-oxo-1,8-naphthyridin-3-yl]-N'-(2,6-diisopropylphenyl)urea N-[1-methyl-4-{3-(2-piperidinoethoxy)phenyl}-1,2-dihydro-2-oxo-1,8-naphthyridin-3-yl]-N'-(2,6-diisopropylphenyl)urea N-(1-methyl-4-butyl-1,2-dihydro-2-oxo-1,8-naphthyridin-3-yl)-N'-(2,6-diisopropylphenyl)urea N-(1-methyl-4-cyclohexyl-1,2-dihydro-2-oxo-1,8-naphthyridin-3-yl)-N'-(2,6-diisopropylphenyl)urea N-[1-methyl-4-(2-pyridyl)-1,2-dihydro-2-oxo-1,8-naphthyridin-3-yl]-N'-(2,6-diisopropylphenyl)urea N-[1-methyl-4-(3-pyridyl)-1,2-dihydro-2-oxo-1,8-naphthyridin-3-yl]-N'-(2,6-diisopropylphenyl)urea N-[1-methyl-4-(4-pyridyl)-1,2-dihydro-2-oxo-1,8-naphthyridin-3-yl]-N'-(2,6-diisopropylphenyl)urea N-[1-methyl-4-(2-furyl)-1,2-dihydro-2-oxo-1,8-naphthyridin-3-yl]-N'-(2,6-diisopropylphenyl)urea N-[1-methyl-4-(3-furyl)-1,2-dihydro-2-oxo-1,8-naphthyridin-3-yl]-N'-(2,6-diisopropylphenyl)urea N-[1-methyl-4-(2-thienyl)-1,2-dihydro-2-oxo-1,8-naphthyridin-3-yl]-N'-(2,6-diisopropylphenyl)urea N-[1-methyl-4-(3-thienyl)-1,2-dihydro-2-oxo-1,8-naphthyridin-3-yl]-N'-(2,6-diisopropylphenyl)urea N-[1-benzyl-4-(3-methoxyphenyl)-1,2-dihydro-2-oxo-1,8-naphthyridin-3-yl]-N'-(2,6-diisopropylphenyl)urea N-[1-benzyl-4-{3-(2-diethylaminoethoxy)phenyl}-1,2-dihydro-2-oxo-1,8-naphthyridin-3-yl]-N'-(2,6-diisopropylphenyl)urea N-[1-benzyl-4-{3-(4-pyridylmethoxy)phenyl}-1,2-dihydro-2-oxo-1,8-naphthyridin-3-yl]-N'-(2,6-diisopropylphenyl)urea N-[1-cyclopropylmethyl-4-(3-methoxyphenyl)-1,2-dihydro-2-oxo-1,8-naphthyridin-3-yl]-N'-(2,6-diisopropylphenyl)urea N-[1-cyclopropylmethyl-4-{3-(2-diethylaminoethoxy)phenyl}-1,2-dihydro-2-oxo-1,8-naphthyridin-3-yl]-N'-(2,6-diisopropylphenyl)urea N-[1-cyclopropylmethyl-4-{3-(4-pyridylmethoxy)phenyl}-1,2-dihydro-2-oxo-1,8-naphthyridin-3-yl]-N'-(2,6-diisopropylphenyl)urea N-[1-cyclopentylmethyl-4-(3-methoxyphenyl)-1,2-dihydro-2-oxo-1,8-naphthyridin-3-yl]-N'-(2,6-diisopropylphenyl)urea N-[1-cyclopentylmethyl-4-{3-(4-pyridylmethoxy)phenyl}-1,2-dihydro-2-oxo-1,8-naphthyridin-3-yl]-N'-(2,6-diisopropylphenyl)urea N-[1-cyclohexylmethyl-4-(3-methoxyphenyl)-1,2-dihydro-2-oxo-1,8-naphthyridin-3-yl]-N'-(2,6-diisopropylphenyl)urea N-[1-cyclohexylmethyl-4-{3-(4-pyridylmethoxy)phenyl}-1,2-dihydro-2-oxo-1,8-naphthyridin-3-yl]-N'-(2,6-diisopropylphenyl)urea N-[1-carboxymethyl-4-(3-methoxyphenyl)-1,2-dihydro-2-oxo-1,8-naphthyridin-3-yl]-N'-(2,6-diisopropylphenyl)urea N-[1-tert-butoxycarbonylmethyl-4-(3-methoxyphenyl)-1,2-dihydro-2-oxo-1,8-naphthyridin-3-yl]-N'-(2,6-diisopropylphenyl)urea N-[1-(4-pyridylmethyl)-4-(3-methoxyphenyl)-1,2-dihydro-2-oxo-1,8-naphthyridin-3-yl]-N'-(2,6-diisopropylphenyl)urea N-[1-(2-pyridylmethyl)-4-(3-methoxyphenyl)-1,2-dihydro-2-oxo-1,8-naphthyridin-3-yl]-N'-(2,6-diisopropylphenyl)urea N-[1-ethyl-4-(3-methoxyphenyl)-1,2-dihydro-2-oxo-1,8-naphthyridin-3-yl]-N'-(2,6-diisopropylphenyl)urea N-[1-ethyl-4-{3-(4-pyridylmethoxy)phenyl}-1,2-dihydro-2-oxo-1,8-naphthyridin-3-yl]-N'-(2,6-diisopropylphenyl)urea N-[1-(2-phenylethyl)-4-(3-methoxyphenyl)-1,2-dihydro-2-oxo-1,8-naphthyridin-3-yl]-N'-(2,6-diisopropylphenyl)urea N-[1-(2-phenylethyl)-4-{3-(4-pyridylmethoxy)phenyl}-1,2-dihydro-2-oxo-1,8-naphthyridin-3-yl]-N'-(2,6-diisopropylphenyl)urea N-[1-(2-methoxyethyl)-4-(3-methoxyphenyl)-1,2-dihydro-2-oxo-1,8-naphthyridin-3-yl]-N'-(2,6-diisopropylphenyl)urea N-[1-(2-hydroxyethyl)-4-(3-methoxyphenyl)-1,2-dihydro-2-oxo-1,8-naphthyridin-3-yl]-N'-(2,6-diisopropylphenyl)urea N-[1-(2-cyanoethyl)-4-(3-methoxyphenyl)-1,2-dihydro-2-oxo-1,8-naphthyridin-3-yl]-N'-(2,6-diisopropylphenyl)urea N-[1-(2-diethylaminoethyl)-4-(3-methoxyphenyl)-1,2-dihydro-2-oxo-1,8-naphthyridin-3-yl]-N'-(2,6-diisopropylphenyl)urea N-[1-propyl-4-(3-methoxyphenyl)-1,2-dihydro-2-oxo-1,8-naphthyridin-3-yl]-N'-(2,6-diisopropylphenyl)urea N-[1-propyl-4-{3-(4-pyridylmethoxy)phenyl}-1,2-dihydro-2-oxo-1,8-naphthyridin-3-yl]-N'-(2,6-diisopropylphenyl)urea N-[1-(2-propenyl)-4-(3-methoxyphenyl)-1,2-dihydro-2-oxo-1,8-naphthyridin-3-yl]-N'-(2,6-diisopropylphenyl)urea N-[1-(2-propenyl)-4-{3-(4-pyridylmethoxy)phenyl}-1,2-dihydro-2-oxo-1,8-naphthyridin-3-yl]-N'-(2,6-diisopropylphenyl)urea N-[1-(2-methyl-2-propenyl)-4-(3-methoxyphenyl)-1,2-dihydro-2-oxo-1,8-naphthyridin-3-yl]-N'-(2,6-diisopropylphenyl)urea N-[1-(2-methyl-2-propenyl)-4-{3-(4-pyridylmethoxy)phenyl}-1,2-dihydro-2-oxo-1,8-naphthyridin-3-yl]-N'-(2,6-diisopropylphenyl)urea N-[1-(3-cyanopropyl)-4-(3-methoxyphenyl)-1,2-dihydro-2-oxo-1,8-naphthyridin-3-yl]-N'-(2,6-diisopropylphenyl)urea N-[1-(3-cyanopropyl)-4-(3-hydroxyphenyl)-1,2-dihydro-2-oxo-1,8-naphthyridin-3-yl]-N'-(2,6-diisopropylphenyl)urea N-[1-(3-cyanopropyl)-4-{3-(2-hydroxyethoxy)phenyl}-1,2-dihydro-2-oxo-1,8-naphthyridin-3-yl]-N'-(2,6-diisopropylphenyl)urea N-[1-(3-cyanopropyl)-4-{3-(2-diethylaminoethoxy)phenyl}-1,2-dihydro-2-oxo-1,8-naphthyridin-3-yl]-N'-(2,6-diisopropylphenyl)urea N-[1-(3-cyanopropyl)-4-{3-(3-hydroxypropoxy)phenyl}-1,2-dihydro-2-oxo-1,8-naphthyridin-3-yl]-N'-(2,6-diisopropylphenyl)urea N-[1-(3-cyanopropyl)-4-[3-{3-(1-imidazolyl)propoxy}phenyl]-1,2-dihydro-2-oxo-1,8-naphthyridin-3-yl]-N'-(2,6-diisopropylphenyl)urea N-[1-(3-hydroxypropyl)-4-(3-methoxyphenyl)-1,2-dihydro-2-oxo-1,8-naphthyridin-3-yl]-N'-(2,6-diisopropylphenyl)urea N-[1-(3-benzyloxypropyl)-4-(3-methoxyphenyl)-1,2-dihydro-2-oxo-1,8-naphthyridin-3-yl]-N'-(2,6-diisopropylphenyl)urea N-[1-(3-aminopropyl)-4-(3-methoxyphenyl)-1,2-dihydro-2-oxo-1,8-naphthyridin-3-yl]-N'-(2,6-diisopropylphenyl)urea N-[1-(3-dimethylaminopropyl)-4-(3-methoxyphenyl)-1,2-dihydro-2-oxo-1,8-naphthyridin-3-yl]-N'-(2,6-diisopropylphenyl)urea N-[1-(3-aminocarbonylpropyl)-4-(3-methoxyphenyl)-1,2-dihydro-2-oxo-1,8-naphthyridin-3-yl]-N'-(2,6-diisopropylphenyl)urea N-[1-(3-acetylaminopropyl)-4-(3-methoxyphenyl)-1,2-dihydro-2-oxo-1,8-naphthyridin-3-yl]-N'-(2,6-diisopropylphenyl)urea N-[1-(3-phthalimidopropyl)-4-(3-methoxyphenyl)-1,2-dihydro-2-oxo-1,8-naphthyridin-3-yl]-N'-(2,6-diisopropylphenyl)urea N-[1-(3-dimethylaminopropyl)-4-(3-methoxyphenyl)-1,2-dihydro-2-oxo-1,8-naphthyridin-3-yl]-N'-(2,6-diisopropylphenyl)urea N-[1-(3-diethylaminopropyl)-4-(3-methoxyphenyl)-1,2-dihydro-2-oxo-1,8-naphthyridin-3-yl]-N'-(2,6-diisopropylphenyl)urea N-[1-(3-piperidinopropyl)-4-(3-methoxyphenyl)-1,2-dihydro-2-oxo-1,8-naphthyridin-3-yl]-N'-(2,6-diisopropylphenyl)urea N-[1-{3-(1-imidazolyl)propyl}-4-(3-methoxyphenyl)-1,2-dihydro-2-oxo-1,8-naphthyridin-3-yl]-N'-(2,6-diisopropylphenyl)urea N-[1-isopropyl-4-(3-methoxyphenyl)-1,2-dihydro-2-oxo-1,8-naphthyridin-3-yl]-N'-(2,6-diisopropylphenyl)urea N-[1-isopropyl-4-{3-(4-pridylmethoxy)phenyl}-1,2-dihydro-2-oxo-1,8-naphthyridin-3-yl]-N'-(2,6-diisopropylphenyl)urea N-[1-butyl-4-(2-methoxyphenyl)-1,2-dihydro-2-oxo-1,8-naphthyridin-3-yl]-N'-(2,6-diisopropylphenyl)urea N-[1-butyl-4-(3-methoxyphenyl)-1,2-dihydro-2-oxo-1,8-naphthyridin-3-yl]-N'-(2,6-diisopropylphenyl)urea N-[1-butyl-4-(4-methoxyphenyl)-1,2-dihydro-2-oxo-1,8-naphthyridin-3-yl]-N'-(2,6-diisopropylphenyl)urea N-[1-butyl-4-(2-hydroxyphenyl)-1,2-dihydro-2-oxo-1,8-naphthyridin-3-yl]-N'-(2,6-diisopropylphenyl)urea N-[1-butyl-4-(3-hydroxyphenyl)-1,2-dihydro-2-oxo-1,8-naphthyridin-3-yl]-N'-(2,6-diisopropylphenyl)urea N-[1-butyl-4-(4-hydroxyphenyl)-1,2-dihydro-2-oxo-1,8-naphthyridin-3-yl]-N'-(2,6-diisopropylphenyl)urea N-[1-butyl-4-(2-aminophenyl)-1,2-dihydro-2-oxo-1,8-naphthyridin-3-yl]-N'-(2,6-diisopropylphenyl)urea N-[1-butyl-4-(3-aminophenyl)-1,2-dihydro-2-oxo-1,8-naphthyridin-3-yl]-N'-(2,6-diisopropylphenyl)urea N-[1-butyl-4-(4-aminophenyl)-1,2-dihydro-2-oxo-1,8-naphthyridin-3-yl]-N'-(2,6-diisopropylphenyl)urea N-[1-butyl-4-(4-bromophenyl)-1,2-dihydro-2-oxo-1,8-naphthyridin-3-yl]-N'-(2,6-diisopropylphenyl)urea N-[1-butyl-4-{3-(2-pyridylmethoxy)phenyl}-1,2-dihydro-2-oxo-1,8-naphthyridin-3-yl]-N'-(2,6-diisopropylphenyl)urea N-[1-butyl-4-{3-(3-pyridylmethoxy)phenyl}-1,2-dihydro-2-oxo-1,8-naphthyridin-3-yl]-N'-(2,6-diisopropylphenyl)urea N-[1-butyl-4-{3-(4-pyridylmethoxy)phenyl}-1,2-dihydro-2-oxo-1,8-naphthyridin-3-yl]-N'-(2,6-diisopropylphenyl)urea N-[1-butyl-4-{3-(2-methylpyridin-3-yl)methoxy)phenyl}-1,2-dihydro-2-oxo-1,8-naphthyridin-3-yl]-N'-(2,6-diisopropylphenyl)urea N-[1-butyl-4-{3-(6-chloropyridin-3-yl)methoxy)phenyl}-1,2-dihydro-2-oxo-1,8-naphthyridin-3-yl]-N'-(2,6-diisopropylphenyl)urea N-[1-butyl-4-{3-(6-chloropyridin-3-yl)methoxy)phenyl}-1,2-dihydro-2-oxo-1,8-naphthyridin-3-yl]-N'-(2,6-diisopropylphenyl)urea N-[1-butyl-4-{3-(2,4-dimethylpyridin-3-yl)methoxy)phenyl}-1,2-dihydro-2-oxo-1,8-naphthyridin-3-yl]-N'-(2,6-diisopropylphenyl)urea N-[1-butyl-4-{3-(2,6-dichloropyridin-4-yl)methoxy)phenyl}-1,2-dihydro-2-oxo-1,8-naphthyridin-3-yl]-N'-(2,6-diisopropylphenyl)urea N-[1-butyl-4-{3-(2-chloropyridin-4-yl)methoxy)phenyl}-1,2-dihydro-2-oxo-1,8-naphthyridin-3-yl]-N'-(2,6-diisopropylphenyl)urea N-[1-butyl-4-{3-(2-chloro-6-methylpyridin-4-yl)methoxy)phenyl}-1,2-dihydro-2-oxo-1,8-naphthyridin-3-yl]-N'-(2,6-diisopropylphenyl)urea N-[1-butyl-4-{3-(2-hydroxyethoxy)phenyl}-1,2-dihydro-2-oxo-1,8-naphthyridin-3-yl]-N'-(2,6-diisopropylphenyl)urea N-[1-butyl-4-{3-(2-acetoxyethoxy)phenyl}-1,2-dihydro-2-oxo-1,8-naphthyridin-3-yl]-N'-(2,6-diisopropylphenyl)urea N-[1-butyl-4-[3-{2-(2-pyridyl)ethoxy}phenyl]-1,2-dihydro-2-oxo-1,8-naphthyridin-3-yl]-N'-(2,6-diisopropylphenyl)urea N-[1-butyl-4-[3-{2-(3-pyridyl)ethoxy}phenyl]-1,2-dihydro-2-oxo-1,8-naphthyridin-3-yl]-N'-(2,6-diisopropylphenyl)urea N-[1-butyl-4-[3-{2-(4-pyridyl)ethoxy}phenyl]-1,2-dihydro-2-oxo-1,8-naphthyridin-3-yl]-N'-(2,6-diisopropylphenyl)urea N-[1-butyl-4-{3-(2-diethylaminoethoxy)phenyl}-1,2-dihydro-2-oxo-1,8-naphthyridin-3-yl]-N'-(2,6-diisopropylphenyl)urea N-[1-butyl-4-{3-(2-dimethylaminoethoxy)phenyl}-1,2-dihydro-2-oxo-1,8-naphthyridin-3-yl]-N'-(2,6-diisopropylphenyl)urea N-[1-butyl-4-{3-(2-piperidinoethoxy)phenyl}-1,2-dihydro-2-oxo-1,8-naphthyridin-3-yl]-N'-(2,6-diisopropylphenyl)urea N-[1-butyl-4-{3-(2-(1-pyrrolidinyl)ethoxy)phenyl}-1,2-dihydro-2-oxo-1,8-naphthyridin-3-yl]-N'-(2,6-diisopropylphenyl)urea N-[1-butyl-4-{3-(2-morpholinoethoxy)phenyl}-1,2-dihydro-2-oxo-1,8-naphthyridin-3-yl]-N'-(2,6-diisopropylphenyl)urea N-[1-butyl-4-{3-(3-chloropropoxy)phenyl}-1,2-dihydro-2-oxo-1,8-naphthyridin-3-yl]-N'-(2,6-diisopropylphenyl)urea N-[1-butyl-4-{3-(3-hydroxypropoxy)phenyl}-1,2-dihydro-2-oxo-1,8-naphthyridin-3-yl]-N'-(2,6-diisopropylphenyl)urea N-[1-butyl-4-{3-(3-acetoxypropoxy)phenyl}-1,2-dihydro-2-oxo-1,8-naphthyridin-3-yl]-N'-(2,6-diisopropylphenyl)urea N-[1-butyl-4-{3-(3-benzyloxypropoxy)phenyl}-1,2-dihydro-2-oxo-1,8-naphthyridin-3-yl]-N'-(2,6-diisopropylphenyl)urea N-[1-butyl-4-{3-(3-phthalimidopropoxy)phenyl}-1,2-dihydro-2-oxo-1,8-naphthyridin-3-yl]-N'-(2,6-diisopropylphenyl)urea N-[1-butyl-4-[3-{3-(2-pyridyl)propoxy}phenyl]-1,2-dihydro-2-oxo-1,8-naphthyridin-3-yl]-N'-(2,6-diisopropylphenyl)urea N-[1-butyl-4-[3-{3-(3-pyridyl)propoxy}phenyl]-1,2-dihydro-2-oxo-1,8-naphthyridin-3-yl]-N'-(2,6-diisopropylphenyl)urea N-[1-butyl-4-[3-{3-(4-pyridyl)propoxy}phenyl]-1,2-dihydro-2-oxo-1,8-naphthyridin-3-yl]-N'-(2,6-diisopropylphenyl)urea N-[1-butyl-4-{3-(3-aminopropoxy)phenyl}-1,2-dihydro-2-oxo-1,8-naphthyridin-3-yl]-N'-(2,6-diisopropylphenyl)urea N-[1-butyl-4-{3-(3-dimethylaminopropoxy)phenyl}-1,2-dihydro-2-oxo-1,8-naphthyridin-3-yl]-N'-(2,6-diisopropylphenyl)urea N-[1-butyl-4-{3-(3-diethylaminopropoxy)phenyl}-1,2-dihydro-2-oxo-1,8-naphthyridin-3-yl]-N'-(2,6-diisopropylphenyl)urea N-[1-butyl-4-{3-(3-piperidinopropoxy)phenyl}-1,2-dihydro-2-oxo-1,8-naphthyridin-3-yl]-N'-(2,6-diisopropylphenyl)urea N-[1-butyl-4-[3-{3-(4-phenyl-1-piperazinyl)propoxy}phenyl]-1,2-dihydro-2-oxo-1,8-naphthyridin-3-yl]-N'-(2,6-diisopropylphenyl)urea N-[1-butyl-4-[3-{3-(1,2,4-triazol-1-yl)propoxy}phenyl]-1,2-dihydro-2oxo-1,8-naphthyridin-3-yl]-N'-(2,6-diisopropylphenyl)urea N-[1-butyl-4-[3-{3-(1-imidazolyl)propoxy}phenyl]-1,2-dihydro-2-oxo-1,8-naphthyridin-3-yl]-N'-(2,6-diisopropylphenyl)urea N-[1-butyl-4-{3-(3-diethylamino-1-propynyl)phenyl}-1,2-dihydro-2-oxo-1,8-naphthyridin-3-yl]-N'-(2,6-diisopropylphenyl)urea N-[1-butyl-4-{3-(3-diethylaminopropyl)phenyl}-1,2-dihydro-2-oxo-1,8-naphthyridin-3-yl]-N'-(2,6-diisopropylphenyl)urea N-[1-butyl-4-{3-(3-hydroxy-1-propynyl)phenyl}-1,2-dihydro-2-oxo-1,8-naphthyridin-3-yl]-N'-(2,6-diisopropylphenyl)urea N-[1-butyl-4-{3-(3-hydroxypropyl)phenyl}-1,2-dihydro-2-oxo-1,8-naphthyridin-3-yl]-N'-(2,6-diisopropylphenyl)urea N-[1-butyl-4-{3-(2-diethylaminoethylthio)phenyl}-1,2-dihydro-2-oxo-1,8-naphthyridin-3-yl]-N'-(2,6-diisopropylphenyl)urea N-[1-butyl-4-(2-pyridyl)-1,2-dihydro-2-oxo-1,8-naphthyridin-3-yl]-N'-(2,6-diisopropylphenyl)urea N-[1-butyl-4-(3-pyridyl)-1,2-dihydro-2-oxo-1,8-naphthyridin-3-yl]-N'-(2,6-diisopropylphenyl)urea N-[1-butyl-4-(4-pyridyl)-1,2-dihydro-2-oxo-1,8-naphthyridin-3-yl]-N'-(2,6-diisopropylphenyl)urea N-[1-isobutyl-4-(3-methoxyphenyl)-1,2-dihydro-2-oxo-1,8-naphthyridin-3-yl]-N'-(2,6-diisopropylphenyl)urea N-[1-isobutyl-4-{3-(4-pyridylmethoxy)phenyl}-1,2-dihydro-2-oxo-1,8-naphthyridin-3-yl]-N'-(2,6-diisopropylphenyl)urea N-[1-(3-butenyl)-4-(3-methoxyphenyl)-1,2-dihydro-2-oxo-1,8-naphthyridin-3-yl]-N'-(2,6-diisopropylphenyl)urea N-[1-(3-butenyl)-4-{3-(4-pyridylmethoxy)phenyl}-1,2-dihydro-2-oxo-1,8-naphthyridin-3-yl]-N'-(2,6-diisopropylphenyl)urea N-[1-(3-methyl-2-butenyl)-4-(3-methoxyphenyl)-1,2-dihydro-2-oxo-1,8-naphthyridin-3-yl]-N'-(2,6-diisopropylphenyl)urea N-[1-(3-methyl-2-butenyl)-4-{3-(2-diethylaminoethoxy)phenyl}-1,2-dihydro-2-oxo-1,8-naphthyridin-3-yl]-N'-(2,6-diisopropylphenyl)urea N-[1-(3-methyl-2-butenyl)-4-{3-(4-pyridylmethoxy)phenyl}-1,2-dihydro-2-oxo-1,8-naphthyridin-3-yl]-N'-(2,6-diisopropylphenyl)urea N-[1-pentyl-4-(3-methoxyphenyl)-1,2-dihydro-2-oxo-1,8-naphthyridin-3-yl]-N'-(2,6-diisopropylphenyl)urea N-[1-pentyl-4-{3-(4-pyridylmethoxy)phenyl}-1,2-dihydro-2-oxo-1,8-naphthyridin-3-yl]-N'-(2,6-diisopropylphenyl)urea N-[1-(4-pentenyl)-4-(3-methoxyphenyl)-1,2-dihydro-2-oxo-1,8-naphthyridin-3-yl]-N'-(2,6-diisopropylphenyl)urea N-[1-(4-pentenyl)-4-{3-(4-pyridylmethoxy)phenyl}-1,2-dihydro-2-oxo-1,8-naphthyridin-3-yl]-N'-(2,6-diisopropylphenyl)urea N-[1-(4-pentynyl)-4-(3-methoxyphenyl)-1,2-dihydro-2-oxo-1,8-naphthyridin-3-yl]-N'-(2,6-diisopropylphenyl)urea N-[1-(4-pentynyl)-4-{3-(4-pyridylmethoxy)phenyl}-1,2-dihydro-2-oxo-1,8-naphthyridin-3-yl]-N'-(2,6-diisopropylphenyl)urea N-[1-(4-methylpentyl)-4-(3-methoxyphenyl)-1,2-dihydro-2-oxo-1,8-naphthyridin-3-yl]-N'-(2,6-diisopropylphenyl)urea N-[1-(4-methylpentyl)-4-{3-(4-pyridylmethoxy)phenyl}-1,2-dihydro-2-oxo-1,8-naphthyridin-3-yl]-N'-(2,6-diisopropylphenyl)urea N-[1-hexyl-4-(3-methoxyphenyl)-1,2-dihydro-2-oxo-1,8-naphthyridin-3-yl]-N'-(2,6-diisopropylphenyl)urea N-[1-hexyl-4-{3-(4-pyridylmethoxy)phenyl}-1,2-dihydro-2-oxo-1,8-naphthyridin-3-yl]-N'-(2,6-diisopropylphenyl)urea N-[1-octyl-4-(3-methoxyphenyl)-1,2-dihydro-2-oxo-1,8-naphthyridin-3-yl]-N'-(2,6-diisopropylphenyl)urea N-[1-octyl-4-{3-(4-pyridylmethoxy)phenyl}-1,2-dihydro-2-oxo-1,8-naphthyridin-3-yl]-N'-(2,6-diisopropylphenyl)urea N-[1-decyl-4-(3-methoxyphenyl)-1,2-dihydro-2-oxo-1,8-naphthyridin-3-yl]-N'-(2,6-diisopropylphenyl)urea N-[1-decyl-4-{3-(4-pyridylmethoxy)phenyl}-1,2-dihydro-2-oxo-1,8-naphthyridin-3-yl]-N'-(2,6-diisopropylphenyl)urea N-[1-methyl-4-(3-benzyloxyphenyl)-1,2-dihydro-2-oxo-1,8-naphthyridin-3-yl]-N'-butylurea N-[1-methyl-4-(3-methoxyphenyl)-1,2-dihydro-2-oxo-1,8-naphthyridin-3-yl]-N'-butylurea N-[1-methyl-4-[3-{3-(4-phenyl-1-piperazinyl)propoxy}phenyl]-1,2-dihydro-2-oxo-1,8-naphthyridin-3-yl]-N'-butylurea N-[1-methyl-4-(2-chlorophenyl)-1,2-dihydro-2-oxo-1,8-naphthyridin-3-yl]-N'-(2,4-difluorophenyl)urea N-[1-methyl-4-(2-chlorophenyl)-1,2-dihydro-2-oxo-1,8-naphthyridin-3-yl]-N'-(2,4,6-trimethylphenyl)urea N-[1-methyl-4-(3-methoxyphenyl)-1,2-dihydro-2-oxo-1,8-naphthyridin-3-yl]-N'-(2,4-difluorophenyl)urea N-[1-methyl-4-(3-methoxyphenyl)-1,2-dihydro-2-oxo-1,8-naphthyridin-3-yl]-N'-(2,4,6-trimethylphenyl)urea N-[1-methyl-4-(3-methoxyphenyl)-1,2-dihydro-2-oxo-1,8-naphthyridin-3-yl]-N'-(2-trifluoromethylphenyl)urea N-[1-methyl-4-(3-methoxyphenyl)-1,2-dihydro-2-oxo-1,8-naphthyridin-3-yl]-N'-(2,6-dichlorophenyl)urea N-[1-methyl-4-(3-methoxyphenyl)-1,2-dihydro-2-oxo-1,8-naphthyridin-3-yl]-N'-(2-methoxy-4-nitrophenyl)urea N-[1-methyl-4-(3-methoxyphenyl)-1,2-dihydro-2-oxo-1,8-naphthyridin-3-yl]-N'-(2-isopropylphenyl)urea N-[1-methyl-4-(3-methoxyphenyl)-1,2-dihydro-2-oxo-1,8-naphthyridin-3-yl]-N'-(2-ethylphenyl)urea N-[1-methyl-4-(3-methoxyphenyl)-1,2-dihydro-2-oxo-1,8-naphthyridin-3-yl]-N'-(2-isopropyl-6-methylphenyl)urea N-[1-methyl-4-(3-methoxyphenyl)-1,2-dihydro-2-oxo-1,8-naphthyridin-3-yl]-N'-(2-chloro-3-pyridyl)urea N-[1-methyl-4-(3-methoxyphenyl)-1,2-dihydro-2-oxo-1,8-naphthyridin-3-yl]-N'-(3,5-dichloro-2-pyridyl)urea N-[1-methyl-4-(3-methoxyphenyl)-1,2-dihydro-2-oxo-1,8-naphthyridin-3-yl]-N'-(8-quinolyl)urea N-[1-methyl-4-(2-chlorophenyl)-1,2-dihydro-2-oxo-1,7-naphthyridin-3-yl]-N'-(2,4,6-trimethylphenyl)urea N-[1-methyl-4-(2-chlorophenyl)-1,2-dihydro-2-oxo-1,7-naphthyridin-3-yl]-N'-(2,6-diisopropylphenyl)urea N-[1-methyl-4-(3-methoxyphenyl)-1,2-dihydro-2-oxo-1,7-naphthyridin-3-yl]-N'-(2,6-diisopropylphenyl)urea N-[1-methyl-4-(2-chlorophenyl)-1,2-dihydro-2-oxo-1,6-naphthyridin-3-yl]-N'-(2,6-diisopropylphenyl)urea N-[1-methyl-4-(2-chlorophenyl)-1,2-dihydro-2-oxo-1,6-naphthyridin-3-yl]-N'-(2,4,6-trimethylphenyl)urea N-[1-methyl-4-(3-methoxyphenyl)-1,2-dihydro-2-oxo-1,6-naphthyridin-3-yl]-N'-(2,6-diisopropylphenyl)urea N-[1-isopropyl-4-(3-methoxyphenyl)-1,2-dihydro-2-oxo-1,6-naphthyridin-3-yl]-N'-(2,6-diisopropylphenyl)urea N-[4-(2-chlorophenyl)-1,8-naphthyridin-3-yl]-N'-(2,6-diisopropylphenyl)urea N-[4-(2-chlorophenyl)-1,7-naphthyridin-3-yl]-N'-(2,6-diisopropylphenyl)urea N-[4-(2-chlorophenyl)-1,6-naphthyridin-3-yl]-N'-(2,6-diisopropylphenyl)urea N-[4-(2-chlorophenyl)-1,7-naphthyridin-3-yl]-N'-(2,4-difluorophenyl)urea 1-methyl-3-benzoylamino-4-(3-methoxyphenyl)-1,2-dihydro-2-oxo-1,8-naphthyridine 1-methyl-3-benzoylamino-4-(3-methoxyphenyl)-1,2-dihydro-2-oxo-1,7-naphthyridine 1-methyl-3-benzoylamino-4-(3-methoxyphenyl)-1,2-dihydro-2-oxo-1,6-naphthyridine 1-methyl-3-phenylacetylamino-4-(3-methoxyphenyl)-1,2-dihydro-2-oxo-1,8-naphthyridine 1-methyl-3-(3-phenylpropionylamino)-4-(3-methoxyphenyl)-1,2-dihydro-2-oxo-1,8-naphthyridine 1-methyl-3-(2,2-dimethyllauroylamino)-4-(3-methoxyphenyl)-1,2-dihydro-2-oxo-1,8-naphthyridine N-[1-benzyl-4-{3-(3-pyridylmethoxy)phenyl}-1,2-dihydro-2-oxo-1,8-naphthyridin-3-yl]-N'-(2,6-diisopropylphenyl)urea N-[1-benzyl-4-{3-(2-methylpyridin-3-yl)methoxy)phenyl}-1,2-dihydro-2-oxo-1,8-naphthyridin-3-yl]-N'-(2,6-diisopropylphenyl)urea N-[1-benzyl-4-[3-{2-(2-pyridyl)ethoxy}phenyl]-1,2-dihydro-2-oxo-1,8-naphthyridin-3-yl]-N'-(2,6-diisopropylphenyl)urea N-[1-benzyl-4-[3-{2-(3-pyridyl)ethoxy}phenyl]-1,2-dihydro-2-oxo-1,8-naphthyridin-3-yl]-N'-(2,6-diisopropylphenyl)urea N-[1-benzyl-4-[3-{2-(4-pyridyl)ethoxy}phenyl]-1,2-dihydro-2-oxo-1,8-naphthyridin-3-yl]-N'-(2,6-diisopropylphenyl)urea N-[1-benzyl-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-benzyl-4-[3-{3-(4-pyridyl)propoxy}phenyl]-1,2-dihydro-2-oxo-1,8-naphthyridin-3-yl]-N'-(2,6-diisopropylphenyl)urea N-[1-benzyl-4-[3-{3-(1,2,4-triazol-1-yl)propoxy}-phenyl]-1,2-dihydro-2-oxo-1,8-naphthyridin-3-yl]-N'-(2,6-diisopropylphenyl)urea N-[1-cyclohexylmethyl-4-{3-(2-diethylaminoethoxy)phenyl]-1,2-dihydro-2-oxo-1,8-naphthyridin-3-yl]-N'-(2,6-diisopropylphenyl)urea N-[1-cyclohexylmethyl-4-{3-(3-pyridylmethoxy)phenyl}-1,2-dihydro-2-oxo-1,8-naphthyridin-3-yl]-N'-(2,6-diisopropylphenyl)urea N-[1-cyclohexylmethyl-4-{3-(2-methylpyridin-3-yl)methoxy)phenyl}-1,2-dihydro-2-oxo-1,8-naphthyridin-3-yl]-N'-(2,6-diisopropylphenyl)urea N-[1-cyclohexylmethyl-4-[3-{2-(2-pyridyl)ethoxy}phenyl]-1,2-dihydro-2-oxo-1,8-naphthyridin-3-yl]-N'-(2,6-diisopropylphenyl)urea N-[1-cyclohexylmethyl-4-[3-{2-(3-pyridyl)ethoxy}phenyl]-1,2-dihydro-2-oxo-1,8-naphthyridin-3-yl]-N'-(2,6-diisopropylphenyl)urea N-[1-cyclohexylmethyl-4-[3-{2-(4-pyridyl)ethoxy}phenyl]-1,2-dihydro-2-oxo-1,8-naphthyridin-3-yl]-N'-(2,6-diisopropylphenyl)urea N-[1-cyclohexylmethyl-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-cyclohexylmethyl-4-[3-{3-(4-pyridyl)propoxy}phenyl]-1,2-dihydro-2-oxo-1,8-naphthyridin-3-yl]-N'-(2,6-diisopropylphenyl)urea N-[1-cyclohexylmethyl-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-(2-phenylethyl)-4-(3-hydroxyphenyl)-1,2-dihydro-2-oxo-1,8-naphthyridin-3-yl]-N'-(2,6-diisopropylphenyl)urea N-[1-(2-phenylethyl)-4-{3-(2-pyridylmethoxy)phenyl}-1,2-dihydro-2-oxo-1,8-naphthyridin-3-yl]-N'-(2,6-diisopropylphenyl)urea N-[1-(2-phenylethyl)-4-{3-(3-pyridylmethoxy)phenyl}-1,2-dihydro-2-oxo-1,8-naphthyridin-3-yl]-N'-(2,6-diisopropylphenyl)urea N-[1-(2-phenylethyl)-4-{3-(2-methylpyridin-3-yl)methoxy)phenyl}1,2-dihydro-2-oxo-1,8-naphthyridin-3-yl]-N'-(2,6-diisopropylphenyl)urea N-[1-(2-phenylethyl)-4-{3-(2,4-dimethylpyridin-3-yl)methoxy)phenyl}-1,2-dihydro-2-oxo-1,8-naphthyridin-3-yl]-N'-(2,6-diisopropylphenyl)urea N-[1-(2-phenylethyl)-4-{3-(2-hydroxyethoxy)phenyl}-1,2-dihydro-2-oxo-1,8-naphthyridin-3-yl]-N'-(2,6-diisopropylphenyl)urea N-[1-(2-phenylethyl)-4-{3-(2-acetoxyethoxy)phenyl}-1,2-dihydro-2-oxo-1,8-naphthyridin-3-yl]-N'-(2,6-diisopropylphenyl)urea N-[1-(2-phenylethyl)-4-[3-{2-(2-pyridyl)ethoxy}phenyl)-1,2-dihydro-2-oxo-1,8-naphthyridin-3-yl]-N'-(2,6-diisopropylphenyl)urea N-[1-(2-phenylethyl)-4-[3-{2-(3-pyridyl)ethoxy}phenyl]-1,2-dihydro-2oxo-1,8-naphthyridin-3-yl]-N'-(2,6-diisopropylphenyl)urea N-[1-(2-phenylethyl)-4-[3-{2-(4-pyridyl)ethoxy}phenyl]-1,2-dihydro-2-oxo-1,8-naphthyridin-3-yl]-N'-(2,6-diisopropylphenyl)urea N-[1-(2-phenylethyl)-4-{3-(2-diethylaminoethoxy)phenyl}-1,2-dihydro-2-oxo-1,8-naphthyridin-3-yl]-N'-(2,6-diisopropylphenyl)urea N-[1-(2-phenylethyl)-4-{3-(2-piperidinoethoxy)phenyl}-1,2-dihydro-2-oxo-1,8-naphthyridin-3-yl]-N'-(2,6-diisopropylphenyl)urea N-[1-(2-phenylethyl)-4-{3-(2-morpholinoethoxy)phenyl}-1,2-dihydro-2-oxo-1,8-naphthyridin-3-yl]-N'-(2,6-diisopropylphenyl)urea N-[1-(2-phenylethyl)-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-(2-phenylethyl)-4-[3-{2-(N-benzyl-N-ethylamino)ethoxy}phenyl]-1,2-dihydro-2-oxo-1,8-naphthyridin-3-yl]-N'-(2,6-diisopropylphenyl)urea N-[1-(2-phenylethyl)-4-{3-(3-hydroxypropoxy)phenyl}-1,2-dihydro-2-oxo-1,8-naphthyridin-3-yl]-N'-(2,6-diisopropylphenyl)urea N-[1-(2-phenylethyl)-4-{3-(3-acetoxypropoxy)phenyl}-1,2-dihydro-2-oxo-1,8-naphthyridin-3-yl]-N'-(2,6-diisopropylphenyl)urea N-[1-(2-phenylethyl)-4-[3-{3-(2-pyridyl)propoxy}phenyl]-1,2-dihydro-2-oxo-1,8-naphthyridin-3-yl]-N'-(2,6-diisopropylphenyl)urea N-[1-(2-phenylethyl)-4-[3-{3-(3-pyridyl)propoxy}phenyl]-1,2-dihydro-2-oxo-1,8-naphthyridin-3-yl]-N'-(2,6-diisopropylphenyl)urea N-[1-(2-phenylethyl)-4-[3-{3-(4-pyridyl)propoxy}phenyl]-1,2-dihydro-2-oxo-1,8-naphthyridin-3-yl]-N'-(2,6-diisopropylphenyl)urea N-[1-(2-phenylethyl)-4-{3-(3-diethylaminopropoxy)phenyl}-1,2-dihydro-2-oxo-1,8-naphthyridin-3-yl]-N'-(2,6-diisopropylphenyl)urea N-[1-(2-phenylethyl)-4-{3-(3-piperidinopropoxy)phenyl}-1,2-dihydro-2-oxo-1,8-naphthyridin-3-yl]-N'-(2,6-diisopropylphenyl)urea N-[1-(2-phenylethyl)-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-(2-phenylethyl)-4-{3-(3-diethylamino-1-propynyl)phenyl}-1,2-dihydro-2-oxo-1,8-naphthyridin-3-yl]-N'-(2,6-diisopropylphenyl)urea N-[1-(2-phenylethyl)-4-{3-(3-diethylaminopropyl)phenyl}-1,2-dihydro-2-oxo-1,8-naphthyridin-3-yl]-N'-(2,6-diisopropylphenyl)urea N-[1-(2-phenylethyl)-4-{3-(3-hydroxy-1-propyl)phenyl}-1,2-dihydro-2-oxo-1,8-naphthyridin-3-yl]-N'-(2,6-diisopropylphenyl)urea N-[1-(2-phenylethyl)-4-{3-(3-hydroxypropyl)phenyl}-1,2-dihydro-2-oxo-1,8-naphthyridin-3-yl]-N'-(2,6-diisopropylphenyl)urea N-[1-(2-phenylethyl)-4-{3-(2-diethylaminoethylthio)phenyl}-1,2-dihydro-2-oxo-1,8-naphthyridin-3-yl]-N'-(2,6-diisopropylphenyl)urea N-[1-propyl-4-{3-(2-diethylaminoethoxy)phenyl}-1,2-dihydro-2-oxo-1,8-naphthyridin-3-yl]-N'-(2,6-diisopropylphenyl)urea N-[1-propyl-4-{3-(3-pyridylmethoxy)phenyl}-1,2-dihydro-2-oxo-1,8-naphthyridin-3-yl]-N'-(2,6-diisopropylphenyl)urea N-[1-propyl-4-{3-(2-methylpyridin-3-yl)methoxy)phenyl}-1,2-dihydro-2-oxo-1,8-naphthyridin-3-yl]-N'-(2,6-diisopropylphenyl)urea N-[1-propyl-4-[3-{-(2-pyridyl)ethoxy}phenyl]-1,2-dihydro-2-oxo-1,8-naphthyridin-3-yl]-N'-(2,6-diisopropylphenyl)urea N-[1-propyl-4-[3-{2-(3-pyridyl)ethoxy}phenyl]-1,2-dihydro-2-oxo-1,8-naphthyridin-3-yl]-N'-(2,6-diisopropylphenyl)urea N-[1-propyl-4-[3-{2-(4-pyridyl)ethoxy}phenyl]-1,2-dihydro-2-oxo-1,8-naphthyridin-3-yl]-N'-(2,6-diisopropylphenyl)urea N-[1-propyl-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-propyl-4-[3-{3-(4-pyridyl)propoxy}phenyl]-1,2-dihydro-2-oxo-1,8-naphthyridin-3-yl]-N'-(2,6-diisopropylphenyl)urea N-[1-propyl-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-(2-methyl-2-propenyl)-4-{3-(2-diethylaminoethoxy)phenyl}-1,2-dihydro-2-oxo-1,8-naphthyridin-3-yl]-N'-(2,6-diisopropylphenyl)urea N-[1-(2-methyl-2-propenyl)-4-{3-(3-pyridylmethoxy) phenyl}-1,2-dihydro-2-oxo-1,8-naphthyridin-3-yl]-N'-(2,6-diisopropylphenyl)urea N-[1-(2-methyl-2-propenyl)-4-{3-(2-methylpyridin-3-yl) methoxy)-phenyl}-1,2-dihydro-2-oxo-1,8-naphthyridin-3-yl]-N'-(2,6-diisopropylphenyl)urea N-[1-(2-methyl-2-propenyl)-4-[3-{2-(2-pyridyl) ethoxy}phenyl]-1,2-dihydro-2-oxo-1,8-naphthyridin-3-yl]-N'-(2,6-diisopropylphenyl)urea N-[1-(2-methyl-2-propenyl)-4-[3-{2-(3-pyridyl) ethoxy}phenyl]-1,2-dihydro-2-oxo-1,8-naphthyridin-3-yl]-N'-(2,6-diisopropylphenyl)urea N-[1-(2-methyl-2-propenyl)-4-[3-{2-(4-pyridyl) ethoxy}phenyl]-1,2-dihydro-2-oxo-1,8-naphthyridin-3-yl]-N'-(2,6-diisopropylphenyl)urea N-[1-(2-methyl-2-propenyl)-4-[3-{2-(1,2,4-triazol-1-yl) ethoxy}phenyl]-1,2-dihydro-2-oxo-1,8-naphthyridin-3-yl]-N'-(2,6-diisopropylphenyl)urea N-[1-(2-methyl-2-propenyl)-4-[3-{3-(4-pyridyl) propoxy}phenyl]-1,2-dihydro-2-oxo-1,8-naphthyridin-3-yl]-N'-(2,6-diisopropylphenyl)urea N-[1-(2-methyl-2-propenyl)-4-[3-{3-(1,2,4-triazol-1-yl) propoxy}phenyl]-1,2-dihydro-2-oxo-1,8-naphthyridin-3-yl]-N'-(2,6-diisopropylphenyl)urea N-[1-isobutyl-4-{3-(2-diethylaminoethoxy)phenyl}-1,2-dihydro-2-oxo-1,8-naphthyridin-3-yl]-N'-(2,6-diisopropylphenyl)urea N-[1-isobutyl-4{-3-(3-pyridylmethoxy)phenyl}-1,2-dihydro-2-oxo-1,8-naphthyridin-3-yl]-N'-(2,6-diisopropylphenyl)urea N-[1-isobutyl-4-{3-(2-methylpyridin-3-yl)methoxy) phenyl}-1,2-dihydro-2-oxo-1,8-naphthyridin-3-yl]-N'-(2,6-diisopropylphenyl)urea N-[1-isobutyl-4-[3-{2-(2-pyridyl)ethoxy}phenyl]-1,2-dihydro-2-oxo-1,8-naphthyridin-3-yl]-N'-(2,6-diisopropylphenyl)urea N-[1-isobutyl-4-[3-{2-(3-pyridyl)ethoxy}phenyl]-1,2-dihydro-2-oxo-1,8-naphthyridin-3-yl]-N'-(2,6-diisopropylphenyl)urea N-[1-isobutyl-4-[3-{2-(4-pyridyl)ethoxy}phenyl]-1,2-dihydro-2-oxo-1,8-naphthyridin-3-yl]-N'-(2,6-diisopropylphenyl)urea N-[1-isobutyl-4-[3-{2-(1,2,4-triazol-1-yl)ethoxy}-phenyl]-1,2-dihydro-2-oxo-1,8-naphthyridin-3-yl]-N'-(2,6-diisopropylphenyl)urea N-[1-isobutyl-4-[3-{3-(4-pyridyl)propoxy}phenyl]-1,2-dihydro-2-oxo-1,8-naphthyridin-3-yl]-N'-(2,6-diisopropylphenyl)urea N-[1-isobutyl-4-[3-{3-(1,2,4-triazol-1-yl) propoxy}phenyl]-1,2-dihydro-2-oxo-1,8-naphthyridin-3-yl]-N'-(2,6-diisopropylphenyl)urea N-[1-(3-phenylpropyl)-4-(3-hydroxyphenyl)-1,2-dihydro-2-oxo-1,8-naphthyridin-3-yl]-N'-(2,6-diisopropylphenyl)urea N-[1-(3-phenylpropyl)-4-{3-(3-pyridylmethoxy)phenyl}-1,2-dihydro-2-oxo-1,8-naphthyridin-3-yl]-N'-(2,6-diisopropylphenyl)urea N-[1-(3-phenylpropyl)-4-{3-(2-methylpyridin-3-yl) methoxy)phenyl}-1,2-dihydro-2-oxo-1,8-naphthyridin-3-yl]-N'-(2,6-diisopropylphenyl)urea N-[1-(3-phenylpropyl)-4-{3-(2,4-dimethylpyridin-3-yl) methoxy)phenyl}-1,2-dihydro-2-oxo-1,8-naphthyridin-3-yl]-N'-(2,6-diisopropylphenyl)urea N-[1-(3-phenylpropyl)-4-{3-(2-hydroxyethoxy)phenyl}-1,2-dihydro-2-oxo-1,8-naphthyridin-3-yl]-N'-(2,6-diisopropylphenyl)urea N-[1-(3-phenylpropyl)-4-{3-(2-acetoxyethoxy)phenyl}-1,2-dihydro-2-oxo-1,8-naphthyridin-3-yl]-N'-(2,6-diisopropylphenyl)urea N-[1-(3-phenylpropyl)-4-[3-{2-(2-pyridyl) ethoxy}phenyl]-1,2-dihydro-2-oxo-1,8-naphthyridin-3-yl]-N'-(2,6-diisopropylphenyl)urea N-[1-(3-phenylpropyl)-4-[3-{2-(3-pyridyl) ethoxy}phenyl]-1,2-dihydro-2-oxo-1,8-naphthyridin-3-yl]-N'-(2,6-diisopropylphenyl)urea N-[1-(3-phenylpropyl)-4-[3-{2-(4-pyridyl) ethoxy}phenyl]-1,2-dihydro-2-oxo-1,8-naphthyridin-3-yl]-N'-(2,6-diisopropylphenyl)urea N-[1-(3-phenylpropyl)-4-{3-(2-diethylaminoethoxy) phenyl}-1,2-dihydro-2-oxo-1,8-naphthyridin-3-yl]-N'-(2,6-diisopropylphenyl)urea N-[1-(3-phenylpropyl)-4-{3-(2-piperidinoethoxy) phenyl}-1,2-dihydro-2-oxo-1,8-naphthyridin-3-yl]-N'-(2,6-diisopropylphenyl)urea N-[1-(3-phenylpropyl)-4-{3-(2-morpholinoethoxy) phenyl}-1,2-dihydro-2-oxo-1,8-naphthyridin-3-yl]-N'-(2,6-diisopropylphenyl)urea N-[1-(3-phenylpropyl)-4-[3-{2-(1,2,4-triazol-1-yl) ethoxy}phenyl]-1,2-dihydro-2-oxo-1,8-naphthyridin-3-yl]-N'-(2,6-diisopropylphenyl)urea N-[1-(3-phenylpropyl)-4-[3-{2-(N-benzyl-N-ethylamino) ethoxy}phenyl]-1,2-dihydro-2-oxo-1,8-naphthyridin-3-yl]-N'-(2,6-diisopropylphenyl)urea N-[1-(3-phenylpropyl)-4-{3-(3-hydroxypropoxy) phenyl}-1,2-dihydro-2-oxo-1,8-naphthyridin-3-yl]-N'-(2,6-diisopropylphenyl)urea N-[1-(3-phenylpropyl)-4-{3-(3-acetoxypropoxy) phenyl}-1,2-dihydro-2-oxo-1,8-naphthyridin-3-yl]-N'-(2,6-diisopropylphenyl)urea N-[1-(3-phenylpropyl)-4-[3-{3-(2-pyridyl) propoxy}phenyl]-1,2-dihydro-2-oxo-1,8-naphthyridin-3-yl]-N'-(2,6-diisopropylphenyl)urea N-[1-(3-phenylpropyl)-4-[3-{3-(3-pyridyl) propoxy}phenyl]-1,2-dihydro-2-oxo-1,8-naphthyridin-3-yl]-N'-(2,6-diisopropylphenyl)urea N-[1-(3-phenylpropyl)-4-[3-{3-(4-pyridyl) propoxy}phenyl]-1,2-dihydro-2-oxo-1,8-naphthyridin-3-yl]-N'-(2,6-diisopropylphenyl)urea N-[1-(3-phenylpropyl)-4-{3-(3-diethylaminopropoxy) phenyl}-1,2-dihydro-2-oxo-1,8-naphthyridin-3-yl]-N'-(2,6-diisopropylphenyl)urea N-[1-(3-phenylpropyl)-4-{3-(3-piperidinopropoxy) phenyl}-1,2-dihydro-2-oxo-1,8-naphthyridin-3-yl]-N'-(2,6-diisopropylphenyl)urea N-[1-(3-phenylpropyl)-4-[3-{3-(1,2,4-triazol-1-yl) propoxy}phenyl]-1,2-dihydro-2-oxo-1,8-naphthyridin-3-yl]-N'-(2,6-diisopropylphenyl)urea N-[1-(3-phenylpropyl)-4-{3-(3-diethylamino-1-propynyl)phenyl}-1,2-dihydro-2-oxo-1,8-naphthyridin-3-yl]-N'-(2,6-diisopropylphenyl)urea N-[1-(3-phenylpropyl)-4-{3-(3-diethylaminopropyl) phenyl}-1,2-dihydro-2-oxo-1,8-naphthyridin-3-yl]-N'-(2,6-diisopropylphenyl)urea N-[1-(3-phenylpropyl)-4-{3-(3-hydroxy-1-propynyl) phenyl}-1,2-dihydro-2-oxo-1,8-naphthyridin-3-yl]-N'-(2,6-diisopropylphenyl)urea N-[1-(3-phenylpropyl)-4-{3-(3-hydroxypropyl)phenyl}-
1,2-dihydro-2-oxo-1,8-naphthyridin-3-yl]-N'-(2,6-
diisopropylphenyl)urea N-[1-(3-phenylpropyl)-4-{3-(2-diethylaminoethylthio)
phenyl}-1,2-dihydro-2-oxo-1,8-naphthyridin-3-yl]-N'-
(2,6-diisopropylphenyl)urea N-[1-(3-acetylaminopropyl)-4-{3-(3-pyridylmethoxy)
phenyl}-1,2-dihydro-2-oxo-1,8-naphthyridin-3-yl]-N'-
(2,6-diisopropylphenyl)urea N-[1-(3-acetylaminopropyl)-4-{3-(2-methylpyridin-3-yl)
methoxy)phenyl}-1,2-dihydro-2-oxo-1,8-
naphthyridin-3-yl]-N'-(2,6-diisopropylphenyl)urea N-[1-(3-acetylaminopropyl)-4-{3-(2,4-dimethylpyridin-
3-yl)methoxy)phenyl}-1,2-dihydro-2-oxo-1,8-
naphthyridin-3-yl]-N'-(2,6-diisopropylphenyl)urea N-[1-(3-acetylaminopropyl)-4-[3-{2-(2-pyridyl)
ethoxy}phenyl]-1,2-dihydro-2-oxo-1,8-naphthyridin-
3-yl]-N'-(2,6-diisopropylphenyl)urea N-[1-(3-acetylaminopropyl)-4-[3-{2-(3-pyridyl)
ethoxy}phenyl]-1,2-dihydro-2-oxo-1,8-naphthyridin-
3-yl]-N'-(2,6-diisopropylphenyl)urea N-[1-(3-acetylaminopropyl)-4-[3-{2-(4-pyridyl)
ethoxy}phenyl]-1,2-dihydro-2-oxo-1,8-naphthyridin-
3-yl]-N'-(2,6-diisopropylphenyl)urea N-[1-(3-acetylaminopropyl)-4-{3-(2-
diethylaminoethoxy)phenyl}-1,2-dihydro-2-oxo-1,8-
naphthyridin-3-yl]-N'-(2,6-diisopropylphenyl)urea N-[1-(3-acetylaminopropyl)-4-{3-(2-piperidinoethoxy)
phenyl}-1,2-dihydro-2-oxo-1,8-naphthyridin-3-yl]-N'-
(2,6-diisopropylphenyl)urea N-[1-(3-acetylaminopropyl)-4-[3-{2-(1,2,4-triazol-1-yl)
ethoxy}phenyl]-1,2-dihydro-2-oxo-1,8-naphthyridin-
3-yl]-N'-(2,6-diisopropylphenyl)urea N-[1-(3-acetylaminopropyl)-4-[3-{3-(2-pyridyl)
propoxy}phenyl]-1,2-dihydro-2-oxo-1,8-naphthyridin-
3-yl]-N'-(2,6-diisopropylphenyl)urea N-[1-(3-acetylaminopropyl)-4-[3-{3-(3-pyridyl)
propoxy}phenyl]-1,2-dihydro-2-oxo-1,8-naphthyridin-
3-yl]-N'-(2,6-diisopropylphenyl)urea N-[1-(3-acetylaminopropyl)-4-[3-{3-(4-pyridyl)
propoxy}phenyl]-1,2-dihydro-2-oxo-1,8-naphthyridin-
3-yl]-N'-(2,6-diisopropylphenyl)urea N-[1-(3-acetylaminopropyl)-4-{3-(3-
diethylaminopropoxy)phenyl}-1,2-dihydro-2-oxo-1,8-
naphthyridin-3-yl]-N'-(2,6-diisopropylphenyl)urea N-[1-(3-acetylaminopropyl)-4-{3-(3-piperidinopropoxy)
phenyl}-1,2-dihydro-2-oxo-1,8-naphthyridin-3-yl]-N'-
(2,6-diisopropylphenyl)urea N-[1-(3-acetylaminopropyl)-4-[3-{3-(1,2,4-triazol-1-yl)
propoxy}phenyl]-1,2-dihydro-2-oxo-1,8-naphthyridin-
3-yl]-N'-(2,6-diisopropylphenyl)urea N-[1-(3-acetylaminopropyl)-4-{3-(3-diethylamino-1-
propynyl)phenyl}-1,2-dihydro-2-oxo-1,8-
naphthyridin-3-yl]-N'-(2,6-diisopropylphenyl)urea N-[1-(3-acetylaminopropyl)-4-{3-(3-
diethylaminopropyl)phenyl}-1,2-dihydro-2-oxo-1,8-
naphthyridin-3-yl]-N'-(2,6-diisopropylphenyl)urea N-[1-(3-acetylaminopropyl)-4-{3-(3-hydroxy-1-
propynyl)phenyl}-1,2-dihydro-2-oxo-1,8-
naphthyridin-3-yl]-N'-(2,6-diisopropylphenyl)urea N-[1-(3-acetylaminopropyl)-4-{3-(3-hydroxypropyl)
phenyl}-1,2-dihydro-2-oxo-1,8-naphthyridin-3-yl]-N'-
(2,6-diisopropylphenyl)urea N-[1-(3-hydroxypropyl)-4-{3-(2-pyridylmethoxy)
phenyl}-1,2-dihydro-2-oxo-1,8-naphthyridin-3-yl]-N'-
(2,6-diisopropylphenyl)urea N-[1-(3-hydroxypropyl)-4-{3-(3-pyridylmethoxy)
phenyl}-1,2-dihydro-2-oxo-1,8-naphthyridin-3-yl]-N'-
(2,6-diisopropylphenyl)urea N-[1-(3-hydroxypropyl)-4-{3-(2-methylpyridin-3-yl)
methoxy)phenyl}-1,2-dihydro-2-oxo-1,8-
naphthyridin-3-yl]-N'-(2,6-diisopropylphenyl)urea N-[1-(3-hydroxypropyl)-4-{3-(2,4-dimethylpyridin-3-yl)
methoxy)-phenyl}-1,2-dihydro-2-oxo-1,8-
naphthyridin-3-yl]-N'-(2,6-diisopropylphenyl)urea N-[1-(3-hydroxypropyl)-4-[3-{2-(2-pyridyl)
ethoxy}phenyl]-1,2-dihydro-2-oxo-1,8-naphthyridin-
3-yl]-N'-(2,6-diisopropylphenyl)urea N-[1-(3-hydroxypropyl)-4-[3-{2-(3-pyridyl)
ethoxy}phenyl]-1,2-dihydro-2-oxo-1,8-naphthyridin-
3-yl]-N'-(2,6-diisopropylphenyl)urea N-[1-(3-hydroxypropyl)-4-[3-{2-(4-pyridyl)
ethoxy}phenyl]-1,2-dihydro-2-oxo-1,8-naphthyridin-
3-yl]-N'-(2,6-diisopropylphenyl)urea N-[1-(3-hydroxypropyl)-4-{3-(2-diethylaminoethoxy)
phenyl}-1,2-dihydro-2-oxo-1,8-naphthyridin-3-yl]-N'-
(2,6-diisopropylphenyl)urea N-[1-(3-hydroxypropyl)-4-{3-(2-piperidinoethoxy)
phenyl}-1,2-dihydro-2-oxo-1,8-naphthyridin-3-yl]-N'-
(2,6-diisopropylphenyl)urea N-[1-(3-hydroxypropyl)-4-[3-{2-(1,2,4-triazol-1-yl)
ethoxy}phenyl]-1,2-dihydro-2-oxo-1,8-naphthyridin-
3-yl]-N'-(2,6-diisopropylphenyl)urea N-[1-(3-hydroxypropyl)-4-[3-{3-(2-pyridyl)
propoxy}phenyl]-1,2-dihydro-2-oxo-1,8-naphthyridin-
3-yl]-N'-(2,6-diisopropylphenyl)urea N-[1-(3-hydroxypropyl)-4-[3-{3-(3-pyridyl)
propoxy}phenyl]-1,2-dihydro-2-oxo-1,8-naphthyridin-
3-yl]-N'-(2,6-diisopropylphenyl)urea N-[1-(3-hydroxypropyl)-4-[3-{3-(4-pyridyl)
propoxy}phenyl]-1,2-dihydro-2-oxo-1,8-naphthyridin-
3-yl]-N'-(2,6-diisopropylphenyl)urea N-[1-(3-hydroxypropyl)-4-{3-(3-diethylaminopropoxy)
phenyl}-1,2-dihydro-2-oxo-1,8-naphthyridin-3-yl]-N'-
(2,6-diisopropylphenyl)urea N-[1-(3-hydroxypropyl)-4-{3-(3-piperidinopropoxy)
phenyl}-1,2-dihydro-2-oxo-1,8-naphthyridin-3-yl]-N'-
(2,6-diisopropylphenyl)urea N-[1-(3-hydroxypropyl)-4-[3-{3-(1,2,4-triazol-1-yl)
propoxy}phenyl]-1,2-dihydro-2-oxo-1,8-naphthyridin-
3-yl]-N'-(2,6-diisopropylphenyl)urea N-[1-(3-hydroxypropyl)-4-{3-(3-diethylamino-1-
propynyl)phenyl}-1,2-dihydro-2-oxo-1,8-
naphthyridin-3-yl]-N'-(2,6-diisopropylphenyl)urea N-[1-(3-hydroxypropyl)-4-{3-(3-diethylaminopropyl)
phenyl}-1,2-dihydro-2-oxo-1,8-naphthyridin-3-yl]-N'-
(2,6-diisopropylphenyl)urea N-[1-(3-hydroxypropyl)-4-{3-(3-hydroxy-1-propynyl)
phenyl}-1,2-dihydro-2-oxo-1,8-naphthyridin-3-yl]-N'-
(2,6-diisopropylphenyl)urea N-[1-(3-hydroxypropyl)-4-{3-(3-hydroxypropyl)
phenyl}-1,2-dihydro-2-oxo-1,8-naphthyridin-3-yl]-N'-
(2,6-diisopropylphenyl)urea N-[1-(3-butenyl)-4-{3-(2-diethylaminoethoxy)phenyl}-1,
2-dihydro-2-oxo-1,8-naphthyridin-3-yl]-N'-(2,6-
diisopropylphenyl)urea N-[1-(3-butenyl)-4-{3-(3-pyridylmethoxy)phenyl}-1,2-dihydro-2-oxo-1,8-naphthyridin-3-yl]-N'-(2,6-diisopropylphenyl)urea N-[1-(3-butenyl)-4-{3-(2-methylpyridin-3-yl)methoxy)phenyl}-1,2-dihydro-2-oxo-1,8-naphthyridin-3-yl]-N'-(2,6-diisopropylphenyl)urea N-[1-(3-butenyl)-4-[3-{2-(2-pyridyl)ethoxy}phenyl]-1,2-dihydro-2-oxo-1,8-naphthyridin-3-yl]-N'-(2,6-diisopropylphenyl)urea N-[1-(3-butenyl)-4-[3-{2-(3-pyridyl)ethoxy}phenyl]-1,2-dihydro-2-oxo-1,8-naphthyridin-3-yl]-N'-(2,6-diisopropylphenyl)urea N-[1-(3-butenyl)-4-[3-{2-(4-pyridyl)ethoxy}phenyl]-1,2-dihydro-2-oxo-1,8-naphthyridin-3-yl]-N'-(2,6-diisopropylphenyl)urea N-[1-(3-butenyl)-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-(3-butenyl)-4-[3-{2-(N-benzyl-N-ethylamino)ethoxy}phenyl]-1,2-dihydro-2-oxo-1,8-naphthyridin-3-yl]-N'-(2,6-diisopropylphenyl)urea N-[1-(3-butenyl)-4-[3-{3-(4-pyridyl)propoxy}phenyl]-1,2-dihydro-2-oxo-1,8-naphthyridin-3-yl]-N'-(2,6-diisopropylphenyl)urea N-[1-(3-butenyl)-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-(3-methyl-2-butenyl)-4-{3-(2-diethylaminoethoxy)phenyl}-1,2-dihydro-2-oxo-1,8-naphthyridin-3-yl]-N'-(2,6-diisopropylphenyl)urea N-[1-(3-methyl-2-butenyl)-4-{3-(3-pyridylmethoxy)phenyl}-1,2-dihydro-2-oxo-1,8-naphthyridin-3-yl]-N'-(2,6-diisopropylphenyl)urea N-[1-(3-methyl-2-butenyl)-4-{3-(2-methylpyridin-3-yl)methoxy)phenyl}-1,2-dihydro-2-oxo-1,8-naphthyridin-3-yl]-N'-(2,6-diisopropylphenyl)urea N-[1-(3-methyl-2-butenyl)-4-[3-{2-(2-pyridyl)ethoxy}phenyl]-1,2-dihydro-2-oxo-1,8-naphthyridin-3-yl]-N'-(2,6-diisopropylphenyl)urea N-[1-(3-methyl-2-butenyl)-4-[3-{2-(3-pyridyl)ethoxy}phenyl]-1,2-dihydro-2-oxo-1,8-naphthyridin-3-yl]-N'-(2,6-diisopropylphenyl)urea N-[1-(3-methyl-2-butenyl)-4-[3-{2-(4-pyridyl)ethoxy}phenyl]-1,2-dihydro-2-oxo-1,8-naphthyridin-3-yl]-N'-(2,6-diisopropylphenyl)urea N-[1-(3-methyl-2-butenyl)-4-[3-{2-(1,2,4-triazol-1-yl)ethoxy}phenyl]- 1,2-dihydro-2-oxo-1,8-naphthyridin-3-yl]-N'-(2,6-diisopropylphenyl)urea N-[1-(3-methyl-2-butenyl)-4-[3-{2-(N-benzyl-N-ethylamino)ethoxy}-phenyl]-1,2-dihydro-2-oxo-1,8-naphthyridin-3-yl]-N'-(2,6-diisopropylphenyl)urea N-[1-(3-methyl-2-butenyl)-4-[3-{3-(4-pyridyl)propoxy}phenyl]-1,2-dihydro-2-oxo-1,8-naphthyridin-3-yl]-N'-(2,6-diisopropylphenyl)urea N-[1-(3-methyl-2-butenyl)-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-(3-methylbutyl)-4-(3-hydroxyphenyl)-1,2-dihydro-2-oxo-1,8-naphthyridin-3-yl]-N'-(2,6-diisopropylphenyl)urea N-[1-(3-methylbutyl)-4-{3-(2-pyridylmethoxy)phenyl}-1,2-dihydro-2-oxo-1,8-naphthyridin-3-yl]-N'-(2,6-diisopropylphenyl)urea N-[1-(3-methylbutyl)-4-{3-(3-pyridylmethoxy)phenyl}-1,2-dihydro-2-oxo-1,8-naphthyridin-3-yl]-N'-(2,6-diisopropylphenyl)urea N-[1-(3-methylbutyl)-4-{3-(2-methylpyridin-3-yl)methoxy)phenyl}-1,2-dihydro-2-oxo-1,8-naphthyridin-3-yl]-N'-(2,6-diisopropylphenyl)urea N-[1-(3-methylbutyl)-4-{3-(2,4-dimethylpyridin-3-yl)methoxy)phenyl}-1,2-dihydro-2-oxo-1,8-naphthyridin-3-yl]-N'-(2,6-diisopropylphenyl)urea N-[1-(3-methylbutyl)-4-{3-(2-hydroxyethoxy)phenyl}-1,2-dihydro-2-oxo-1,8-naphthyridin-3-yl]-N'-(2,6-diisopropylphenyl)urea N-[1-(3-methylbutyl)-4-{3-(2-acetoxyethoxy)phenyl}-1,2-dihydro-2-oxo-1,8-naphthyridin-3-yl]-N'-(2,6-diisopropylphenyl)urea N-[1-(3-methylbutyl)-4-[3-{2-(2-pyridyl)ethoxy}phenyl]-1,2-dihydro-2-oxo-1,8-naphthyridin-3-yl]-N'-(2,6-diisopropylphenyl)urea N-[1-(3-methylbutyl)-4-[3-{2-(3-pyridyl)ethoxy}phenyl]-1,2-dihydro-2-oxo-1,8-naphthyridin-3-yl]-N'-(2,6-diisopropylphenyl)urea N-[1-(3-methylbutyl)-4-[3-{2-(4-pyridyl)ethoxy}phenyl]-1,2-dihydro-2-oxo-1,8-naphthyridin-3-yl]-N'-(2,6-diisopropylphenyl)urea N-[1-(3-methylbutyl)-4-{3-(2-diethylaminoethoxy)phenyl}-1,2-dihydro-2-oxo-1,8-naphthyridin-3-yl]-N'-(2,6-diisopropylphenyl)urea N-[1-(3-methylbutyl)-4-{3-(2-piperidinoethoxy)phenyl}-1,2-dihydro-2-oxo-1,8-naphthyridin-3-yl]-N'-(2,6-diisopropylphenyl)urea N-[1-(3-methylbutyl)-4-{3-(2-morpholinoethoxy)phenyl}-1,2-dihydro-2-oxo-1,8-naphthyridin-3-yl]-N'-(2,6-diisopropylphenyl)urea N-[1-(3-methylbutyl)-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-(3-methylbutyl)-4-[3-{2-(N-benzyl-N-ethylamino)ethoxy}phenyl]-1,2-dihydro-2-oxo-1,8-naphthyridin-3-yl]-N'-(2,6-diisopropylphenyl)urea N-[1-(3-methylbutyl)-4-{3-(3-hydroxypropoxy)phenyl}-1,2-dihydro-2-oxo-1,8-naphthyridin-3-yl]-N'-(2,6-diisopropylphenyl)urea N-[1-(3-methylbutyl)-4-{3-(3-acetoxypropoxy)phenyl}-1,2-dihydro-2-oxo-1,8-naphthyridin-3-yl]-N'-(2,6-diisopropylphenyl)urea N-[1-(3-methylbutyl)-4-[3-{3-(2-pyridyl)propoxy}phenyl]-1,2-dihydro-2-oxo-1,8-naphthyridin-3-yl]-N'-(2,6-diisopropylphenyl)urea N-[1-(3-methylbutyl)-4-[3-{3-(3-pyridyl)propoxy}phenyl]-1,2-dihydro-2-oxo-1,8-naphthyridin-3-yl]-N'-(2,6-diisopropylphenyl)urea N-[1-(3-methylbutyl)-4-[3-{3-(4-pyridyl)propoxy}phenyl]-1,2-dihydro-2-oxo-1,8-naphthyridin-3-yl]-N'-(2,6-diisopropylphenyl)urea N-[1-(3-methylbutyl)-4-{3-(3-diethylaminopropoxy)phenyl}-1,2-dihydro-2-oxo-1,8-naphthyridin-3-yl]-N'-(2,6-diisopropylphenyl)urea N-[1-(3-methylbutyl)-4-{3-(3-piperidinopropoxy)phenyl}-1,2-dihydro-2-oxo-1,8-naphthyridin-3-yl]-N'-(2,6-diisopropylphenyl)urea N-[1-(3-methylbutyl)-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-(3-methylbutyl)-4-{3-(3-diethylamino-1-propynyl) phenyl}-1,2-dihydro-2-oxo-1,8-naphthyridin-3-yl]-N'-(2,6-diisopropylphenyl)urea N-[1-(3-methylbutyl)-4-{3-(3-diethylaminopropyl) phenyl}-1,2-dihydro-2-oxo-1,8-naphthyridin-3-yl]-N'-(2,6-diisopropylphenyl)urea N-[1-(3-methylbutyl)-4-{3-(3-hydroxy-1-propynyl) phenyl}-1,2-dihydro-2-oxo-1,8-naphthyridin-3-yl]-N'-(2,6-diisopropylphenyl)urea N-[1-(3-methylbutyl)-4-{3-(3-hydroxypropyl)phenyl}-1,2-dihydro-2-oxo-1,8-naphthyridin-3-yl]-N'-(2,6-diisopropylphenyl)urea N-[1-(3-methylbutyl)-4-{3-(2-diethylaminoethylthio) phenyl}-1,2-dihydro-2-oxo-1,8-naphthyridin-3-yl]-N'-(2,6-diisopropylphenyl)urea N-[1-(4-pentenyl)-4-(3-hydroxyphenyl)-1,2-dihydro-2-oxo-1,8-naphthyridin-3-yl]-N'-(2,6-diisopropylphenyl)urea N-[1-(4-pentenyl)-4-{3-(2-pyridylmethoxy)phenyl}-1,2-dihydro-2-oxo-1,8-naphthyridin-3-yl]-N'-(2,6-diisopropylphenyl)urea N-[1-(4-pentenyl)-4-{3-(3-pyridylmethoxy)phenyl}-1,2-dihydro-2-oxo-1,8-naphthyridin-3-yl]-N'-(2,6-diisopropylphenyl)urea N-[1-(4-pentenyl)-4-{3-(2-methylpyridin-3-yl)methoxy) phenyl}-1,2-dihydro-2-oxo-1,8-naphthyridin-3-yl]-N'-(2,6-diisopropylphenyl)urea N-[1-(4-pentenyl)-4-{3-(2,4-dimethylpyridin-3-yl) methoxy)phenyl}-1,2-dihydro-2-oxo-1,8-naphthyridin-3-yl]-N'-(2,6-diisopropylphenyl)urea N-[1-(4-pentenyl)-4-{3-(2-hydroxyethoxy)phenyl}-1,2-dihydro-2-oxo-1,8-naphthyridin-3-yl]-N'-(2,6-diisopropylphenyl)urea N-[1-(4-pentenyl)-4-{3-(2-acetoxyethoxy)phenyl}-1,2-dihydro-2-oxo-1,8-naphthyridin-3-yl]-N'-(2,6-diisopropylphenyl)urea N-[1-(4-pentenyl)-4-[3-{2-(2-pyridyl)ethoxy}phenyl]-1,2-dihydro-2-oxo-1,8-naphthyridin-3-yl]-N'-(2,6-diisopropylphenyl)urea N-[1-(4-pentenyl)-4-[3-{2-(3-pyridyl)ethoxy}phenyl]-1,2-dihydro-2-oxo-1,8-naphthyridin-3-yl]-N'-(2,6-diisopropylphenyl)urea N-[1-(4-pentenyl)-4-[3-{2-(4-pyridyl)ethoxy}phenyl]-1,2-dihydro-2-oxo-1,8-naphthyridin-3-yl]-N'-(2,6-diisopropylphenyl)urea N-[1-(4-pentenyl)-4-{3-(2-diethylaminoethoxy)phenyl}-1,2-dihydro-2-oxo-1,8-naphthyridin-3-yl]-N'-(2,6-diisopropylphenyl)urea N-[1-(4-pentenyl)-4-{3-(2-dimethylaminoethoxy) phenyl}-1,2-dihydro-2-oxo-1,8-naphthyridin-3-yl]-N'-(2,6-diisopropylphenyl)urea N-[1-(4-pentenyl)-4-{3-(2-piperidinoethoxy)phenyl}-1,2-dihydro-2-oxo-1,8-naphthyridin-3-yl]-N'-(2,6-diisopropylphenyl)urea N-[1-(4-pentenyl)-4-{3-(2-(1-pyrrolidinyl)ethoxy) phenyl}-1,2-dihydro-2-oxo-1,8-naphthyridin-3-yl]-N'-(2,6-diisopropylphenyl)urea N-[1-(4-pentenyl)-4-{3-(2-morpholinoethoxy)phenyl}-1,2-dihydro-2-oxo-1,8-naphthyridin-3-yl]-N'-(2,6-diisopropylphenyl)urea N-[1-(4-pentenyl)-4-[3-{2-(1,2,4-triazol-1-yl) ethoxy}phenyl]-1,2-dihydro-2-oxo-1,8-naphthyridin-3-yl]-N'-(2,6-diisopropylphenyl)urea N-[1-(4-pentenyl)-4-[3-{2-(N-benzyl-N-ethylamino) ethoxy}phenyl]-1,2-dihydro-2-oxo-1,8-naphthyridin-3-yl]-N'-(2,6-diisopropylphenyl)urea N-[1-(4-pentenyl)-4-{3-(3-hydroxypropoxy)phenyl}-1,2-dihydro-2-oxo-1,8-naphthyridin-3-yl]-N'-(2,6-diisopropylphenyl)urea N-[1-(4-pentenyl)-4-{3-(3-acetoxypropoxy)phenyl}-1,2-dihydro-2-oxo-1,8-naphthyridin-3-yl]-N'-(2,6-diisopropylphenyl)urea N-[1-(4-pentenyl)-4-[3-{3-(2-pyridyl)propoxy}phenyl]-1,2-dihydro-2-oxo-1,8-naphthyridin-3-yl]-N'-(2,6-diisopropylphenyl)urea N-[1-(4-pentenyl)-4-[3-{3-(3-pyridyl)propoxy}phenyl]-1,2-dihydro-2-oxo-1,8-naphthyridin-3-yl]-N'-(2,6-diisopropylphenyl)urea N-[1-(4-pentenyl)-4-[3-{3-(4-pyridyl)propoxy}phenyl]-1,2-dihydro-2-oxo-1,8-naphthyridin-3-yl]-N'-(2,6-diisopropylphenyl)urea N-[1-(4-pentenyl)-4-{3-(3-dimethylaminopropoxy) phenyl}-1,2-dihydro-2-oxo-1,8-naphthyridin-3-yl]-N'-(2,6-diisopropylphenyl)urea N-[1-(4-pentenyl)-4-{3-(3-diethylaminopropoxy) phenyl}-1,2-dihydro-2-oxo-1,8-naphthyridin-3-yl]-N'-(2,6-diisopropylphenyl)urea N-[1-(4-pentenyl)-4-{3-(3-piperidinopropoxy)phenyl}-1,2-dihydro-2-oxo-1,8-naphthyridin-3-yl]-N'-(2,6-diisopropylphenyl)urea N-[1-(4-pentenyl)-4-[3-{3-(1,2,4-triazol-1-yl) propoxy}phenyl]-1,2-dihydro-2-oxo-1,8-naphthyridin-3-yl]-N'-(2,6-diisopropylphenyl)urea N-[1-(4-pentenyl)-4-{3-(3-diethylamino-1-propynyl) phenyl}-1,2-dihydro-2-oxo-1,8-naphthyridin-3-yl]-N'-(2,6-diisopropylphenyl)urea N-[1-(4-pentenyl)-4-{3-(3-diethylaminopropyl)phenyl}-1,2-dihydro-2-oxo-1,8-naphthyridin-3-yl]-N'-(2,6-diisopropylphenyl)urea N-[1-(4-pentenyl)-4-{3-(3-hydroxy-1-propynyl)phenyl}-1,2-dihydro-2-oxo-1,8-naphthyridin-3-yl]-N'-(2,6-diisopropylphenyl)urea N-[1-(4-pentenyl)-4-{3-(3-hydroxypropyl)phenyl}-1,2-dihydro-2-oxo-1,8-naphthyridin-3-yl]-N'-(2,6-diisopropylphenyl)urea N-[1-(4-pentenyl)-4-{3-(2-diethylaminoethylthio) phenyl}-1,2-dihydro-2-oxo-1,8-naphthyridin-3-yl]-N'-(2,6-diisopropylphenyl)urea N-[1-(4-pentynyl)-4-{3-(2-diethylaminoethoxy)phenyl}-1,2-dihydro-2-oxo-1,8-naphthyridin-3-yl]-N'-(2,6-diisopropylphenyl)urea N-[1-(4-pentynyl)-4-{3-(3-pyridylmethoxy)phenyl}-1,2-dihydro-2-oxo-1,8-naphthyridin-3-yl]-N'-(2,6-diisopropylphenyl)urea N-[1-(4-pentynyl)-4-{3-(2-methylpyridin-3-yl)methoxy) phenyl}-1,2-dihydro-2-oxo-1,8-naphthyridin-3-yl]-N'-(2,6-diisopropylphenyl)urea N-[1-(4-pentynyl)-4-[3-{2-(2-pyridyl)ethoxy}phenyl]-1,2-dihydro-2-oxo-1,8-naphthyridin-3-yl]-N'-(2,6-diisopropylphenyl)urea N-[1-(4-pentynyl)-4-[3-{2-(3-pyridyl)ethoxy}phenyl]-1,2-dihydro-2-oxo-1,8-naphthyridin-3-yl]-N'-(2,6-diisopropylphenyl)urea N-[1-(4-pentynyl)-4-[3-{2-(4-pyridyl)ethoxy}phenyl]-1,2-dihydro-2-oxo-1,8-naphthyridin-3-yl]-N'-(2,6-diisopropylphenyl)urea N-[1-(4-pentynyl)-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-(4-pentynyl)-4-[3-{3-(4-pyridyl)propoxy}phenyl]-1,2-dihydro-2-oxo-1,8-naphthyridin-3-yl]-N'-(2,6-diisopropylphenyl)urea N-[1-(4-pentynyl)-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-(4-methylpentyl)-4-{3-(2-diethylarninoethoxy)phenyl}-1,2-dihydro-2-oxo-1,8-naphthyridin-3-yl]-N'-(2,6-diisopropylphenyl)urea 5 N-[1-(4-methylpentyl)-4-{3-(3-pyridylmethoxy)phenyl}-1,2-dihydro-2-oxo-1,8-naphthyridin-3-yl]-N'-(2,6-diisopropylphenyl)urea N-[1-(4-methylpentyl)-4-{3-(2-methylpyridin-3-yl)methoxy)phenyl}-1,2-dihydro-2-oxo-1,8-naphthyridin-3-yl]-N'-(2,6-diisopropylphenyl)urea N-[1-(4-methylpentyl)-4-[3-{2-(2-pyridyl)ethoxy}phenyl}-1,2-dihydro-2-oxo-1,8-naphthyridin-3-yl]-N'-(2,6-diisopropylphenyl)urea N-[1-(4-methylpentyl)-4-[3-{2-(3-pyridyl)ethoxy}phenyl}-1,2-dihydro-2-oxo-1,8-naphthyridin-3-yl]-N'-(2,6-diisopropylphenyl)urea N-[1-(4-methylpentyl)-4-[3-{2-(4-pyridyl)ethoxy}phenyl}-1,2-dihydro-2-oxo-1,8-naphthyridin-3-yl]-N'-(2,6-diisopropylphenyl)urea N-[1-(4-methylpentyl)-4-[3-{2-(1,2,4-triazol-1-yl)ethoxy}phenyl]-1,2-dihydro-2-oxo-1,8-naphthyridin-3-yl]-N'-(2,6-diisopropylphenyl)urea N-[1-(4-methylpentyl)-4-[3-{3-(4-pyridyl)propoxy}phenyl]-1,2-dihydro-2-oxo-1,8-naphthyridin-3-yl]-N'-(2,6-diisopropylphenyl)urea N-[1-(4-methylpentyl)-4-[3-{3-(1,2,4-triazol-1-yl)propoxy}phenyl]-1,2-dihydro-2-oxo-1,8-naphthyridin-3-yl]-N'-(2,6-diisopropylphenyl)urea N-[1-methyl-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-(2-pyridylmethyl)-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-(3-pyridymethyl)-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-(4-pyridylmethyl)-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-ethyl-4-[3-{3-(1-pyrrolidinyl)-1-propynyl}phenyl}-1,2-dihydro-2-oxo-1,8-naphthyridin-3-yl]-N'-(2,6-diisopropylphenyl)urea N-[1-propyl-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-isobutyl-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-pentyl-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-(3-acetylaminopropyl)-4-[3-{3-(1-pyrrolidinyl)-1-propynyl}phenyl]-1,2-dihydro-2-oxo-1,8-naphthyridin-3-yl]-N'-(2,6-diisopropylphenyl)urea N-[1-(3-hydroxypropyl)-4-[3-{3-(1-pyrrolidinyl)-1-propynyl}phenyl]-1,2-dihydro-2-oxo-1,8-naphthyridin-3-yl]-N'-(2,6-diisopropylphenyl)urea

BEST MODE FOR CARRYING OUT THE INVENTION

The present invention is illustrated by Reference Examples and Examples, but should not be construed to be limited thereto.

EXAMPLE 1

Preparation of N-[4-(2-chlorophenyl)-1,7-naphthyridin-3-yl]-N'-(2,4-difluorophenyl)urea:

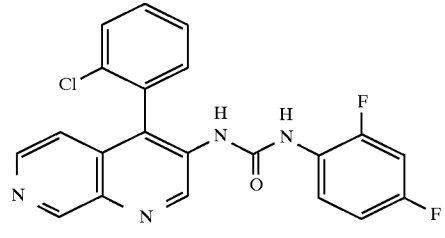

A solution of 3-amino-4-(2-chlorophenyl)-1,7-naphthyridine (169 mg, 0.66 mmol) and 2,4-difluorophenylisocyanate (102 mg, 0.66 mmol) in tetrahydrofuran (50 ml) was refluxed for 8 hours. The mixture was concentrated, and the residue was purified by column chromatography (silica gel; methanol:chloroform=1:9), and recrystallized from hexane to give the title compound (98 mg, 0.24 mmol) as colorless powder.

m.p. 213°–216° C.; $^1$H-NMR δ (DMSO-d$_6$) 10.52 (1H, br), 8.25 (1H, d, J=5.0 Hz), 8.04–8.08 (2H, m), 7.59–7.75 (2H, m), 7.17–7.46 (4H, m), 6.91–7.00 (1H, m), 6.67–6.74 (0.5H, m), 6.62 (1H, d, J=5.0 Hz), 6.30–6.36 (0.5H, m); IR (KBr) 1683, 1596, 1508, 1400 cm$^{-1}$

EXAMPLE 2

Preparation of N-[1-methyl-4-(2-chlorophenyl)-1,2-dihydro-2-oxo-1,8-naphthyridin-3-yl]-N'-(2,4-difluorophenyl)urea

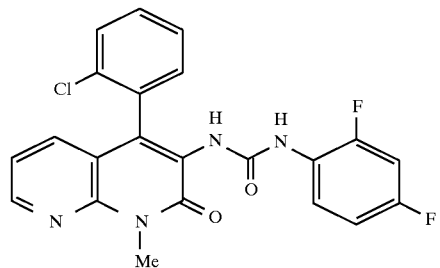

A solution of 1-methyl-4-(2-chlorophenyl)-1,2-dihydro-2-oxo-1,8-naphthyridine-3-carboxylic acid (315 mg, 1 mmol), diphenylphosphoryl azide (330 mg, 1.2 mmol) and triethylamine (101 mg, 1 mmol) in benzene (4 ml) was stirred at room temperature for 0.5 hour, and then refluxed for 0.5 hour. After allowed to stand for cooling, to the mixture was added 2,4-difluoroaniline (152 mg, 1.2 mmol), and the mixture was stirred at room temperature for 0.5 hour, and then stirred under reflux for two hours. After allowed to stand for cooling, the mixture was washed with water, washed with a saturated aqueous sodium chloride solution, dried over anhydrous magnesium sulfate, and concentrated under reduced pressure. The resulting solid was recrystallized from isopropanol to give the title compound (288 mg, 0.65 mmol) as a colorless crystal.

m.p. 225°–226° C. $^1$H-NMR δ (CDCl$_3$) 8.61 (1H, dd, J=4.6 Hz, 1.7 Hz), 7.66–7.75 (2H, m), 7.38–7.56 (6H, m), 7.16 (1H, dd, J=7.9 Hz, 4.6 Hz), 6.67–677 (2H, m), 4.00 (3H, s); IR (KBr) 1715, 1636, 1613, 1584, 1584, 1550, 1500, 1434 cm$^{-1}$

EXAMPLE 3

Preparation of N-[1-methyl-4-(2-chlorophenyl)-1,2-dihydro-2-oxo-1,8-naphthyridin-3-yl]-N'-(2,4,6-trimethylphenyl)urea

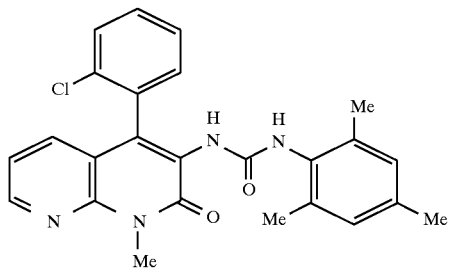

The title compound was obtained in the same manner as in Example 2 from 1-methyl-4-(2-chlorophenyl)-1,2-dihydro-2-oxo-1,8-naphthyridine-3-carboxylic acid and 2,4,6-trimethylaniline.

m.p. >250° C.; $^1$H-NMR δ (CDCl$_3$) 8.55 (1H, dd, J=4.6 Hz, 2.0 Hz), 7.37–7.53 (5H, m), 7.10 (1H, dd, J=7.9 Hz, 4.6 Hz), 6.91 (2H, brs), 6.36 (0.7H, br), 5.73 (0.7H, br), 3.91 (3H, s), 2.27 (6H, brs), 2.02 (3H, brs); IR (KBr) 3271, 1658, 1634, 1554, 1458, 1118 cm$^{-1}$

EXAMPLE 4

Preparation of N-[1-methyl-4-(2-chlorophenyl)-1,2-dihydro-2-oxo-1,8-naphthyridin-3-yl]-N'-(2,6-diisopropylphenyl)urea

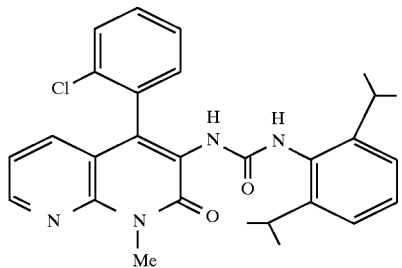

The title compound was obtained in the same manner as in Example 2 from 1-methyl-4-(2-chlorophenyl)-1,2-dihydro-2-oxo-1,8-naphthyridine-3-carboxylic acid and 2,6-diisopropylaniline.

m.p. 193°–196° C.; $^1$H-NMR δ (CDCl$_3$) 8.54 (1H, br), 7.53–7.57 (1H, m), 7.03–7.46 (8H, m), 6.47 (0.7H, brs), 5.65 (0.7H, brs), 3.88 (3H, brs), 3.22 (m) and 2.94 (m) (total 1H), 1.02–1.38 (12H, m); IR (KBr) 3342, 2963, 1714, 1629, 1608, 1581, 1509, 1461 cm$^{-1}$

EXAMPLE 5

Preparation of N-[1-methyl-4-(2-chlorophenyl)-1,2-dihydro-2-oxo-1,7-naphthyridin-3-yl]-N'-(2,4,6-trimethylphenyl)urea

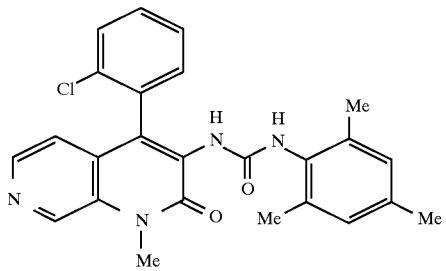

A solution of 1-methyl-4-(2-chlorophenyl)-1,2-dihydro-2-oxo-1,7-naphthyridine-3-carboxylic acid (315 mg, 1 mmol), diphenylphosphoryl azide (330 mg, 1.2 mmol) and triethylamine (101 mg, 1 mmol) in N,N-dimethylformamide (DMF, 5 ml) was stirred at room temperature for 0.5 hour, and stirred at 80°–90° C. for 0.5 hour. After allowed to stand for cooling, to the mixture was added 2,4,6-trimethylaniline (162 mg, 1.2 mmol), and the mixture was stirred at room temperature for 0.5 hour, and then stirred at 80–90° C. for two hours. After allowed to stand for cooling, the mixture was diluted with ethyl acetate, washed with water, washed with a saturated aqueous sodium chloride solution, dried over anhydrous magnesium sulfate, and concentrated under reduced pressure. The resulting solid was recrystallized from ethanol to give the title compound (350 mg, 0.78 mmol) as a colorless crystal.

m.p. 222°–224° C.; $^1$H-NMR δ (CDCl$_3$) 8.83 (1H, s), 8.36 (1H, d, J=5.3 Hz), 7.50–7.54 (1H, m), 7.38–7.43 (3H, m), 7.02 (1H, d, J=5.3 Hz), 6.93 (1H, brs), 6.62 (0.5H, br), 5.68 (0.5H, br), 3.86 (3H, brs), 2.27 (6H, brs), 2.05 (3H, brs); IR (KBr) 1658, 1638, 1545, 1432 cm$^{-1}$

EXAMPLE 6

Preparation of N-[1-methyl-4-(2-chlorophenyl)-1,2-dihydro-2-oxo-1,7-naphthyridin-3-yl]-N'-(2,6-diisopropylphenyl)urea

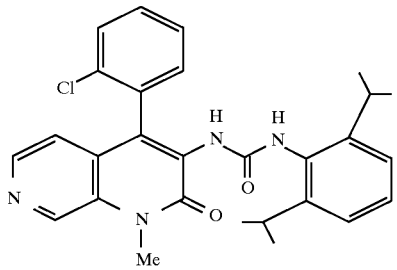

The title compound was obtained in the same manner as in Example 5 from 1-methyl-4-(2-chlorophenyl)-1,2-dihydro-2-oxo-1,7-naphthyridine-3-carboxylic acid and 2,6-diisopropylaniline.

m.p. 153°–154° C.; $^1$H-NMR δ (CDCl$_3$) 8.83 (1H, br), 8.34 (1H, d, J=5.6 Hz), 7.01–7.61 (7H, m), 6.97 (1H, d, J=5.6 Hz), 6.72 (0.7H, br), 5.80 (0.7H, br), 3.80 (3H, s), 3.21 (1H, m), 2.96 (1H, m), 1.03–1.36 (12H, m); IR (KBr) 2963, 1645, 1591, 1505 cm$^{-1}$

EXAMPLE 7

Preparation of N-[1-methyl-4-(3-methoxyphenyl)-1,2-dihydro-2-oxo-1,8-naphthyridin-3-yl]-N'-(2,6-diisopropylphenyl)urea

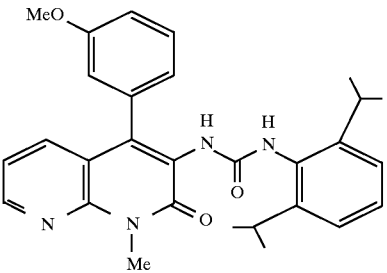

A solution of 1-methyl-4-(3-methoxyphenyl)-1,2-dihydro-2-oxo-1,8-naphthyridine-3-carboxylic acid (315 mg, 1 mmol), diphenylphosphoryl azide (330 mg, 1.2 mmol) and triethylamine (101 mg, 1 mmol) in toluene (4 ml) was stirred at room temperature for 0.5 hour, and then refluxed for 0.5 hour. After allowed to stand for cooling, to the mixture was added 2,6-diisopropylaniline (216 mg, 1.2 mmol), and the mixture was stirred at room temperature for 0.5 hour, and then stirred under reflux for two hours. After allowed to stand for cooling, the mixture was diluted with ethyl acetate, washed with water, washed with a saturated aqueous sodium chloride solution, and dried over anhydrous magnesium sulfate. The resultant was concentrated under reduced pressure, and the residue was purified by silica gel column chromatography (ethyl acetate:hexane =1:1), and crystallized from diethyl ether to give the title compound (302 mg, 0.62 mmol) as a colorless crystal.

m.p. 169°–170° C.; $^1$H-NMR δ (CDCl$_3$) 7.64–7.72 (1H, m), 6.85–7.39 (8H, m), 6.11 (OSH, br), 5.90 (0.5H, br), 3.92 (s) and 3.86 (s) (total 3H), 3.84 (3H, s), 2.85–3.15 (2H, m), 1.08–1.29 (12H, m); IR (KBr) 2964, 1716, 1654, 1509 cm$^{-1}$

EXAMPLE 8

Preparation of N-[4-(3-methoxyphenyl)-1,2-dihydro-2-oxo-1,8-naphthyridin-3-yl]-N'-(2,6-diisopropylphenyl)urea

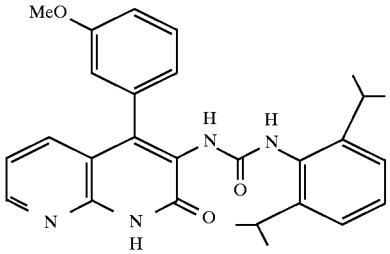

The title compound was obtained in the same manner as in Example 7 from 4-(3-methoxyphenyl)-1,2-dihydro-2-oxo-1,8-naphthyridine-3-carboxylic acid and 2,6-diisopropylaniline.

$^1$H-NMR δ (CDCl$_3$) 11.45 (1H, brs), 8.58 (1H, br), 7.65 (1H, br), 6.96–7.40 (7H, m), 6.03 (1H, br), 3.84 (3H, s), 2.96 (br) and 3.18 (br) (total 2H), 1.07–1.20 (12H, br)

EXAMPLE 9

Preparation of N-[1-methyl-4-(4-methoxyphenyl)-1,2-dihydro-2-oxo-1,8-naphthyridin-3-yl]-N'-(2,6-diisopropylphenyl)urea

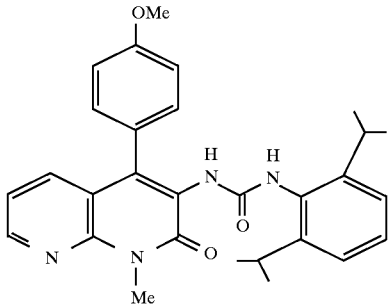

The title compound was obtained in the same manner as in Example 7 from 1-methyl-4-(4-methoxyphenyl)-1,2-dihydro-2-oxo-1,8-naphthyridine-3-carboxylic acid and 2,6-diisopropylaniline.

m.p. 179°–182° C.;

EXAMPLE 10

Preparation of N-[1-isopropyl-4-(3-methoxyphenyl)-1,2-dihydro-2-oxo-1,8-naphthyridin-3-yl]-N'-(2,6-diisopropylphenyl)urea

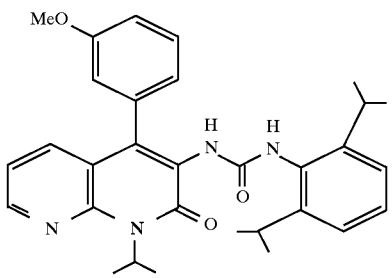

The title compound was obtained in the same manner as in Example 7 from 1-isopropyl-4-(3-methoxyphenyl)-1,2-dihydro-2-oxo-1,8-naphthyridine-3-carboxylic acid and 2,6-diisopropylaniline.

$^1$H-NMR δ (DMSO-d$_6$) 8.58 (1H, dd, J=4.6 Hz, 2.0 Hz), 7.75 (2H, br), 7.62 (1H, dd, J=4.6 Hz, 2.0 Hz), 7.40 (1H, dd, J=7.9 Hz, 7.9 Hz), 7.24 (1H, dd, J=7.9Hz, 4.6 Hz), 7.13–7.18 (1H, m), 7.00–7.05 (3H, m), 6.91–6.98 (2H, m), 6.10 (1H, br), 3.77 (3H, s), 2.86–2.96 (2H, m), 1.63 (6H, d, J=6.9 Hz), 1.08 (12H, br)

EXAMPLE 11

Preparation of N-[1-(2-methoxyethyl)-4-(3-methoxphenyl)-1,2-dihydro-2-oxo-1,8-naphthyridin-3-yl]-N'-(2,6-diisopropylphenyl)urea

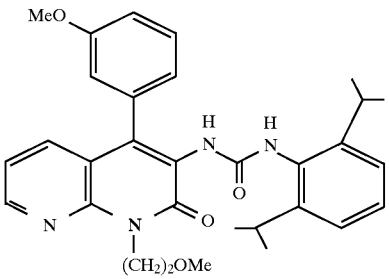

The title compound was obtained in the same manner as in Example 7 from 1-(2-methoxyethyl)-4-(3-methoxyphenyl)-1,2-dihydro-2-oxo-1,8-naphthyridine-3-carboxylic acid and 2,6-diisopropylaniline.

m.p. 164°–165° C.

EXAMPLE 12

Preparation of N-[1-methyl-4-(3-methoxyphenyl)-1,2-dihydro-2-oxo-1,8-naphthyridin-3-yl]-N'-(2,4-difluorophenyl)urea

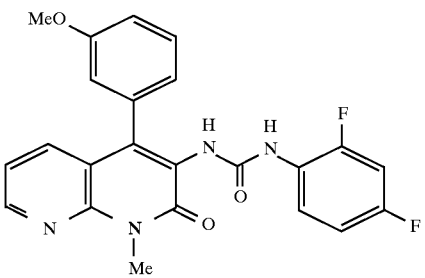

The title compound was obtained in the same manner as in Example 7 from 1-methyl-4-(3-methoxyphenyl)-1,2-dihydro-2-oxo-1,8-naphthyridine-3-carboxylic acid and 2,4-difluoroaniline.

m.p. 203°–205° C.

EXAMPLE 13

Preparation of N-[1-methyl-4-(3-methoxyphenyl)-1,2-dihydro-2-oxo-1,8-naphthyridin-3-yl]-N'-(2,4,6-trimethylphenyl)urea

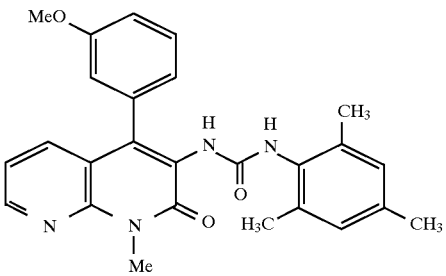

The title compound was obtained in the same manner as in Example 7 from 1-methyl-4-(3-methoxyphenyl)-1,2-dihydro-2-oxo-1,8-naphthyridine-3-carboxylic acid and 2,4,6-trimethylaniline.

m.p. >230° C.; IR (KBr) 2956, 1654, 1585, 1547, 1460, 1254 cm$^{-1}$

EXAMPLE 14

Preparation of N-[1-methyl-4-(3-methoxyphenyl)-1,2-dihydro-2-oxo-1,8-naphthyridin-3-yl]-N'-(2-trifluoromethylphenyl)urea

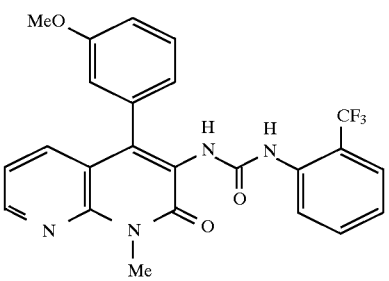

The title compound was obtained in the same manner as in Example 7 from 1-methyl-4-(3-methoxyphenyl)-1,2-dihydro-2-oxo-1,8-naphthyridine-3-carboxylic acid and 2-trifluoromethylaniline.

$^1$H-NMR δ (CDCl$_3$) 8.60 (1H, dd, J=4.6 Hz, 2.0 Hz), 7.78 (1H, dd, J=8.3 Hz, J=2.0 Hz), 7.70 (1H, d, J=8.3 Hz), 7.32–7.54 (4H, m), 7.12–7.17 (3H, m), 6.9–6.98 (3H, m), 3.85 (3H, s), 3.80 (3H, s)

EXAMPLE 15

Preparation of N-[1-methyl-4-(3-methoxyphenyl)-1,2-dihydro-2-oxo-1,8-naphthyridin-3-yl]-N'-(2,6-dichlorophenyl)urea

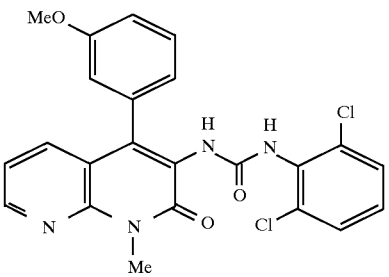

The title compound was obtained in the same manner as in Example 7 from 1-methyl-4-(3-methoxyphenyl)-1,2-dihydro-2-oxo-1,8-naphthyridine-3-carboxylic acid and 2,6-dichloroaniline.

m.p. 207°–208° C.

EXAMPLE 16

Preparation of N-[1-methyl-4-(3-methoxyphenyl)-1,2-dihydro-2-oxo-1,8-naphthyridin-3-yl]-N'-(2-chloro-3-pyridyl)urea

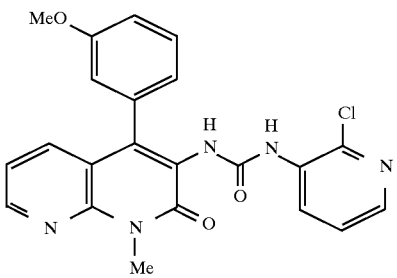

The title compound was obtained in the same manner as in Example 7 from 1-methyl-4-(3-methoxyphenyl)-1,2-dihydro-2-oxo-1,8-naphthyridine-3-carboxylic acid and 3-amino-2-chloropyridine.

m.p. >230° C.; IR (KBr) 1652, 1587, 1535, 1459, 1390, 1260 cm$^{-1}$

EXAMPLE 17

Preparation of N-[1-methyl-4-(3-methoxyphenyl)-1,2-dihydro-2-oxo-1,8-naphthyridin-3-yl]-N'-(3,5-dichloro-2-pyridyl)urea

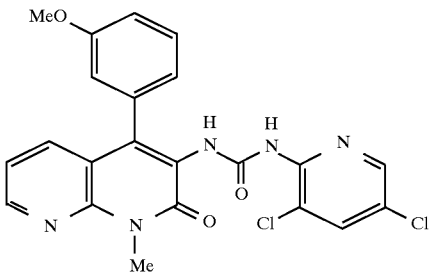

The title compound was obtained in the same manner as in Example 7 from 1-methyl-4-(3-methoxyphenyl)-1,2-dihydro-2-oxo-1,8-naphthyridine-3-carboxylic acid and 2-amino-3,5-dichloropyridine.

m.p. 78°–79° C.

EXAMPLE 18

Preparation of N-[1-methyl-4-(3-methoxyphenyl)-1,2-dihydro-2-oxo-1,8-naphthyridin-3-yl]-N'-(8-quinolyl)urea

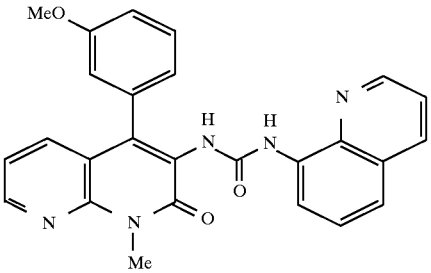

The title compound was obtained in the same manner as in Example 7 from 1-methyl-4-(3-methoxyphenyl)-1,2-dihydro-2-oxo-1,8-naphthyridine-3-carboxylic acid and 8-aminoquinoline.

m.p. >250° C.; IR (KBr) 2924, 1710, 1661, 1641, 1545 cm$^{-1}$

EXAMPLE 19

Preparation of N-[1-methyl-4-(3-methoxyphenyl)-1,2-dihydro-2-oxo-1,8-naphthyridin-3-yl]-N'-(2-methoxy-4-nitrophenyl)urea

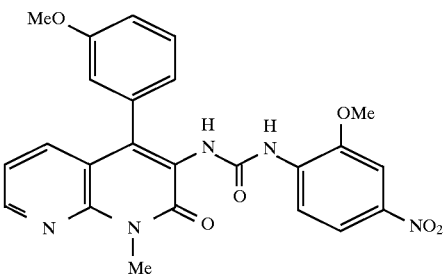

The title compound was obtained in the same manner as in Example 7 from 1-methyl-4-(3-methoxyphenyl)-1,2-dihydro-2-oxo-1,8-naphthyridine-3-carboxylic acid and 2-methoxy-4-nitroaniline.

m.p. >250° C.; IR (KBr) 1715, 1664, 1645, 1588, 1550 cm$^{-1}$

EXAMPLE 20

Preparation of N-[1-methyl-4-(3-methoxyphenyl)-1,2-dihydro-2-oxo-1,8-naphthyridin-3-yl]-N'-(2-isopropylphenyl)urea

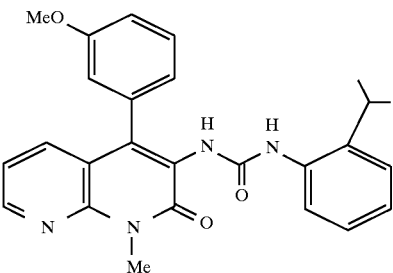

The title compound was obtained in the same manner as in Example 7 from 1-methyl-4-(3-methoxyphenyl)-1,2-dihydro-2-oxo-1,8-naphthyridine-3-carboxylic acid and 2-isopropylaniline.

m.p. 208°–209° C.

EXAMPLE 21

Preparation of N-[1-methyl-4-(3-methoxyphenyl)-1,2-dihydro-2-oxo-1,8-naphthyridin-3-yl]-N'-(2-ethylphenyl)urea

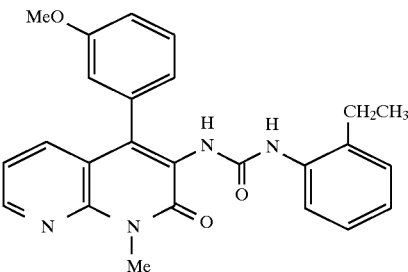

The title compound was obtained in the same manner as in Example 7 from 1-methyl-4-(3-methoxyphenyl)-1,2-dihydro-2-oxo-1,8-naphthyridine-3-carboxylic acid and 2-ethylaniline.

m.p. 212°–212.5° C.

EXAMPLE 22

Preparation of N-[1-methyl-4-(3-methoxyphenyl)-1,2-dihydro-2-oxo-1,8-naphthyridin-3-yl]-N'-(2-isopropyl-6-methylphenyl)urea

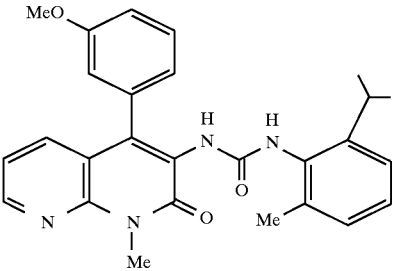

The title compound was obtained in the same manner as in Example 7 from 1-methyl-4-(3-methoxyphenyl)-1,2-dihydro-2-oxo-1,8-naphthyridine-3-carboxylic acid and 2-isopropyl-6-methylaniline.

m.p. 196°–198° C.

EXAMPLE 23

Preparation of N-[1-methyl-4-(3-methoxyphenyl)-1,2-dihydro-2-oxo-1,8-naphthyridin-3-yl]-N'-butylurea

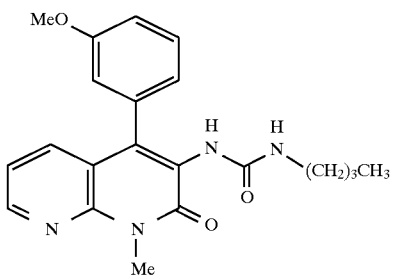

The title compound was obtained in the same manner as in Example 1 from 1-methyl-4-(3-methoxyphenyl)-1,2-dihydro-2-oxo-1,8-naphthyridine-3-carboxylic acid and butylamine.

m.p. 208°–210° C.

EXAMPLE 24

Preparation of N-[1-methyl-4-(2-methoxyphenyl)-1,2-dihydro-2-oxo-1,8-naphthyridin-3-yl]-N'-(2,6-diisopropylphenyl)urea

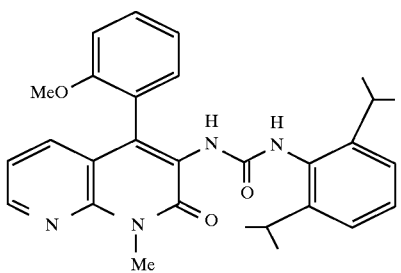

The title compound was obtained in the same manner as in Example 5 from 1-methyl-4-(2-methoxyphenyl)-1,2-dihydro-2-oxo-1,8-naphthyridine-3-carboxylic acid and 2,6-diisopropylaniline.

m.p. 179°–180° C.

EXAMPLE 25

Preparation of N-[1-butyl-4-(3-methoxyphenyl)-1,2-dihydro-2-oxo-1,8-naphthyridin-3-yl]-N'-(2,6-diisopropylphenyl)urea

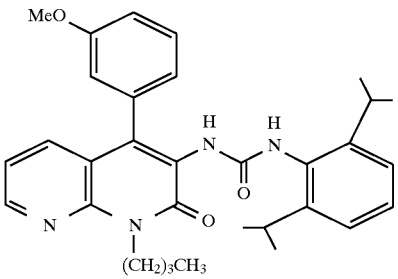

The title compound was obtained in the same manner as in Example 5 from 1-butyl-4-(3-methoxyphenyl)-1,2-dihydro-2-oxo-1,8-naphthyridine-3-carboxylic acid and 2,6-diisopropylaniline.

m.p. 179°–182° C.

EXAMPLE 26

Preparation of N-[1-pentyl-4-(3-methoxyphenyl)-1,2-dihydro-2-oxo-1,8-naphthyridin-3-yl]-N'-(2,6-diisopropylphenyl)urea

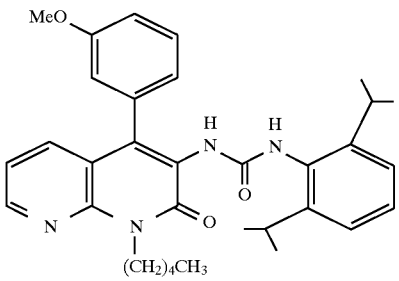

The title compound was obtained in the same manner as in Example 5 from 1-pentyl-4-(3-methoxyphenyl)-1,2-dihydro-2-oxo-1,8-naphthyridine-3-carboxylic acid and 2,6-diisopropylaniline.

m.p. 189°–190° C.

EXAMPLE 27

Preparation of N-[1-(3-methylbutyl)-4-(3-methoxyphenyl)-1,2-dihydro-2-oxo-1,8-naphthyridin-3-yl]-N'-(2,6-diisopropylphenyl)urea

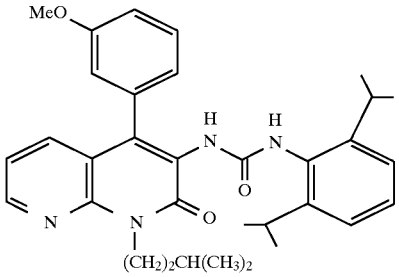

The title compound was obtained in the same manner as in Example 5 from 1-(3-methylbutyl)-4-(3-methoxyphenyl)-1,2-dihydro-2-oxo-1,8-naphthyridine-3-carboxylic acid and 2,6-diisopropylaniline.

m.p. 189.5°–191° C.

EXAMPLE 28

Preparation of N-[1-butyl-4-(3-pyridyl)-1,2-dihydro-2-oxo-1,8-naphthyridin-3-yl]-N'-(2,6-diisopropylphenyl)urea

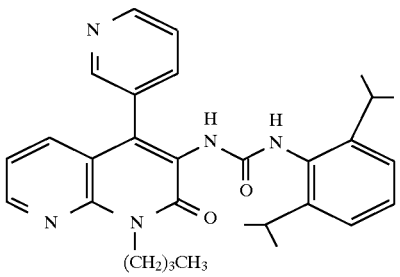

The title compound was obtained in the same manner as in Example 5 from 1-butyl-4-(3-pyridyl)-1,2-dihydro-2-oxo-1,8-naphthyridine-3-carboxylic acid and 2,6-diisopropylaniline.

Hydrochloride: m.p. 170°–172° C.

EXAMPLE 29

Preparation of N-[1-(3-cyanopropyl)-4-(3-methoxyphenyl)-1,2-dihydro-2-oxo-1,8-naphthyridin-3-yl]-N'-(2,6-diisopropylphenyl)urea

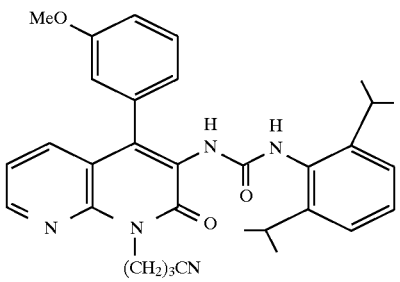

The title compound was obtained in the same manner as in Example 5 from 1-(3-cyanopropyl)-4-(3-methoxyphenyl)-1,2-dihydro-2-oxo-1,8-naphthyridine-3-carboxylic acid and 2,6-diisopropylaniline.

m.p. 187°–188.5° C.

EXAMPLE 30

Preparation of N-(1-methyl-4-phenyl-1,2-dihydro-2-oxo-1,8-naphthyridin-3-yl)-N'-(2,6-diisopropylphenyl)urea

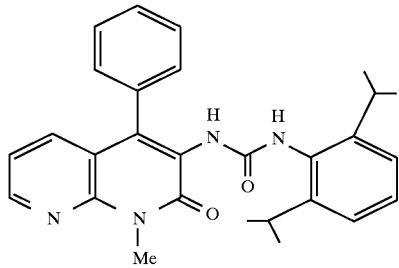

To a solution of N-[1-methyl-4-(2-chlorophenyl)-1,2-dihydro-2-oxo-1,8-naphthyridin-3-yl]-N'-(2,6-diisopropylphenyl)urea (350 mg, 0.72 mmol) in methanol (20 ml) were added ammonium formate (135 mg, 2.15 mmol) and 10% palladium-carbon (100 mg), and the mixture was refluxed for 4 hours. After allowed to stand for cooling, the mixture was filtered through a cerite pad, and the filtrate was concentrated under reduced pressure. To the residue was added dilute aqueous ammonia, and the mixture was extracted with ethyl acetate. The extract was washed with water, washed with a saturated aqueous sodium chloride solution, dried over anhydrous magnesium sulfate, concentrated under reduced pressure, and crystallized from diethyl ether to give the title compound (249 mg, mmol) as a colorless powder.

m.p. 188°–190.5° C.

EXAMPLE 31

Preparation of N-(1-methyl-4-(3-hydroxyphenyl)-1,2-dihydro-2-oxo-1,8-naphthyridin-3-yl)-N'-(2,6-diisopropylphenyl)urea

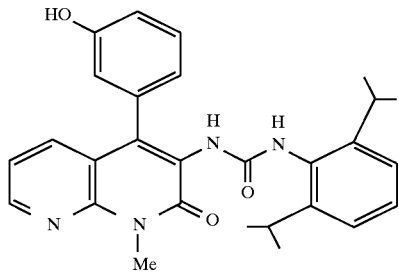

To a solution of N-[1-methyl-4-(3-methoxyphenyl)-1,2-dihydro-2-oxo-1,8-naphthyridin-3-yl]-N'-(2,6-diisopropylphenyl)urea (1310 mg, 2.7 mmol) in methylene chloride (20 ml) was added dropwise boron tribromide (1.7 g, 6.75 mmol) at 0° C., and the mixture was stirred for 6 hours. The mixture was poured into a saturated aqueous sodium hydrogen carbonate solution, and the mixture was extracted with methylene chloride. The extract was washed with water, washed with a saturated aqueous sodium chloride solution, and dried over anhydrous magnesium sulfate. The residue was concentrated under reduced pressure, purified by silica gel column chromatography (3% methanol in chloroform), and crystallized from diethyl ether/hexane to give the title compound (830 mg, 1.76 mmol) as a colorless powder.

m.p. 152°–155° C.

EXAMPLE 32

Preparation of N-(1-butyl-4-(3-hydroxyphenyl)-1,2-dihydro-2-oxo-1,8-naphthyridin-3-yl)-N'-(2,6-diisopropylphenyl)urea

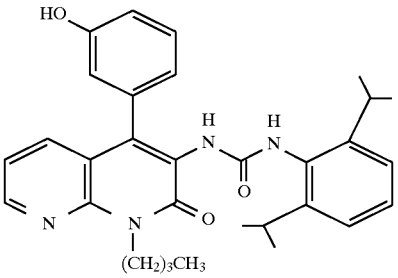

The title compound was obtained in the same manner as in Example 31 from N-[1-butyl-4-(3-methoxyphenyl)-1,2-dihydro-2-oxo-1,8-naphthyridin-3-yl]-N'-(2,6-diisopropylphenyl)urea.

m.p. 136°–140° C.

EXAMPLE 33

Preparation of N-(1-methyl-4-(3-hydroxyphenyl)-1,2-dihydro-2-oxo-1,8-naphthyridin-3-yl)-N'-butylurea

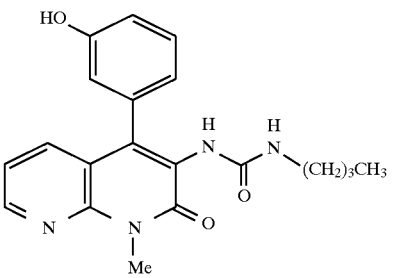

The title compound was obtained in the same manner as in Example 31 from N-[1-methyl-4-(3-methoxyphenyl)-1,2-dihydro-2-oxo-1,8-naphthyridin-3-yl]-N'-butylurea.

m.p. 178°–180.5° C.

EXAMPLE 34

Preparation of N-[1-butyl-4-{3-(2-acetoxyethoxy)phenyl}-1,2-dihydro-2-oxo-1,8-naphthyridin-3-yl]-N'-(2,6-diisopropylphenyl)urea

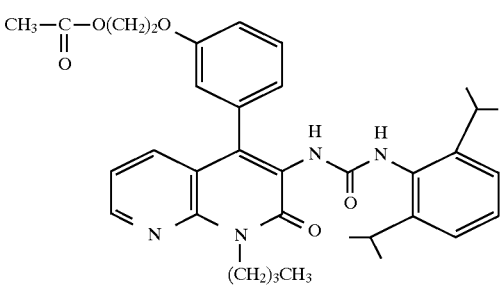

To a solution of N-(1-butyl-4-(3-hydroxyphenyl)-1,2-dihydro-2-oxo-1,8-naphthyridin-3-yl)-N'-(2,6- diisopropylphenyl)urea (300 mg, 0.59 mmol) in DMF (10 ml) was added sodium hydride (NaH, 23 mg, 0.59 mmol), and the mixture was stirred at room temperature for 0.5 hour. To the mixture was added 2-bromoethyl acetate (98 mg, 0.59 mmol), and the mixture was stirred at 40°–50° C. for 6 hours. After allowed to stand for cooling, the mixture was poured into water, extracted with ethyl acetate, and the extract was washed with water, washed with a saturated aqueous sodium chloride solution, and dried over anhydrous magnesium sulfate. The residue was concentrated under reduced pressure, and purified by silica gel column chromatography (3% methanol in chloroform) to give the title compound (209 mg, 0.35 mmol) as a colorless powder.

$^1$H-NMR δ (CDCl$_3$) 8.53 (1H, br), 7.65 (1H, br), 6.98–7.44 (9H, m), 6.27 (0.5H, br), 5.72 (0.5H, br), 4.53 (2H, br), 4.44 (2H, m), 4.20 (2H, m), 3.06 (2H, br), 2.11 (3H, s), 1.72 (2H, br), 1.45 (2H, m), 1.11–1.24 (12H, m), 0.96 (3H, t, J=7.3 Hz)

EXAMPLE 35

Preparation of N-[1-methyl-4-[3-{3-(4-phenyl-1-piperazinyl)propoxy}-phenyl]-1,2-dihydro-2-oxo-1,8-naphthyridin-3-yl]-N'-(2,6-diisopropylphenyl)urea

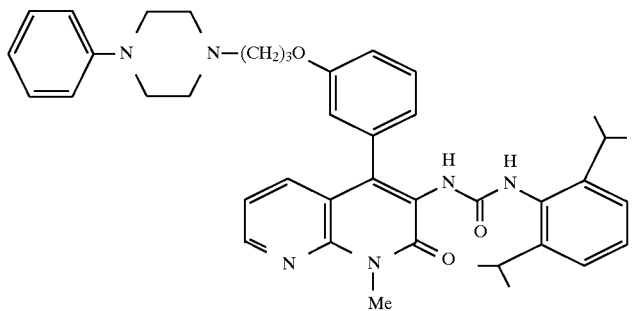

The title compound was obtained in the same manner as in Example 34 from N-{1-methyl-4-(3-hydroxyphenyl)-1,2-dihydro-2-oxo-1,8-naphthyridin-3-yl }-N'-(2,6-diisopropylphenyl)urea and 1-(3-chloropropyl)-4-phenylpiperazine.

$^1$H-NMR δ (CDCl$_3$) 8.54 (1H, m), 7.65 (1H, m), 6.83–7.42 (14H, m), 6.10 (0.5H, br), 5.77 (1H, br), 4.09 (2H, t, J=6.3 Hz), 3.87 (3H, br), 3.22 (4H, br), 2.51–3.10 (2H, br), 2.64 (6H, br), 2.05 (2H, t, J=6.3 Hz), 1.11–1.25 (12H, br)

EXAMPLE 36

Preparation of N-[1-methyl-4-{3-(2-acetoxyethoxy)phenyl}-1,2-dihydro-2-oxo-1,8-naphthyridin-3-yl]-N'-(2,6-diisopropylphenyl)urea

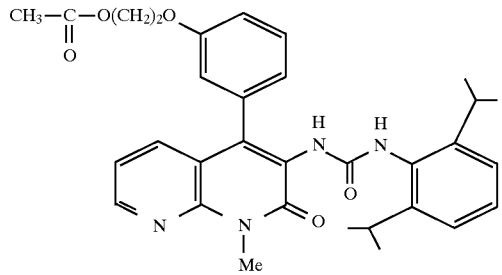

The title compound was obtained in the same manner as in Example 34 from N-{1-methyl-4-(3-hydroxyphenyl)-1,2-dihydro-2-oxo-1,8-naphthyridin-3-yl}-N'-(2,6-diisopropylphenyl)urea and 2-bromoethyl acetate.

$^1$H-NMR δ (CDCl$_3$) 8.53 (1H, m), 7.62–7.74 (1H, m), 6.87–7.40 (9H, m), 6.13 (0.5H, br), 5.93 (0.5H, br), 4.43 (2H, m), 4.20 (2H, m), 3.93 (3H, br), 2.94–3.21 (2H, br), 2.11 (3H, s), 1.08–1.26 (12H, br)

EXAMPLE 37

Preparation of N-[1-butyl-4-{3-(3-phthalimidopropoxy)phenyl}-1,2-dihydro-2-oxo-1,8-naphthyridin-3-yl]-N'-(2,6-diisopropylphenyl)urea

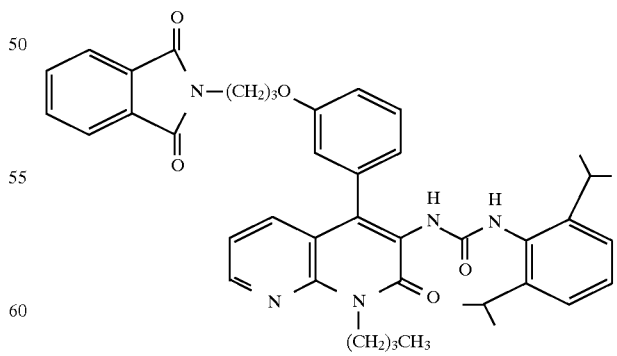

The title compound was obtained in the same manner as in Example 34 from N-{1-butyl-4-(3-hydroxyphenyl)-1,2-dihydro-2-oxo-1,8-naphthyridin-3-yl } -N'-(2,6-diisopropylphenyl)urea and N-(3-bromopropyl)phthalimide.

$^1$H-NMR δ (CDCl$_3$) 8.52 (1H, br), 7.79–7.82 (2H, m), 7.64–7.68 (3H, m), 6.82–7.36 (9H, m), 6.21 (0.5H, br), 5.78 (0.5H, br), 4.54 (2H, br), 4.07 (2H, t, J=5.9 Hz), 3.91 (2H, t, J=6.9 Hz), 2.95–3.20 (2H, br), 2.23 (2H, m), 1.73 (2H, m), 1.56 (2H, m), 1.09–1.9 (12H, m), 0.97 (3H, brt, J=7.3 Hz)

EXAMPLE 38

Preparation of N-[1-methyl-4-[3-{3-(4-phenyl-1-piperazinyl)propoxy}-phenyl]-1,2-dihydro-2-oxo-1,8-naphthyridin-3-yl]-N'-butylurea

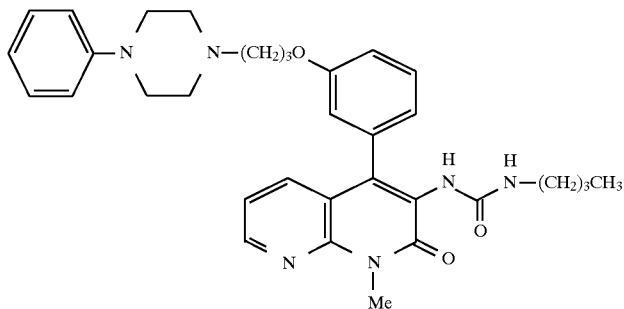

The title compound was obtained in the same manner as in Example 34 from N-{1-methyl-4-(3-hydroxyphenyl)-1,2-dihydro-2-oxo-1,8-naphthyridin-3-yl}-N'-butylurea and 1-(3-chloropropyl)-4-phenylpiperazine.

m.p. 120.5°–121.5° C.

EXAMPLE 39

Preparation of N-[1-butyl-4-{3-(3-chloropropoxy)phenyl}-1,2-dihydro-2-oxo-1,8-naphthyridin-3-yl]-N'-(2,6-diisopropylphenyl)urea

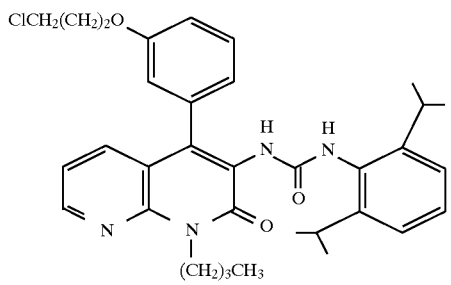

To a solution of N-{1-butyl-4-(3-hydroxyphenyl)-1,2-dihydro-2-oxo-1,8-naphthyridin-3-yl}-N'-(2,6-diisopropylphenyl)urea (1000 mg, 1.95 mmol) and 1-bromo-3-chloropropane (460 mg, 2.93 mmol) in DMF (10 ml) was added potassium carbonate (673 mg, 4.88 mmol), and the mixture was stirred at 50°–60° C. for 6 hours. After allowed to stand for cooling, the mixture was poured into water, extracted with ethyl acetate, washed with water, washed with a saturated aqueous sodium chloride solution, and dried over anhydrous sodium sulfate. The residue was concentrated under reduced pressure, purified by silica gel column chromatography (ethyl acetate:hexane=50:50), and crystallized from hexane to give the title compound (1020 mg, 1.73 mmol) as a colorless powder.

m.p. 138°–140° C.

EXAMPLE 40

Preparation of N-[1-(3-cyanopropyl)-4-{3-(3-chloropropoxy)phenyl}-1,2-dihydro-2-oxo-1,8-naphthyridin-3-yl]-N'-(2,6-diisopropylphenyl)urea

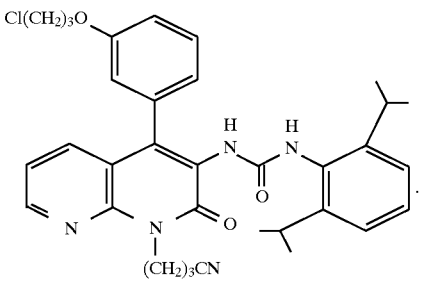

The title compound was obtained in the same manner as in Example 39 from N-{1-(3-cyanopropyl)-4-(3-hydroxyphenyl)-1,2-dihydro-2-oxo-1,8-naphthyridin-3-yl}-N'-(2,6-diisopropylphenyl)urea and 1-bromo-3-chloropropane.

$^1$H-NMR δ (CD$_3$OD) 8.60 (1H, d, J=4.6 Hz), 7.72 (1H, d, J=6.3 Hz), 7.45 (1H, dd, J=7.9 Hz, 7.9 Hz), 7.07–7.25 (5H, m), 6.96 (2H, br), 4.78 (2H, t, J=6.6 Hz), 4.16 (2H, t, J=6.6 Hz), 3.75 (2H, t, J=6.6 Hz), 2.95–3.05 (2H, m), 2.60 (2H, t, J=7.2 Hz)

EXAMPLE 41

Preparation of N-[1-butyl-4-{3-(3-dimethylaminopropoxy)phenyl}-1,2-dihydro-2-oxo-1,8-naphthyridin-3-yl]-N'-(2,6-diisopropylphenyl)urea

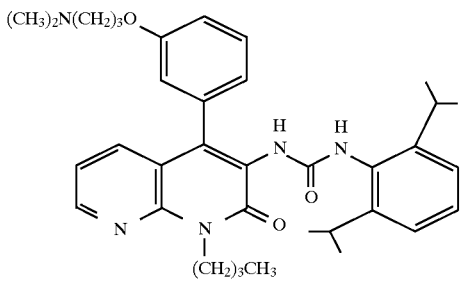

To a suspension of N-{1-butyl-4-(3-hydroxyphenyl)-1,2-dihydro-2-oxo-1,8-naphthyridin-3-yl}-N'-(2,6-diisopropylphenyl)urea (200 mg, 0.4 mmol), potassium carbonate (166 mg, 1.2 mmol), and sodium iodide (5 mg) in DMF (10 ml) was added 3-dimethylaminopropyl chloride hydrochloride (63 mg) at room temperature, and the mixture was stirred at 60°–70° C. for 10 hours. After allowed to stand for cooling, the mixture was poured into water, extracted with ethyl acetate, washed with water, washed with a saturated aqueous sodium chloride solution, and dried over anhydrous magnesium sulfate. The residue was concentrated under reduced pressure, and purified by silica gel column chromatography (10% methanol in chloroform) to give the title compound (88 mg, 0.15 mmol).

$^1$H-NMR δ (DMSO-$d_6$) 8.59 (1H, d, J=3.3 Hz), 7.76 (1H, s), 7.74 (1H, s), 7.61 (1H, d, J=6.6 Hz), 7.38 (1H, dd, J=7.6 Hz, 7.6 Hz), 7.12–7.26 (2H, m), 6.98–7.04 (3H, m), 6.85–6.91 (2H, m), 4.52 (2H, br), 3.99 (2H, brt, J=6.9 Hz), 2.85–2.95 (2H, m), 2.38 (2H, t, J=6.9 Hz), 1.82–1.91 (2H, m), 1.65–1.75 (2H, m), 1.37–1.47(2H, m), 0.95–1.00 (15H, m)

EXAMPLE 42

Preparation of N-[1-methyl-4-(3-benzyloxyphenyl)-1,2-dihydro-2-oxo-1,8-naphthyridin-3-yl]-N'-butylurea

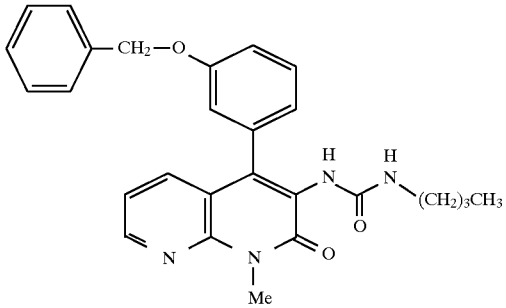

The title compound was obtained in the same manner as in Example 41 from N-[1-methyl-4-(3-hydroxyphenyl)-1,2-dihydro-2-oxo-1,8-naphthyridin-3-yl]-N'-butylurea and benzyl bromide.

m.p. 183°–184° C.

EXAMPLE 43

Preparation of N-[1-butyl-4-{3-(4-pyridylmethoxy)phenyl}1-1,2-dihydro-2-oxo-1,8-naphthyridin-3-yl]-N'-(2,6-diisopropylphenyl)urea

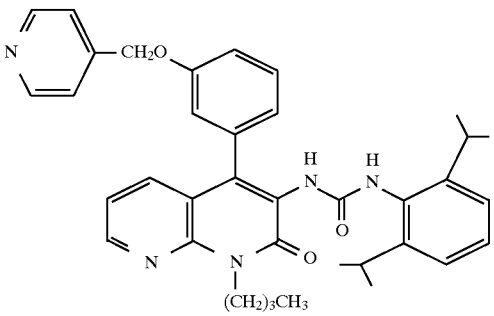

The title compound was obtained in the same manner as in Example 41 from N-{1-butyl-4-(3-hydroxyphenyl)-1,2-dihydro-2-oxo-1,8-naphthyridin-3-yl}-N'-(2,6-diisopropylphenyl)urea and 4-picolyl chloride hydrochloride.

m.p. 157°–158° C.

EXAMPLE 44

Preparation of N-[1-butyl-4-{3-(2-pyridylmethoxy)phenyl}-1,2-dihydro-2-oxo-1,8-naphthyridin-3-yl]-N'-(2,6-diisopropylphenyl)urea

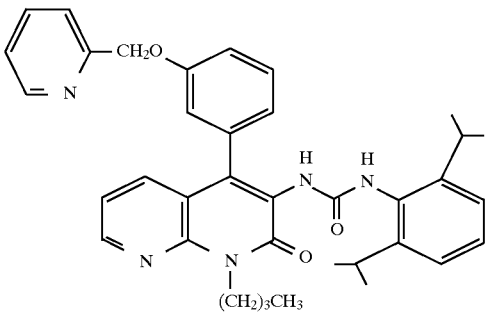

The title compound was obtained in the same manner as in Example 41 from N-{1-butyl-4-(3-hydroxyphenyl)-1,2-dihydro-2-oxo-1,8-naphthyridin-3-yl}-N'-(2,6-diisopropylphenyl)urea and 2-picolyl chloride hydrochloride.

Hydrochloride: m.p. 145°–146° C.

EXAMPLE 45

Preparation of N-[1-butyl-4-{3-(3-piperidinopropoxy)phenyl}-1,2-dihydro-2-oxo-1,8-naphthyridin-3-yl]-N'-(2,6-diisopropylphenyl)urea

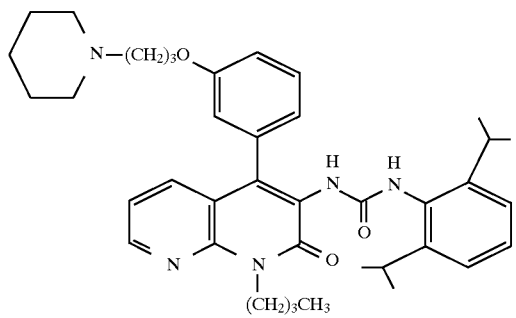

The title compound was obtained in the same manner as in Example 41 from N-{1-butyl-4-(3-hydroxyphenyl)-1,2-dihydro-2-oxo-1,8-naphthyridin-3-yl}-N'-(2,6-diisopropylphenyl)urea and N-(3-chloropropyl)piperidine hydrochloride.

Hydrochloride: m.p. 142°–145° C.

EXAMPLE 46

Preparation of N-[1-butyl-4-{3-(2-diethylaminoethoxy)phenyl}-1,2-dihydro-2-oxo-1,8-naphthyridin-3-yl]-N'-(2,6-diisopropylphenyl)urea

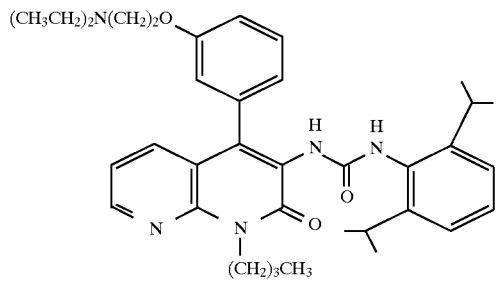

The title compound was obtained in the same manner as in Example 41 from N-{1-butyl-4-(3-hydroxyphenyl)-1,2-dihydro-2-oxo-1,8-naphthyridin-3-yl}-N'-(2,6-diisopropylphenyl)urea and 2-diethylaminoethyl chloride hydrochloride.

Hydrochloride: m.p. 141°–144° C.

EXAMPLE 47

Preparation of N-[1-butyl-4-{3-(2-dimethylaminoethoxy)phenyl}-1,2-dihydro-2-oxo-1,8-naphthyridin-3-yl]-N'-(2,6-diisopropylphenyl)urea

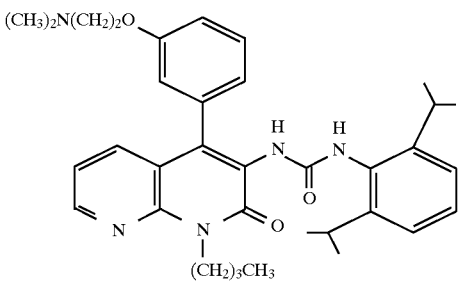

The title compound was obtained in the same manner as in Example 41 from N-{1-butyl-4-(3-hydroxyphenyl)-1,2-dihydro-2-oxo-1,8-naphthyridin-3-yl}-N'-(2,6-diisopropylphenyl)urea and 2-dimethylaminoethyl chloride hydrochloride.

$^1$H-NMR δ (CD$_3$OD) 8.59 (1H, d, J=4.6 Hz), 7.72 (1H, d, J=6.3 Hz), 7.44 (1H, dd, J=8.3H, 8.3 Hz), 7.15–7.22 (3H, m), 7.07 (2H, d, J=7.3 Hz), 6.98 (2H, m, 4.64 (2H, t, J=7.6 Hz), 4.15 (2H, t, J=5.0 Hz), 2.96 (2H, sep, J=6.9 Hz), 2.83 (2H, t, J=5.0 Hz), 1.70–1.81 (2H, m), 1.40–1.55 (2H, m), 1.10 (12H, d, J=6.9 Hz), 1.02 (3H, t, J=7.3 Hz)

EXAMPLE 48

Preparation of N-[1-butyl-4-{3-(3-benzyloxypropoxy)phenyl}-1,2-dihydro-2-oxo-1,8-naphthyridin-3-yl]-N'-(2,6-diisopropylphenyl)urea

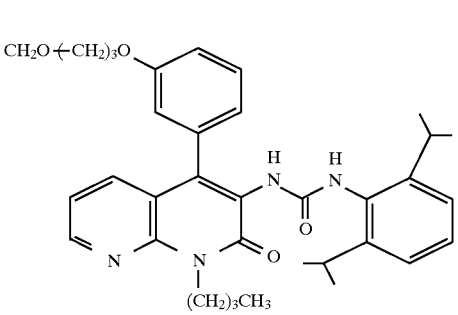

The title compound was obtained in the same manner as in Example 41 from N-{1-butyl-4-(3-hydroxyphenyl)-1,2-dihydro-2-oxo-1,8-naphthyridin-3-yl}-N'-(2,6-diisopropylphenyl)urea and benzyl 3-bromopropyl ether.

$^1$H-NMR δ (CD$_3$OD) 8.58 (1H, br), 7.72 (1H, d, J=8.3 Hz), 7.39 (1H, t, J=7.9 Hz), 6.94–7.29 (12H, m), 4.63 (2H, t, J=7.6 Hz), 4.12 (2H, t, J=5.9 Hz), 3.66 (2H, t, J=5.9 Hz), 2.90–3.00 (2H, m), 2.00–2.10 (2H, m), 1.73–1.85 (2H, m), 1.48–1.56 (2H, m), 1.10 (12H, d, J=6.9 Hz), 1.02 (3H, t, J=7.3 Hz)

EXAMPLE 49

Preparation of N-[1-(3-cyanopropyl)-4-{3-(2-acetoxyethoxy)phenyl}-1,2-dihydro-2-oxo-1,8-naphthyridin-3-yl]-N'-(2,6-diisopropylphenyl)urea

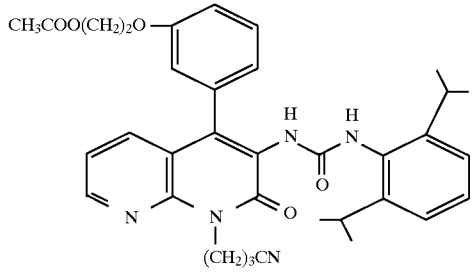

The title compound was obtained in the same manner as in Example 41 from N-{1-(3-cyanopropyl)-4-(3-hydroxyphenyl)-1,2-dihydro-2-oxo-1,8-naphthyridin-3-yl}-N'-(2,6-diisopropylphenyl)urea and 2-bromoethyl acetate.

$^1$H-NMR δ (CD$_3$OD) 8.60 (1H, d, J=2.6 Hz), 7.72 (1H, d, J=6.3Hz), 7.46 (1H, dd, J=7.9 Hz, 7.9 Hz), 7.07–7.25 (5H, m), 6.98 (2H, br), 4.78 (2H, t, J=6.9 Hz), 4.38 (2H, t, J=5.0 Hz), 4.22 (2H, t, J=5.0 Hz), 2.86–3.00 (2H, m), 2.60 (2H, t, J=7.3 Hz), 2.10–2.22 (2H, m), 2.05 (3H, s), 1.11 (12H, brd, J=5.9 Hz)

EXAMPLE 50

Preparation of N-[1-(3-cyanopropyl)-4-{3-(2-diethylaminoethoxy)-phenyl}-1,2-dihydro-2-oxo-1,8-naphthyridin-3-yl]-N'-(2,6-diisopropylphenyl)urea

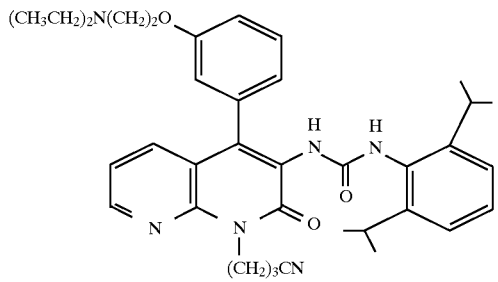

The title compound was obtained in the same manner as in Example 41 from N-{1-(3-cyanopropyl)-4-(3-hydroxyphenyl)-1,2-dihydro-2-oxo-1,8-naphthyridin-3-yl}-N'-(2,6-diisopropylphenyl)urea and 2-diethylaminoethyl chloride hydrochloride.

$^1$H-NMR δ (CD$_3$OD) 8.58 (1H, dd, J=4.6 Hz, 1.6 Hz), 7.70 (1H, dd, J=7.9 Hz, 1.6 Hz), 7.45 (1H, dd, J=7.9 Hz, 7.9 Hz), 7.06–7.22 (5H, m), 6.96 (2H, br), 4.75 (2H, t, J=6.9 Hz), 4.14 (2H, t, J=4 Hz), 2.92–3.04 (4H, m), 2.69 (4H, q, J=6.9 Hz), 2.57 (2H, t, J=6.9 Hz), 2.12–2.02 (2H, m), 1.06–1.12 (18H, m)

EXAMPLE 51

Preparation of N-[1-butyl-4-{3-(2-hydroxyethoxy)phenyl}-1,2-dihydro-2-oxo-1,8-naphthyridin-3-yl]-N'-(2,6-diisopropylphenyl)urea

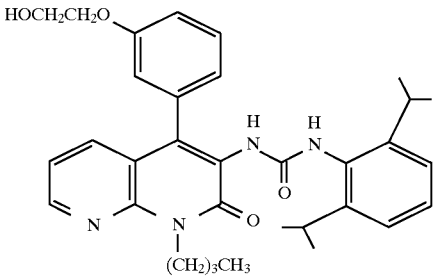

To a solution of N-[1-butyl-4-{3-(2-acetoxyethoxy)phenyl}-1,2-dihydro-2-oxo-1,8-naphthyridin-3-yl]-N'-(2,6-diisopropylphenyl)urea (196 mg, 0.33 mmol) in methanol (10 ml) was added potassium carbonate (11 mg), and the mixture was stirred at room temperature for 4 hours. To the mixture was added water, and the mixture was extracted with ethyl acetate. The extract was washed with water, washed with a saturated aqueous sodium chloride solution, and dried over anhydrous magnesium sulfate. The residue was concentrated under reduced pressure, and crystallized from ether/hexane to give the title compound (145 mg, 0.26 mmol).

m.p. 106°–110° C.

EXAMPLE 52

Preparation of N-[1-methyl-4-{3-(2-hydroxyethoxy)phenyl}-1,2-dihydro-2-oxo-1,8-naphthyridin-3-yl]-N'-(2,6-diisopropylphenyl)urea

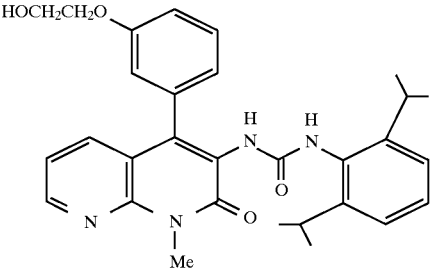

The title compound was obtained in the same manner as in Example 51 from N-[1-methyl-4-{3-(2-acetoxyethoxy)phenyl}-1,2-dihydro-2-oxo-1,8-naphthyridin-3-yl]-N'-(2,6-diisopropylphenyl)urea.

$^1$H-NMR δ (CDCl$_3$) 8.53 (1H, dd, J=3.6 Hz), 7.42 (1H, m), 6.89–7.42 (9H, m), 6.11 (0.5H, br), 5.86 (0.5H, br), 4.13 (2H, br), 3.96 (3H, br), 3.87 (2H, br), 2.90–3.25 (2H, br), 1.09–1.29 (12H, m)

EXAMPLE 53

Preparation of N-[1-(3-cyanopropyl)-4-{3-(2-hydroxyethoxy)phenyl}-1,2-dihydro-2-oxo-1,8-naphthyridin-3-yl]-N'-(2,6-diisopropylphenyl)urea

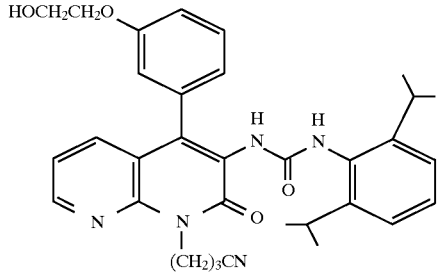

The title compound was obtained in the same manner as in Example 51 from N-[1-(3-cyanopropyl)-4-{3-(2-acetoxyethoxy)phenyl}-1,2-dihydro-2-oxo-1,8-naphthyridin-3-yl}-N'-(2,6-diisopropylphenyl)urea.

$^1$H-NMR δ (CD$_3$OD) 8.60 (1H, d, J=4.6 Hz), 7.73 (1H, d, J=6.3 Hz), 7.45 (1H, dd, J=8.3 Hz, 8.3 Hz), 7.07–7.25 (5H, m), 6.95–6.98 (2H, m), 4.78 (2H, t, J=6.9 Hz), 4.08 (2H, t, J=4.9 Hz), 3.87 (2H, t, J=4.9 Hz), 2.93–3.04 (2H, m), 2.60 (2H, t, J=7.3 Hz), 1.12 (12H, br)

EXAMPLE 54

Preparation of N-[1-butyl-4-{3-(3-hydroxypropoxy)phenyl}-1,2-dihydro-2-oxo-1,8-naphthyridin-3-yl]-N'-(2,6-diisopropylphenyl)urea

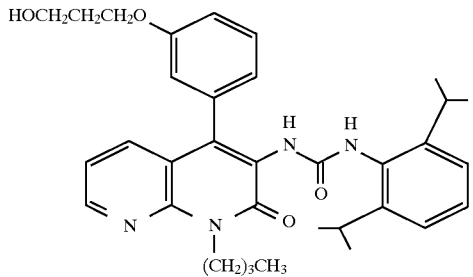

To a solution of N-[1-butyl-4-{3-(3-benzyloxypropoxy)phenyl}-1,2-dihydro-2-oxo-1,8-naphthyridin-3-yl]-N'-(2,6-diisopropylphenyl)urea (316 mg, 0.48 mmol) in methanol (20 ml) were added ammonium formate (91 mg, 1.44 mmol) and 10% palladium-carbon (100 mg), and the mixture was refluxed for 10 hours. After allowed to stand for cooling, the mixture was filtered through a cerite pad, and the filtrate was concentrated under reduced pressure. The residue was dissolved in ethyl acetate, and the mixture was washed with water, washed with a saturated aqueous sodium chloride solution, and dried over anhydrous magnesium sulfate. The residue was concentrated under reduced pressure, purified by silica gel column chromatography (1–3% methanol in chloroform), and crystallized from ether/hexane to give the title compound (85 mg, 0.15 mmol).

$^1$H-NMR δ (CD$_3$OD) 8.58 (1H, dr), 7.72 (1H, d, J=8.3 Hz), 7.42 (1H, t, J=8.3 Hz), 7.06–7.20 (5H, m), 6.95 (2H, br), 4.63 (2H, t, J=7.3 Hz), 4.10 (2H, t, J=6.3 Hz), 3.72 (2H, t, J=5.9 Hz), 2.96 (2H, sep, J=6.6 Hz), 1.99 (2H, t, J=6.3 Hz), 1.78 (2H, br), 1.47 (2H, br), 1.10 (12H, d, J=6.6 Hz), 1.02 (3H, t, J=7.3 Hz)

EXAMPLE 55

Preparation of N-[1-butyl-4-{3-(3-aminopropoxy)phenyl}-1,2-dihydro-2-oxo-1,8-naphthyridin-3-yl]-N'-(2,6-diisopropylphenyl)urea

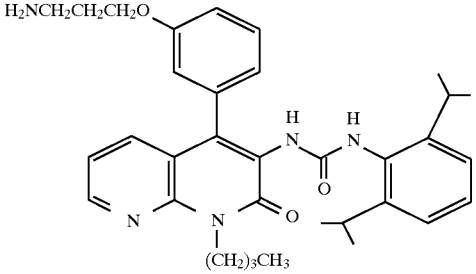

To a solution of N-[1-butyl-4-{3-(3-phthalimidopropoxy)phenyl}-1,2-dihydro-2-oxo-1,8-naphthyridin-3-yl]-N'-(2,6-diisopropylphenyl)urea (157 mg, 0.22 mmol) in ethanol (10 ml) was added hydrazine monohydrate (100 mg, 2 mmol), and the mixture was stirred at room temperature for 3 hours. The precipitates were removed by filtration, and the filtrate was concentrated under reduced pressure. To the residue was added methylene chloride, and the insoluble materials were removed by filtration, and the filtrate was concentrated under reduced pressure. The residue was purified by silica gel column chromatography (10% methanol in chloroform) to give the title compound (58 mg, 0.10 mmol).

Hydrochloride: m.p. 106°–110° C.

EXAMPLE 56

Preparation of N-[1-butyl-4-[3-{3-(1-imidazolyl)propoxy}phenyl]-1,2-dihydro-2-oxo-1,8-naphthyridin-3-yl]-N'-(2,6-diisopropylphenyl)urea

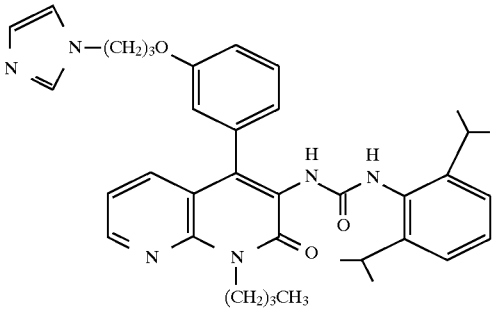

To a suspension of imidazole (97 mg, 1.43 mmol), potassium carbonate (246 mg, 1.78 mmol) and sodium iodide (35 mg) in DMF (20 ml) was added N-[1-(butyl-4-{3-(3-chloropropoxy)phenyl}-1,2-dihydro-2-oxo-1,8-naphthyridin-3-yl]-N'-(2,6-diisopropylphenyl)urea (700 mg, 1.19 mmol), and the mixture was stirred at 50°–60° C. for 10 hours. After allowed to stand for cooling, the mixture was poured into water, extracted with ethyl acetate, and the extract was washed with water, washed with a saturated aqueous sodium chloride solution, and dried over magnesium sulfate. The residue was concentrated under reduced pressure, and purified by silica gel column chromatography (5% methanol in chloroform) to give the title compound (286 mg, 0.46 mmol).

$^1$H-NMR δ (DMSO-d$_6$) 8.60 (1H, d, J=4.6 Hz), 7.76 (1H, s), 7.74 (1H, s), 7.61 (1H, d, J=7.0 Hz), 7.60 (1H, s), 7.40

(1H, dd, J=7.9 Hz, 7.9 Hz), 7.12–7.26 (3H, m), 7.02–7.05 (3H, m), 6.86–6.93 (3H, m), 4.53 (2H, br), 4.08–4.14 (2H, m), 3.93 (2H, t, J=5.6 Hz), 2.85–2.95 (2H, m), 2.20 (2H, br), 1.72 (2H, br), 1.39–1.47 (2H, m) 0.97–1.24 (15H, m)

EXAMPLE 57

Preparation of N-[1-butyl-4-[3-{3-(1,2,4-triazol-1-yl)propoxy}phenyl]- 1,2-dihydro-2-oxo-1,8-naphthyridin-3-yl]-N'-(2,6-diisopropylphenyl)urea

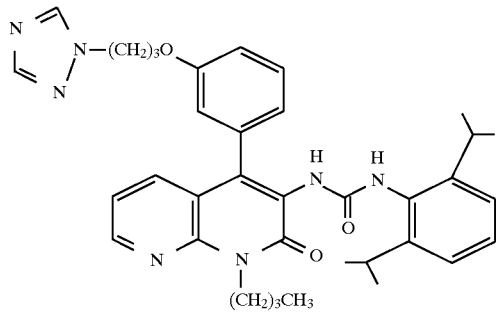

The title compound was obtained in the same manner as in Example 56 from N-[1-butyl-4-{3-(3-chloropropoxy) phenyl}-1,2-dihydro-2-oxo-1,8-naphthyridin-3-yl]-N'-(2,6-diisopropylphenyl)urea and 1,2,4-triazole.

$^1$H-NMR δ (CD$_3$OD) 8.60 (1H, d, J=3.0 Hz), 8.43 (1H, s), 7.96 (1H, s), 7.71 (1H, d, J=7.9 Hz), 7.43 (1H, dd, J=7.9 Hz, 7.9 Hz), 6.94–7.23 (7H, m), 4.64 (2H, brt, J=4.6 Hz), 4.44 (2H, brt, J=4.4 Hz), 4.03 (2H, br), 2.90–3.05 (2H, m), 2.37 (2H, m), 1.75–1.85 (2H, m), 1.45–1.56 (2H, m), 0.99–1.11 (15H, m)

EXAMPLE 58

Preparation of N-[1-(3-phthalimidopropyl)-4-(3-methoxyphenyl)-1,2-dihydro-2-oxo-1,8-naphthyridin-3-yl]-N'-(2,6-diisopropylphenyl)urea

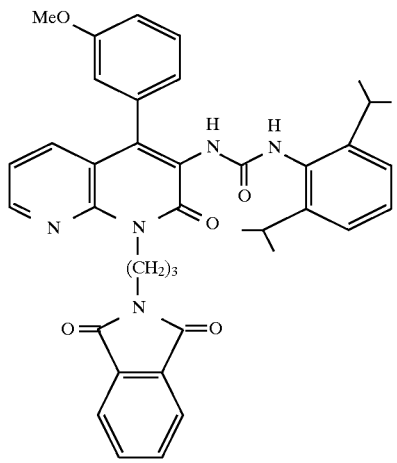

To a solution of N-[4-(3-methoxyphenyl)-1,2-dihydro-2-oxo-1,8-naphthyridin-3-yl]-N'-(2,6-diisopropylphenyl)urea (200 mg, 0.43 mmol) and N-(3-bromopropyl)phthalimide (133 mg, 0.50 mmol) in DMF (10 ml) was added potassium carbonate (114 mg, 0.83 mmol), and the mixture was stirred at 50°–60° C. for one hour. After allowed to stand for cooling, the mixture was poured into water, and the mixture was extracted with ethyl acetate. The extract was washed with water, washed with a saturated aqueous sodium chloride solution, and dried over anhydrous magnesium sulfate. The residue was concentrated under reduced pressure, purified by silica gel column chromatography (1–3% methanol in chloroform), and crystallized from hexane to give the title compound (229 mg, 0.35 mmol).

$^1$H-NMR δ (CD$_3$OD) 8.40 (1H, dd, J=4.6 Hz, 1.7 Hz), 7.78–7.96 (4H, m), 7.72 (1H, dd, J=7.9 Hz, 1.7 Hz), 7.48 (1H, dd, J=8.2 Hz, 7.9 Hz), 7.04–7.27 (5H, m), 6.93–7.02 (2H, m), 4.66–4.78 (2H, m), 3.90 (2H, t, J=6.9 Hz), 3.87 (3H, s), 3.02 (2H, sept, J=6.6 Hz), 2.17–2.35 (2H, m), 1.13 (12H, brd, J=6.6 Hz)

EXAMPLE 59

Preparation of N-[1-(3-aminopropyl)-4-(3-methoxyphenyl)-1,2-dihydro-2-oxo-1,8-naphthyridin-3-yl]-N'-(2,6-diisopropylphenyl)urea

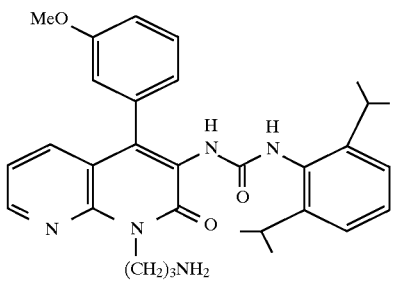

The title compound was obtained in the same manner as in Example 55 from N-[1-(phthalimidopropyl)-4-(3-methoxyphenyl)-1,2-dihydro-2-oxo-1,8-naphthyridin-3-yl}-N'-(2,6-diisopropylphenyl)urea.

$^1$H-NMR δ (CD$_3$OD) 8.40 (1H, dd, J=4.6 Hz, 1.7 Hz), 7.78–7.96 (4H, m), 7.72 (1H, dd, J=7.9 Hz, 1.7 Hz), 7.48 (1H, dd, J=8.2 Hz, 7.9 Hz), 7.04–7.27 (5H, m), 6.93–7.02 (2H, m), 4.66–4.78 (2H, m), 3.90 (2H, t, J=6.9 Hz), 3.87 (3H, s), 3.02 (2H, sept, J=6.6 Hz), 2.17–2.35 (2H, m), 1.13 (12H, brd, J=6.6 Hz)

EXAMPLE 60

Preparation of N-[1-(3-acetylaminopropyl)-4-(3-methoxyphenyl)-1,2-dihydro-2-oxo-1,8-naphthyridin-3-yl]-N'-(2,6-diisopropylphenyl)urea

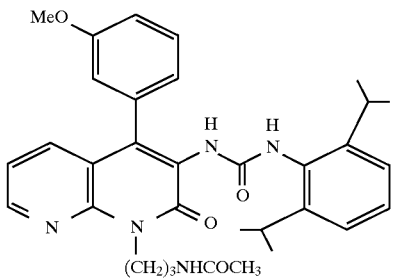

N-[1-(3-Aminopropyl)-4-(3-methoxyphenyl)-1,2-dihydro-2-oxo-1,8-naphthyridin-3-yl]-N'-(2,6-diisopropylphenyl)urea (50 mg, 0.1 mmol) was dissolved in pyridine (1 ml), and thereto was added acetic anhydride (0.5 ml). The mixture was stirred for 40 minutes, and concentrated under reduced pressure. The residue was purified by preparative thin layer chromatography to give the title compound (49 mg, 0.09 mmol).

¹H-NMR δ (CD₃OD) 8.65 (1H, dd, J=4.6H, 1.7 Hz), 7.77 (1H, dd, J=7.9H, 1.7 Hz), 7.50 (1H, dd, J=8.2 Hz, 8.2 Hz), 7.05–7.36 (5H, m), 6.95–7.03 (2H, m), 4.78 (2H, t, J=6.6 Hz), 3.88 (3H, s), 3.04 (2H, sept, J=6.6 Hz), 2.79 (2H, t, J=6.9 Hz), 2.00–2.18 (2H, m), 1.15 (12H, brd, J=6.6 Hz)

EXAMPLE 61

Preparation of N-[1-(3-benzyloxypropyl)-4-(3-methoxyphenyl)-1,2-dihydro-2-oxo-1,8-naphthyridin-3-yl]-N'-(2,6-diisopropylphenyl)urea

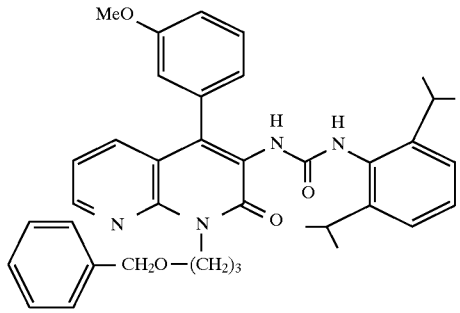

The title compound was obtained in the same manner as in Example 5 from 1-(3-benzyloxypropyl)-4-(3-methoxyphenyl)-1,2-dihydro-2-oxo-1,8-naphthyridine-3-carboxylic acid and 2,6-diisopropylaniline.

¹H-NMR δ (CD₃OD) 8.63 (1H, dd, J=4.6 Hz, 2.0 Hz), 7.75 (1H, dd, J=7.9 Hz, 2.0 Hz), 7.48 (1H, dd, J=8.3 Hz, 7.6 Hz), 7.03–7.40 (10H, m), 6.90–7.00 (2H, m), 4.82 (2H, t, J=7.3 Hz), 4.52 (2H, s), 3.87 (3H, s), 3.71 (2H, t, J=5.9 Hz), 3.03 (2H, sept, J=6.6 Hz), 2.18 (2H, m), 1.14 (12H, brd, J=6.6 Hz)

EXAMPLE 62

Preparation of N-[1-(3-hydroxypropyl)-4-(3-methoxyphenyl)-1,2-dihydro-2-oxo-1,8-naphthyridin-3-yl]-N'-(2,6-diisopropylphenyl)urea

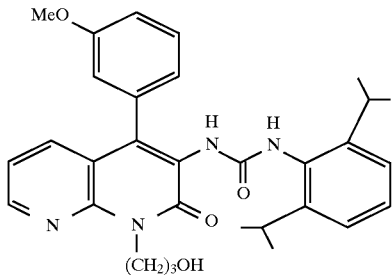

To a solution of N-[1-(3-benzyloxypropyl)-4-(3-methoxyphenyl)-1,2-dihydro-2-oxo-1,8-naphthyridin-3-yl]-N'-(2,6-diisopropylphenyl)urea (1.31 g, 2.12 mmol) in ethanol (80 ml) was added 10% palladium-carbon (150 mg), and the mixture was stirred at room temperature under hydrogen atmosphere for three hours. To the mixture was added 12N hydrochloric acid (1 ml), and the mixture was further stirred at room temperature under hydrogen atmosphere for two hours. The mixture was filtered through a cerite pad, and the filtrate was concentrated under reduced pressure. The residue was purified by silica gel column chromatography (1–3% methanol in chloroform) to give the title compound (1.12 g, 2.12 mmol).

¹H-NMR δ (CD₃OD) 8.65 (1H, dd, J=4.6 Hz, 1.7 Hz), 7.79 (1H, dd, J=7.9 Hz, 1.7 Hz), 7.49 (1H, dd, J=8.2 Hz, 8.2 Hz), 7.05–7.35 (5H, m), 6.95–7.04 (2H, m), 4.79 (2H, t, J=7.3 Hz), 3.87 (3H, s), 3.71 (2H, t, J=6.3 Hz), 3.03 (2H, sept, J=6.3 Hz), 2.10 (2H, m), 1.15 (12H, brd, J=6.3 Hz)

EXAMPLE 63

Preparation of N-[(1-tert-butoxycarbonylmethyl)-4-(3-methoxyphenyl)-1,2-dihydro-2-oxo-1,8-naphthyridin-3-yl]-N'-(2,6-diisopropylphenyl)urea

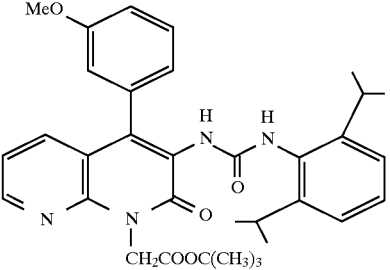

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and tert-butyl bromoacetate.

¹H-NMR a (CD₃OD) 8.59 (1H, dd, J=4.6 Hz, 1.7 Hz), 7.78 (1H, dd, J=7.9 Hz, 1.9 Hz), 7.51 (1H, dd, J=7.9 Hz, 7.9 Hz), 6.95–7.35 (7H, m), 5.32 (2H, s), 3.88 (3H, s), 2.93–3.12 (2H, m), 1.53 (9H, s), 1.14 (12H, d, J=6.6 Hz)

EXAMPLE 64

Preparation of N-[1-carboxymethyl-4-(3-methoxyphenyl)-1,2-dihydro-2-oxo-1,8-naphthyridin-3-yl]-N'-(2,6-diisopropylphenyl)urea

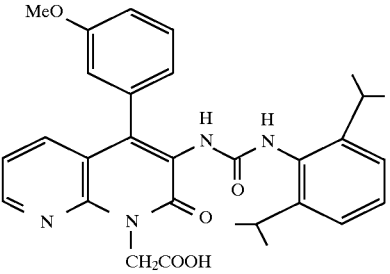

To a solution of N-[(1-tert-butoxycarbonylmethyl)-4-(3-methoxyphenyl)-1,2-dihydro-2-oxo-1,8-naphthyridin-3-yl]-N'-(2,6-diisopropylphenyl)urea (110 mg, 0.19 mmol) in methylene chloride (20 ml) was added trifluoroacetic acid (1 ml, 13 mmol), and the mixture was stirred at room temperature for 1.5 hour. The mixture was concentrated under reduced pressure, diluted with water, and basified with 4N aqueous NaOH solution, and washed with ethyl acetate. The aqueous layer was acidified with 2N aqueous HCl solution, extracted with ethyl acetate, washed with a saturated aqueous sodium chloride solution, and dried over anhydrous magnesium sulfate. The residue was concentrated under reduced pressure, and purified by preparative thin layer chromatography to give the title compound (41 mg, 0.77 mmol).

$^1$H-NMR δ (CD$_3$OD) 8.50–8.65 (1H, m), 7.78 (1H, d, J=7.6 Hz), 7.50 (1H, dd, J=7.9 Hz, 7.9 Hz), 6.96–7.38 (7H, m), 5.40 (2H, s), 3.88 (3H, s), 2.92 (2H, m), 1.14 (12H, d, J=6.3 Hz)

EXAMPLE 65

Preparation of N-[1-(2-hydroxyethyl)-4-(3-methoxyphenyl)-1,2-dihydro-2-oxo-1,8-naphthyridin-3-yl]-N'-(2,6-diisopropylphenyl)urea

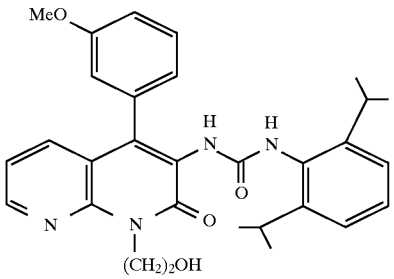

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 2-bromoethanol.

$^1$H-NMR δ (CD$_3$OD) 8.63 (1H, dd, J=4.6 Hz, 1.6 Hz), 7.76 (1H, dd, J=7.9 Hz, 1.7 Hz), 7.50 (1H, dd, J=7.9 Hz, 7.9 Hz), 6.95–7.35 (7H, m), 4.89 (2H, t, J=6.3 Hz), 3.98 (2H, t, J=6.3 Hz), 3.87 (3H, s), 2.92–3.13 (2H, m), 1.15 (12H, d, J=6.6 Hz)

EXAMPLE 66

Preparation of N-[1-(4-pyridylmethyl)-4-(3-methoxyphenyl)-1,2-dihydro-2-oxo-1,8-naphthyridin-3-yl]-N'-(2,6-diisopropylphenyl)urea

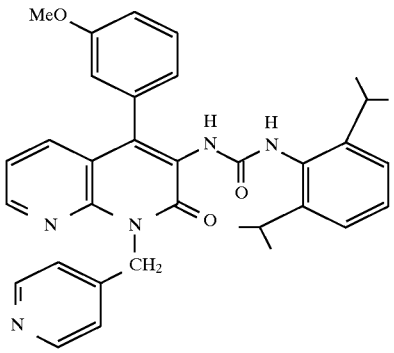

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 4-picolyl chloride hydrochloride.

$^1$H-NMR δ (CD$_3$OD) 8.57 (1H, dd, J=4.6 Hz, 1.7 Hz), 8.40–8.50 (2H, m), 7.97 (1H, dd, J=7.9 Hz, 1.7 Hz), 7.51 (1H, dd, J=8.6 Hz, 7.9 Hz), 7.38–7.48 (2H, m), 6.99–7.35 (7H, m), 5.94 (2H, s), 3.88 (3H, s), 2.93–3.13 (2H, m), 1.14 (12H, d, J=6.3 Hz)

EXAMPLE 67

Preparation of N-[1-(3-dimethylaminopropyl)-4-(3-methoxyphenyl)-1,2-dihydro-2-oxo-1,8-naphthyridin-3-yl]-N'-(2,6-diisopropylphenyl)urea

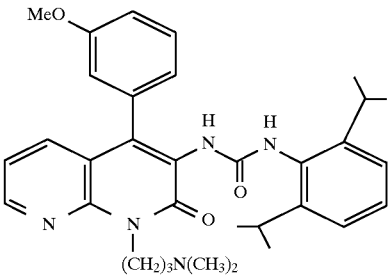

To a solution of N-[1-(3-aminopropyl)-4-(3-methoxyphenyl)-1,2-dihydro-2-oxo-1,8-naphthyridin-3-yl]-N'-(2,6-diisopropylphenyl)urea (100 mg, 0.19 mmol) in methanol (5 ml) were added successively 30% HCl in ethanol (1 ml), 37% aqueous formaldehyde solution (46 mg, 0.57 mmol) and sodium borohydride (36 mg, 0.57 mmol), and the mixture was stirred at room temperature for three hours. The mixture was poured into water, and the mixture was basified with conc. aqueous ammonia, and extracted with ethyl acetate. The extract was washed with a saturated aqueous sodium chloride solution, and dried over anhydrous magnesium sulfate. The residue was concentrated under reduced pressure, and purified by preparative thin layer chromatography to give the title compound (79 mg, 0.14 mmol).

$^1$H-NMR δ (CD$_3$OD) 8.65 (1H, dd, J=4.6 Hz, 1.7 Hz), 7.77 (1H, dd, J=7.9H, 1.7 Hz), 7.49 (1H, dd, J=7.9 Hz, 7.9 Hz), 6.95–7.35 (7H, m), 4.65–4.78 (2H, m), 3.87 (3H, s), 2.95–3.10 (2H, m), 2.52–2.68 (2H, m), 2.37 (6H, s), 2.00–2.15 (2H, m), 1.15 (12H, d, J=6.6 Hz)

EXAMPLE 68

Preparation of N-[1-(3-aminocarbonylpropyl)-4-(3-methoxyphenyl)-1,2-dihydro-2-oxo-1,8-naphthyridin-3-yl]-N'-(2,6-diisopropylphenyl)urea

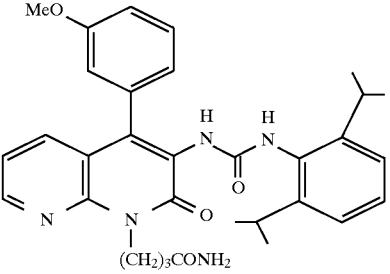

To a solution of N-[1-(3-cyanopropyl)-4-(3-methoxyphenyl)-1,2-dihydro-2-oxo-1,8-naphthyridin-3-yl]-N'-(2,6-diisopropylphenyl)urea (100 mg, 0.19 mmol) in methanol-acetone (3 ml) were added 10% aqueous sodium carbonate solution (1 ml) and 30% hydrogen peroxide (1 ml), and the mixture was stirred at room temperature for three hours. The mixture was poured into water, and extracted with ethyl acetate. The extract was washed with a saturated aqueous sodium chloride solution, and dried over anhydrous magnesium sulfate. The residue was concentrated under reduced pressure, and purified by preparative thin layer chromatography to give the title compound (96 mg, 0.17 mmol).

$^1$H-NMR δ (DMSO-d$_6$) 8.52–8.68 (1H, m), 7.68–7.85 (2H, m), 7.55–7.68 (1H, m), 6.60–7.50 (10H, m), 4.40–4.65 (2H, m), 3.77 (3H, s), 2.80–3.00 (2H, m), 2.10–2.30 (2H, m), 1.80–2.07 (2H, m), 1.03 (brs, 12H)

EXAMPLE 69

Preparation of N-[1-{3-cyanopropyl)-4-{3-(2-pyridylmethoxy)phenyl 3-1,2-dihydro-2-oxo-1,8-naphthyridin-3-yl]-N'-(2,6-diisopropylphenyl)urea

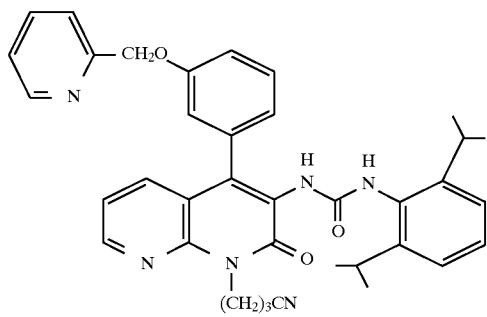

The title compound was obtained in the same manner as in Example 41 from N-[1-(3-cyanopropyl)-4-(3-hydroxyphenyl)-1,2-dihydro-2-oxo-1,8-naphthyridin-3-yl]-N'-(2,6-diisopropylphenyl)urea and 2-picolyl chloride hydrochloride.

Hydrochloride: m.p. 151°–154° C.

EXAMPLE 70

Preparation of N-[1-(2-pyridylmethyl)-4-(3-methoxyphenyl)-1,2-dihydro-2-oxo-1,8-naphthyridin-3-yl]-N'-(2,6-diisopropylphenyl)urea

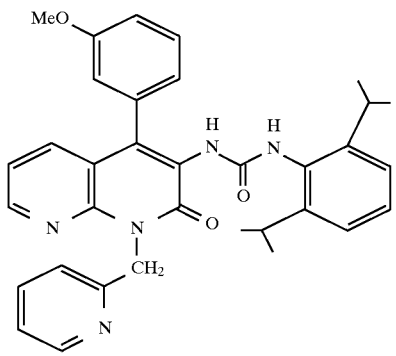

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 4-picolyl chloride hydrochloride.

$^1$H-NMR δ (CD$_3$OD) 8.50 (1H, dd J=4.6 Hz, 1.7 Hz), 8.44 (1H, m), 7.72–7.83 (2H, m), 7.52 (1H, dd, J=8.3 Hz, 7.9 Hz), 7.00–7.38 (9H, m), 6.02 (2H, s), 3.89 (3H, s), 2.90–3.13 (2H, m), 1.12 (12H, brs)

EXAMPLE 71

Preparation of N-[1-(3-piperidinopropyl)-4-(3-methoxyphenyl)-1,2-dihydro-2-oxo-1,8-naphthyridine-3-yl]-N'-(2,6-diisopropylphenyl)urea

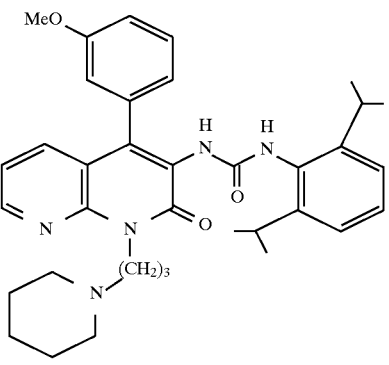

To a solution of N-(3-chloropropyl)piperidine hydrochloride (422 mg, 2.13 mmol) in DMF (30 ml) was added sodium bromide (330 mg, 3.20 mmol), and the mixture was stirred at about 120° C. for one hour, and then cooled to about 20° C. To the mixture were added successively N-[4-(3-methoxyphenyl)-1,2-dihydro-2-oxo-1,8-naphthyridin-3-yl]-N'-(2,6-diisopropylphenyl)urea (100 mg, 0.21 mmol), potassium carbonate (147 mg, 1.06 mmol) and potassium iodide (35 mg, 0.21 mmol), and the mixture was stirred at about 50° C. for three hours. To the mixture was added sodium bromide (660 mg, 6.40 mmol), and the mixture was stirred at about 80° C. for 4.5 hours, and cooled. The mixture was poured into water, and the mixture was extracted with ethyl acetate, washed with a saturated aqueous sodium chloride solution, and dried over anhydrous magnesium sulfate. The residue was concentrated under reduced pressure, and purified by preparative thin layer chromatography to give the title compound (77 mg, 0.12 mmol).

$^1$H-NMR δ (CD$_3$OD) 8.63 (1H, dd, J=4.6 Hz, 1.7 Hz), 7.76 (1H, dd, J=7.9 Hz, 1.7 Hz), 7.49 (1H, dd, J=8.3 Hz, 7.9 Hz), 6.95–7.30 (7H, m), 4.71 (2H, t, J=7.3 Hz), 3.87 (3H, s), 2.95–3.12 (2H, m), 2.40–2.80 (6H, m), 2.00–2.20 (2H, m), 1.40–1.80 (6H, m), 0.95–1.30 (12H, t, J=5.9 Hz)

EXAMPLE 72

Preparation of N-[1-(3-diethylaminopropyl)-4-(3-methoxyphenyl)-1,2-dihydro-2-oxo-1,8-naphthyridin-3-yl]-N'-(2,6-diisopropylphenyl)urea

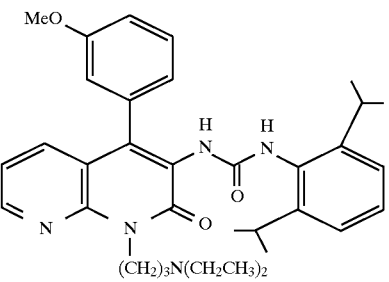

The title compound was obtained in the same manner as in Example 71 from N-[4-(3-methoxyphenyl)-1,2-dihydro-2-oxo-1,8-naphthyridin-3-yl]-N'-(2,6-diisopropylphenyl)urea and 3-diethylaminopropyl chloride hydrochloride.

$^1$H-NMR δ (CD$_3$OD) 8.64 (1H, dd, J=4.6 Hz, 1.7 Hz), 7.76 (1H, dd, J=7.9 Hz, 1.7 Hz), 7.50 (1H, dd, J=8.3 Hz, 8.3 Hz), 6.93–7.33 (7H, m), 4.71 (2H, t, J=7.3 Hz), 3.88 (3H, s), 2.95–3.10 (2H, m), 2.85–2.93 (2H, m), 2.80 (4H, q, J=7.3 Hz), 2.00–2.20 (2H, m), 1.00–1.30 (18H, m)

EXAMPLE 73

Preparation of N-[1-butyl-4-{3-(3-diethylaminopropoxy)phenyl}-1,2-dihydro-2-oxo-1,8-naphthyridin-3-yl]-N'-(2,6-diisopropylphenyl)urea

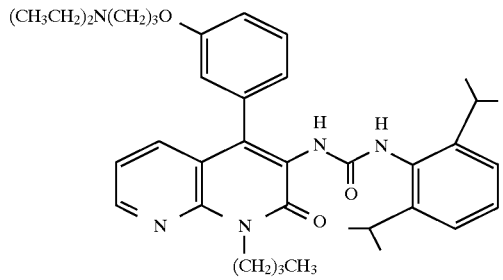

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 3-diethylaminopropyl chloride hydrochloride.

Hydrochloride: $^1$H-NMR δ (DMSO-d$_6$) 9.90 (1H, brs), 8.50–8.70 (1H, m), 7.80 (1H, brs), 7.50–7.65 (1H, m), 7.35–7.45 (1H, m), 6.72–7.30 (7H, m), 4.40–4.62 (2H, m), 3.92–4.18 (2H, m), 2.70–3.22 (8H, m), 2.00–2.21 (2H, m), 1.56–1.83 (2H, m), 1.30–1.50 (2H, m), 0.60–1.30 (21H, m)

EXAMPLE 74

Preparation of N-[1-butyl-4-[3-{2-(1-pyrrolidinyl)ethoxy}phenyl]-1,2-dihydro-2-oxo-1,8-naphthyridin-3-yl]-N'-(2,6-diisopropylphenyl)urea

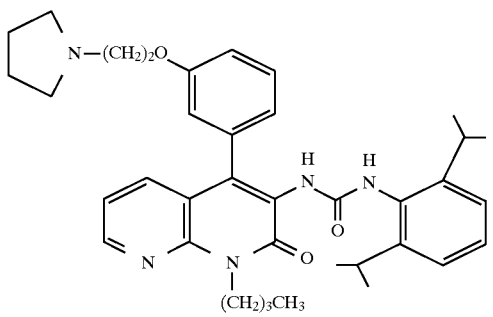

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 2-(1-pyrrolidinyl)ethyl chloride hydrochloride.

Hydrochloride: $^1$H-NMR δ (DMSO-d$_6$) 8.55–8.65 (1H, m), 7.75–7.90 (1H, m), 7.55–7.65 (1H, m), 7.35–7.48 (1H, m), 6.85–7.20 (8H, m), 4.43–4.60 (2H, m), 4.25–4.30 (2H, m), 3.40–3.65 (4H, m), 2.75–3.15 (4H, m), 1.56–2.10 (6H, m), 1.25–1.53 (2H, m), 0.80–1.20 (15H, m)

EXAMPLE 75

Preparation of N-[1-butyl-4-{3-(2-piperidinoethoxy)phenyl}-1,2-dihydro-2-oxo-1,8-naphthyridin-3-yl]-N'-(2,6-diisopropylphenyl)urea

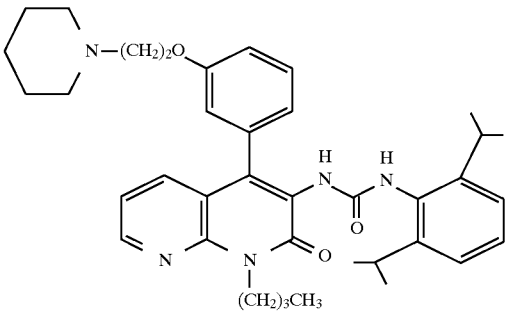

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 2-piperidinoethyl chloride hydrochloride.

Hydrochloride: m.p. 154°–156° C.

EXAMPLE 76

Preparation of N-[1-(3-tert-butoxycarbonylaminopropyl)-4-(3-methoxyphenyl)-1,2-dihydro-2-oxo-1,8-naphthyridin-3-yl]-N'-(2,6-diisopropylphenyl)urea

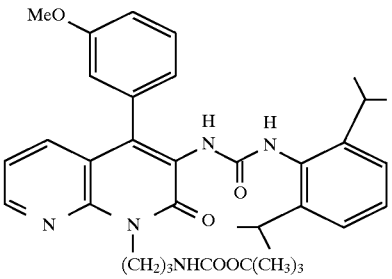

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 3-tert-butoxycarbonylaminopropyl iodide.

$^1$H-NMR δ (CD$_3$OD) 8.64 (1H, dd, J=5.0 Hz, 1.7 Hz), 7.77 (1H, dd, J=8.3 Hz, 1.7 Hz), 7.49 (1H, dd, J=8.3 Hz, 7.6 Hz), 6.95–7.35 (7H, m), 4.74 (2H, t, J=6.9 Hz), 3.87 (3H, s), 3.20 (2H, t, J=6.6 Hz), 2.95–3.10 (2H, m), 1.90–2.10 (2H, m), 1.49 (9H, s), 1.15 (12H, brd, J=6.3 Hz)

EXAMPLE 77

Preparation of N-[1-{3-(imidazol-1-yl)propyl}-4-(3-methoxyphenyl)-1,2-dihydro-2-oxo-1,8-naphthyridin-3-yl]-N'-(2,6-diisopropylphenyl)urea

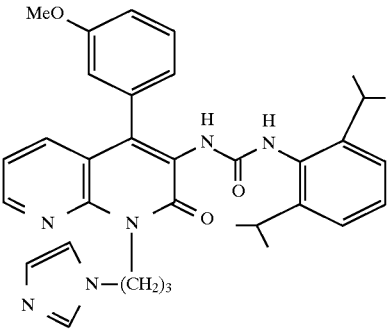

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 3-(imidazol-1-yl)propyl bromide hydrobromide.

Hydrochloride: $^1$H-NMR δ (DMSO-$d_6$) 9.20 (1H, brs), 8.57 (1H, dd, J=4.6 Hz, 1.3 Hz), 7.55–8.00 (6H, m), 7.37–7.48 (1H, m), 7.22–7.32 (1H, m), 7.11–7.18 (1H, m), 6.98–7.09 (3H, m), 6.86–6.94 (2H, m), 4.47–4.62 (2H, m), 4.20–4.40 (2H, m), 3.38 (3H, s), 2.84–2.98 (2H, m), 2.25–2.40 (2H, m), 1.02 (12H, d, J=5.9 Hz)

EXAMPLE 78

Preparation of N-[1-butyl-4-{3-(2-morpholinoethoxy)phenyl}-1,2-dihydro-2-oxo-1,8-naphthyridin-3-yl]-N'-(2,6-diisopropylphenyl)urea

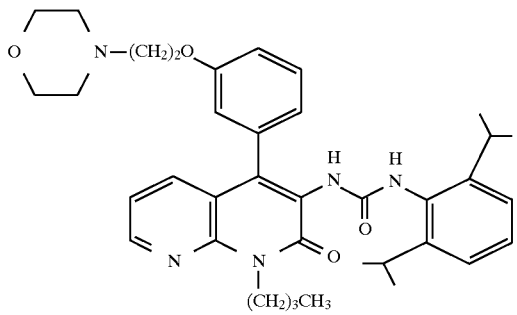

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 2-morpholinoethyl chloride hydrochloride.

$^1$H-NMR δ (CD$_3$OD) 8.64 (1H, d, J=4.6 Hz, 1.7 Hz), 7.75 (1H, d, J=7.9 Hz, 1.7 Hz), 7.48 (1H, dd, J=8.2 Hz, 7.9 Hz), 6.95–7.20 (7H, m), 4.60–4.70 (2H, m), 4.21 (2H, t, J=5.6 Hz), 3.65–3.80 (4H, m), 2.94–3.10 (2H, m), 2.85 (2H, t, J=5.6 Hz), 2.52–2.70 (4H, m), 1.70–1.93 (2H, m), 1.43–1.65 (2H, m), 1.14 (12H, d, J=6.6 Hz), 1.06 (3H, t, J=7.3 Hz)

EXAMPLE 79

Preparation of N-[1-(3-methylbutyl)-4-(3-hydroxyphenyl)-1,2-dihydro-2-oxo-1,8-naphthyridin-3-yl]-N'-(2,6-diisopropylphenyl)urea

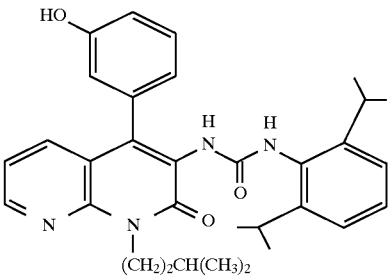

The title compound was obtained in the same manner as in Example 31 from N-[1-(3-methylbutyl)-4-(3-methoxyphenyl)-1,2-dihydro-2-oxo-1,8-naphthyridin-3-yl]-N'-(2,6-diisopropylphenyl)urea.

$^1$H-NMR δ (DMSO-$d_6$) 9.52 (1H, s), 7.71 (1H, d, J=6.3 Hz), 7.43 (1H, dd, J=8.3 Hz, 7.9 Hz), 7.71 (2H, brs), 7.63 (1H, dd, J=7.9 Hz, 1.7 Hz), 7.23–7.30 (2H, m), 7.15 (1H, t, J=7.3 Hz), 7.04 (2H, d, J=7.3 Hz), 6.85 (1H, dd, J=7.9 Hz, 1.7Hz), 6.72–6.77 (3H, m), 4.54 (2H, t, J=7.3 Hz), 2.95 (2H, sep, J=6.6 Hz), 1.59–1.74 (3H, m), 0.99–1.05 (18H, m)

EXAMPLE 80

Preparation of N-[1-(3-methylbutyl)-4-{3-(2-diethylaminoethoxy)-phenyl}-1,2-dihydro-2-oxo-1,8-naphthyridin-3-yl]-N'-(2,6-diisopropylphenyl)urea

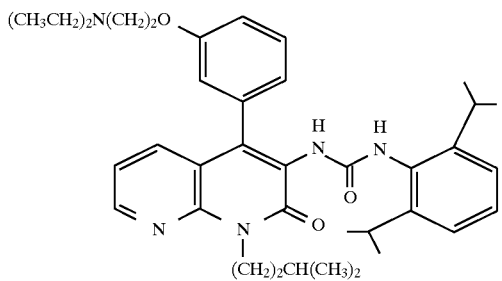

The title compound was obtained in the same manner as in Example 41 from N-[1-(3-methylbutyl)-4-(3-hydroxyphenyl)-1,2-dihydro-2-oxo-1,8-naphthyridin-3-yl]-N'-(2,6-diisopropylphenyl)urea and 2-diethylaminoethyl chloride hydrochloride.

$^1$H-NMR δ (CD$_3$OD) 8.59 (1H, brs), 7.71 (1H, d, J=6.3 Hz), 7.43 (1H, dd, J=8.3 Hz, 7.9 Hz), 7.05–7.20 (5H, m), 6.97 (2H, brs), 4.64 (2H, m), 4.13 (2H, m), 2.90–3.01 (4H, m), 2.63–2.69 (2H, m), 1.69–1.80 (3H, m), 1.03–1.11 (24H, m)

EXAMPLE 81

Preparation of N-[1-isobutyl-4-(3-methoxyphenyl)-1,2-dihydro-2-oxo-1,8-naphthyridin-3-yl]-N'-(2,6-diisopropylphenyl)urea

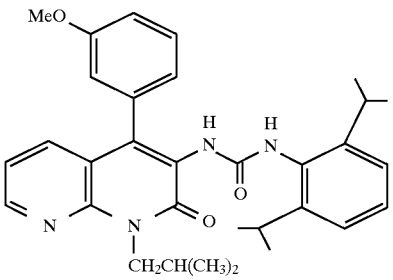

To a solution of N-[4-(3-methoxyphenyl)-1,2-dihydro-2-oxo-1,8-naphthyridin-3-yl]-N'-(2,6-diisopropylphenyl)urea (100 mg, 0.21 mmol) in DMF (5 ml) were added potassium carbonate (1.39 g, 10.1 mmol), potassium iodide (10 mg, 0.07 mmol) and 1-bromo-2-methylpropane (58 mg, 0.43 mmol), and the mixture was stirred at room temperature for five hours. The mixture was poured into water, and the mixture was extracted with ethyl acetate. The extract was washed with water, washed with a saturated aqueous sodium chloride solution, and dried over anhydrous magnesium sulfate. The resultant was concentrated under reduced pressure, and the residue was purified by silica gel column chromatography (1–3% methanol in chloroform) to give the title compound (71 mg, 0.13 mmol).

$^1$H-NMR δ (CD$_3$OD) 8.61 (1H, dd, J=4.6 Hz, 1.7 Hz), 7.76 (1H, dd, J=7.9 Hz, 1.7 Hz), 7.49 (1H, dd, J=8.3 Hz, 8.2 Hz), 6.93–7.30 (7H, m), 4.56 (2H, d, J=7.6Hz), 3.87 (3H, s), 2.90–3.10 (2H, m), 2.30–2.52 (1H, m), 1.15 (12H, d, J=6.6 Hz), 1.03 (6H, d, J=6.6 Hz)

EXAMPLE 82

Preparation of N-[1-(3-methyl-2-butenyl)-4-(3-methoxyphenyl)-1,2-dihydro-2-oxo-1,8-naphthyridin-3-yl]-N'-(2,6-diisopropylphenyl)urea

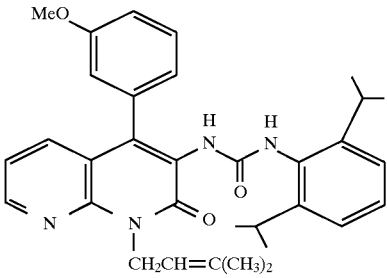

The title compound was obtained in the same manner as in Example 81 from N-[4-(3-methoxyphenyl)-1,2-dihydro-2-oxo-1,8-naphthyridin-3-yl]-N'-(2,6-diisopropylphenyl)urea and 4-bromo-2-methyl-2-butene.

$^1$H-NMR δ (CD$_3$OD) 8.63 (1H, dd, J=4.3 Hz, 1.7 Hz), 7.75 (1H, dd, J=7.9 Hz, 1.7 Hz), 7.49 (1H, dd, J=8.6 Hz, 7.9 Hz), 6.90–7.30 (7H, m), 5.36–5.50 (1H, m), 5.26–5.36 (2H, m), 3.87 (3H, s), 2.95–3.15 (2H, m), 2.01 (3H, s), 1.75 (3H, s), 1.15 (12H, d, J=6.6 Hz)

EXAMPLE 83

Preparation of N-[1-(4-methylpentyl)-4-(3-methoxyphenyl)-1,2-dihydro-2-oxo-1,8-naphthyridin-3-yl]-N'-(2,6-diisopropylphenyl)urea

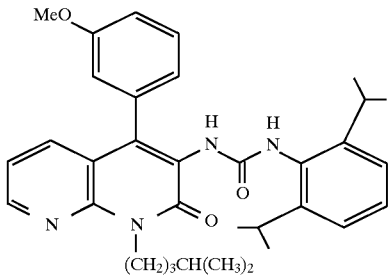

The title compound was obtained in the same manner as in Example 81 from N-[4-(3-methylphenyl)-1,2-dihydro-2-oxo-1,8-naphthyridin-3-yl]-N'-(2,6-diisopropylphenyl)urea and 1-bromo-4-methylpentane.

$^1$H-NMR δ (CD$_3$OD) 8.63 (1H, dd, J=4.6 Hz, 1.7 Hz), 7.75 (1H, dd, J=8.2 Hz, 1.9 Hz), 7.48 (1H, dd, J=8.2 Hz, 7.9 Hz), 6.90–7.30 (7H, m), 4.53–4.70 (2H, m), 3.87 (3H, s), 2.90–3.10 (2H, m), 1.76–1.95 (2H, m), 1.60–1.75 (1H, m), 1.30–1.50 (2H, m), 1.15 (12H, d, J=6.3 Hz), 0.97 (6H, d, J=6.6 Hz)

EXAMPLE 84

Preparation of N-[1-butyl-4-[3-{2-(1-piperazinyl)ethoxy}phenyl]-1,2-dihydro-2-oxo-1,8-naphthyridin-3-yl]-N'-(2,6-diisopropylphenyl)urea (a) Preparation of N-[1-butyl-4-[3-{2-(4-tert-butoxycarbonyl-1-piperazinyl)ethoxy}phenyl]-1,2-dihydro-2-oxo-1,8-naphthyridin-3-yl]-N'-(2,6-diisopropylphenyl)urea

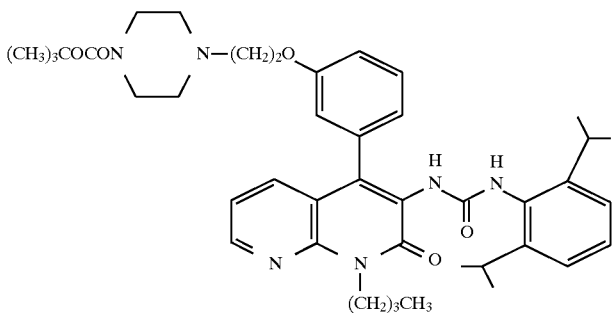

The title compound was obtained in the same manner as in Example 41 from N-[4-(3-hydroxyphenyl)-1,2-dihydro-2-oxo-1,8-naphthyridin-3-yl]-N'-(2,6-diisopropylphenyl)urea and 1-tert-butoxycarbonyl-4-(2-chloroethyl)piperazine.

$^1$H-NMR δ (CD$_3$OD) 8.63 (1H, dd, J=4.6 Hz, 1.7 Hz), 7.75 (1H, dd, J=7.9 Hz, 1.7 Hz), 7.47 (1H, dd, J=8.2 Hz, 7.9 Hz), 7.04–7.30 (5H, m), 6.93–7.04 (2H, m), 4.60–4.73 (2H, m), 4.05–4.10 (2H, m), 3.38–3.53 (4H, m), 2.92–3.10 (2H, m), 2.55–2.68 (2H, m), 2.36–2.54 (4H, m), 1.95–2.10 (2H, m), 1.70–1.90 (2H, m), 1.45–1.62 (2H, m), 1.49 (9H, s), 1.15 (12H, d, J=6.6 Hz), 1.05 (3H, t, J=7.3 Hz)

(b) Preparation of N-[1-butyl-4-[3-{2-(1-piperazinyl)ethoxy}phenyl]-1,2-dihydro-2-oxo-1,8-naphthyridin-3-yl]-N'-(2,6-diisopropylphenyl)urea

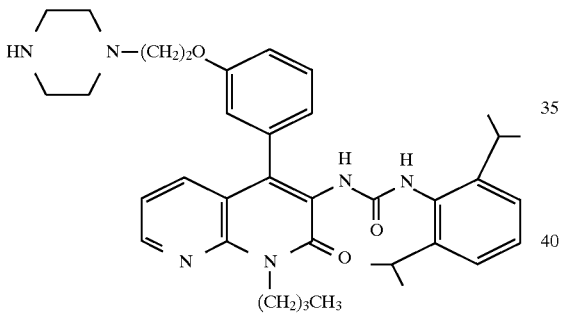

To a solution of N-[1-butyl-4-[3-{2-(4-tert-butoxycarbonyl-1-piperazinyl)-ethoxy}phenyl]-1,2-dihydro-2-oxo-1,8-naphthyridin-3-yl]-N'-(2,6-diisopropylphenyl)urea (26 mg, 0.035 mmol) in methylene chloride (5 ml) was added trifluoroacetic acid (1 ml, 13 mmol), and the mixture was stirred at room temperature for two hours. The mixture was concentrated under reduced pressure to remove the solvent, and to the residue was added 5% aqueous ammonia (50 ml), and the mixture was extracted with ethyl acetate. The extract was washed with water, washed with a saturated aqueous sodium chloride solution, and dried over anhydrous magnesium sulfate. The resultant was concentrated under reduced pressure, and the residue was purified by thin layer chromatography (20% methanol in chloroform) to give the title compound (13 mg, 0.20 mmol).

$^1$H-NMR δ (CD$_3$OD) 8.65 (1H, dd, J=4.6 Hz, 1.7 Hz), 7.76 (1H, dd, J=7.9 Hz, 1.7 Hz), 7.48 (1H, dd, J=8.3 Hz, 8.2 Hz), 7.17–7.30 (2H, m), 7.04–7.16 (3H, m), 6.95–7.02 (2H, m), 4.60–4.73 (2H, m), 4.00–4.18 (2H, m), 2.98–3.10 (2H, m), 2.85–2.97 (4H, m), 2.40–2.68 (7H, m), 1.96–2.13 (2H, m), 1.72–1.92 (2H, m), 1.46–1.64 (2H, m), 1.15 (12H, brs, J=6.6 Hz), 1.06 (3H, t, J=7.3 Hz)

EXAMPLE 85

Preparation of N-[1-butyl-4-(3-methoxyphenyl)-1,2-dihydro-2-oxo-1,8-naphthyridin-3-yl]-N'-(2,4,6-trifluorophenyl)urea

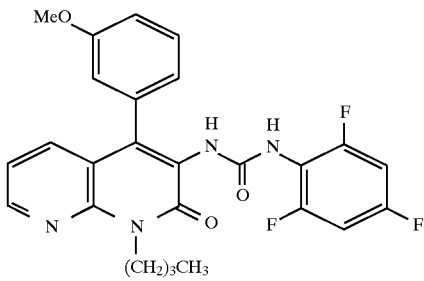

The title compound was obtained in the same manner as in Example 5 from 1-butyl-4-(3-methoxyphenyl)-1,2-dihydro-2-oxo-1,8-naphthyridine-3-carboxylic acid and 2,4,6-trifluoroaniline.

m.p. 189°–190° C.

EXAMPLE 86

Preparation of N-[1-(4-pentenyl)-4-(3-methoxyphenyl)-1,2-dihydro-2-oxo-1,8-naphthyridin-3-yl]-N'-(2,6-diisopropylphenyl)urea

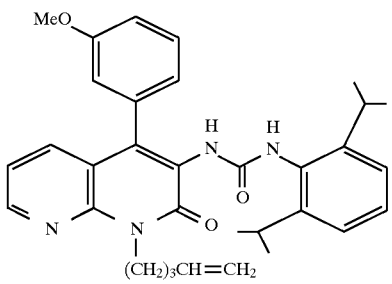

The title compound was obtained in the same manner as in Example 81 from N-[4-(3-methoxyphenyl)-1,2-dihydro-2-oxo-1,8-naphthyridin-3-yl]-N'-(2,6-diisopropylphenyl)urea and 5-bromo-1-pentene.

$^1$H-NMR δ (CD$_3$OD) 8.64 (1H, dd, J=4.6 Hz, 1.7 Hz), 7.77 (1H, dd, J=8.3 Hz, 2.0 Hz), 7.49 (1H, dd, J=8.3 Hz, 7.9 Hz), 7.05–7.30 (5H, m), 6.95–7.02 (2H, m), 5.85–6.05 (1H, m), 5.08–5.20 (1H, m), 4.96–5.09 (1H, m), 4.63–4.75 (2H, m), 3.87 (3H, s), 2.59–3.13 (2H, m), 2.16–2.37 (2H, m), 1.82–2.05 (2H, m), 1.15 (12H, brd, J=5.9 Hz),

EXAMPLE 87

Preparation of N-[1-(2-phenoxyethyl)-4-(3-methoxyphenyl)-1,2-dihydro-2-oxo-1,8-naphthyridin-3-yl]-N'-(2,6-diisopropylphenyl)urea

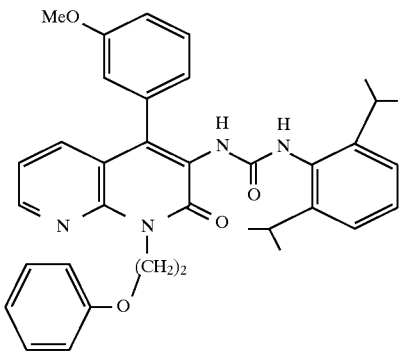

To a solution of N-[4-(3-methoxyphenyl)-1,2-dihydro-2-oxo-1,8-naphthyridin-3-yl]-N'-(2,6-diisopropylphenyl)urea (500 mg, 1.06 mmol) in DMF (10 ml) were added β-bromophenetole (256 mg, 1.28 mmol) and potassium carbonate (441 mg, 3.19 mmol), and the mixture was stirred at 40°–50° C. for 10 hours. The mixture was allowed to stand for cooling, and then poured into water. The mixture was extracted with ethyl acetate, and the extract was washed with water, washed with a saturated aqueous sodium chloride solution, and dried over anhydrous magnesium sulfate. The resultant was concentrated under reduced pressure, and the residue was purified by silica gel column chromatography (1–3% methanol in chloroform), and crystallized from ether to give the title compound (446 mg, 0.77 mmol) as a colorless crystal.

m.p. 168°–169.5° C.

EXAMPLE 88

Preparation of N-[1-butyl-4-{3-(3-methylaminopropoxy)phenyl}-1,2-dihydro-2-oxo-1,8-naphthyridin-3-yl]-N'-(2,6-diisopropylphenyl)urea (a) Preparation of N-[1-butyl-4-[3-{3-(N-tert-butoxycarbonyl-N-methyl-amino)propoxy}phenyl]-1,2-dihydro-2-oxo-1,8-naphthyridin-3-yl]-N'-(2,6-diisopropylphenyl)urea

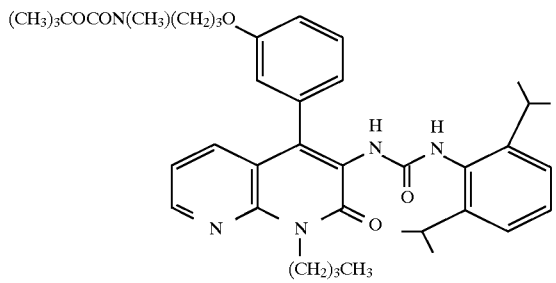

The title compound was obtained in the same manner as in Example 41 from N-[4-(3-hydroxyphenyl)-1,2-dihydro-2-oxo-1,8-naphthyridin-3-yl]-N'-(2,6-diisopropylphenyl)urea and (N-tert-butoxycarbonyl-N-methylamino)propyl iodide.

$^1$H-NMR δ (CD$_3$OD) 8.64 (1H, dd, J=4.6 Hz, 1.7 Hz), 7.70–7.80 (1H, m), 7.48 (1H, dd, J=8.3 Hz, 7.9 Hz), 7.16–7.18 (2H, m), 7.04–7.16 (3H, m), 6.97–7.03 (2H, m), 4.60–4.73 (2H, m), 3.98–4.13 (2H, m), 3.40–3.55 (2H, m), 2.95–3.11 (2H, m), 2.90 (3H, m), 1.97–2.12 (2H, m), 1.73–1.90 (2H, m), 1.45–1.60 (2H, m), 1.45 (9H, s), 1.15 (12H, d, J=6.6 Hz), 1.06 (3H, t, J=7.6 Hz)

(b) Preparation of N-[1-butyl-4-{3-(3-methylaminopropoxy)phenyl}-1,2-dihydro-2-oxo-1,8-naphthyridin-3-yl]-N'-(2,6-diisopropylphenyl)urea

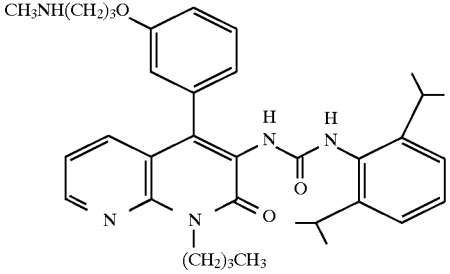

The title compound was obtained in the same manner as in Example 84-(b) from N-[1-butyl-4-[3-{3-(N-tert-butoxycarbonyl-N-methylamino)propoxy}-phenyl]-1,2-dihydro-2-oxo-1,8-naphthyridin-3-yl]-N'-(2,6-diisopropylphenyl)urea.

$^1$H-NMR δ (DMSO-d$_6$) 8.61 (1H, dd, J=4.6 Hz, 1.7 Hz), 7.76 (2H, brs), 7.55–7.65 (1H, m), 7.39 (1H, dd, J=8.3 Hz, 7.9 Hz), 7.25 (1H, dd, J=7.6 Hz, 4.6 Hz), 7.10–7.19 (1H, m), 6.96–7.08 (3H, m), 6.85–6.94 (2H, m), 4.42–4.60 (2H, m), 3.90–4.10 (2H, m), 2.80–3.00 (2H, m), 2.68 (2H, t, J=6.9 Hz), 2.32 (3H, s), 1.82–1.98 (2H, m), 1.60–1.80 (2H, m), 1.30–1.53 (2H, m), 1.02 (12H, brs), 0.96 (3H, 7.3 Hz)

EXAMPLE 89

Preparation of N-[1-butyl-4-(3-hydroxyphenyl)-1,2-dihydro-2-oxo-1,8-naphthyridin-3-yl]-N'-(2,4,6-trifluorophenyl)urea

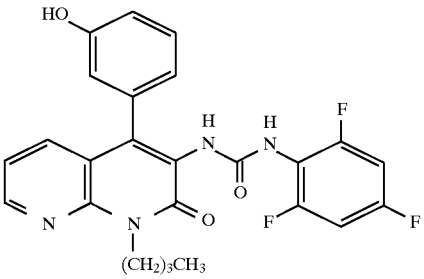

The title compound was obtained in the same manner as in Example 31 from N-[1-butyl-4-(3-methoxyphenyl)-1,2-dihydro-2-oxo-1,8-naphthyridin-3-yl]-N'-(2,4,6-trifluorophenyl)urea.

$^1$H-NMR δ (CD$_3$OD) 8.62 (1H, dd, J=4.6 Hz, 2.0 Hz), 7.74 (1H, dd, J=7.9 Hz, 2.0 Hz), 7.34 (1H, dd, J=7.9 Hz, 7.9 Hz), 7.20–7.24 (1H, m), 6.78–6.92 (5H, m), 4.62 (2H, t, J=7.6 Hz), 1.72–1.81 (2H, m), 1.42–1.52 (2H, m), 1.01 (3H, t, J=7.3 Hz)

EXAMPLE 90

Preparation of N-[1-butyl-4-{3-(2-diethylaminoethoxy)phenyl}-1,2-dihydro-2-oxo-1,8-naphthyridin-3-yl]-N'-(2,4,6-trifluorophenyl)urea

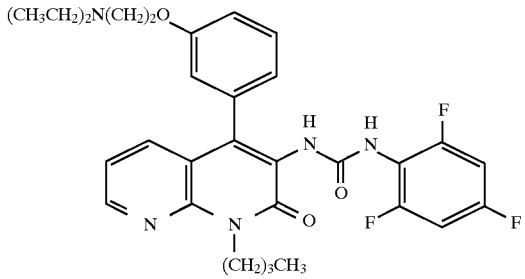

The title compound was obtained in the same manner as in Example 41 from N-[1-butyl-4-(3-hydroxyphenyl)-1,2-dihydro-2-oxo-1,8-naphthyridin-3-yl]-N'-(2,4,6-trifluorophenyl)urea and 2-diethylaminoethyl chloride hydrochloride.

m.p. 132°–135° C.

EXAMPLE 91

Preparation of N-[1-butyl-4-{3-(2-diisopropylaminoethoxy)phenyl}-1,2-dihydro-2-oxo-1,8-naphthyridin-3-yl]-N'-(2,6-diisopropylphenyl)urea

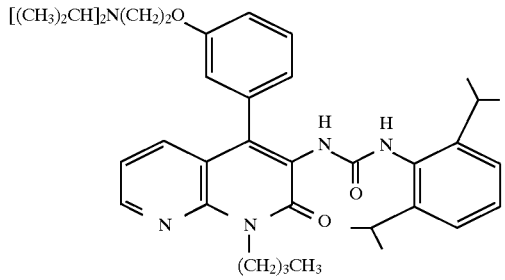

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 2-diisopropylaminoethyl chloride hydrochloride.

$^1$H-NMR δ (DMSO-$d_6$) 8.60 (1H, dd, J=4.6 Hz, 1.7 Hz), 7.68–7.80 (2H, m), 7.55–7.65 (1H, m), 7.39 (1H, dd, J=7.9 Hz, 7.9 Hz), 7.24 (1H, dd, J=8.3 Hz, 5.0 Hz), 7.09–7.19 (1H, m), 6.97–7.08 (3H, m), 6.82–6.97 (2H, m), 4.44–4.58 (2H, m), 3.75–3.98 (2H, m), 2.83–3.09 (4H, m), 2.70–2.82 (2H, m), 1.60–1.80 (2H, m), 1.30–1.52 (2H, m), 0.80–1.17 (27H, m)

EXAMPLE 92

Preparation of N-[1-(2-methyl-2-propenyl)-4-(3-methoxyphenyl)-1,2-dihydro-2-oxo-1,8-naphthyridin-3-yl]-N'-(2,6-diisopropylphenyl)urea

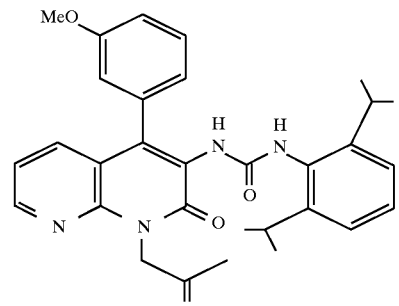

The title compound was obtained in the same manner as in Example 58 from N-[4-(3-methoxyphenyl)-1,2-dihydro-2-oxo-1,8-naphthyridin-3-yl]-N'-( 2,6-diisopropylphenyl)urea and 3-bromo-2-methylpropene.

$^1$H-NMR δ (DMSO-$d_6$) 8.56 (1H, dd, J=4.6 Hz, 1.9 Hz), 7.76 (1H, brs), 7.73 (1H, brs), 7.64 (1H, dd, J=7.9 Hz, 1.7 Hz), 7.42 (1H, dd, J=8.3 Hz, 8.3 Hz), 7.24 (1H, dd, J=7.9 Hz, 4.6 Hz), 7.10–7.20 (1H, m), 6.88–7.09 (5H, m), 5.04 (2H, brs), 4.74 (1H, brs), 4.41 (1H, brs), 3.78 (3H, s), 2.84–3.02 (2H, m), 1.83 (3H, brs), 0.80–1.20 (12H, m)

EXAMPLE 93

Preparation of N-[1-butyl-4-(3-bromophenyl)-1,2-dihydro-2-oxo-1,8-naphthyridin-3-yl]-N'-(2,6-diisopropylphenyl)urea

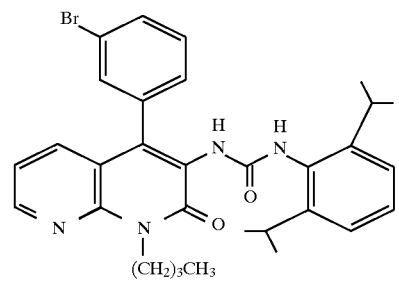

The title compound was obtained in the same manner as in Example 5 from 1-butyl-4-(3-bromophenyl)-1,2-dihydro-2-oxo-1,8-naphthyridin-3-carboxylic acid and 2,6-diisoporopylaniline.

m.p. 208°–210° C.

EXAMPLE 94

Preparation of N-[1-cyclopropylmethyl-4-(3-methoxyphenyl)-1,2-dihydro-2-oxo-1,8-naphthyridin-3-yl]-N'-(2,6-diisopropylphenyl)urea

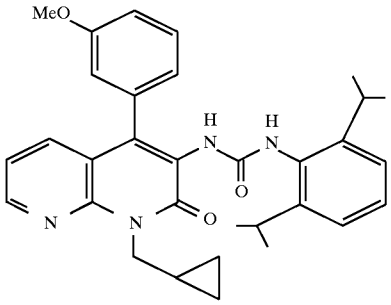

To a solution of N-[4-(3-methoxyphenyl)-1,2-dihydro-2-oxo-1,8-naphthyridin-3-yl]-N'-(2,6-diisopropylphenyl)urea (400 mg, 0.85 mmol) in DMF (10 ml) were added potassium carbonate (141 mg, 1.02 mmol), potassium iodide (28 mg, 0.17 mmol), and (bromomethyl)cyclopropane (138 mg, 1.02 mmol), and the mixture was stirred at 40°–50° C. for 10 hours. After allowed to stand for cooling, the mixture was poured into water, and the mixture was extracted with ethyl acetate. The extract was washed with water, washed with a saturated aqueous sodium chloride solution, and dried over anhydrous magnesium sulfate. The resultant was concentrated under reduced pressure, and the residue was purified by silica gel column chromatography (1% methanol in chloroform), and crystallized from ether to give the title compound (354 mg, 0.67 mmol) as a colorless crystal.
m.p. 190°–190.5° C.

EXAMPLE 95

Preparation of N-[1-butyl-4-[3-{2-(N-benzyl-N-ethylamino)ethoxy}-phenyl]-1,2-dihydro-2-oxo-1,8-naphthyridin-3-yl]-N'-(2,6-diisopropylphenyl)urea

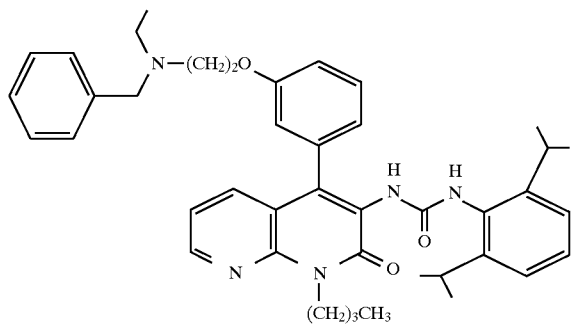

To a solution of N-[1-butyl-4-(3-hydroxyphenyl)-1,2-dihydro-2-oxo-1,8-naphthyridin-3-yl]-N'-(2,6-diisopropylphenyl)urea (200 mg, 0.39 mmol) in DMSO (8 ml) were added 2-(N-benzyl-N-ethylamino)ethyl chloride hydrochloride (182 mg, 0.78 mmol) and potassium t-butoxide (132 mg, 1.17 mmol), and the mixture was stirred at room temperature for five hours. The mixture was poured into water, and the mixture was extracted with ethyl acetate. The extract was washed with water, washed with a saturated aqueous sodium chloride solution, and dried over anhydrous magnesium sulfate. The resultant was concentrated under reduced pressure, and the residue was purified by silica gel column chromatography (hexane:ethyl acetate=1:1) to give the title compound (218 mg, 0.32 mmol).

Hydrochloride: $^1$H-NMR δ (DMSO-$d_6$) 11.51 (1H, brs), 8.62 (1H, dd, J=4.6 Hz, 1.7 Hz), 7.78–7.90 (2H, m), 7.55–7.70 (3H, m), 7.22–7.32 (1H, m), 6.90–7.20 (6H, m), 4.46–4.60 (2H, m), 4.30–4.45 (4H, m), 3.32–3.60 (2H, m), 3.05–3.25 (2H, m), 2.78–3.02 (2H, m), 1.60–1.80 (2H, m), 1.34–1.42 (2H, m), 1.27 (3H, t, J=7.3 Hz), 0.80–1.15 (15H, m)

EXAMPLE 96

Preparation of N-[1-butyl-4-{3-(2-ethylaminoethoxy)phenyl}-1,2-dihydro-2-oxo-1,8-naphthyridin-3-yl]-N'-(2,6-diisopropylphenyl)urea

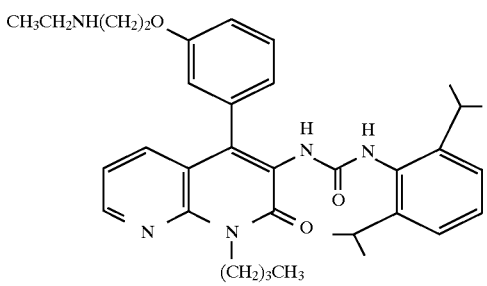

To a solution of N-[1-butyl-4-[3-{2-(N-benzyl-N-ethylamino)ethoxy)-phenyl]-1,2-dihydro-2-oxo-1,8-naphthyridin-3-yl]-N'-(2,6-diisopropylphenyl)urea (129 mg, 0.191 mmol) in ethanol (10 ml) were added 12N aqueous hydrochloric acid solution (1 ml) and 10% palladium-carbon (210 mg), and the mixture was stirred at room temperature under hydrogen atmosphere for five hours. The mixture was filtered through a cerite pad, and the filtrate was concentrated. To the concentrated resultant was added aqueous ammonia, and the mixture was extracted with ethyl acetate. The extract was washed with water, washed with a saturated aqueous sodium chloride solution, and dried over anhydrous magnesium sulfate. The reside was concentrated under reduced pressure, and the residue was purified by thin layer chromatography (10% methanol in chloroform) to give the title compound (63 mg, 0.10 mmol).

Hydrochloride: $^1$H-NMR δ (DMSO-$d_6$) 8.80 (2H, brs), 8.58–8.66 (1H, m), 7.85 (1H, brs), 7.82 (1H, brs), 7.57–7.65 (1H, m), 7.44 (1H, dd, J=8.9 Hz, 7.5 Hz), 7.22–7.31 (1H, m), 6.90–7.20 (6H, m), 4.43–4.60 (2H, m), 4.15–4.30 (2H, m), 2.75–3.10 (4H, m), 1.60–1.80 (2H, m), 1.30–1.54 (2H, m), 1.18 (3H, t, J=7.3 Hz), 0.90–1.15 (15H, m)

EXAMPLE 97

Preparation of N-[1-butyl-4-{3-(3-hydroxy-1-propynyl)phenyl}-1,2-dihydro-2-oxo-1,8-naphthyridin-3-yl]-N'-(2,6-diisopropylphenyl)urea

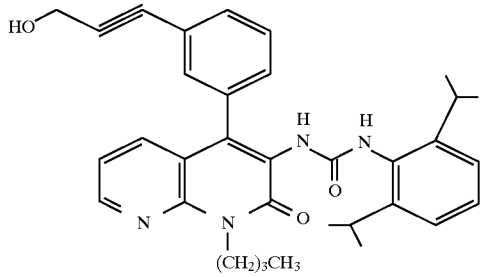

A mixture of N-[1-butyl-4-(3-bromophenyl)-1,2-dihydro-2-oxo-1,8-naphthyridin-3-yl]-N'-(2,6-diisopropylphenyl)urea (575 mg, 1 mmol), propargyl alcohol (168 mg, 3 mmol), copper (I) iodide (38 mg, 0.2 mmol), triphenylphosphine (52 mg, 0.2 mmol), bis(triphenylphosphine)palladium (II) chloride (14 mg, 0.02 mmol), triethylamine (5 ml) and acetonitrile (5 ml) was heated under reflux for five hours. After allowed to stand for cooling, the mixture was diluted with a mixture of tetrahydrofuran and ethyl acetate, and the mixture was filtered through a cerite pad. The filtrate was concentrated under reduced pressure, and the residue was dissolved in ethyl acetate. The resultant was washed with 0.1N aqueous hydrochloric acid solution, washed with water, washed with a saturated aqueous sodium chloride solution, and dried over anhydrous magnesium sulfate. The resultant was concentrated under reduced pressure, and the residue was purified by silica gel column chromatography (hexane:ethyl acetate=7:3~5:5), and further purified by thin layer chromatography (hexane:ethyl acetate=5:5) to give the title compound (16 mg, 0.03 mmol).

$^1$H-NMR δ (CD$_3$OD) 8.60 (1H, dd, J=4.6 Hz, 1.7 Hz), 7.66 (1H, dd, J=7.9 Hz, 1.7 Hz), 7.49–7.56 (3H, m), 7.37 (1H, d, J=7.3 Hz), 7.15–7.23 (2H, m), 7.07 (2H, d, J=7.3 Hz), 4.64 (2H, t, J=7.6 Hz), 4.39 (2H, s), 2.91 (2H, br), 1.74–1.85 (2H, m), 1.46–1.54 (2H, m), 1.10 (12H, d, J=6.9 Hz), 1.02 (3H, t, J=7.3 Hz)

EXAMPLE 98

Preparation of N-[1-butyl-4-{3-(3-hydroxypropyl)phenyl}-1,2-dihydro-2-oxo-1,8-naphthyridin-3-yl]-N'-(2,6-diisopropylphenyl)urea

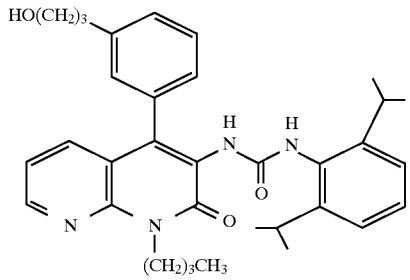

To a solution of N-[1-butyl-4-{3-(3-hydroxy-1-propynyl)phenyl}-1,2-dihydro-2-oxo-1,8-naphthyridin-3-yl]-N'-(2,6-diisopropylphenyl)urea (10 mg, 0.02 mmol) in methanol (3 ml) were added ammonium formate (5 mg, 0.08 mmol) and 10% palladium-carbon (5 mg), and the mixture was heated under reflux for five hours. After allowed to stand for cooling, the mixture was filtered through a cerite pad, and the filtrate was concentrated. The concentrated residue was diluted with ethyl acetate, and washed with water, washed with a saturated aqueous sodium chloride solution, and dried over anhydrous magnesium sulfate. The residue was concentrated under reduced pressure, and further purified by thin layer chromatography (hexane:ethyl acetate=5:5) to give the title compound (6 mg, 0.02 mmol).

m.p. 188°–189° C.

EXAMPLE 99

Preparation of N-[1-butyl-4-{3-(3-diethylamino-1-propynyl)phenyl}-1,2-dihydro-2-oxo-1,8-naphthyridin-3-yl]-N'-(2,6-diisopropylphenyl)urea

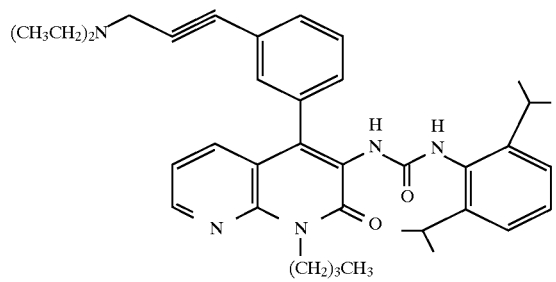

A mixture of N-[1-butyl-4-(3-bromophenyl)-1,2-dihydro-2-oxo-1,8-naphthyridin-3-yl]-N'-(2,6-diisopropylphenyl)urea (4.6 g, 8 mmol), 3-diethylamino-3-propyne (2.67 g, 24 mmol), copper (I) iodide (122 mg, 0.64 mmol), triphenylphosphine (335 mg, 1.28 mmol), 10% palladium-carbon (336 mg), triethylamine (30 ml), acetonitrile (30 ml), and DMF (30 ml) was heated under reflux for six hours. After allowed to stand for cooling, the mixture was filtered through a cerite pad. The filtrate was concentrated under reduced pressure, and the residue was dissolved in ethyl acetate (500 ml). The mixture was washed with water, washed with a 0.5N aqueous hydrochloric acid solution, washed with water, washed with a saturated aqueous sodium chloride solution, and dried over anhydrous sodium sulfate. The resultant was concentrated under reduced pressure, and the residue was purified by silica gel column chromatography (0–4% methanol in chloroform) to give the title compound (3.05g, 5.0 mmol).

$^1$H-NMR δ (CD$_3$OD) 8.60 (1H, d, J=3.3 Hz), 7.06–7.68 (9H, m), 4.64 (2H, t, J=7.6 Hz), 3.66 (2H, s), 2.85 (2H, m), 2.66 (4H, q, J=7.3 Hz), 1.74–1.82 (2H, m), 1.43–1.54 (2H, m), 1.09–1.14 (18H, m), 1.02 (3H, t, J=7.3 Hz)

EXAMPLE 100

Preparation of N-[1-butyl-4-{3-(3-diethylaminopropyl)phenyl}-1,2-dihydro-2-oxo-1,8-naphthyridin-3-yl]-N'-(2,6-diisopropylphenyl)urea

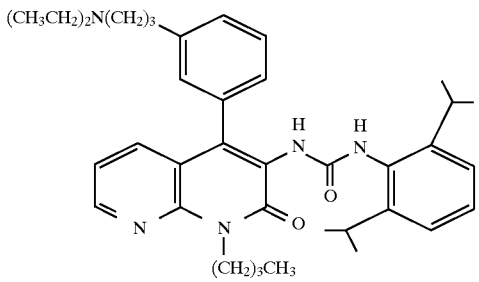

The title compound was obtained in the same manner as in Example 98 from N-[1-butyl-4-{3-(3-diethylamino-1-propynyl)phenyl}-1,2-dihydro-2-oxo-1,8-naphthyridin-3-yl]-N'-(2,6-diisopropylphenyl)urea.

$^1$H-NMR δ (CD$_3$OD) 8.60 (1H, dd, J=4.6 Hz, 1.7 Hz), 7.71 (1H, dd, J=7.9 Hz, 1.7 Hz), 7.47 (1H, dd, J=7.9 Hz, 7.6 Hz), 7.35 (1H, d, J=7.9 Hz), 7.07–7.26 (6H, m), 4.65 (2H, t, J=7.6 Hz), 3.02 (2H, br), 2.73–2.93 (8H, m), 1.89–2.02 (2H, m) 1.74–1.86 (2H, m), 1.45–1.56 (2H, m), 0.99–1.19 (21H, m)

Simultaneously, N-[1-butyl-4-(3-propylphenyl)-1,2-dihydro-2-oxo-1,8-naphthyridin-3-yl]-N'-(2,6-diisopropylphenyl)urea was also prepared.

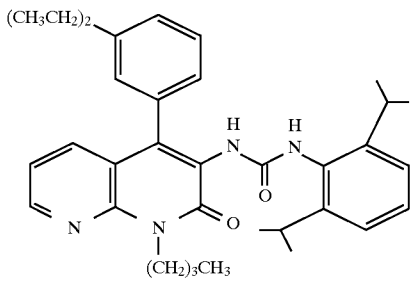

$^1$H-NMR δ (CD$_3$OD) 8.59 (1H, d, J=4.6 Hz), 7.55–7.68 (2H, m), 7.44 (1H, dd, J=8.3 Hz, 7.6 Hz), 7.32 (1H, d, J=7.6 Hz), 7.07–7.23 (5H, m), 4.63 (2H, t, J=7.6 Hz), 2.98 (2H, br), 2.68 (2H, t, J=7.6 Hz), 1.66–1.79 (4H, m), 1.45–1.54 (2H, m), 1.10 (12H, d, J=6.9 Hz), 1.02 (3H, t,=7.3 Hz), 0.98 (3H, t, J=7.3 Hz)

EXAMPLE 101

Preparation of N-[1-(N,N-diethylaminocarbonylmethyl)-4-(3-methoxyphenyl)-1,2-dihydro-2-oxo-1,8-naphthyridin-3-yl]-N'-(2,6-diisopropylphenyl)urea

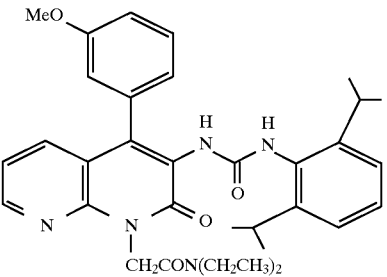

The title compound was obtained from N-[4-(3-methoxyphenyl)-1,2-dihydro-2-oxo-1,8-naphthyridin-3-yl]-N'-(2,6-diisopropylphenyl)urea and 2-chloro-N,N-diethylacetamide.

IR (KBr) 2996, 1662, 1597, 1537, 1486 cm$^{-1}$

EXAMPLE 102

Preparation of N-[1-(2-methylpropyl)-4-(3-hydroxyphenyl)-1,2-dihydro-2-oxo-1,8-naphthyridin-3-yl]-N'-(2,6-diisopropylphenyl)urea

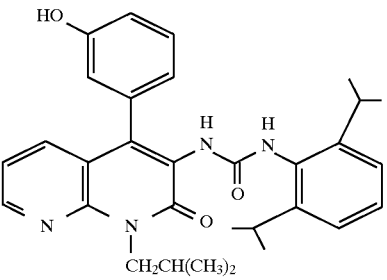

The title compound was obtained in the same manner as in Example 31 from N-[1-(2-methylpropyl)-4-(3-methoxyphenyl)-1,2-dihydro-2-oxo-1,8-naphthyridin-3-yl]-N'-(2,6-diisopropylphenyl)urea.

$^1$H-NMR δ (CD$_3$OD) 8.62 (1H, dd, J=4.6 Hz, J=1.6 Hz), 7.78 (1H, dd, J=7.9 Hz, 1.7 Hz), 7.39 (1H, dd, J=7.9 Hz, 7.6 Hz), 7.10–7.30 (4H, m), 6.80–7.00 (3H, m), 4.55 (2H, d, J=7.6 Hz), 2.95–3.15 (2H, m), 2.30–2.55 (1H, m), 1.10–1.30 (12H, m), 1.03 (6H, d, J=6.9 Hz)

EXAMPLE 103

Preparation of N-[1-(4-methylpentyl)-4-(3-hydroxyphenyl)-1,2-dihydro-2-oxo-1,8-naphthyridin-3-yl]-N'-(2,6-diisopropylphenyl)urea

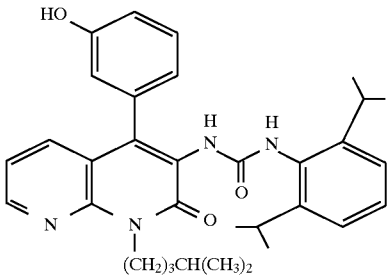

The title compound was obtained in the same manner as in Example 31 from N-[1-(4-methylpentyl)-4-(3-methoxyphenyl)-1,2-dihydro-2-oxo-1,8-naphthyridin-3-yl]-N'-(2,6-diisopropylphenyl)urea.

$^1$H-NMR δ (CD$_3$OD) 8.64 (1H, dd, J=4.6 Hz, 2.0 Hz), 7.78 (1H, dd, J=7.9 Hz, 1.7 Hz), 7.39 (1H, dd, J=8.2 Hz, 7.6 Hz), 7.18–7.30 (2H, m), 7.08–7.15 (2H, m), 6.80–7.00 (3H, m), 4.56–4.70 (2H, m), 3.00–3.15 (2H, m), 1.75–1.93 (2H, m), 1.60–1.74 (1H, m), 1.32–1.50 (2H, m), 1.05–1.30 (12H, m), 0.98 (6H, d, J=6.3 Hz)

EXAMPLE 104

Preparation of N-[1-(2-methylpropyl)-4-{3-(2-diethylaminoethoxy)phenyl}-1,2-dihydro-2-oxo-1,8-naphthyridin-3-yl]-N'-(2,6-diisopropylphenyl)urea

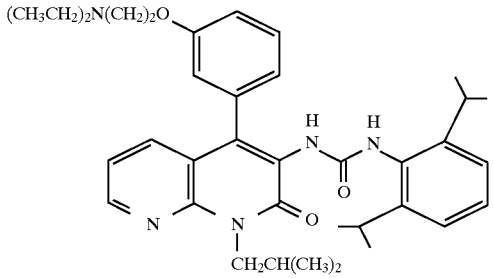

The title compound was obtained in the same manner as in Example 41 from N-[1-(2-methylpropyl)-4-(3-hydroxyphenyl)-1,2-dihydro-2-oxo-1,8-naphthyridin-3-yl]-N'-(2,6-diisopropylphenyl)urea and 2-diethylaminoethyl chloride hydrochloride.

Hydrochloride: $^1$H-NMR δ (DMSO-d$_6$) 10.41 (1H, brs), 8.60 (1H, dd, J=4.6 Hz, 1.7 Hz), 7.85 (2H, brs), 7.61 (1H, dd, J=8.2 Hz, 1.7 Hz), 7.44 (1H, dd, J=7.9 Hz, 7.9 Hz), 7.24 (1H, dd, J=7.9 Hz, 4.6 Hz), 6.90–7.20 (6H, m), 4.26–4.50 (4H, m), 3.40–3.53 (2H, m), 3.05–3.30 (4H, m), 2.80–3.00 (2H, m), 2.20–2.40 (1H, m), 1.21 (6H, t, J=7.3 Hz), 0.91–1.10 (12H, m), 0.94 (6H, d, J=6.6 Hz)

EXAMPLE 105

Preparation of N-[1-(2-methylpropyl)-4-{3-(4-pyridylmethoxy)phenyl}-1,2-dihydro-2-oxo-1,8-naphthyridin-3-yl]-N'-(2,6-diisopropylphenyl)urea

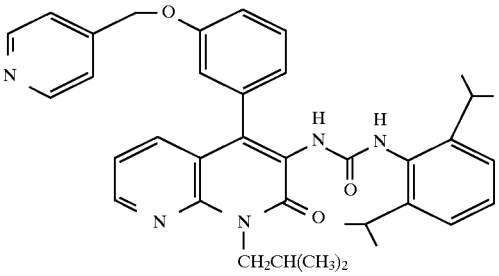

The title compound was obtained in the same manner as in Example 41 from N-[1-(2-methylpropyl)-4-(3-hydroxyphenyl)-1,2-dihydro-2-oxo-1,8-naphthyridin-3-yl]-N'-(2,6-diisopropylphenyl)urea and 4-picolyl chloride hydrochloride.

Hydrochloride: $^1$H-NMR δ (DMSO-d$_6$) 8.80 (2H, brd, J=6.6 Hz), 8.60 (1H, dd, J=4.6 Hz, 1.7 Hz), 7.94 (2H, brd, J=6.6 Hz), 7.85 (1H, brs), 7.82 (1H, brs), 7.57 (1H, dd, J=7.9 Hz, 1.3 Hz), 7.46 (1H, dd, J=7.9 Hz, J=7.9 Hz), 7.21 (1H, dd, J=7.9 Hz, 4.6 Hz), 7.10–7.20 (2H, m), 6.95–7.08 (3H, m), 5.44 (2H, s), 4.41 (2H, d, J=6.9 Hz), 2.90 (2H, brs), 2.20–2.40 (1H, m), 1.00 (12H, m), 0.94 (6H, d, J=6.6 Hz)

EXAMPLE 106

Preparation of N-[1-(4-methylpentyl)-4-{3-(4-pyridylmethoxy)phenyl}-1,2-dihydro-2-oxo-1,8-naphthyridin-3-yl]-N'-(2,6-diisopropylphenyl)urea

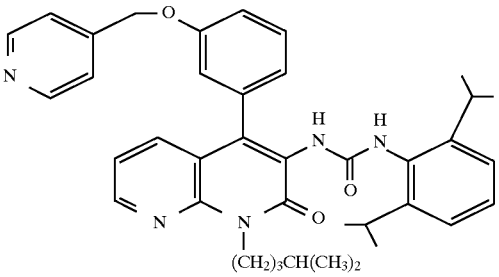

The title compound was obtained in the same manner as in Example 41 from N-[1-(4-methylpentyl)-4-(3-hydroxyphenyl)-1,2-dihydro-2-oxo-1,8-naphthyridin-3-yl]-N'-(2,6-diisopropylphenyl)urea and 4-picolyl chloride hydrochloride.

Hydrochloride: $^1$H-NMR δ (DMSO-d$_6$) 8.79 (2H, brd, J=6.3 Hz), 8.61 (1H, dd, J=4.6 Hz, 1.7 Hz), 7.93 (2H, brd, J=6.3 Hz), 7.85 (1H, brs), 7.82 (1H, brs), 7.57 (1H, dd, J=7.9 Hz, 1.9 Hz), 7.46 (1H, dd, J=7.9 Hz, 7.9 Hz), 7.22 (1H, dd, J=7.9 Hz, 4.6 Hz), 7.10–7.20 (2H, m), 6.95–7.08 (4H, m), 5.43 (2H, s), 4.40–4.60 (2H, m), 2.8–3.00 (2H, m), 1.50–1.85 (3H, m), 1.20–1.40 (2H, m), 1.00 (12H, brs), 0.90 (6H, d, J=6.6 Hz)

EXAMPLE 107

Preparation of N-[1-(3-methylbutyl)-4-{3-(4-pyridylmethoxy)phenyl}-1,2-dihydro-2-oxo-1,8-naphthyridin-3-yl]-N'-(2,6-diisopropylphenyl)urea

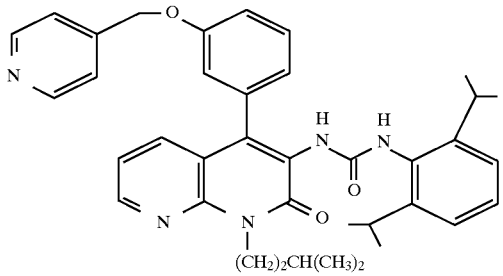

The title compound was obtained in the same manner as in Example 41 from N-[1-(3-methylbutyl)-4-(3-hydroxyphenyl)-1,2-dihydro-2-oxo-1,8-naphthyridin-3-yl]-N'-(2,6-diisopropylphenyl)urea and 4-picolyl chloride hydrochloride.

$^1$H-NMR δ (CD$_3$OD) 8.59 (1H, d, J=2.6 Hz), 8.50 (2H, d, J=6.3 Hz), 7.60 (1H, d, J=6.6 Hz), 7.51 (2H, d, J=6.3 Hz), 7.46 (1H, d, J=7.9 Hz), 6.99–7.17 (7H, m), 5.22 (2H, s), 4.66 (2H, t, J=7.6 Hz), 2.95 (2H, br), 1.61–1.82 (3H, m), 1.04–1.12 (18H, m)

EXAMPLE 108

Preparation of N-[1-propyl-4-(3-methoxyphenyl)-1,2-dihydro-2-oxo-1,8-naphthyridin-3-yl]-N'-(2,6-diisopropylphenyl)urea

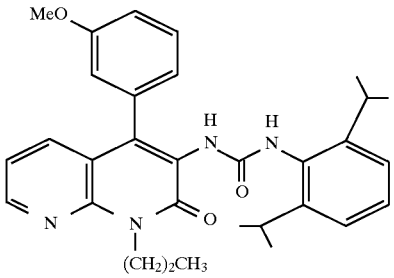

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 1-iodopropane.

m.p. 198.5°–200° C.

EXAMPLE 109

Preparation of N-[1-hexyl-4-(3-methoxyphenyl)-1,2-dihydro-2-oxo-1,8-naphthyridin-3-yl]-N'-(2,6-diisopropylphenyl)urea

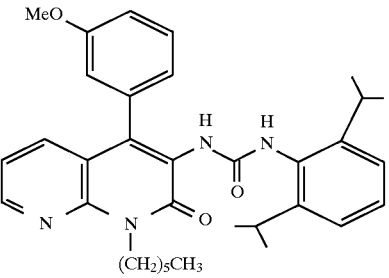

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 1-bromohexane.

m.p. 163.5°–165° C.

EXAMPLE 110

Preparation of N-[1-(3-phenylpropyl)-4-(3-methoxyphenyl)-1,2-dihydro-2-oxo-1,8-naphthyridin-3-yl]-N'-(2,6-diisopropylphenyl)urea

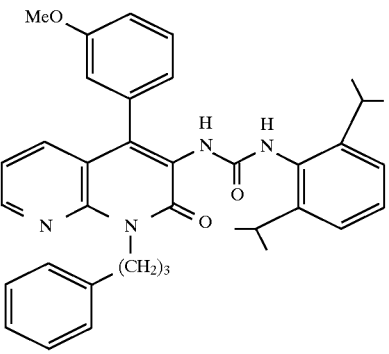

The title compound was obtained in the same manner as in Example 94 from N-[4-(3-methoxyphenyl)-1,2-dihydro-2-oxo-1,8-naphthyridin-3-yl]-N'-(2,6-diisopropylphenyl)urea and 1-bromo-3-phenylpropane.

m.p. 166°–167° C.

EXAMPLE 111

Preparation of N-[1-ethyl-4-(3-methoxyphenyl)-1,2-dihydro-2-oxo-1,8-naphthyridin-3-yl]-N'-(2,6-diisopropylphenyl)urea

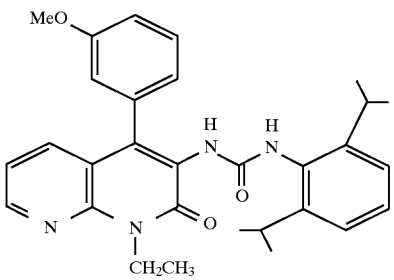

The title compound was obtained in the same manner as in Example 58 from N-[4-(3-methoxyphenyl)-1,2-dihydro-2-oxo-1,8-naphthyridin-3-yl]-N'-(2,6-diisopropylphenyl)urea and 1-iodoethane.

m.p. 194°–195° C.

EXAMPLE 112

Preparation of N-[1-(2-phenylethyl)-4-(3-methoxyphenyl)-1,2-dihydro-2-oxo-1,8-naphthyridin-3-yl]-N'-(2,6-diisopropylphenyl)urea

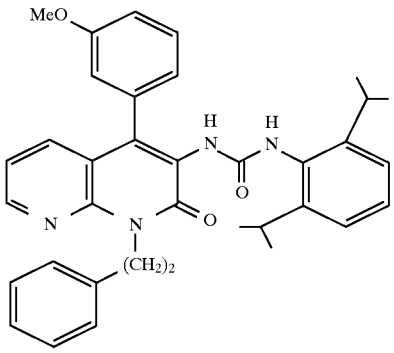

The title compound was obtained in the same manner as in Example 94 from N-[4-(3-methoxyphenyl)-1,2-dihydro-2-oxo-1,8-naphthyridin-3-yl]-N'-(2,6-diisopropylphenyl)urea and 1-bromo-3-phenylethane.

m.p. 149°–150° C.

EXAMPLE 113

Preparation of N-[1-butyl-4-{3-(3-pyridylmethoxy)phenyl}-1,2-dihydro-2-oxo-1,8-naphthyridin-3-yl]-N'-(2,6-diisopropylphenyl)urea

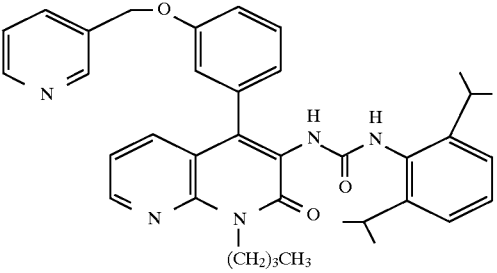

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 3-picolyl chloride hydrochloride.

$^1$H-NMR δ (CD$_3$OD) 8.63 (1H, brs), 8.59 (1H, d, J=4.6 Hz), 8.50 (1H, d, J=4.6 Hz), 7.42–7.50 (2H, m), 6.99–7.20 (7H, m), 5.19 (2H, s), 4.64 (2H, t, J=7.6 Hz), 2.97 (2H, br), 1.70–1.83 (2H, m), 1.42–1.60 (2H, m), 1.09 (12H, d, J=6.6 Hz), 1.02 (3H, t, J=7.3 Hz)

EXAMPLE 114

Preparation of N-[1-cyclohexylmethyl-4-(3-methoxyphenyl)-1,2-dihydro-2-oxo-1,8-naphthyridin-3-yl]-N'-(2,6-diisopropylphenyl)urea

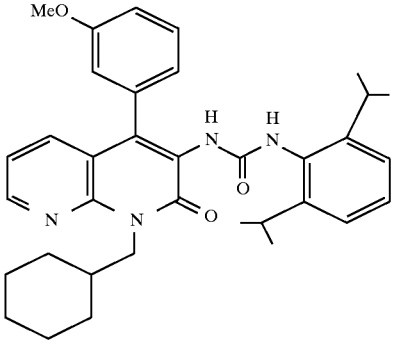

The title compound was obtained in the same manner as in Example 94 from N-[4-(3-methoxyphenyl)-1,2-dihydro-2-oxo-1,8-naphthyridin-3-yl]-N'-(2,6-diisopropylphenyl)urea and bromomethylcyclohexane.

m.p. 209°–210° C.

EXAMPLE 115

Preparation of N-[1-(4-methylpentyl)-4-{3-(2-diethylaminoethoxy)-phenyl}-1,2-dihydro-2-oxo-1,8-naphthyridin-3-yl]-N'-(2,6-diisopropylphenyl)urea

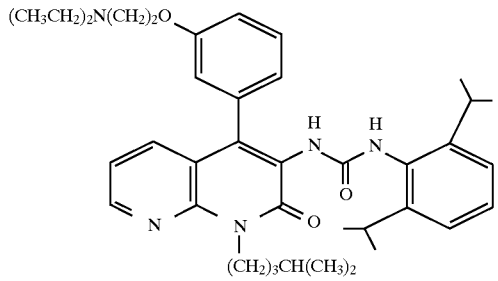

The title compound was obtained in the same manner as in Example 41 from N-[1-(4-methylpentyl)-4-(3-hydroxyphenyl)-1,2-dihydro-2-oxo-1,8-naphthyridin-3-yl]-N'-(2,6-diisopropylphenyl)urea and 2-diethylaminoethyl chloride hydrochloride.

Hydrochloride: $^1$H-NMR δ (DMSO-$d_6$) 10.64 (1H, brs), 8.55–8.68 (1H, m), 7.79–8.02 (2H, m), 7.55–7.68 (1H, m), 7.44 (1H, dd, J=8.3 Hz, 7.9 Hz), 7.25 (1H, dd, J=7.9 Hz, 4.6 Hz), 6.86–7.20 (6H, m), 4.30–4.60 (4H, m), 3.38–3.61 (2H, m), 3.02–3.27 (6H, m), 2.80–3.00 (2H, m), 1.50–1.85 (3H, m), 1.35–1.40 (2H, m), 1.21 (6H, t, J=6.9 Hz), 1.02 (12H, brs), 0.89 (6H, d, J=6.6 Hz)

EXAMPLE 116

Preparation of N-[1-(2-propenyl)-4-(3-methoxyphenyl)-1,2-dihydro-2-oxo-1,8-naphthyridin-3-yl]-N'-(2,6-diisopropylphenyl)urea

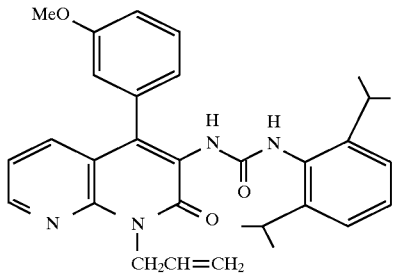

The title compound was obtained in the same manner as in Example 81 from N-[4-(3-methoxyphenyl)-1,2-dihydro-2-oxo-1,8-naphthyridin-3-yl]-N'-(2,6-diisopropylphenyl)urea and allyl bromide.

$^1$H-NMR δ (CD$_3$OD) 8.52–8.68 (1H, m), 7.70–7.82 (1H, m), 7.49 (1H, dd, J=8.3 Hz, 7.9 Hz), 6.95–7.30 (7H, m), 5.95–6.20 (1H, m), 5.10–5.40 (4H, m), 3.87 (3H, s), 2.90–3.15 (2H, m), 1.15 (12H, d, J=6.6 Hz)

EXAMPLE 117

Preparation of N-[1-(3-butenyl)-4-(3-methoxyphenyl)-1,2-dihydro-2-oxo-1,8-naphthyridin-3-yl]-N'-(2,6-diisopropylphenyl)urea

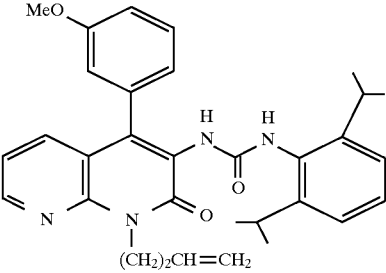

The title compound was obtained in the same manner as in Example 81 from N-[4-(3-methoxyphenyl)-1,2-dihydro-2-oxo-1,8-naphthyridin-3-yl]-N'-(2,6-diisopropylphenyl)urea and 4-bromo-1-butene.

$^1$H-NMR δ (CD$_3$OD) 8.63 (1H, dd, J=4.6 Hz, 1.3 Hz), 7.76 (1H, dd, J=7.9 Hz, 1.7 Hz), 7.48 (1H, dd, J=8.2 Hz, 7.9 Hz), 6.94–7.30 (7H, m), 5.88–6.10 (1H, m), 5.00–5.21 (2H, m), 4.66–4.80 (2H, m), 3.87 (3H, s), 2.90–3.13 (2H, m), 2.50–2.70 (2H, m), 1.15 (12H, d, J=6.3 Hz)

EXAMPLE 118

Preparation of N-[1-butyl-4-[3-{(3,5-dimethyl-4-methoxypyridin-2-yl)methoxy}phenyl]-1,2-dihydro-2-oxo-1,8-naphthyridin-3-yl]-N'-(2,6-diisopropylphenyl)urea

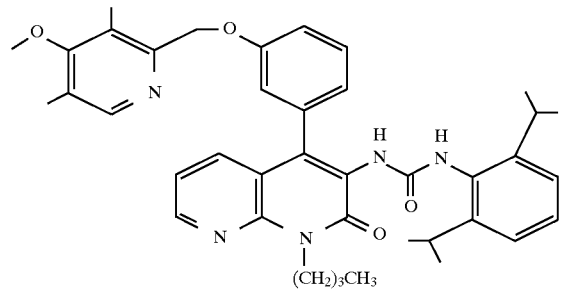

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 2-chloromethyl-3,5-dimethyl-4-methoxypyridine.

Hydrochloride: $^1$H-NMR δ (DMSO-$d_6$) 8.60 (1H, d, J=4.6 Hz), 8.53 (1H, s), 7.87 (1H, s), 7.81 (1H, s), 7.60 (1H, d, J=6.6 Hz), 7.45 (1H, dd, J=7.9 Hz, 7.9 Hz), 7.00–7.25 (7H, m), 5.38 (2H, s), 4.54 (2H, brs), 3.97 (3H, s), 2.90 (2H, br), 2.37 (3H, s), 2.30 (3H, s), 1.72 (2H, m), 1.43 (2H, m), 0.95–1.01 (15H, m)

EXAMPLE 119

Preparation of N-[1-decyl-4-(3-methoxyphenyl)-1,2-dihydro-2-oxo-1,8-naphthyridin-3-yl]-N'-(2,6-diisopropylphenyl)urea

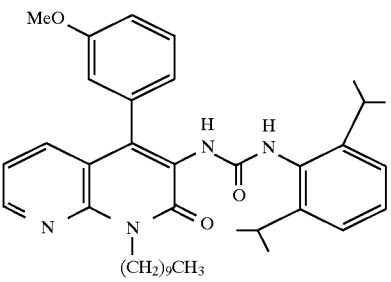

The title compound was obtained in the same manner as in Example 94 from N-[4-(3-methoxyphenyl)-1,2-dihydro-2-oxo-1,8-naphthyridin-3-yl]-N'-(2,6-diisopropylphenyl)urea and 1-bromodecane.

m.p. 119°–122° C.

EXAMPLE 120

Preparation of N-[1-butyl-4-[3-{3-(3-pyridyl)propoxy}phenyl]-1,2-dihydro-2-oxo-1,8-naphthyridin-3-yl]-N'-(2,6-diisopropylphenyl)urea

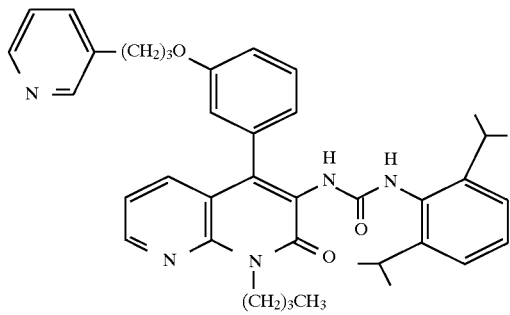

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 1-iodo-3-(3-pyridyl)propane.

$^1$H-NMR δ (CD$_3$OD) 8.60 (1H, d, J=4.3 Hz), 8.41 (1H, s), 8.34 (1H, d, J=2.3 Hz), 7.70–7.73 (2H, m), 7.43 (1H, dd, J=8.3 Hz, 7.6 Hz), 7.32 (1H, dd, J=8.3 Hz, 5.0 Hz), 6.94–7.23 (7H, m), 4.64 (2H, t, J=7.6 Hz), 4.08 (2H, m), 2.83–2.99 (4H, m), 2.14 (2H, m), 1.79 (2H, m), 1.54 (2H, m), 1.10 (12H, d, J=6.9 Hz), 1.02 (3H, t, J=7.3 Hz)

EXAMPLE 121

Preparation of N-[1-butyl-4-(3-propoxyphenyl)-1,2-dihydro-2-oxo-1,8-naphthyridin-3-yl]-N'-(2,6-diisopropylphenyl)urea

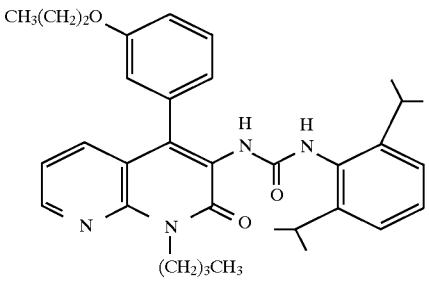

To a suspension of N-{1-butyl-4-(3-hydroxyphenyl)-1,2-dihydro-2-oxo-1,8-naphthyridin-3-yl }-N'-(2,6-diisopropylphenyl)urea (300 mg, 0.58 mmol), potassium carbonate (96 mg, 0.7 mmol) and potassium iodide (19 mg) in DMF (5 ml) was added 1-iodopropane (99 mg, 0.58 mmol) at room temperature, and the mixture was stirred at 40°–50° C. for five hours. After allowed to stand for cooling, the mixture was poured into water, and the mixture was extracted with ethyl acetate. The extracted was washed with water, washed with a saturated aqueous sodium chloride solution, and dried over anhydrous magnesium sulfate. The resultant was concentrated under reduced pressure, and the residue was purified by silica gel column chromatography (20% ethyl acetate in hexane), and crystallized from ether/hexane to give the title compound (253 mg, 0.48 mmol).

m.p. 154°–155.5° C.

EXAMPLE 122

Preparation of N-[1-butyl-4-(3-hexyloxyphenyl)-1,2-dihydro-2-oxo-1,8-naphthyridin-3-yl]-N'-(2,6-diisopropylphenyl)urea

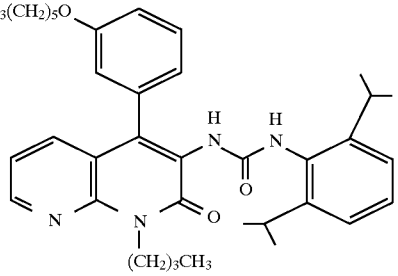

The title compound was obtained in the same manner as in Example 121 from N-[1-butyl-4-(3-hydroxyphenyl)-1,2-dihydro-2-oxo-1,8-naphthyridin-3-yl]-N'-(2,6-diisopropylphenyl)urea and 1-iodohexane.

m.p. 115°–117° C.

EXAMPLE 123

Preparation of N-[1-butyl-4-(3-benzyloxyphenyl)-1,2-dihydro-2-oxo-1,8-naphthyridin-3-yl]-N'-(2,6-diisopropylphenyl)urea

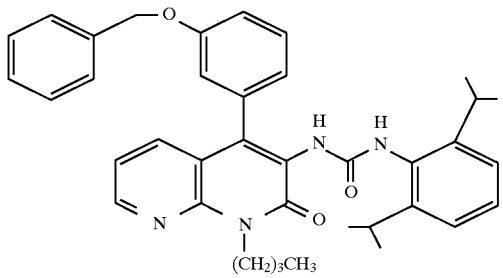

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and benzyl bromide.

m.p. 178°–179° C.

EXAMPLE 124

Preparation of N-[1-butyl-4-(3-cyclohexylmethoxyphenyl)-1,2-dihydro-2-oxo-1,8-naphthyridin-3-yl]-N'-(2,6-diisopropylphenyl)urea

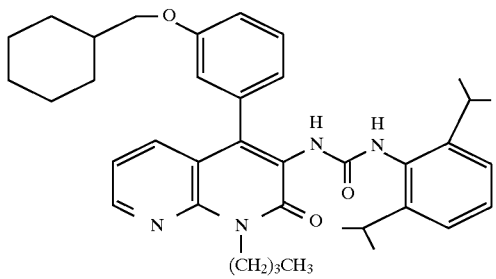

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and bromomethylcyclohexane.

m.p. 102°–106° C.

EXAMPLE 125

Preparation of N-[1-(4-pentenyl)-4-(3-hydroxyphenyl)-1,2-dihydro-2-oxo-1,8-naphthyridin-3-yl]-N'-(2,6-diisopropylphenyl)urea

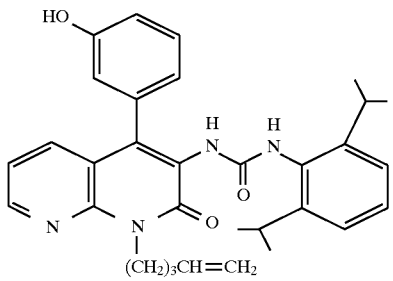

The title compound was obtained in the same manner as in Example 31 from N-[1-(4-pentenyl)-4-(3-methoxyphenyl-1,2-dihydro-2-oxo-1,8-naphthyridin-3-yl]-N'-(2,6-diisopropylphenyl)urea.

$^1$H-NMR δ (DMSO-$d_6$) 9.52 (1H, s), 8.61 (1H, dd, J=4.3 Hz, 1.3 Hz), 7.71 (1H, s), 7.70 (1H, s), 7.63 (1H, dd, J=7.9 Hz, 1.3 Hz), 7.20–7.35 (3H, m), 7.10–7.20 (1H, m), 7.00–7.08 (2H, m), 6.80–6.90 (1H, m), 6.67–6.79 (2H, m), 5.80–6.00 (1H, m), 4.90–5.20 (2H, m), 4.39–4.61 (2H, m), 2.85–3.06 (2H, m), 2.05–2.28 (2H, m), 1.72–1.93 (2H, m), 1.3 (12H, d, J=6.3 Hz)

EXAMPLE 126

Preparation of N-[1-(4-pentenyl)-4-{3-(4-pyridylmethoxy)phenyl}-1,2-dihydro-2-oxo-1,8-naphthyridin-3-yl]-N'-(2,6-diisopropylphenyl)urea

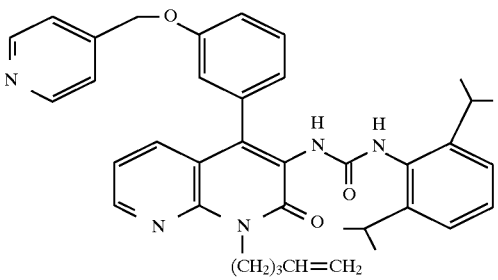

The title compound was obtained in the same manner as in Example 41 from N-[1-(4-pentenyl)-4-(3-hydroxyphenyl)-1,2-dihydro-2-oxo-1,8-naphthyridin-3-yl]-N'-(2,6-diisopropylphenyl)urea and 4-picolyl chloride hydrochloride.

Hydrochloride: $^1$H-NMR δ (DMSO-$d_6$) 8.07–8.80 (2H, m), 8.62 (1H, dd, J=4.3 Hz, 1.7 Hz), 7.73–7.89 (4H, m), 7.52–7.62 (1H, m), 7.46 (1H, dd, J=8.6 Hz, 7.9 Hz), 7.22 (1H, dd, J=7.9 Hz, 4.6 Hz), 7.11–7.20 (2H, m), 6.95–7.09 (4H, m), 5.78–6.00 (1H, m), 5.38 (2H, s), 4.95–5.19 (2H, m), 4.45–4.61 (2H, m), 2.08–3.00 (2H, m), 2.10–2.28 (2H, m), 1.73–1.92 (2H, m), 0.85–1.17 (12H, m)

EXAMPLE 127

Preparation of N-[1-(4-methylpentyl)-4-[3-{2-(N-benzyl-N-ethylamino)-ethoxy}phenyl]-1,2-dihydro-2-oxo-1,8-naphthyridin-3-yl]-N'-(2,6-diisopropylphenyl)urea

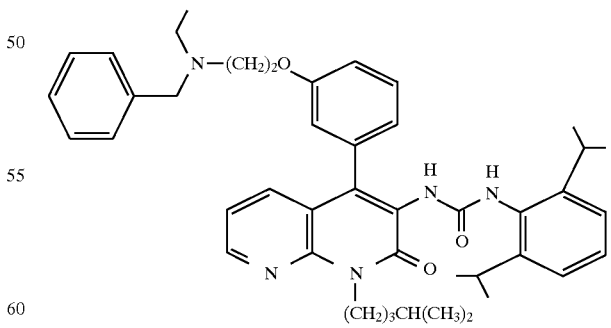

The title compound was obtained in the same manner as in Example 41 from N-[1-(4-methylpentyl)-4-(3-hydroxyphenyl)-1,2-dihydro-2-oxo-1,8-naphthyridin-3-yl]-N'-(2,6-diisopropylphenyl)urea and 2-(N-benzyl-N-ethyl) ethyl chloride hydrochloride.

Hydrochloride: ¹H-NMR δ (DMSO-d₆) 10.81 (1H, brs), 8.62 (1H, dd, J=4.6 Hz, 1.3 Hz), 7.79–7.91 (2H, m), 7.55–7.74 (3H, m), 7.35–7.51 (5H, m), 7.25 (1H, dd, J=7.6 Hz, 4.6 Hz), 6.90–7.20 (5H, m), 4.29–4.60 (6H, m), 3.33–3.55 (2H, m), 3.02–3.27 (2H, m), 2.80–3.00 (2H, m), 1.53–1.83 (3H, m), 1.20–1.40 (2H, m), 1.28 (3H, t, J=7.3 Hz), 0.94–1.15 (12H, m), 0.90 (6H, d, J=6.3 Hz)

EXAMPLE 128

Preparation of N-[1-(4-pentenyl)-4-{3-(2-diethylaminoethoxy)phenyl}-1,2-dihydro-2-oxo-1,8-naphthyridin-3-yl]-N'-(2,6-diisopropylphenyl)urea

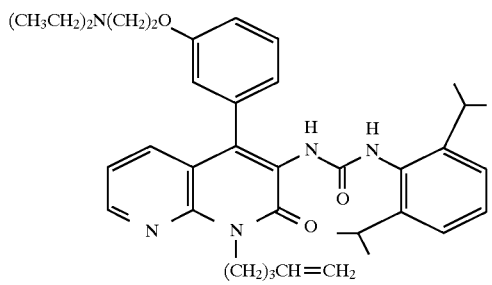

The title compound was obtained in the same manner as in Example 41 from N-[1-(4-pentenyl)-4-(3-hydroxyphenyl)-1,2-dihydro-2-oxo-1,8-naphthyridin-3-yl]-N'-(2,6-diisopropylphenyl)urea and 2-diethylaminoethyl chloride hydrochloride.

Hydrochloride: ¹H-NMR δ (DMSO-d₆) 9.99 (1H, brs), 8.62 (1H, dd, J=4.3 Hz, 1.7 Hz), 7.85 (1H, brs), 7.83 (1H, brs), 7.62 (1H, dd, J=8.3 Hz, 1.7 Hz), 7.45 (1H, dd, J=8.3 Hz, 8.3 Hz), 7.27 (1H, dd, J=7.9 Hz, 4.6 Hz), 6.90–7.11 (6H, m), 5.80–6.00 (1H, m), 4.95–5.19 (2H, m), 4.48–4.64 (2H, m), 4.28–4.44 (2H, m), 3.40–3.57 (2H, m), 3.06–3.27 (4H, m), 2.79–3.02 (2H, m), 2.09–2.29 (2H, m), 1.72–1.94 (2H, m), 1.20 (6H, t, J=7.3 Hz), 1.85–1.14 (12H, m)

EXAMPLE 129

Preparation of N-[1-butyl-4-(3-methylphenyl)-1,2-dihydro-2-oxo-1,8-naphthyridin-3-yl]-N'-(2,6-diisopropylphenyl)urea

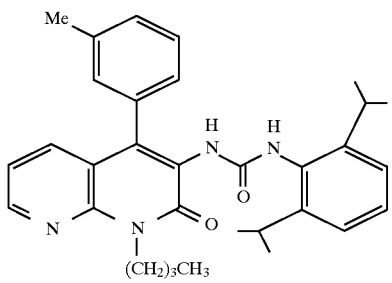

The title compound was obtained in the same manner as in Example 5 from 1-butyl-4-(3-methylphenyl)-1,2-dihydro-2-oxo-1,8-naphthyridine-3-carboxylic acid and 2,6-diisopropylaniline.

m.p. 214°–215° C.

EXAMPLE 130

Preparation of N-[1-octyl-4-(3-methoxyphenyl)-1,2-dihydro-2-oxo-1,8-naphthyridin-3-yl]-N'-(2,6-diisopropylphenyl)urea

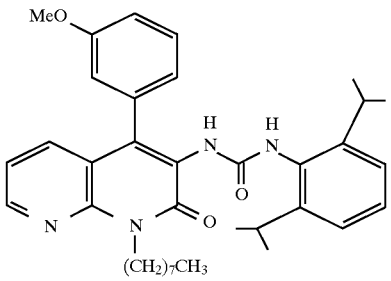

The title compound was obtained in the same manner as in Example 81 from N-[4-(3-methoxyphenyl)-1,2-dihydro-2-oxo-1,8-naphthyridin-3-yl]-N'-(2,6-diisopropylphenyl)urea and bromooctane.

¹H-NMR δ (DMSO-d₆) 8.59 (1H, dd, J=4.6 Hz, 2.0 Hz), 7.74 (2H, s), 7.63 (1H, d, J=7.9 Hz), 7.41 (1H, dd, J=8.3 Hz, 7.9 Hz), 7.24 (1H, dd, J=8.3 Hz, 4.6 Hz), 7.15 (1H, t, J=7.3 Hz), 7.04 (3H, m), 6.92 (2H, brs), 4.51 (2H, t, J=7.3 Hz), 3.77 (3H, s), 2.92 (2H, sep, J=6.9 Hz), 1.73 (2H, br), 1.27–1.37 (10H, br), 1.02 (12H, br), 0.85 (3H, brt, J=6.9 Hz)

EXAMPLE 131

Preparation of N-[1-butyl-4-{3-(quinolin-2-ylmethoxy)phenyl}-1,2-dihydro-2-oxo-1,8-naphthyridin-3-yl]-N'-(2,6-diisopropylphenyl)urea

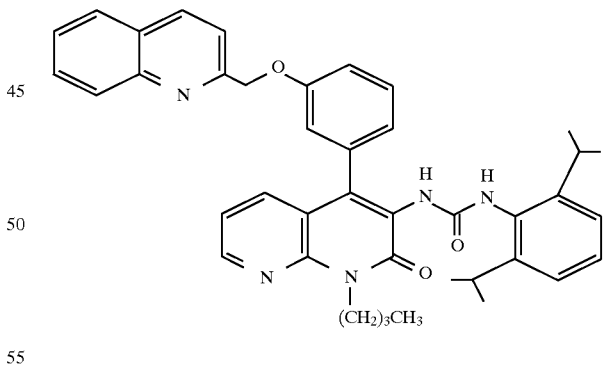

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 2-(chloromethyl)quinoline hydrochloride.

¹H-NMR δ (DMSO-d₆) 8.48–8.60 (2H, m), 8.05 (1H, dd, J=8.3 Hz, 3.3 Hz), 7.62–7.86 (5H, m), 7.41–7.48 (2H, m), 6.95–7.26 (8H, m), 5.44 (2H, s), 4.51 (2H, t, J=7.3 Hz), 2.94 (2H, br), 1.71 (2H, br), 1.44 (2H, m), 0.95–1.03 (15H, m)

EXAMPLE 132

Preparation of N-[1-(4-pentenyl)-4-{3-(2-pyridylmethoxy)phenyl}-1,2-dihydro-2-oxo-1,8-naphthyridin-3-yl]-N'-(2,6-diisopropylphenyl)urea

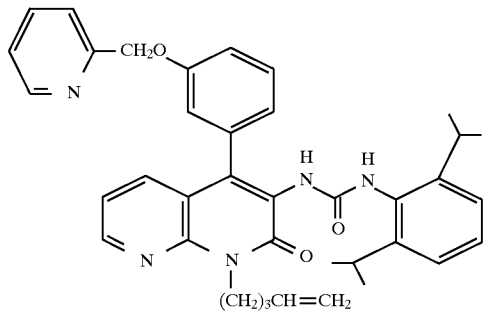

The title compound was obtained in the same manner as in Example 41 from N-[1-(4-pentenyl)-4-(3-hydroxyphenyl)-1,2-dihydro-2-oxo-1,8-naphthyridin-3-yl]-N'-(2,6-diisopropylphenyl)urea and 2-picolyl chloride hydrochloride.

Hydrochloride: $^1$H-NMR δ (DMSO-$d_6$) 8.65–8.74 (1H, m), 8.61 (1H, dd, J=4.6 Hz, 1.7 Hz), 8.02–8.15 (1H, m), 7.82 (1H, brs), 7.81 (1H, brs), 7.72–7.80 (1H, m), 7.51–7.65 (2H, m), 7.45 (1H, dd, J=7.9 Hz, 7.9 Hz), 7.22 (1H, dd, J=7.9 Hz, 4.6 Hz), 7.10–7.20 (2H, m), 6.94–7.09 (1H, m), 5.76–6.00 (1H, m), 5.32 (2H, s), 4.92–5.20 (2H, m), 4.35–4.65 (2H, m), 2.79–3.01 (2H, m), 2.05–2.28 (2H, m), 1.70–1.91 (2H, m), 0.78–1.15 (12H, brs)

EXAMPLE 133

Preparation of N-[1-(4-pentenyl)-4-{3-(3-pyridylmethoxy)phenyl}-1,2-dihydro-2-oxo-1,8-naphthyridin-3-yl]-N'-(2,6-diisopropylphenyl)urea

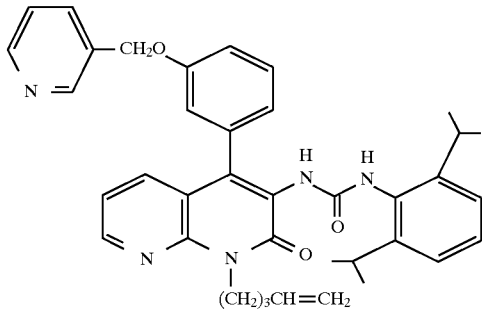

The title compound was obtained in the same manner as in Example 41 from N-[1-(4-pentenyl)-4-(3-hydroxyphenyl)-1,2-dihydro-2-oxo-1,8-naphthyridin-3-yl]-N'-(2,6-diisopropylphenyl)urea and 3-picolyl chloride hydrochloride.

Hydrochloride: $^1$H-NMR δ (DMSO-$d_6$) 8.90–8.96 (1H, m), 8.75–8.84 (1H, m), 8.62 (1H, dd, J=4.6 Hz, 2.0 Hz), 8.38–8.48 (1H, m), 7.86 (1H, dd, J=7.9 Hz, 5.6 Hz), 7.84 (2H, brs), 7.57 (1H, dd, J=7.9 Hz, 1.7 Hz), 7.45 (1H, dd, J=7.9 Hz, 7.9 Hz), 7.24 (1H, dd, J=8.3 Hz, 4.6 Hz), 7.11–7.12 (2H, m), 6.90–7.10 (5H, m), 5.78–6.00 (1H, m), 5.32 (2H, s), 4.93–5.18 (2H, m), 4.41–4.61 (2H, m), 2.80–3.02 (2H, m), 2.08–2.28 (2H, m), 1.72–1.92 (2H, m), 0.70–1.15 (12H, m)

EXAMPLE 134

Preparation of N-[1-(4-pentenyl)-4-{3-(3-piperidinopropoxy)phenyl}-1,2-dihydro-2-oxo-1,8-naphthyridin-3-yl]-N'-(2,6-diisopropylphenyl)urea

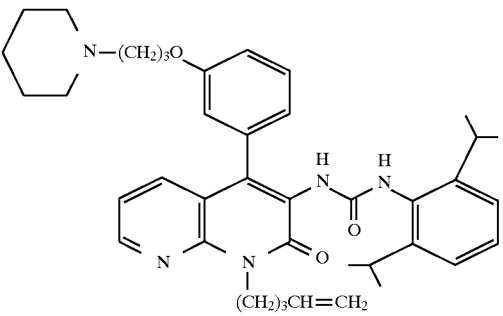

The title compound was obtained in the same manner as in Example 41 from N-[1-(4-pentenyl)-4-(3-hydroxyphenyl)-1,2-dihydro-2-oxo-1,8-naphthyridin-3-yl]-N'-(2,6-diisopropylphenyl)urea and N-(3-chloropropyl)-piperidine hydrochloride.

Hydrochloride: $^1$H-NMR δ (DMSO-$d_6$) 10.83 (1H, brs), 8.62 (1H, dd, J=4.6 Hz, 1.3 Hz), 7.83 (1H, brs), 7.82 (1H, brs), 7.58–7.68 (1H, m), 7.42 (1H, dd, J=7.9 Hz, 7.6 Hz), 7.26 (1H, dd, J=7.9 Hz, 4.6 Hz), 7.11–7.20 (1H, m), 6.99–7.09 (3H, m), 6.87–6.98 (2H, m), 5.80–6.00 (1H, m), 4.93–5.19 (2H, m), 4.42–4.62 (2H, m), 3.96–4.15 (2H, m), 3.35–3.52 (2H, m), 3.02–3.22 (2H, m), 2.70–3.00 (3H, m), 2.05–2.28 (4H, m), 1.55–1.94 (8H, m), 1.25–1.47 (1H, m), 1.02 (12H, brs)

EXAMPLE 135

Preparation of N-[1-(4-methylpentyl)-4-{3-(2-ethylaminoethoxy)-phenyl}-1,2-dihydro-2-oxo-1,8-naphthyridin-3-yl]-N'-(2,6-diisopropylphenyl)urea

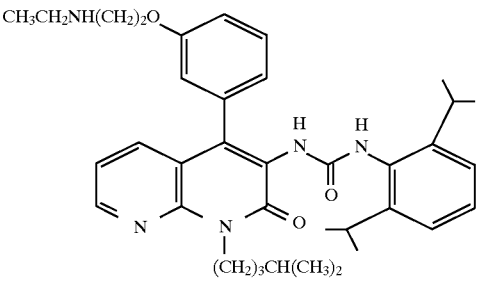

The title compound was obtained in the same manner as in Example 62 from N-[1-(4-methylpentyl)-4-[3-{2-(N-benzyl-N-ethylamino)ethoxy}phenyl]-1,2-dihydro-2-oxo-1,8-naphthyridin-3-yl]-N'-(2,6-diisopropylphenyl)urea.

Hydrochloride: $^1$H-NMR δ (DMSO-$d_6$) 8.92 (2H, brs), 8.62 (1H, dd, J=4.6 Hz, 1.7 Hz), 7.72 (1H, brs), 7.71 (1H, brs), 7.61 (1H, dd, J=7.9 Hz, 1.7 Hz), 7.44 (1H, dd, J=8.3 Hz, 7.9 Hz), 7.25 (1H, dd, J=7.9 Hz, 4.6 Hz), 6.85–7.20 (6H, m), 4.38–4.58 (2H, m), 4.16–4.33 (2H, m), 3.20–3.40 (2H, m), 2.78–3.10 (4H, m), 1.50–1.83 (3H, m), 1.25–1.40 (2H, m), 1.19 (3H, t, J=7.3 Hz), 0.93–1.13 (12H, m), 0.90 (6H, d, J=6.6 Hz)

EXAMPLE 136

Preparation of N-[1-butyl-4-{3-(2-methyl-3-pyridylmethoxy)phenyl}-1,2-dihydro-2-oxo-1,8-naphthyridin-3-yl]-N'-(2,6-diisopropylphenyl)urea

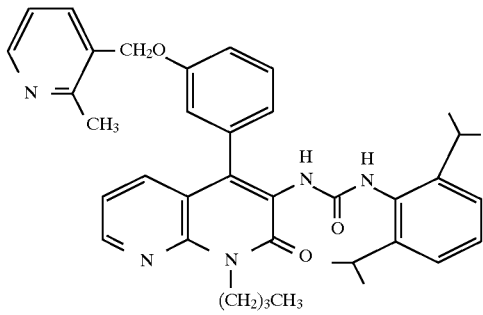

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 2-methyl-3-picolyl chloride hydrochloride.

$^1$H-NMR δ (DMSO-d$_6$) 8.67 (1H, d, J=4.3 Hz), 8.61 (1H, dd, J=4.6 Hz, 1.7 Hz), 8.44 (1H, d, J=7.6 Hz), 7.86 (1H, s), 7.82 (1H, s), 7.74 (1H, dd, J=6.9 Hz, 6.6 Hz), 7.59 (1H, d, J=6.3 Hz), 7.45 (1H, d, J=7.9 Hz, 7.9 Hz), 6.98–7.26 (7H, m), 5.30 (2H, s), 4.53 (2H, t, J=7.6 Hz), 2.90 (2H, m), 2.74 (3H, s), 1.72 (2H, m), 1.45 (2H, m), 0.95–1.12 (15H, m)

EXAMPLE 137

Preparation of N-[1-butyl-4-[3-{3-(4-pyridyl)propoxy}phenyl]-1,2-dihydro-2-oxo-1,8-naphthyridin-3-yl]-N'-(2,6-diisopropylphenyl)urea

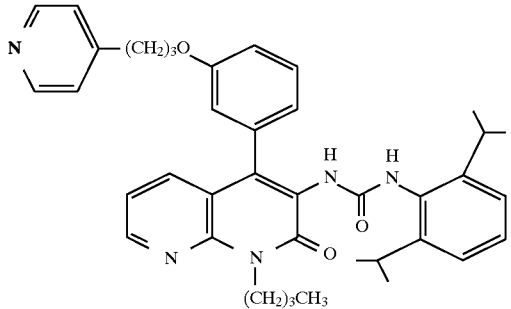

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 3-(4-pyridyl)propyl bromide hydrochloride.

m.p. 138°–140° C.

EXAMPLE 138

Preparation of N-[1-butyl-4-[3-{2-(2-pyridyl)ethoxy}phenyl]-1,2-dihydro-2-oxo-1,8-naphthyridin-3-yl]-N'-(2,6-diisopropylphenyl)urea

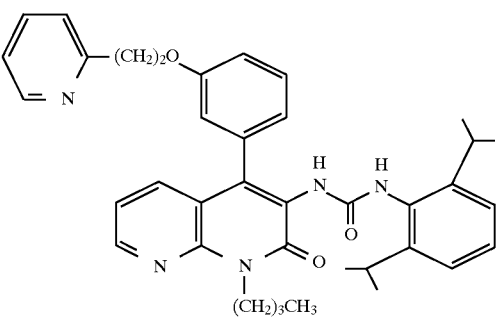

To a solution of N-[1-butyl-4-(3-hydroxyphenyl)-1,2-dihydro-2-oxo-1,8-naphthyridin-3-yl]-N'-(2,6-diisopropylphenyl)urea (300 mg, 0.58 mmol), 2-pyridinethanol (71 mg, 0.58 mmol) in THF (5 ml) were added triphenylphosphine (152 mg, 0.58 mmol), and diethyl azodicarboxylate (101 mg, 0.58 mmol), and the mixture was stirred at room temperature for 40 hours. The mixture was poured into water, and extracted with ethyl acetate. The extract was washed with water, washed with a saturated aqueous sodium chloride solution, and dried over anhydrous magnesium sulfate. The resultant was concentrated under reduced pressure, and the residue was purified by silica gel column chromatography (ethyl acetate:hexane=5:5) and thin layer chromatography to give the title compound (43 mg, 0.07 mmol).

$^1$H-NMR δ (CD$_3$OD) 8.58 (1H, d, J=4.6 Hz), 8.44 (1H, d, J=4.3 Hz), 7.68–7.76 (2H, m), 7.41 (2H, m), 6.93–7.28 (8H, m), 4.62 (2H, t, J=7.3 Hz), 4.37 (2H, t, J=6.3 Hz), 3.24 (2H, t, J=6.3 Hz), 2.93 (2H, br), 1.75 (2H, m), 1.47 (2H, m), 1.26 (12H, br), 1.00 (3H, t, J=7.3 Hz)

EXAMPLE 139

Preparation of N-[1-butyl-4-[3-{(2,4-dimethylpyridin-3-yl)methoxy}-phenyl]-1,2-dihydro-2-oxo-1,8-naphthyridin-3-yl]-N'-(2,6-diisopropylphenyl)urea

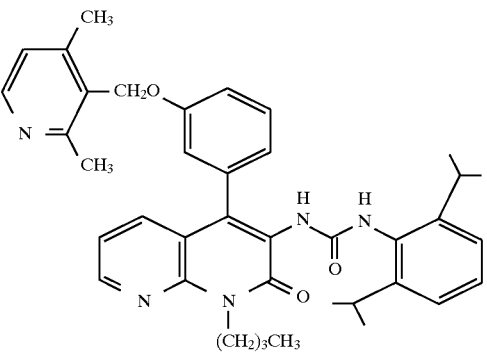

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and 3-chloromethyl-2,4-dimethylpyridine hydrochloride.

Hydrochloride: ¹H-NMR δ (DMSO-d₆) 8.65 (1H, d, J=5.9 Hz), 8.62 (1H, dd, J=4.6 Hz, 1.7 Hz), 7.78–7.86 (3H, m), 7.64 (1H, dd, J=7.9 Hz, 1.7 Hz), 7.47 (1H, dd, J=7.9 Hz, 7.9 Hz), 7.02–7.28 (7H, m), 5.26 (2H, brs), 4.53 (2H, t, J=7.3 Hz), 2.92 (2H, m), 2.76 (3H, s), 2.60 (3H, s), 1.69 (2H, m), 1.44 (2H, m), 1.00 (12H, brs), 0.97 (3H, t, J=7.3 Hz)

EXAMPLE 140

Preparation of N-[1-butyl-4-[3-{2-(3-pyridyl)ethoxy}phenyl]-1,2-dihydro-2-oxo-1,8-naphthyridin-3-yl]-N'-(2,6-diisopropylphenyl)urea

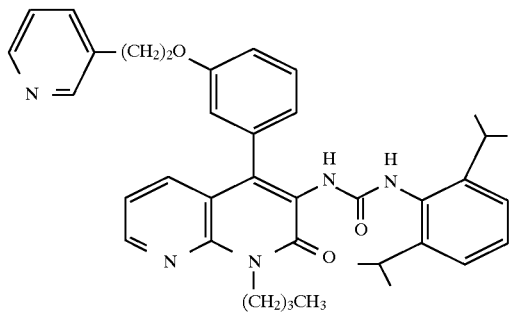

The title compound was obtained in the same manner as in Example 138 from N-[1-butyl-4-(3-hydroxyphenyl)-1,2-dihydro-2-oxo-1,8-naphthyridin-3-yl]-N'-(2,6-diisopropylphenyl)urea and 3-pyridinethanol.

¹H-NMR δ (CD₃OD) 8.58 (1H, dd, J=4.6 Hz, J=1.7 Hz), 8.49 (1H, s), 8.37 (1H, d, J=4.0 Hz), 7.80 (1H, d, J=7.9 Hz), 7.52–7.60 (3H, m), 7.37 (1H, m), 6.93–7.21 (6H, m), 4.62 (2H, t, J=6.3 Hz), 2.91 (2H, m), 1.78 (2H, m), 1.47 (2H, m), 1.04 (15H, br)

EXAMPLE 141

Preparation of N-[1-(4-pentenyl)-4-{3-(3-dimethylaminopropoxy)-phenyl}-1,2-dihydro-2-oxo-1,8-naphthyridin-3-yl]-N'-(2,6-diisopropylphenyl)urea

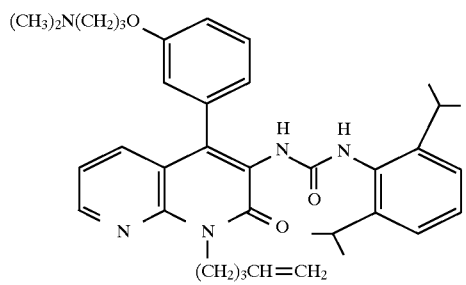

The title compound was obtained in the same manner as in Example 41 from N-[1-(4-pentenyl)-4-(3-hydroxyphenyl)-1,2-dihydro-2-oxo- 1,8-naphthyridin-3-yl]-N'-(2,6-diisopropylphenyl)urea and 3-dimethylaminopropyl chloride hydrochloride.

Hydrochloride:
¹H-NMR δ (DMSO-d₆) 10.35 (1H, brs), 8.62 (1H, dd, J=4.6 Hz, 1.7 Hz), 7.83 (1H, brs), 7.82 (1H, brs), 7.62 (1H, dd, J=7.9 Hz, 1.7 Hz), 7.41 (1H, dd, J=8.3 Hz, 7.6 Hz), 7.26 (1H, dd, J=7.9 Hz, 4.6 Hz), 7.11–7.20 (1H, m), 7.00–7.09 (3H, m), 6.85–6.99 (2H, m), 5.78–6.00 (1H, m), 4.93–5.20 (2H, m), 4.40–4.66 (2H, m), 3.09–3.28 (2H, m), 2.81–3.02 (2H, m), 2.73 (6H, d, J=5.0 Hz), 2.03–2.28 (4H, m), 1.71–1.94 (2H, m), 0.75–1.20 (12H, m)

EXAMPLE 142

Preparation of N-[1-(4-pentenyl)-4-[3-{2-(N-benzyl-N-ethylamino)-ethoxy}phenyl]-1,2-dihydro-2-oxo-1,8-naphthyridin-3-yl]-N'-(2,6-diisopropylphenyl)urea

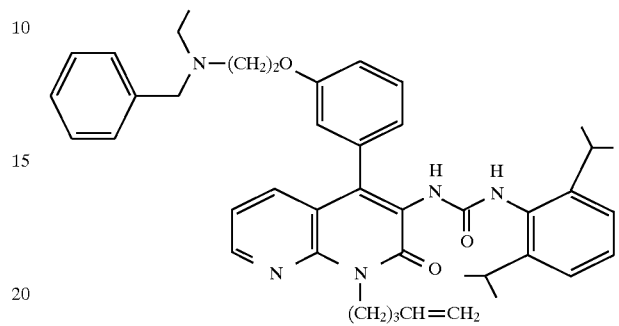

The title compound was obtained in the same manner as in Example 41 from N-[1-(4-pentenyl)-4-(3-hydroxyphenyl)-1,2-dihydro-2-oxo-1,8-naphthyridin-3-yl]-N'-(2,6-diisopropylphenyl)urea and 2-(N-benzyl-N-ethyl-amino)ethyl chloride hydrochloride.

Hydrochloride: ¹H-NMR δ (DMSO-d₆) 10.75 (1H, brs), 8.62 (1H, dd, J=4.6 Hz, 1.7 Hz), 7.85 (1H, brs), 7.55–7.72 (3H, m), 7.37–7.52 (4H, m), 7.26 (1H, d, J=7.9 Hz, J=4.6 Hz), 6.89–7.20 (7H, m), 5.80–6.00 (1H, m), 4.93–5.19 (2H, m), 4.30–4.62 (6H, m), 3.35–3.54 (2H, m), 3.05–3.25 (2H, m), 2.80–3.00 (2H, m), 2.08–2.28 (2H, m), 1.72–1.93 (2H, m), 1.83 (3H, brt, J=6.9 Hz), 0.80–1.16 (12H, brs)

EXAMPLE 143

Preparation of N-[1-(4-pentenyl)-4-[3-{2-(pyrrolidin-1-yl)ethoxy}-phenyl]-1,2-dihydro-2-oxo-1,8-naphthyridin-3-yl]-N'-(2,6-diisopropylphenyl)urea

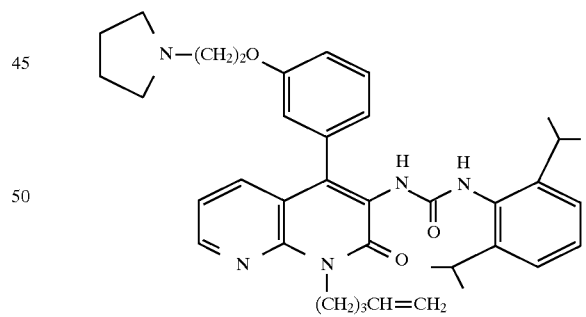

The title compound was obtained in the same manner as in Example 41 from N-[1-(4-pentenyl)-4-(3-hydroxyphenyl)-1,2-dihydro-2-oxo-1,8-naphthyridin-3-yl]-N'-(2,6-diisopropylphenyl)urea and N-(2-chloroethyl)pyrrolidine hydrochloride.

Hydrochloride: ¹H-NMR δ (DMSO-d₆) 10.62 (1H, brs), 8.57–8.69 (1H, m), 7.86 (2H, brs), 7.58–7.70 (1H, m), 7.38–7.51 (1H, m), 7.22–7.32 (1H, m), 6.88–7.21 (6H, m), 5.80–6.00 (1H, m), 4.92–5.20 (2H, m), 4.45–4.62 (2H, m), 4.26–4.42 (2H, m), 3.45–3.66 (4H, m), 2.78–3.20 (4H, m), 2.06–2.29 (2H, m), 1.69–2.05 (4H, m), 1.02 (12H, brs)

EXAMPLE 144

Preparation of N-[1-(4-pentynyl)-4-(3-methoxyphenyl)-1,2-dihydro-2-oxo-1,8-naphthyridin-3-yl]-N'-(2,6-diisopropylphenyl)urea (a) Preparation of N-[1-(5-trimethylsilyl-4-pentynyl)-4-(3-methoxyphenyl)-1,2-dihydro-2-oxo-1,8-naphthyridin-3-yl]-N'-(2,6-diisopropylphenyl)urea

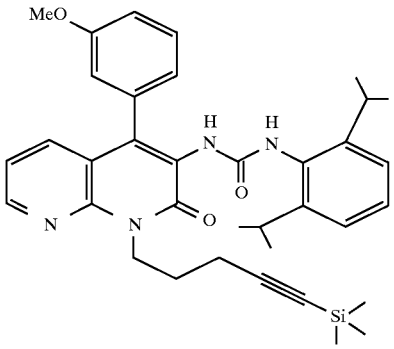

The title compound was obtained in the same manner as in Example 94 from N-[4-(3-methoxyphenyl)-1,2-dihydro-2-oxo-1,8-naphthyridin-3-yl]-N'-(2,6-diisopropylphenyl)urea and 5-(p-toluenesulfonyloxy)-1-trimethylsilyl-1-pentyne.

$^1$H-NMR δ (CD$_3$OD) 8.65 (1H, dd, J=4.3 Hz, 1.7 Hz), 7.76 (1H, dd, J=7.9 Hz, 1.7 Hz), 7.49 (1H, dd, J=8.3 Hz, 7.9 Hz), 6.95–7.35 (7H, m), 4.70–7.83 (2H, m), 3.87 (3H, s), 2.95–3.13 (2H, m), 2.44 (2H, t, J=7.3 Hz), 1.98–2.16 (2H, m), 1.15 (12H, brd, J=6.3 Hz), 0.17 (9H, s)

(b) Preparation of N-[1-(4-pentynyl)-4-(3-methoxyphenyl)-1,2-dihydro-2-oxo-1,8-naphthyridin-3-yl]-N'-(2,6-diisopropylphenyl)urea

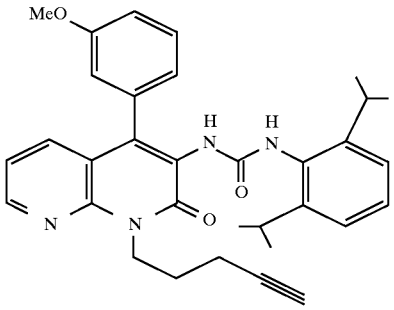

To a solution of N-[1-(5-trimethylsilyl-4-pentynyl)-4-(3-methoxyphenyl)-1,2-dihydro-2-oxo-1,8-naphthyridin-3-yl]-N'-(2,6-diisopropylphenyl)urea (81 mg, 0.133 mmol) in DMF (4 ml) was added potassium fluoride (138 mg, 2.38 mmol), and the mixture was stirred at room temperature for 7 hours. The mixture was poured into water, and extracted with ethyl acetate. The extract was washed with a saturated aqueous sodium chloride solution, and dried over anhydrous magnesium sulfate. The resultant was concentrated under reduced pressure, and purified by preparative thin layer chromatography to give the title compound (58 mg, 0.14 mmol).

$^1$H-NMR δ (DMSO-d$_6$) 8.61 (1H, dd, J=8.1 Hz, 1.5 Hz), 7.75 (2H, brs), 7.62 (1 H, dd, J=8.1 Hz, 1.1 Hz), 7.42 (1H, dd, J=8.1 Hz, 8.1 Hz), 7.26 (1H, dd, J=7.8 Hz, 4.5 Hz), 7.10–7.21 (1H, m), 6.98–7.10 (3H, m), 6.85–6.97 (2H, m), 4.42–4.70 (2H, m), 2.77–3.00 (2H, m), 2.82 (1H, t, J=2.4 Hz), 2.24–2.40 (2H, m), 1.77–2.05 (2H, m), 1.02 (12H, brs)

EXAMPLE 145

Preparation of N-[1-butyl-4-(3-fluorophenyl)-1,2-dihydro-2-oxo-1,8-naphthyridin-3-yl]-N'-(2,6-diisopropylphenyl)urea

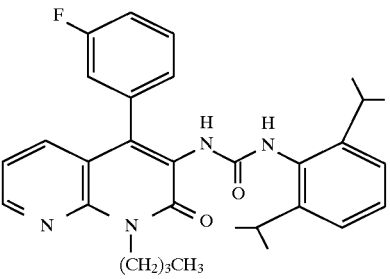

The title compound was obtained in the same manner as in Example 5 from 1-butyl-4-(3-fluorophenyl)-1,2-dihydro-2-oxo-1,8-naphthyridine-3-carboxylic acid and 2,6-diisopropylaniline.

m.p. 201°–202° C.

EXAMPLE 146

Preparation of N-[1-butyl-4-{3-(3-dipropylamino-1-propynyl)phenyl}-1,2-dihydro-2-oxo-1,8-naphthyridin-3-yl]-N'-(2,6-diisopropylphenyl)urea

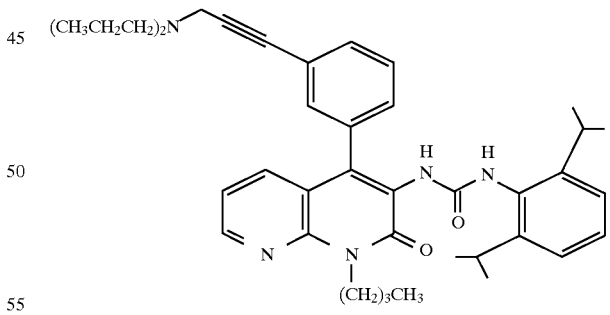

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 3-dipropylamino-1-propyne.

Hydrochloride: m.p. 201°–202° C.

EXAMPLE 147

Preparation of N-[1-butyl-4-{3-(3-amino-3-methyl-1-butynyl)phenyl}-1,2-dihydro-2-oxo-1,8-naphthyridin-3-yl]-N'-(2,6-diisopropylphenyl)urea

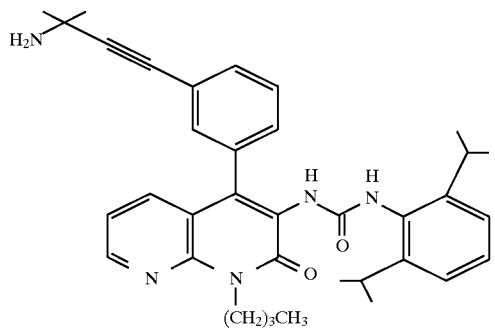

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 3-amino-3-methyl-1-butyne.

Hydrochloride: m.p. 170°–172° C.

EXAMPLE 148

Preparation of N-[1-butyl-4-[3-{3-(N-benzyl-N-methylamino)-1-propynyl}phenyl]-1,2-dihydro-2-oxo-1,8-naphthyridin-3-yl]-N'-(2,6-diisopropylphenyl)urea

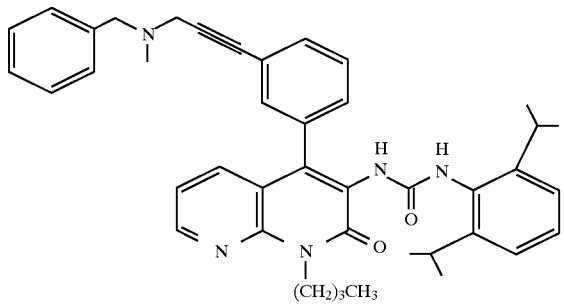

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 3-(N-benzyl-N-methylamino)-1-propyne.

Hydrochloride: m.p. 140°–142° C.

EXAMPLE 149

Preparation of N-[1-butyl-4-[3-{2-(aminocyclohexan-1-yl)ethynyl}-phenyl]-1,2-dihydro-2-oxo-1,8-naphthyridin-3-yl]-N'-(2,6-diisopropylphenyl)urea

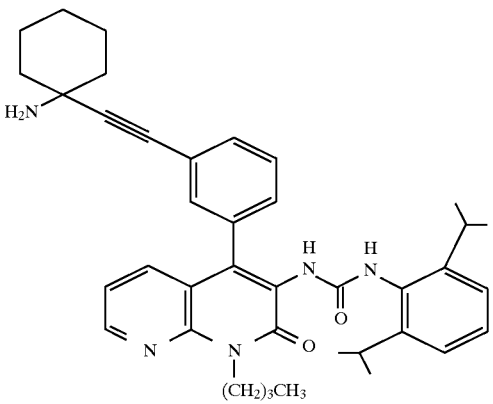

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 1-ethynylcyclohexylamine.

Hydrochloride: m.p. 171°–172° C.

EXAMPLE 150

Preparation of N-[1-butyl-4-{3-(3-amino-3-ethyl-1-pentynyl)phenyl}-1,2-dihydro-2-oxo-1,8-naphthyridin-3-yl]-N'-(2,6-diisopropylphenyl)urea

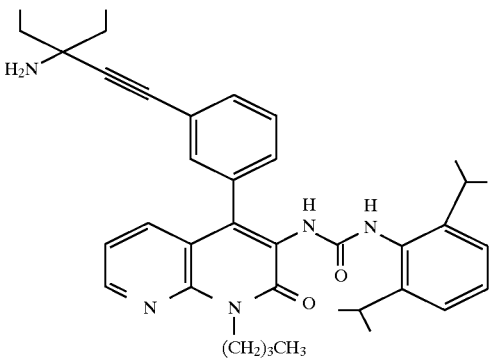

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 3-amino-3-ethyl-1-pentyne.

Hydrochloride: m.p. 164°–165° C.

EXAMPLE 151

Preparation of N-[1-butyl-4-{3-(3-tert-butoxycarbonylamino-1-propynyl)-phenyl}-1,2-dihydro-2-oxo-1,8-naphthyridin-3-yl]-N'-(2,6-diisopropylphenyl)urea

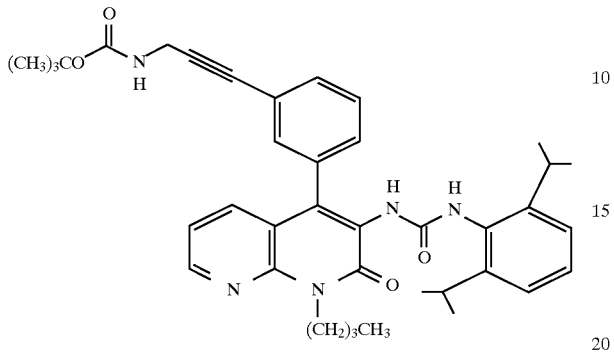

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 3-tert-butoxycarbonylamino-1-propyne.

$^1$H-NMR δ (CDCl$_3$) 8.61 (1H, dd, J=4.6 Hz, 1.6 Hz), 7.89 (1H, br), 7.81 (1H, br), 7.01–7.56 (9H, m), 4.50–4.53 (2H, m), 3.95–3.97 (2H, m), 2.71–2.92 (2H, m), 1.71–1.80 (2H, m), 1.30–1.51 (11H, m), 0.94–1.07 (12H, m)

EXAMPLE 152

Preparation of N-[1-butyl-4-{3-(3-amino-1-propynyl)phenyl}-1,2-dihydro-2-oxo-1,8-naphthyridin-3-yl]-N'-(2,6-diisopropylphenyl)urea

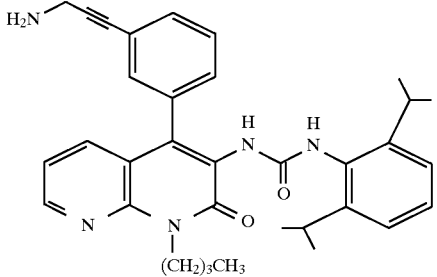

To a solution of N-[1-butyl-4-{3-(3-tert-butoxycarbonylamino-1-propynyl)phenyl}-1,2-dihydro-2-oxo-1,8-naphthyridin-3-yl]-N'-(2,6-diisopropyl-phenyl)urea (104 mg, 0.16 mmol) in chloroform (5 ml) was added trifluoroacetic acid (1 ml) at under ice-cooling. The mixture was warmed to room temperature, and then stirred for 1.5 hour. The mixture was concentrated under reduced pressure to remove the solvent, and to the residue was added 5% aqueous sodium chloride solution. The mixture was treated with aqueous ammonia to be converted into a free form, and then extracted with ethyl acetate. The oily layer was washed with 5% aqueous sodium chloride solution, and dried over anhydrous magnesium sulfate. The resultant was concentrated under reduced pressure, and the residue was purified by silica gel column chromatography (4% methanol in chloroform) to give the title compound (64 mg, 0.12 mmol).

Hydrochloride: $^1$H-NMR δ (DMSO-d$_6$) 8.62 (1H, d, J=3.7 Hz), 8.35 (2H, brs), 8.03 (1H, s), 7.90 (1H, s), 7.54 (1H, s), 7.52 (2H, s), 7.41–7.42 (2H, m), 7.27 (1H, dd, J=8.1 Hz, 4.8 Hz), 7.13–7.19 (1H, m), 7.03 (2H, d, J=7.9 Hz), 4.52–4.57 (2H, m), 3.98 (2H, d, J=4.8 Hz), 2.85 (1H, brs), 2.76 (1H, brs), 1.68–1.78 (2H, m), 1.40–1.47 (2H, m), 0.92–1.04 (15H, m)

EXAMPLE 153

Preparation of N-[1-butyl-4-{3-(3-methylamino-3-methyl-1-butynyl)-phenyl}-1,2-dihydro-2-oxo-1,8-naphthyridin-3-yl]-N'-(2,6-diisopropylphenyl)urea

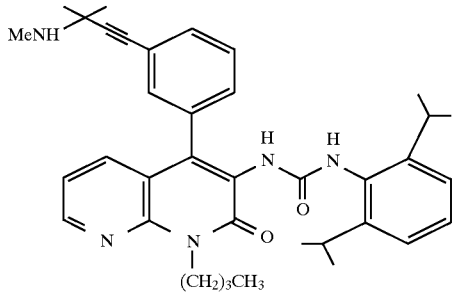

The title compound was obtained in the same manner as in Example 67 from N-[1-butyl-4-{3-(3-amino-3-methyl-1-butynyl)phenyl}-1,2-dihydro-2-oxo-1,8-naphthyridin-3-yl]-N'-(2,6-diisopropylphenyl)urea and formaldehyde.

Hydrochloride: $^1$H-NMR δ (DMSO-d$_6$) 9.36 (2H, brs), 8.62 (1H, d, J=3.9 Hz), 8.03 (1H, s), 7.89 (1H, s), 7.51–7.55 (3H, m), 7.40–7.44 (2H, m), 7.25–7.29 (1H, m), 7.13–7.19 (1H, m), 7.04 (2H, d, J=7.5 Hz), 4.54 (2H, t, J=7.5 Hz), 3.12 (2H, brs), 2.76 (2H, brs), 1.66–1.75 (2H, m), 1.66 (6H, s), 1.40–1.47 (2H, m), 1.25 (3H, t, J=7.2 Hz), 0.95–1.14 (15H, m)

EXAMPLE 154

Preparation of N-[1-butyl-4-{3-(3-dimethylamino-1-propynyl)phenyl}-1,2-dihydro-2-oxo-1,8-naphthyridin-3-yl]-N'-(2,6-diisopropylphenyl)urea

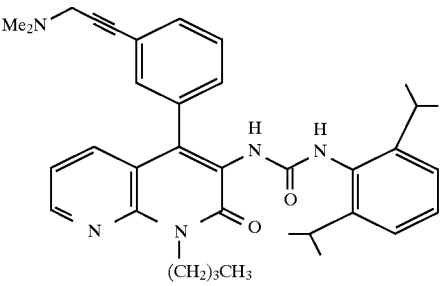

The title compound was obtained in the same manner as in Example 67 from N-[1-butyl-4-{3-(3-amino-1-propynyl)phenyl}-1,2-dihydro-2-oxo-1,8-naphthyridin-3-yl]-N'-(2,6-diisopropylphenyl)urea and formaldehyde.

Hydrochloride: $^1$H-NMR δ (DMSO-d$_6$) 10.62 (1H, brs), 8.62–8.63 (1H, m), 8.00 (1H, s), 7.89 (1H, s), 7.50–7.63 (4H, m), 7.43 (1H, d, J=7.3 Hz), 7.27 (1H, dd, J=7.7 Hz, J=4.4 Hz), 7.13–7.18 (1H, m), 7.03 (2H, d, J=7.5 Hz), 4.52–4.57 (2H, m), 4.32 (2H, s), 2.84 (2H, s), 2.73–2.84 (2H, m), 1.70–1.75 (2H, m), 1.39–1.47 (2H, m), 0.95–1.11 (15H, m)

EXAMPLE 155

Preparation of N-[1-butyl-4-{3-(3-diethylamino-3-methyl-1-butynyl)-phenyl}-1,2-dihydro-2-oxo-1,8-naphthyridin-3-yl]-N'-(2,6-diisopropylphenyl)urea

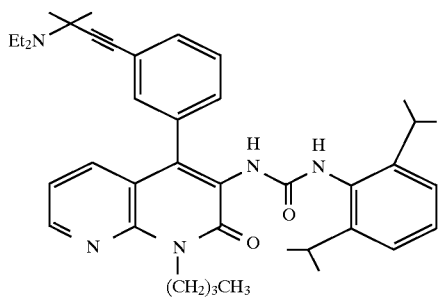

To a solution of N-[1-butyl-4-{3-(3-amino-3-methyl-1-butynyl)phenyl}-1,2-dihydro-2-oxo-1,8-naphthyridin-3-yl]-N'-(2,6-diisopropylphenyl)urea (126 mg, 0.22 mmol) in DMF were added potassium carbonate (300 mg, 2.18 mmol) and iodoethane (102 mg, 0.654 mmol), and the mixture was stirred at room temperature for one hour. The mixture was warmed to 50° C., and then stirred for five hours. The mixture was further stirred at room temperature for 12 hours, and poured into water. The mixture was extracted with ethyl acetate, and the extract was washed with 5% aqueous sodium hydrogen carbonate solution, 5% aqueous sodium chloride solution, and concentrated under reduced pressure. The residue was purified by silica gel column chromatography (1% methanol in chloroform) to give the title compound (25 mg, 0.04 mmol).

Hydrochloride: m.p. 144°–146° C.

EXAMPLE 156

Preparation of N-[1-butyl-4-{3-(3-diethylamino-3-ethyl-1-pentynyl)-phenyl}-1,2-dihydro-2-oxo-1,8-naphthyridin-3-yl]-N'-(2,6-diisopropylphenyl)urea

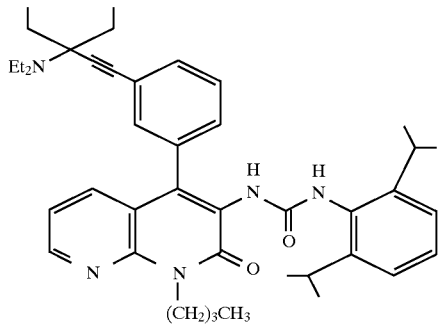

The title compound was obtained in the same manner as in Example 155 from N-[1-butyl-4-{3-(3-amino-3-ethyl-1-pentynyl)phenyl}-1,2-dihydro-2-oxo-1,8-naphthyridin-3-yl]-N'-(2,6-diisopropylphenyl)urea and iodoethane.

Hydrochloride: m.p. 137°–139° C.

EXAMPLE 157

Preparation of N-[1-butyl-4-[3-{2-(N,N-diethylaminocyclohexan-1-yl)-ethynyl}phenyl]-1,2-dihydro-2-oxo-1,8-naphthyridin-3-yl]-N'-(2,6-diisopropylphenyl)urea

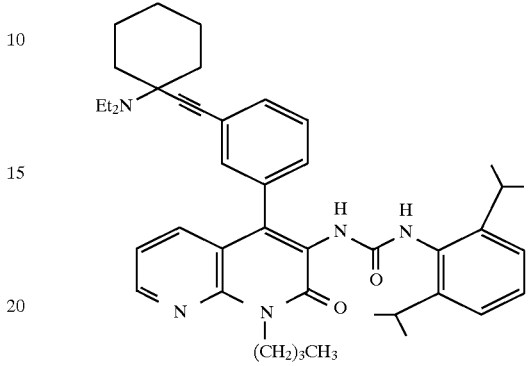

The title compound was obtained in the same manner as in Example 155 from N-[1-butyl-4-[3-{2-(aminocyclohexan-1-yl)ethynyl}phenyl]-1,2-dihydro-2-oxo-1,8-naphthyridin-3-yl]-N'-(2,6-diisopropylphenyl)urea and iodoethane.

Hydrochloride: m.p. 208°–212° C.

EXAMPLE 158

Preparation of N-[1-butyl-4-{3-(3-methylamino-1-propynyl)phenyl}-1,2-dihydro-2-oxo-1,8-naphthyridin-3-yl]-N'-(2,6-diisopropylphenyl)urea

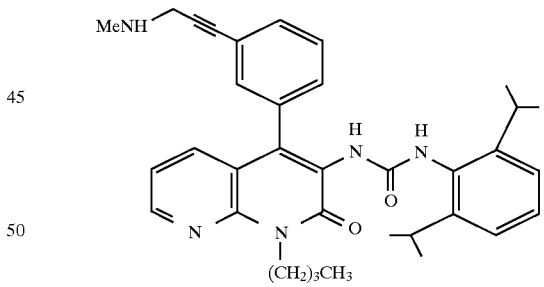

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 3-methylamino-1-propyne.

Hydrochloride: $^1$H-NMR δ (DMSO-$d_6$) 9.19 (2H, brs), 8.61–8.63 (1H, m), 8.02 (1H, s), 7.90 (1H, s), 7.55 (2H, s), 7.53 (1H, s), 7.44 (1H, s), 7.42 (1H, brs), 7.25–7.29 (1H, m), 7.13–7.18 (1H, m), 7.03 (2H, d, J=7.7 Hz), 4.52–4.57 (2H, m), 4.11–4.15 (2H, m), 2.73–2.76 (2H, m), 2.62 (3H, t, J=5.5 Hz), 1.71–1.76 (2H, m), 1.40–1.47 (2H, m), 0.96–1.12 (15H, m)

EXAMPLE 159

Preparation of N-[1-butyl-4-{3-(4-chlorobutoxy)phenyl}-1,2-dihydro-2-oxo-1,8-naphthyridin-3-yl]-N'-(2,6-diisopropylphenyl)urea

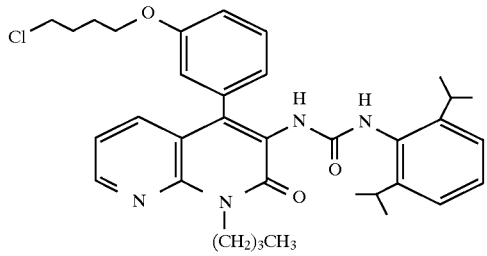

The title compound was obtained in the same manner as in Example 39 from N-[1-butyl-4-(3-hydroxyphenyl)-1,2-dihydro-2-oxo-1,8-naphthyridin-3-yl]-N'-(2,6-diisopropylphenyl)urea and 1-bromo-3-chlorobutane.

$^1$H-NMR δ (DMSO-d$_6$) 8.59 (1H, dd, J=4.6 Hz, 1.7 Hz), 7.76 (1H, brs), 7.74 (1H, brs), 7.62 (1H, d, J=6.6 Hz), 7.24 (1H, dd, J=7.9 Hz, 4.6 Hz), 7.12–7.18 (1H, m), 6.97–7.02 (3H, m), 6.89 (2H, br), 4.52 (2H, t, J=7.3 Hz), 4.00 (2H, br), 3.67 (2H, br), 2.91 (2H, m), 1.86 (2H, m), 1.72 (2H, br), 1.42 (2H, m), 1.02 (12H, br), 0.97 (3H, t, J=7.3 Hz)

EXAMPLE 160

Preparation of N-[1-butyl-4-[3-{4-(1,2,4-triazol-1-yl)butoxy}phenyl]-1,2-dihydro-2-oxo-1,8-naphthyridin-3-yl]-N'-(2,6-diisopropylphenyl)urea

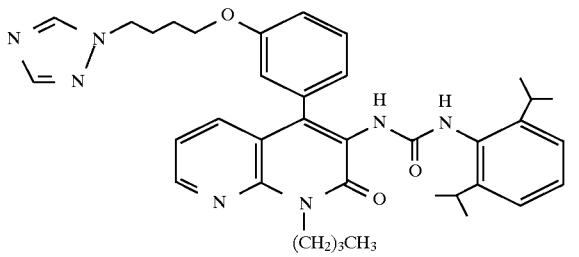

The title compound was obtained in the same manner as in Example 56 from N-[1-butyl-4-{3-(4-chlorobutoxy)phenyl}-1,2-dihydro-2-oxo-1,8-naphthyridin-3-yl]-N'-(2,6-diisopropylphenyl)urea and 1,2,4-triazole.

Hydrochloride: $^1$H-NMR δ (DMSO-d$_6$) 8.60 (1H, dd, J=4.6 Hz, 1.7 Hz), 8.50 (1H, s), 7.93 (1H, s), 7.77 (1H, brs), 7.74 (1H, brs), 7.61 (1H, dd, J=8.1 Hz, 1.7 Hz), 7.39 (1H, dd, J=7.9 Hz, 7.9 Hz), 7.24 (1H, dd, J=7.9 Hz, 4.6 Hz), 7.13 (1H, m), 6.98–7.04 (3H, m), 6.86–6.91 (2H, m), 4.52 (2H, t, J=7.3 Hz), 4.23 (2H, t, J=6.8 Hz), 3.98 (2H, t, J=6.1 Hz), 2.90 (2H, m), 1.93 (2H, m), 1.65–1.72 (4H, m), 1.43 (2H, m), 1.00 (12H, br), 0.97 (3H, t, J=7.5 Hz)

Example 161

Preparation of N-[1-butyl-4-[3-{2-(p-toluenesulfonyloxy)ethoxy}phenyl]-1,2-dihydro-2-oxo-1,8-naphthyridin-3-yl]-N'-(2,6-diisopropylphenyl)urea

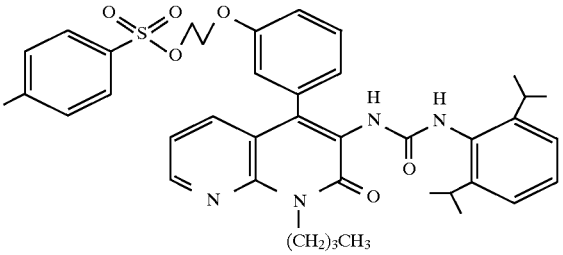

To a solution of N-[1-butyl-4-{3-(2-hydroxyethoxy)phenyl}-1,2-dihydro-2-oxo-1,8-naphthyridin-3-yl]-N'-(2,6-diisopropylphenyl)urea (2.02 g, 3.63 mmol) in THF (20 ml) were added p-toluenesulfonyl chloride (0.69 g, 3.63 mmol) and triethylamine (0.40 g, 3.99 mmol), and the mixture was stirred at 40°–50° C. for 8 hours. The mixture was poured into water, and extracted with ethyl acetate. The extract was washed with water, washed with a saturated aqueous sodium chloride solution, and dried over anhydrous magnesium sulfate. The resultant was concentrated under reduced pressure, and the residue was purified by silica gel column chromatography (ethyl acetate:hexane=1:1) to give the title compound (1.40 g, 1.97 mmol).

$^1$H-NMR δ (DMSO-d$_6$) 8.60 (1H, dd, J=4.6 Hz, 1.5 Hz), 7.74–7.80 (4H, m), 7.57 (1H, d, J=7.0 Hz), 7.45 (2H, d, J=8.4 Hz), 7.37 (11H, dd, J=8.1 Hz, 7.9 Hz), 7.24 (1H, dd, J=7.9 Hz, 4.8 Hz), 7.15 (1H, d, J=7.5 Hz), 7.03 (2H, d, J=7.5 Hz), 6.90–6.94 (2H, m), 6.75 (1H, br), 4.52 (2H, t, J=7.3 Hz), 4.34 (2H, br), 4.15 (2H, br), 2.88 (2H, m), 1.70 (2H, m), 1.42 (2H, m), 0.99 (12H, br), 0.97 (3H, t, J=7.2 Hz)

EXAMPLE 162

Preparation of N-[1-butyl-4-[3-{2-(1,2,4-triazol-1-yl)ethoxy}phenyl]-1,2-dihydro-2-oxo-1,8-naphthyridin-3-yl]-N'-(2,6-diisopropylphenyl)urea

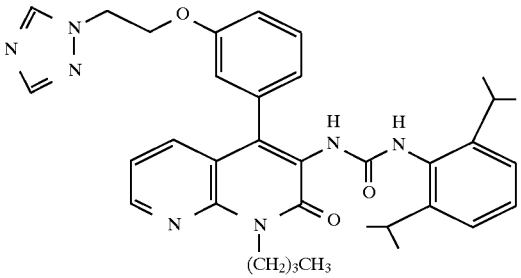

The title compound was obtained in the same manner as in Example 56 from N-[1-butyl-4-[3-{2-(p-toluenesulfonyloxy)ethoxy}phenyl]-1,2-dihydro-2-oxo-1,8-naphthyridin-3-yl]-N'-(2,6-diisopropylphenyl)urea and 1,2,4-triazole.

Hydrochloride: $^1$H-NMR δ (DMSO-d$_6$) 8.64 (1H, brs), 8.60 (1H, dd, J=4.6 Hz, 1.7 Hz), 8.04 (1H, brs), 7.79 (1H, brs), 7.76 (1H, brs), 7.58 (1H, dd, J=8.1 Hz, 1.7 Hz), 7.38 (1H, dd, J=7.9 Hz, 7.9 Hz), 7.24 (1H, dd, J=8.1 Hz, 4.6 Hz), 7.14 (1H, t, J=7.5 Hz), 6.98–7.03 (3H, m), 6.88–6.93 (2H, m), 4.59 (2H, m), 4.52 (2H, t, J=7.5 Hz), 2.85 (2H, m), 1.70 (2H, m), 1.43 (2H, m), 0.97 (15H, br)

EXAMPLE 163

Preparation of N-[1-butyl-4-{3-(2-propynyloxy) phenyl}-1,2-dihydro-2-oxo-1,8-naphthyridin-3-yl]-N'-(2,6-diisopropylphenyl)urea

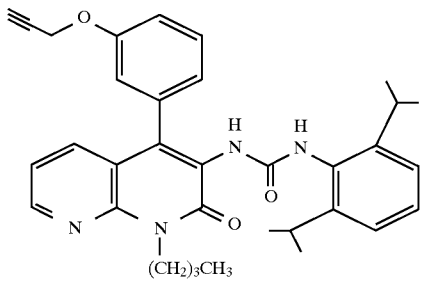

The title compound was obtained in the same manner as in Example 41 from N-[1-butyl-4-(3-hydroxyphenyl)-1,2-dihydro-2-oxo-1,8-naphthyridin-3-yl]-N'-(2,6-diisopropylphenyl)urea and propargyl bromide.

$^1$H-NMR δ (DMSO-d$_6$) 8.61 (1H, d, J=4.6 Hz), 7.77 (1H, s), 7.75 (1H, s), 7.64 (1H, d, J=6.3 Hz), 7.43 (1H, dd, J=8.3 Hz, 7.9 Hz), 7.25 (1H, dd, J=8.3 Hz, 4.6 Hz), 6.96–7.18 (6H, m), 4.79 (2H, d, J=2.3 Hz), 4.52 (2H, t, J=7.3 Hz), 3.60 (1H, s), 2.92 (2H, m), 1.70 (2H, m), 1.46 (2H, m), 1.03 (12H, br), 1.00 (3H, t, J=7.3 Hz)

EXAMPLE 164

Preparation of N-[1-butyl-4-[3-{(4-diethylamino-2-butynyl)oxy}phenyl]-1,2-dihydro-2-oxo-1,8-naphthyridin-3-yl]-N'-(2,6-diisopropylphenyl)urea

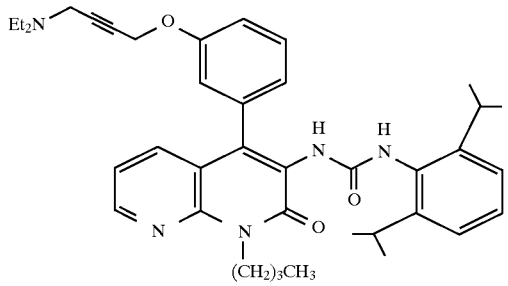

To a solution of N-[1-butyl-4-{3-(2-propynyloxy) phenyl}-1,2-dihydro-2-oxo-1,8-naphthyridin-3-yl]-N'-(2,6-diisopropylphenyl)urea (1.0 g, 1.82 mmol) in dioxane (10 ml) were added paraformaldehyde (0.37 g), diethylamine (0.26 g, 3.63 mmol) and copper (I) iodide, and the mixture was stirred at room temperature for two hours. To the mixture was added ether, and the mixture was filtered through a cerite pad. The filtrate was concentrated under reduced pressure, and the residue was purified by silica gel column chromatography (2% methanol in chloroform) to give the title compound (1.05 g, 1.65 mmol).

$^1$H-NMR δ (DMSO-d$_6$) 8.61 (1H, dd, J=4.2 Hz, 1.7 Hz), 7.78 (1H, brs), 7.76 (1H, brs), 7.62 (1H, dd, J=8.1 Hz, 1.5 Hz), 7.42 (1H, dd, J=7.9 Hz, 7.9 Hz), 7.24 (1H, dd, J=7.9 Hz, 4.6 Hz), 6.94–7.18 (5H, m), 4.81 (2H, brs), 4.53 (2H, t, J=7.4 Hz), 3.37 (2H, brs), 2.94 (2H, m), 2.33 (4H, q, J=7.2 Hz), 1.70 (2H, m), 1.44 (2H, m), 1.03 (12H, br), 0.97 (3H, t, J=7.3 Hz), 0.86 (6H, t, J=7.2 Hz)

EXAMPLE 165

Preparation of N-[1-butyl-4-[3-{(cis-4-diethylamino-2-butenyl)oxy}-phenyl]-1,2-dihydro-2-oxo-1,8-naphthyridin-3-yl]-N'-(2,6-diisopropylphenyl)urea

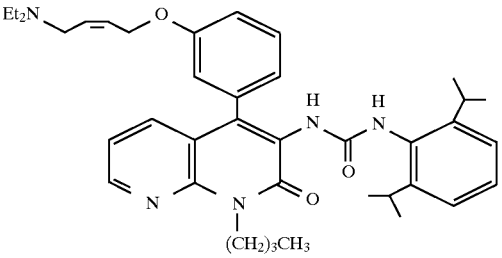

A suspension of N-[1-butyl-4-[3-{(4-diethylamino-2-butynyl)oxy}-phenyl]-1,2-dihydro-2-oxo-1,8-naphthyridin-3-yl]-N'-(2,6-diisopropylphenyl)urea (300 mg, 0.45 mmol), a Lindlar catalyst (distributed by Sigma Alderich Japan, 20 mg) in methanol (20 ml) was stirred at room temperature under hydrogen atmosphere for six hours. The mixture was filtered through a cerite pad, and the filtrate was concentrated under reduced pressure. The resultant was dissolved in chloroform, and the mixture was washed with a dilute aqueous ammonia, washed with water, washed with a saturated aqueous sodium chloride solution, dried over anhydrous magnesium sulfate, and concentrated under reduced pressure. The residue was purified by silica gel column chromatography (3–8% methanol in chloroform) to give the title compound (280 mg, 0.43 mmol).

$^1$H-NMR δ (DMSO-d$_6$) 8.62 (1H, dd, J=4.6 Hz, 1.8 Hz), 7.75 (1H, s), 7.62 (1H, dd, J=8.1 Hz, 1.8 Hz), 7.40 (1H, dd, J=8.1lHz, 8.1 Hz), 7.25 (1H, dd, J=8.8 Hz, 4.6 Hz), 7.15 (1H, t, J=7.6 Hz), 7.02–7.05 (3H, m), 6.90–6.93 (2H, m), 5.75 (1H, br), 5.67 (1H, dt, J=11.2 Hz, J=6.2 Hz), 4.65 (2H, br), 4.52 (2H, t, J=7.4 Hz), 3.13 (2H, br), 2.91 (2H, m), 2.45 (4H, br), 1.71 (2H, m), 1.42 (2H, m), 0.90–1.08 (2H, m)

EXAMPLE 166

Preparation of N-[1-butyl-4-{3-(cis-3-diethylamino-1-propenyl)phenyl}-1,2-dihydro-2-oxo-1,8-naphthyridin-3-yl]-N'-(2,6-diisopropylphenyl)urea

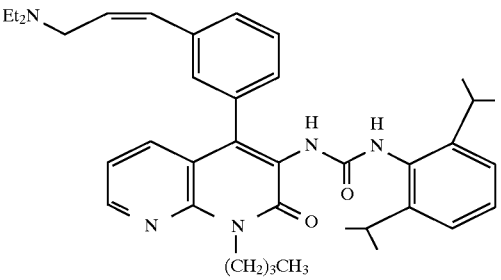

The title compound was obtained in the same manner as in Example 165 from N-[1-butyl-4-(3-diethylamino-1-propynylphenyl)-1,2-dihydro-2-oxo-1,8-naphthyridin-3-yl]-N'-(2,6-diisopropylphenyl)urea.

$^1$H-NMR δ (CD$_3$OD) 8.60 (1H, m), 7.66 (1H, d, J=6.6 Hz), 7.53 (1H, dd, J=7.7 Hz, 7.7 Hz), 7.38 (1H, d, J=7.5 Hz), 7.36 (2H, m), 7.15–7.22 (2H, m), 7.06 (2H, d, J=7.3 Hz), 6.72 (1H, d, J=11.6 Hz), 5.81 (1H, dt, J=11.6 Hz, 5.1 Hz), 4.64 (2H, b, J=7.5 Hz), 3.47 (2H, d, J=5.1 Hz), 2.90 (2H, br), 2.50 (4H, m), 1.80 (2H, m), 1.50 (2H, m), 0.92–1.09 (21H, m)

EXAMPLE 167

Preparation of N-[1-butyl-4-{3-(3-bromo-1-propynyl)phenyl}-1,2-dihydro-2-oxo-1,8-naphthyridin-3-yl]-N'-(2,6-diisopropylphenyl)urea

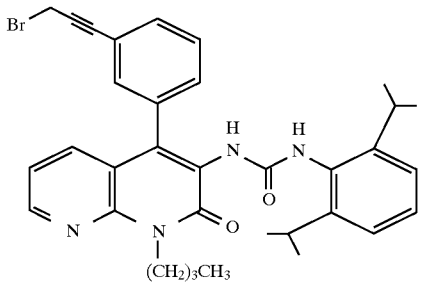

To a solution of N-[1-butyl-4-{3-(3-hydroxy-1-propynyl)phenyl}-1,2-dihydro-2-oxo-1,8-naphthyridin-3-yl]-N'-(2,6-diisopropylphenyl)urea (90 mg, 0.16 mmol) in methylene chloride (1.5 ml) were added carbon tetrabromide (81 mg, 0.245 mmol) and triphenylphosphine (51 mg, 0.196 mmol) under ice-cooling, and the mixture was stirred for 30 minutes. To the mixture was added water, and the mixture was extracted with ethyl acetate. The extract was washed with a saturated aqueous sodium chloride solution, dried over anhydrous magnesium sulfate, and concentrated under reduced pressure. The residue was purified by silica gel column chromatography (ethyl acetate:hexane: 1:5) to give the title compound (53 mg, 0.086 mmol).

$^1$H-NMR δ (CD$_3$OD) 8.58 (1H, d, J=3.9 Hz), 7.66 (lH, d, J=7.9 Hz), 7.38–7.56 (4H, m), 7.15–7.17 (2H, m), 7.07 (2H, d, J=7.5 Hz), 4.64 (2H, t, J=6.8 Hz), 4.27 (2H, s), 1.73–1.81 (2H, m), 1.42–1.52(2H, m), 1.10–1.11 (12H, m), 1.01 (3H, t, J=7.3 Hz)

EXAMPLE 168

Preparation of N-[1-butyl-4-[3-{3-(1-pyrrolidinyl)-1-propynyl}phenyl}-1,2-dihydro-2-oxo-1,8-naphthyridin-3-yl]-N'-(2,6-diisopropylphenyl)urea

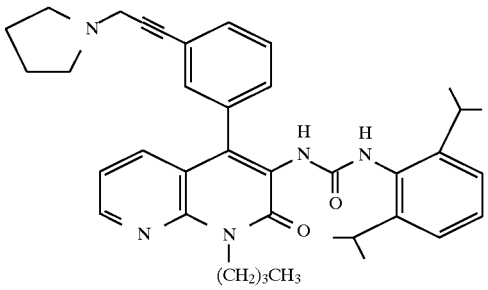

To a solution of N-[1-butyl-4-{3-(3-bromo-1-propynyl)phenyl}-1,2-dihydro-2-oxo-1,8-naphthyridin-3-yl]-N'-(2,6-diisopropylphenyl)urea (400 mg, 0.65 mmol) in THF (5 ml) was added pyrrolidine (139 mg, 1.96 mmol), and the mixture was stirred at room temperature for four hours. To the mixture was added water, and the mixture was extracted with ethyl acetate. The extract was washed with water, washed with a saturated aqueous sodium chloride solution, dried over anhydrous magnesium sulfate, and concentrated under reduced pressure. The residue was purified by silica gel chromatography (ethyl acetate) to give the title compound (340 mg, 0.56 mmol).

Hydrochloride: 1H-NMR δ (DMSO-d$_6$) 11.04 (1H, br), 8.62 (1H, d, J=4.6 Hz), 8.01 (1H, brs), 7.90 (1H, brs), 7.41–7.61 (5H, m), 7.27 (1H, dd, J=7.9 Hz, 4.6 Hz), 7.16 (1H, t, J=7.5 Hz), 7.03 (2H, d, J=7.5 Hz), 4.54 (2H, t, J=7.5 Hz), 4.38 (2H, s), 3.53 (2H, br), 3.14 (2H, br), 2.89 (2H, br), 2.00 (4H, br), 1.73 (2H, m), 1.43 (2H, m), 0.95–1.09 (15H, m)

EXAMPLE 169

Preparation of N-[1-butyl-4-[3-{3-(N,N-dihexylamine)-1-propynyl)-phenyl}-1,2-dihydro-2-oxo-1,8-naphthyridin-3-yl]-N'-(2,6-diisopropylphenyl)urea

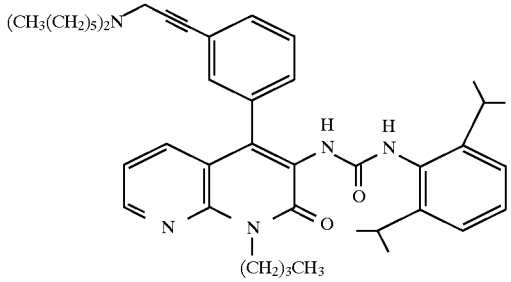

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and dihexylamine.

Hydrochloride: $^1$H-NMR δ (DMSO-d$_6$) 8.61 (1H, m), 8.04 (1H, brs), 7.90 (1H, brs), 7.42–7.59 (5H, m), 7.26 (1H, m), 7.15 (1H, t, J=7.2 Hz), 7.02 (2H, d, J=7.2 Hz), 4.54 (2H, t, J=7.7 Hz), 4.35 (2H, br), 3.14 (4H, br), 2.77 (2H, br), 1.70 (6H, br), 1.43 (2H, m), 1.28 (12H, br), 0.95–1.03 (15H, m), 0.83 (6H, br)

EXAMPLE 170

Preparation of N-[1-butyl-4-[3-{3-(N-benzyl-N-ethylamino)-1-propynyl}-phenyl]-1,2-dihydro-2-oxo-1,8-naphthyridin-3-yl]-N'-(2,6-diisopropylphenyl)urea

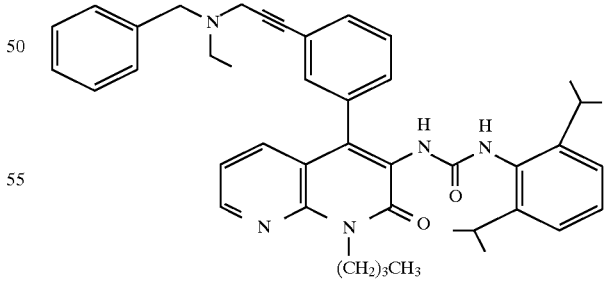

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and N-ethylbenzylamine.

Hydrochloride: $^1$H-NMR δ (DMSO-d$_6$) 11.16 (1H, br), 8.62 (1H, d, J=4.2 Hz), 8.03 (1H, brs), 7.91 (1H, brs), 7.45–7.63 (10H, m), 7.37 (1H, dd, J=7.7 Hz, J=4.4 Hz), 7.15 (1H, t, J=7.5 Hz), 7.03 (2H, d, J=7.5 Hz), 4.55 (2H, t, J=7.4 Hz), 4.26–4.43 (3H, m), 4.10 (1H, brd, J=18 Hz), 3.21 (2H, br), 2.80 (2H, m), 1.73 (2H, m), 1.43 (2H, m), 1.32 (3H, br), 0.96–1.08 (15H, m)

EXAMPLE 171

Preparation of N-[1-butyl-4-[3-{3-(1-piperidinyl)-1-propynyl)phenyl}-1,2-dihydro-2-oxo-1,8-naphthyridin-3-yl]-N'-(2,6-diisopropylphenyl)urea

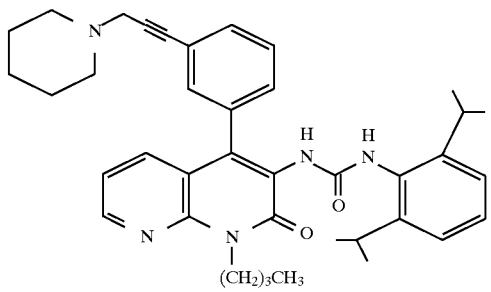

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and piperidine.

Hydrochloride: m.p. 160°–162° C.

EXAMPLE 172

Preparation of N-[1-butyl-4-[3-{3-(4-methyl-1-piperazinyl)-1-propynyl}-phenyl]-1,2-dihydro-2-oxo-1,8-naphthyridin-3-yl]-N'-(2,6-diisopropylphenyl)urea

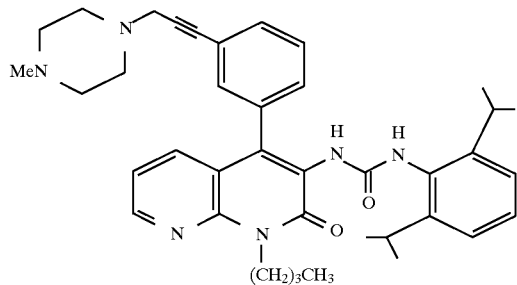

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and 1-methylpiperazine.

Hydrochloride: m.p. 157°–161° C.

EXAMPLE 173

Preparation of N-[1-butyl-4-[3-{3-(N,N-dibenzylamino)-1-propynyl}-phenyl]-1,2-dihydro-2-oxo-1,8-naphthyridin-3-yl]-N'-(2,6-diisopropylphenyl)urea

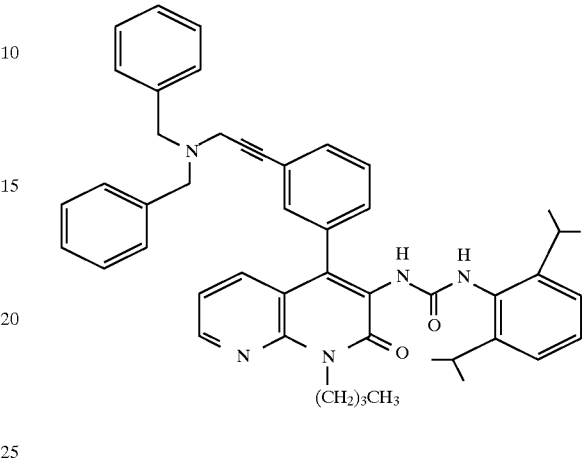

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and dibenzylamine.

Hydrochloride: IR (KBr) 2962, 2870, 1704, 1646, 1585, 1500, 1456 cm$^{-1}$

EXAMPLE 174

Preparation of N-[1-butyl-4-[3-{3-(1-homopiperidinyl)-1-propynyl}-phenyl]-1,2-dihydro-2-oxo-1,8-naphthyridin-3-yl]-N'-(2,6-diisopropylphenyl)urea

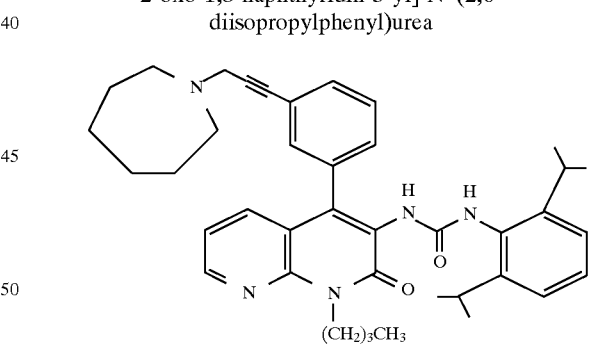

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and homopiperidine.

Hydrochloride: $^1$H-NMR δ (DMSO-$d_6$) 10.88 (1H, br), 8.62 (1H, dd, J=4.6 Hz, 1.7 Hz), 8.02 (1H, brs), 7.91 (1H, brs), 7.51–7.62 (3H, m), 7.49 (1H, br), 7.42 (1H, d, J=7.5 Hz), 7.26 (1H, dd, J=8.1 Hz, 4.6 Hz), 7.15 (1H, t, J=7.5 Hz), 7.03 (2H, d, J=7.5 Hz), 4.54 (2H, t, J=7.3 Hz), 4.34 (2H, d, J=4.2 Hz), 3.48 (2H, m), 3.20 (3H, m), 2.79 (2H, br), 1.85 (4H, br), 1.57–1.78 (6H, m), 1.43 (2H, m), 0.96–1.03 (15H, m)

EXAMPLE 175

Preparation of N-[1-butyl-4-[3-{3-(4-benzyl-1-piperazinyl)-1-propynyl}-phenyl]-1,2-dihydro-2-oxo-1,8-naphthyridin-3-yl]-N'-(2,6-diisopropylphenyl)urea

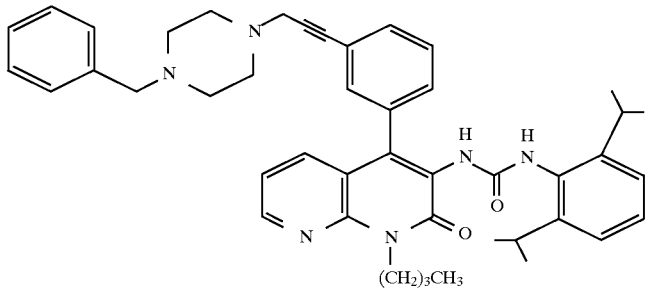

The title compound was obtained in the same manner as in Example 168 from N-[1-butyl-4-{3-(3-bromo-1propynyl)phenyl}-1,2-dihydro-2-oxo-1,8-naphthyridin-3-yl]-N'-(2,6-diisopropylphenyl)urea and 1-benzylpiperazine.

Hydrochloride: $^1$H-NMR δ (DMSO-$d_6$) 8.61 (1H, dd, J=4.6 Hz, 1.3 Hz), 7.96 (1H, brs), 7.91 (1H, brs), 7.37–7.64 (11H, m), 7.26 (1H, dd, J=7.9 Hz, 4.6 Hz), 7.15 (1H, t, J=7.7 Hz), 7.03 (2H, d, J=7.7 Hz), 4.53 (2H, t, J=7.2 Hz), 4.33 (2H, br), 4.04 (2H, br), 3.23–3.37 (8H, br), 2.81 (2H, m), 1.74 (2H, m), 1.42 (2H, m), 0.95–1.03 (15H, m)

EXAMPLE 176

Preparation of N-[1-butyl-4-[3-{3-(3-azabicyclo[3.3.2]nonan-3-yl)-1-propynyl}phenyl]-1,2-dihydro-2-oxo-1,8-naphthyridin-3-yl]-N'-(2,6-diisopropylphenyl)urea

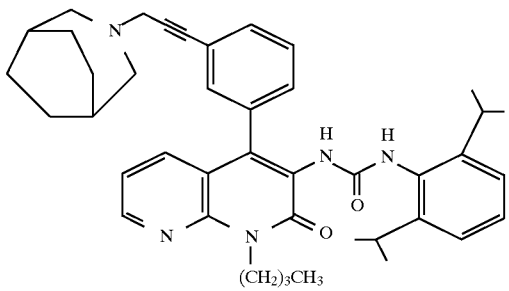

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and 3-azabicyclo[3.3.2]-nonane.

Hydrochloride: m.p. 171°–176° C.

EXAMPLE 177

Preparation of N-[1-butyl-4-[3-{3-(N-ethyl-N-propylamino)-1-propynyl}-phenyl]-1,2-dihydro-2-oxo-1,8-naphthyridin-3-yl]-N'-(2,6-diisopropylphenyl)urea

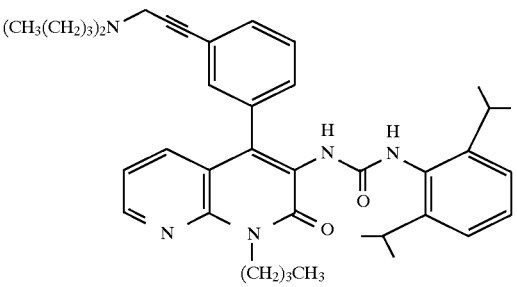

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and N-ethylpropylamine.

Hydrochloride: m.p. 163°–166.5° C.

EXAMPLE 178

Preparation of N-[1-butyl-4-[3-{3-(dibutylamino)-1-propynyl}phenyl]-1,2-dihydro-2-oxo-1,8-naphthyridin-3-yl]-N'-(2,6-diisopropylphenyl)urea The title compound was obtained in the same manner as in Example 168 from N-[1-butyl-4-{3-(3-bromo-1- propynyl)phenyl}-1,2-dihydro-2-oxo-1,8-naphthyridin-3-yl]-N'-(2,6-diisopropylphenyl)urea and dibutylamine.

Hydrochloride: m.p. 138°–141.5° C.

EXAMPLE 179

Preparation of N-[1-butyl-4-[3-{3-(diisopropylamino)-1-propynyl}phenyl]-1,2-dihydro-2-oxo-1,8-naphthyridin-3-yl]-N'-(2,6-diisopropylphenyl)urea

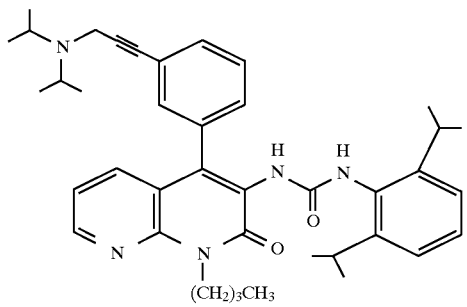

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and diisopropylamine.

Hydrochloride: m.p. 152°–154° C.

EXAMPLE 180

Preparation of N-[1-butyl-4-[3-{3-di(2-ethoxyethyl)amino-1-propynyl}phenyl]-1,2-dihydro-2-oxo-1,8-naphthyridin-3-yl]-N'-(2,6-diisopropylphenyl)urea

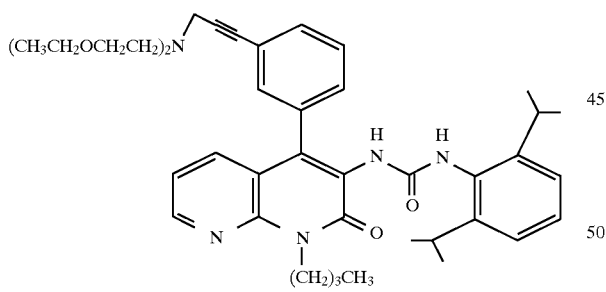

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and di(2-ethoxyethyl)amine.

Hydrochloride: $^1$H-NMR δ (DMSO-$d_6$) 10.68 (1H, br), 8.62 (1H, d, J=4.6 Hz), 8.03 (1H, brs), 7.91 (1H, brs), 7.51–7.61 (3H, m), 7.49 (1H, brs), 7.43 (1H, d, J=7.0 Hz), 7.26 (1H, dd, J=7.9 Hz, 4.6 Hz), 7.15 (1H, t, J=7.7 Hz), 7.03 (2H, d, J=7.7 Hz), 4.54 (2H, t, J=7.3 Hz), 4.41 (2H, brs), 3.76 (4H, brs), 3.45–3.52 (8H, m), 2.80 (2H, br), 1.73 (2H, m), 1.45 (2H, m), 1.12 (6H, t, J=7.0Hz), 0.95–1.03 (15H, m)

EXAMPLE 181

Preparation of N-[1-butyl-4-(4-bromophenyl)-1,2-dihydro-2-oxo-1,8-naphthyridin-3-yl]-N'-(2,6-diisopropylphenyl)urea

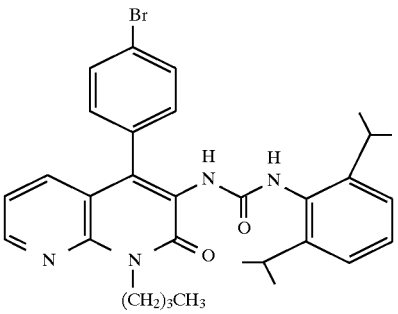

The title compound was obtained in the same manner as in Example 5 from 1-butyl-4-(4-bromophenyl)-1,2-dihydro-2-oxo-1,8-naphthyridine-3-carboxylic acid and 2,6-diisopropylaniline.

m.p. 193°–195° C.

EXAMPLE 182

Preparation of N-[1-butyl-4-{4-(3-diethylamino-1-propynyl)phenyl}-1,2-dihydro-2-oxo-1,8-naphthyridin-3-yl]-N'-(2,6-diisopropylphenyl)urea

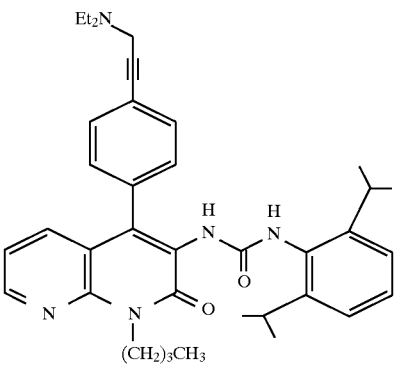

The title compound was obtained in the same manner as in Example 99 from N-[1-butyl-4-(4-bromophenyl)-1,2-dihydro-2-oxo-1,8-naphthyridin-3-yl]-N'-(2,6-diisopropylphenyl)urea and 3-diethylamino-1-propyne.

Hydrochloride: m.p. 208°–210° C.

EXAMPLE 183

Preparation of N-[1-butyl-4-[3-{3-(morpholin-4-yl)-1-propynyl)phenyl}-1,2-dihydro-2-oxo-1,8-naphthyridin-3-yl]-N'-(2,6-diisopropylphenyl)urea

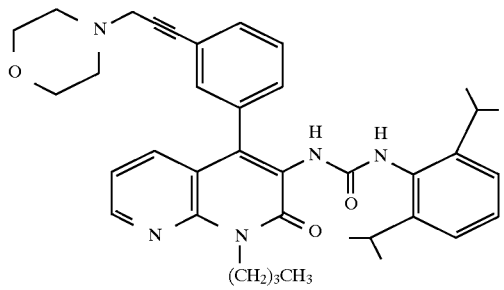

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea.

Hydrochloride: m.p. 212°–214° C.

EXAMPLE 184

Preparation of N-[1-butyl-4-{3-(3-hexylamino-1-propynyl)phenyl}-1,2-dihydro-2-oxo-1,8-naphthyridin-3-yl]-N'-(2,6-diisopropylphenyl)urea

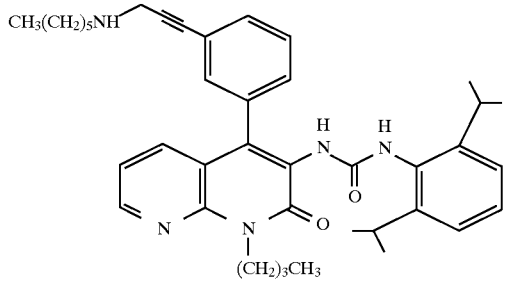

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and hexylamine.

Hydrochloride: m.p. 187°–189° C.

EXAMPLE 185

Preparation of N-[1-butyl-4-{3-(4-phthalimido-1-butynyl)phenyl}-1,2-dihydro-2-oxo-1,8-naphthyridin-3-yl]-N'-(2,6-diisopropylphenyl)urea

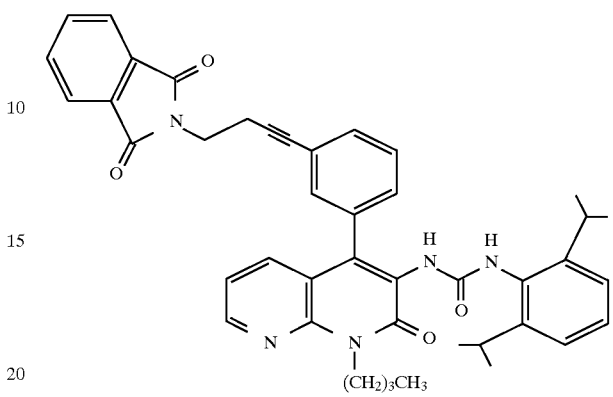

The title compound was obtained in the same manner as in Example 99 from N-[1-butyl-4-(3-bromophenyl)-1,2-dihydro-2-oxo-1,8-naphthyridin-3-yl]-N'-(2,6-diisopropylphenyl)urea and 4-phthalimido-1-butyne.

$^1$H-NMR δ (OD$_3$OD) 8.61 (1H, dd, J=4.8 Hz, 1.7 Hz), 7.78–7.85 (3H, m), 7.71–7.74 (1H, m), 7.62 (1H, dd, J=8.1 Hz, 1.7 Hz), 7.39–7.42 (2H, m), 7.14–7.31 (5H, m), 7.03 (2H, d, J=7.5 Hz), 4.64 (2H, t, J=7.7 Hz), 3.94 (2H, t, J=6.8 Hz), 2.84 (2H, t, J=5.0 Hz), 1.77–1.80 (2H, m), 1.46–1.54 (2H, m). 1.00–1.18 (15H, m)

EXAMPLE 186

Preparation of N-[1-butyl-4-{3-(4-amino-1-butynyl)phenyl}-1,2-dihydro-2-oxo-1,8-naphthyridin-3-yl]-N'-(2,6-diisopropylphenyl)urea

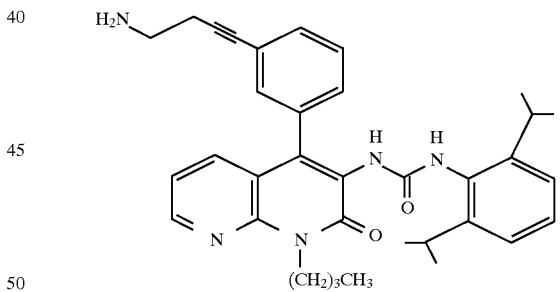

To a solution of N-[1-butyl-4-{3-(4-phthalimido-1-butynyl)phenyl}-1,2-dihydro-2-oxo-1,8-naphthyridin-3-yl]-N'-(2,6-diisopropylphenyl)urea (50 mg, 0.072 mmol) in ethanol (1 ml) was added 30% methylamine ethanol solution (1.0 ml), and the mixture was stirred at room temperature. The mixture was concentrated under reduced pressure to remove the solvent, and the residue was purified by silica gel column chromatography (5% methanol in chloroform) to give the title compound (33 mg, 0.058 mmol).

$^1$H-NMR δ (OD$_3$OD) 8.49 (1H, dd, J=4.6 Hz, 1.7 Hz), 7.56 (1H, dd, J=8.1 Hz, 1.7 Hz), 7.31–7.43 (3H, m), 7.23 (1H, d, J=7.3 Hz), 7.01–7.12 (2H, m), 6.97 (2H, d, J=7.3 Hz), 4.52 (2H, t, J=7.5 Hz), 2.47 (2H, t, J=6.4 Hz), 1.63–1.73 (2H, m), 1.33–1.45 (2H, m), 1.00 (12H, d, J=6.4 Hz), 0.91 (3H, t, J=7.3 Hz)

EXAMPLE 187

Preparation of N-[1-butyl-4-{3-(3-cyclohexylamino-1-propynyl)phenyl}-1,2-dihydro-2-oxo-1,8-naphthyridin-3-yl]-N'-(2,6-diisopropylphenyl)urea

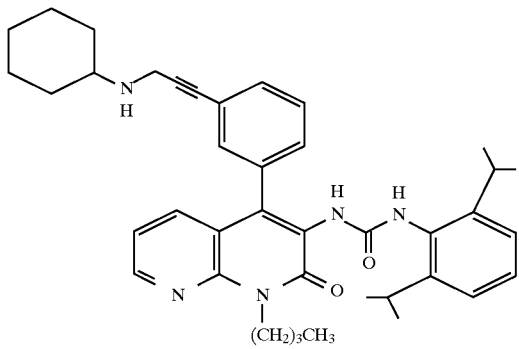

The title compound was obtained in the same manner as in Example 168 from N-[1-butyl-4-{3-(3-bromo-1-propynyl)phenyl)-1,2-dihydro-2-oxo-1,8-naphthyridin-3-yl]-N'-(2,6-diisopropylphenyl)urea and cyclohexylamine.

Hydrochloride: m.p. 186°–187° C.

EXAMPLE 188

Preparation of N-[1-butyl-4-[3-{3-(3-pyridylmethylamino)-1-propynyl}phenyl]-1,2-dihydro-2-oxo-1,8-naphthyridin-3-yl]-N'-(2,6-diisopropylphenyl)urea

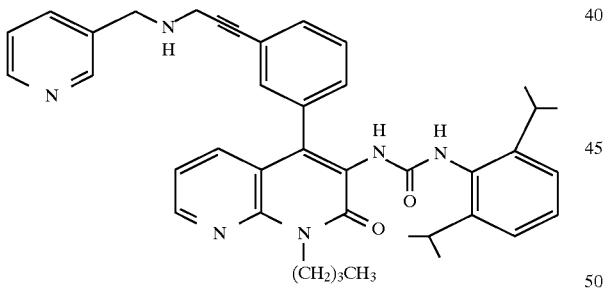

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and 3-(aminomethyl)pyridine.

Hydrochloride: $^1$H-NMR δ (DMSO-$d_6$) 10.29 (2H, brs), 8.98 (1H, s), 8.79 (1H, s), 8.63 (1H, d, J=3.9 Hz), 8.46 (1H, d, J=7.3 Hz), 8.03 (1H, s), 7.97 (1H, s), 7.83 (1H, dd, J=7.0 Hz, 7.0 Hz), 7.53–7.59 (3H, m), 7.48 (1H, s), 7.42 (1H, d, J=7.2 Hz), 7.28 (1H, dd, J=7.9 Hz, 5.0 Hz), 7.16 (1H, dd, J=7.3 Hz, 7.3 Hz), 7.03 (2H, d, J=7.3 Hz), 4.54 (2H, t, J=7.5 Hz), 4.42 (2H, s), 4.21 (2H, s), 4.20 (2H, s), 2.80 (2H, brs) 1.76 (2H, m), 1.40–1.47 (2H, m), 0.95–1.03 (15H, m)

EXAMPLE 189

Preparation of N-[1-butyl-4-[3-{3-(2-diethylaminoethyl)amino-1-propynyl}phenyl]-1,2-dihydro-2-oxo-1,8-naphthyridin-3-yl]-N'-(2,6-diisopropylphenyl)urea

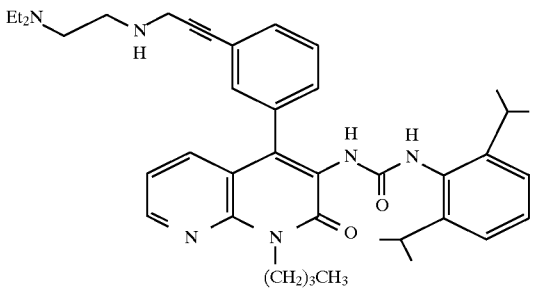

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and N,N-diethylethylenediamine.

Hydrochloride: $^1$H-NMR δ (CD$_3$OD) 8.62 (1H, dd, J=4.6 Hz, 1.7 Hz), 7.54–7.66 (4H, m), 7.47 (1H, d, J=7.7 Hz), 7.22 (1H, dd, J=8.1 Hz, 4.6 Hz), 7.17 (1H, d, J=7.7 Hz 7.08 (2H, d, J=7.5 Hz), 4.65 (2H, t, J=7.5 Hz), 4.30 (2H, s), 3.65 (2H, t, J=7.9 Hz), 3.51 (2H, t, J=7.7 Hz), 2.87 (2H, brd), 1.77–1.87 (2H, m), 1.46–1.54 (2H, m), 1.29–1.40 (6H, m), 1.02–1.10 (15H, m)

EXAMPLE 190

Preparation of N-[1-butyl-4-{3-(3-ethylamino-1-propynyl)phenyl}-1,2-dihydro-2-oxo-1,8-naphthyridin-3-yl]-N'-(2,6-diisopropylphenyl)urea

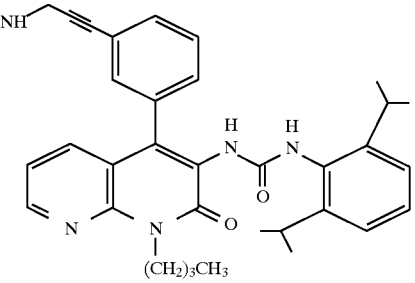

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and ethylamine.

Hydrochloride: 158°–160° C.

EXAMPLE 191

Preparation of N-[1-butyl-4-{3-(4-diethylamino-1-butynyl)phenyl}-1,2-dihydro-2-oxo-1,8-naphthyridin-3-yl]-N'-(2,6-diisopropylphenyl)urea

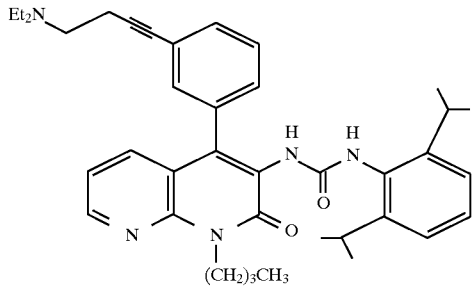

The title compound was obtained in the same manner as in Example 155 from N-[1-butyl-4-{3-(4-amino-1-butynyl)phenyl}-1,2-dihydro-2-oxo-1,8-naphthyridin-3-yl]-N'-(2,6-diisopropylphenyl)urea and iodoethyl.

Hydrochloride: $^1$H-NMR δ (DMSO-$d_6$) 10.44 (1H, brs), 8.62 (1H, d, J=4.4 Hz), 7.97 (1H, s), 7.89 (1H, s), 7.55 (1H, d, J=7.7 Hz), 7.49 (2H, d, J=4.4 Hz), 7.26 (1H, dd, J=7.7 Hz, 4.4 Hz), 7.16 (1H, dd, J=7.7 Hz, 7.7 Hz), 7.03 (2H, d, J=7.7 Hz), 4.54 (2H, t, J=7.2 Hz), 3.29 (2H, m), 3.15–3.17 (4H, m), 3.00 (2H, t, J=7.3 Hz), 2.82 (2H, brs), 1.73 (2H, m), 1.40–1.47 (2H, m), 1.22 (6H, t, J=7.3 Hz), 0.95–1.04 (15H, m)

EXAMPLE 192

Preparation of N-[1-butyl-4-[3-{3-(2-pyridylmethylamino)-1-propynyl}-phenyl]-1,2-dihydro-2-oxo-1,8-naphthyridin-3-yl]-N'-(2,6-diisopropylphenyl)-urea

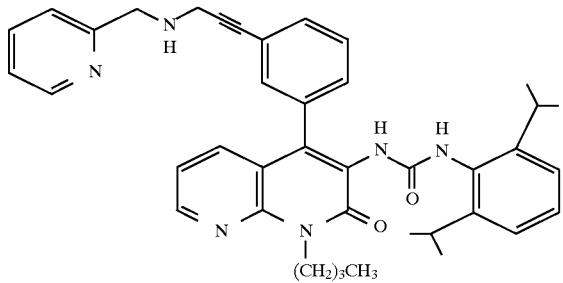

The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and 2-(aminomethyl)-pyridine.

Hydrochloride: $^1$H-NMR δ (CD$_3$OD) 8.59–8.64 (2H, m), 7.85 (1H, ddd, J=7.9 Hz, 7.9 Hz, J=1.84 Hz), 7.63 (1H, d, J=6.4 Hz), 7.39–7.62 (6H, m), 7.22 (1H, dd, J=7.9 Hz, J=5.5 Hz), 7.18 (1H, dd, J=7.7 Hz, 7.7 Hz), 7.07 (2H, d, J=5.5 Hz), 4.65 (2H, t, J=7.7 Hz), 4.50 (2H, s), 4.28 (2H, s), 2.88 (2H, brd), 1.72–1.82 (2H, m), 1.44–1.54 (2H, m), 1.08 (12H, m), 1.03 (3H, t, J=7.5 Hz)

EXAMPLE 193

Preparation of N-[1-butyl-4-[3-{3-(4-pyridylmethylamino)-1-propynyl}-phenyl]-1,2-dihydro-2-oxo-1,8-naphthyridin-3-yl]-N'-(2,6-diisopropylphenyl)-urea The title compound was obtained in the same manner as in Example 168 from N-[1-butyl-4-{3-(3-bromo-1-propynyl)phenyl}-1,2-dihydro-2-oxo-1,8-naphthyridin-3-yl]-N'-(2,6-diisopropylphenyl)urea and 4-(aminomethyl)-pyridine.

Hydrochloride: $^1$H-NMR δ (CD$_3$OD) 8.88 (2H, d, J=4.6 Hz), 8.61 (1H, d, J=9.4 Hz), 8.18 (2H, d, J=4.6 Hz), 7.55–7.63 (4H, m), 7.48 (1H, d, J=7.7 Hz), 7.22 (1H, dd, J×7.9 Hz, J=4.4 Hz), 7.17 (2H, d, J=7.9 Hz), 7.07 (2H, d, J=7.9 Hz), 4.70 (2H, s), 4.65 (2H, t, J=7.9 Hz), 4.35 (2H, s), 2.86 (2H, br), 1.80 (2H, m), 1.49–1.52 (2H, m), 1.09 (12H, brs), 1.03 (3H, t, J=7.3 Hz)

EXAMPLE 194

Preparation of N-[1-butyl-4-[3-{3-(N-(3-pyridylmethyl)-N-methylamino)-1-propynyl}-phenyl]-1,2-dihydro-2-oxo-1,8-naphthyridin-3-yl]-N'-(2,6-diisopropylphenyl)urea The title compound was obtained in the same manner as in Example 67 from N-[1-butyl-4-[3-{3-(3-pyridylmethylamino)-1-propynyl}phenyl]-1,2-dihydro-2-oxo-1,8-naphthyridin-3-yl]-N'-(2,6-diisopropylphenyl)urea and formaldehyde.

Hydrochloride: $^1$H-NMR δ (CD$_3$OD) 9.04 (1H, m), 8.73 (1H, m), 8.62 (1H, d, J=5.1 Hz), 7.94 (1H, m), 7.57–7.67 (4H, m), 7.49 (1H, d, J=8.3 Hz), 7.16–7.25 (3H, m), 7.09 (2H, m), 4.64–4.68 (4H, m), 4.38 (2H, s), 2.85 (2H, br), 3.02 (3H, s), 1.80–1.87 (2H, m), 1.46–1.52 (2H, m), 1.00–1.09 (12H, m), 1.03 (3H, t, J=7.3 Hz)

EXAMPLE 195

Preparation of N-[1-butyl-4-[3-{3-(N-(2-pyridylmethyl)-N-methylamino)-1-propynyl}-phenyl]-1,2-dihydro-2-oxo-1,8-naphthyridin-3-yl]-N'-(2,6-diisopropylphenyl)urea

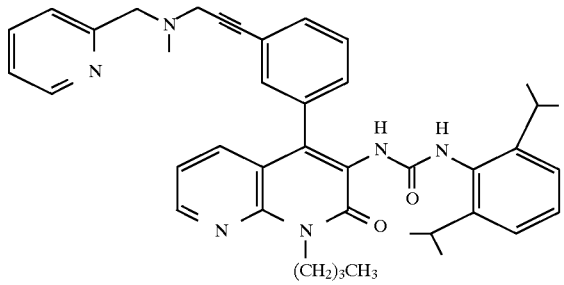

The title compound was obtained in the same manner as in Example 67 from N-[1-butyl-4-[3-{3-(2-pyridylmethylamino)-1-propynyl}phenyl]-1,2-dihydro-2-oxo-1,8-naphthyridin-3-yl]-N'-(2,6-diisopropylphenyl)urea and formaldehyde.

Hydrochloride: $^1$H-NMR δ (CD$_3$OD) 8.69 (1H, d, J=4.2 Hz), 8.62 (1H, d, J=3.3 Hz), 7.92 (1H, d, J=7.9 Hz), 7.49–7.68 (7H, m), 7.16–7.21 (2H, m), 7.08 (2H, m), 4.66 (2H, t, J=7.7 Hz), 4.62 (2H, s), 4.40 (2H, s), 3.02 (2H, br), 3.02 (3H, s), 1.80 (2H, m, 1.49–1.52 (2H, m), 1.08 (12H, brs), 1.03 (3H, t, J=7.3 Hz)

EXAMPLE 196

Preparation of N-[1-butyl-4-[3-{3-(N-(4-pyridylmethyl)-N-methylamino)-1-propynyl}-phenyl]-1,2-dihydro-2-oxo-1,8-naphthyridin-3-yl]-N'-(2,6-diisopropylphenyl)urea

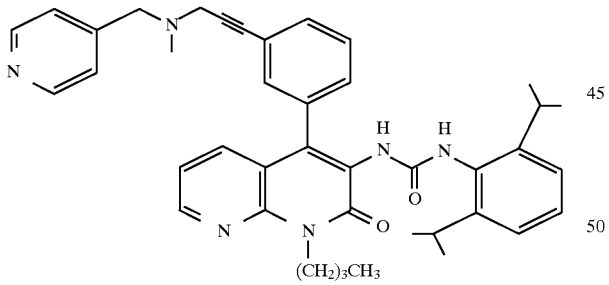

The title compound was obtained in the same manner as in Example 67 from N-[1-butyl-4-[3-{3-(4-pyridylmethylamino)-1-propynyl}phenyl]-1,2-dihydro-2-oxo-1,8-naphthyridin-3-yl]-N'-(2,6-diisopropylphenyl)urea and formaldehyde.

Hydrochloride: $^1$H-NMR δ (CD$_3$OD) 8.87 (2H, d, J=5.7 Hz), 8.62 (1H, d, J=4.8 Hz), 8.27 (2H, d, J=5.7 Hz), 7.56–7.70 (4H, m), 7.49 (1H, d, J=7.5 Hz), 7.23 (1H, dd, J=9.2 Hz, 7.2 Hz), 7.21 (1H, dd, J=6.8 Hz, 6.8 Hz), 7.07 (2H, d, J=8.4 Hz), 4.75 (2H, s), 4.66 (2H, t, J=7.2 Hz), 4.38 (2H, s), 3.03 (3H, s), 1.80 (2H, m), 1.52 (2H, m), 1.05–1.08 (12H, m), 1.03 (3H, t, J=7.3 Hz)

EXAMPLE 197

Preparation of N-[1-butyl-4-{3-(3-diethylamino-1-propynyl)phenyl}-1,2-dihydro-2-oxo-1,8-naphthyridin-3-yl]-N'-(2-isopropylphenyl)urea

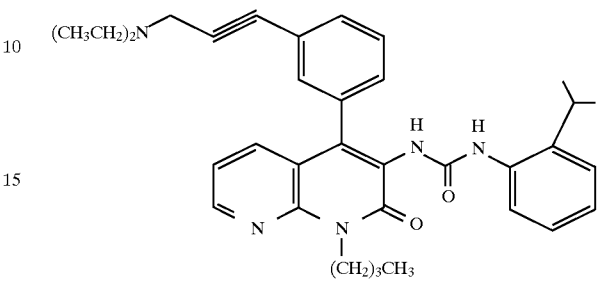

The title compound was obtained in the same manner as in Example 99 from N-[1-butyl-4-(3-bromophenyl)-1,2-dihydro-2-oxo-1,8-naphthyridin-3-yl]-N'-(2-isopropylphenyl)urea and 3-diethylamino-1-propynyl.

Hydrochloride: m.p. 138°–140° C.

EXAMPLE 198

Preparation of N-[1-butyl-4-{3-(3-diethylamino-1-propynyl)phenyl}-1,2-dihydro-2-oxo-1,8-naphthyridin-3-yl]-N'-(2,4,6-trimethylphenyl)urea

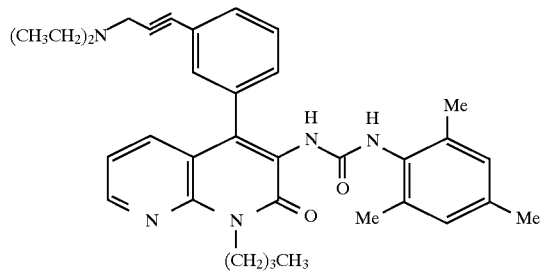

The title compound was obtained in the same manner as in Example 99 from N-[1-butyl-4-(3-bromophenyl)-1,2-dihydro-2-oxo-1,8-naphthyridin-3-yl]-N'-(2,4,6-trimethylphenyl)urea and 3-diethylamino-1-propynyl.

$^1$H-NMR δ (DMSO-d$_6$) 8.61 (1H, dd, J=4.8 Hz, 1.8 Hz), 7.76 (1H, s), 7.56–7.63 (2H, m), 7.47 (2H, d, J=5.1 Hz), 7.32–7.38 (2H, m), 7.25 (1H, dd, J=9.8 Hz, 7.9 Hz), 6.77 (2H, s), 4.51 (2H, brs), 3.59 (2H, s), 2.17 (3H, s), 1.92 (6H, s), 1.71 (2H, brs), 1.38–1.46 (2H, m), 1.01 (6H, t, J=7.2 Hz), 0.97 (3H, t, J=7.2 Hz)

EXAMPLE 199

Preparation of N-[1-butyl-4-{3-(3-diethylamino-1-propynyl)phenyl}-1,2-dihydro-2-oxo-1,8-naphthyridin-3-yl]-N'-(2,4,6-trifluorophenyl)urea

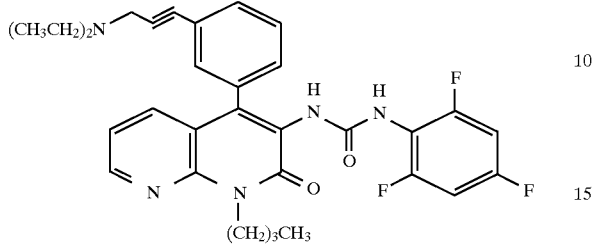

The title compound was obtained in the same manner as in Example 99 from N-[1-butyl-4-(3-bromophenyl)-1,2-dihydro-2-oxo-1,8-naphthyridin-3-yl]-N'-(2,4,6-trifluorophenyl)urea and 3-diethylamino-1-propynyl.

$^1$H-NMR δ (CD$_3$OD) 8.61 (1H, dd, J=4.8 Hz, 1.8 Hz), 7.67 (1H, dd, J=8.1 Hz, 1.8 Hz), 7.44–7.55 (4H, m), 7.35 (1H, ddd, J=7.0 Hz, 2.0 Hz, 2.0 Hz), 7.22 (1H, dd, J=8.1 Hz, 4.8 Hz), 6.84 (1H, dd, J=9.0 Hz, 7.5 Hz), 4.61 (2H, t, J=7.5 Hz), 3.67 (2H, s), 2.67 (2H, q, J=7.2 Hz), 1.72–1.82 (2H, m), 1.41–1.54 (2H, m), 1.12 (6H, t, J=7.3 Hz), 1.00 (3H, t, J=7.2 Hz)

EXAMPLE 200

Preparation of N-[1-butyl-4-{3-(3-diethylamino-1-propynyl)phenyl}-1,2-dihydro-2-oxo-1,8-naphthyridin-3-yl]-N'-(2,4-difluorophenyl)urea

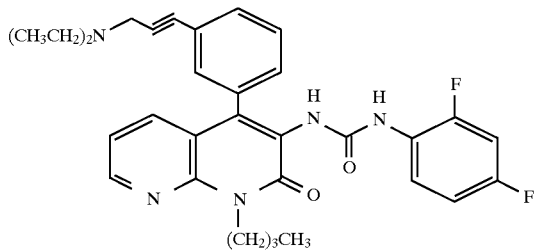

The title compound was obtained in the same manner as in Example 99 from N-[1-butyl-4-(3-bromophenyl)-1,2-dihydro-2-oxo-1,8-naphthyridin-3-yl]-N'-(2,4-difluorophenyl)urea and 3-diethylamino-1-propynyl.

$^1$H-NMR δ (CD$_3$OD) 8.60 (1H, dd, J=4.6 Hz, 1.7 Hz), 7.76 (1H, ddd, J=9.2 Hz, 9.2 Hz, 5.9 Hz), 7.65 (1H, dd, J=8.1 Hz, 1.8 Hz), 7.45–7.51 (3H, m), 7.33–7.37 (1H, m), 7.21 (1H, dd, J=7.9 Hz, 4.6 Hz), 6.89 (1H, ddd, J=8.6 Hz, 8.6 Hz, 2.8 Hz), 6.77 (1H, dd, J=8.1 Hz, 8.1 Hz), 4.56 (2H, t, J=7.9 Hz), 3.61 (2H, s), 2.60 (4H, q, J=7.3 Hz), 1.69–1.76 (2H, m), 1.41–1.48 (2H, m), 1.07 (6H, t, J=7.2 Hz), 0.98 (3H, t, J=7.5 Hz)

EXAMPLE 201

Preparation of N-[1-butyl-4-(3-bromophenyl)-1,2-dihydro-2-oxo-1,8-naphthyridin-3-yl]-N'-(2-isopropylphenyl)urea

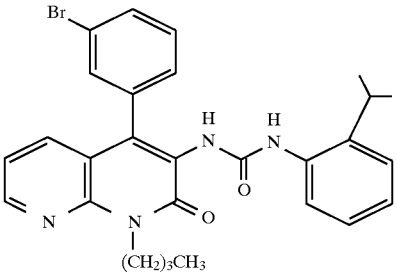

The title compound was obtained in the same manner as in Example 5 from 1-butyl-4-(3-bromophenyl)-1,2-dihydro-2-oxo-1,8-naphthyridine-3-carboxylic acid and 2-isopropylaniline.

$^1$H-NMR δ (DMSO-d$_6$) 8.63 (1H, dd, J=4.8 Hz, 1.7 Hz), 8.13 (1H, s), 8.08 (1H, s), 7.60–7.65 (2H, m), 7.57 (1H, s), 7.47 (1H, dd, J=7.7 Hz, 7.7 Hz), 7.73 (1H, d, J=7.7 Hz), 7.28 (1H, dd, J=8.1 Hz, 4.8 Hz), 7.17–7.22 (2H, m), 7.04–7.07 (2H, m), 4.53 (2H, t, J=7.2 Hz), 2.92 (1H, sep, J=6.8 Hz), 1.66–1.68 (2H, m), 1.28–1.41 (2H, m), 1.00 (12H, brs), 0.94 (3H, t, J=7.2 Hz)

EXAMPLE 202

Preparation of N-[1-butyl-4-(3-bromophenyl)-1,2-dihydro-2-oxo-1,8-naphthyridin-3-yl]-N'-(2,4,6-trimethylphenyl)urea

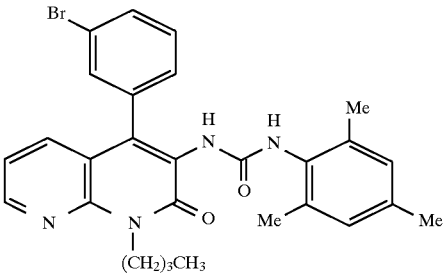

The title compound was obtained in the same manner as in Example 5 from 1-butyl-4-(3-bromophenyl)-1,2-dihydro-2-oxo-1,8-naphthyridine-3-carboxylic acid and 2,4,6-trimethylaniline.

$^1$H-NMR δ (DMSO-d$_6$) 8.63 (1H, s), 7.93 (1H, s), 7.82 (1H, s), 7.55–7.65 (3H, m), 7.43–7.48 (1H, m), 7.34–7.36 (1H, m), 7.24–7.29 (1H, m), 7.11 (2H, d, J=5.9 Hz), 6.78 (2H, s), 4.52 (2H, s), 3.33 (2H, m), 2.18 (3H, s), 1.92 (6H, s), 1.71 (2H, m), 1.41 (2H, m), 0.97 (3H, t, J=7.3 Hz)

EXAMPLE 203

Preparation of N-[1-butyl-4-(3-bromophenyl)-1,2-dihydro-2-oxo-1,8-naphthyridin-3-yl]-N'-(2,4,6-trifluorophenyl)urea

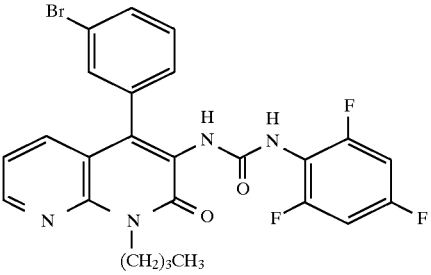

The title compound was obtained in the same manner as in Example 5 from 1-butyl-4-(3-bromophenyl)-1,2-dihydro-2-oxo-1,8-naphthyridine-3-carboxylic acid and 2,4,6-trifluoroaniline.

$^1$H-NMR δ (DMSO-$d_6$) 8.63 (1H, dd, J=4.8 Hz, 1.7 Hz), 8.18 (1H, s), 8.05 (1H, s), 7.64 (1H, d, J=7.9 Hz), 7.57 (1H, dd, J=7.9 Hz, 1.7 Hz), 7.54 (1H, dd, J=1.7 Hz, 1.7 Hz), 7.45 (1H, dd, J=7.9 Hz, 7.9 Hz), 7.34 (1H, d, J=7.9 Hz), 7.26 (1H, dd, J=8.1 Hz, 4.8 Hz), 7.15 (2H, dd, J=9.0 Hz, 7.7 Hz), 4.49 (2H, t, J=7.5 Hz), 1.64–1.71 (2H, m), 1.36–1.43 (2H, m), 0.95 (3H, t, J=7.2 Hz)

EXAMPLE 204

Preparation of N-[1-butyl-4-(3-bromophenyl)-1,2-dihydro-2-oxo-1,8-naphthyridin-3-yl]-N'-(2,4-difluorophenyl)urea

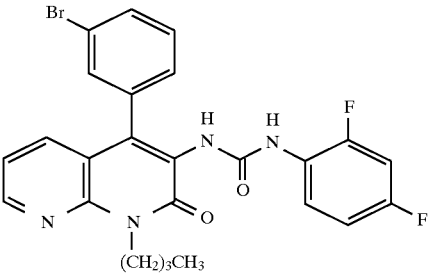

The title compound was obtained in the same manner as in Example 5 from 1-butyl-4-(3-bromophenyl)-1,2-dihydro-2-oxo-1,8-naphthyridine-3-carboxylic acid and 2,4-difluoroaniline.

$^1$H-NMR δ (DMSO-$d_6$) 8.68 (1H, dd, J=1.7 Hz), 8.63 (1H, dd, J=4.6 Hz, 1.7 Hz), 8.19 (1H, s), 7.76 (1H, ddd, J=9.2 Hz, 9.2 Hz, 6.1 Hz), 7.63 (1H, d, J=8.1 Hz), 7.55–7.58 (2H, m), 7.47 (1H, dd, J=7.7 Hz, 7.7 Hz), 7.73 (1H, d, J=7.5 Hz), 7.27 (1H, dd, J=8.1 Hz, 4.8 Hz), 7.23 (1H, ddd, J=11.6 Hz, 9.0 Hz, 2.0 Hz), 6.95 (1H, dd, J=8.4 Hz, 8.4 Hz), 4.50 (2H, t, J=7.3 Hz), 1.64–1.74 (2H, m), 1.33–1.46 (1H, m), 0.95 (3H, t, J=7.3 Hz)

REFERENCE EXAMPLE 1

Preparation of 3-amino-4-(2-chlorophenyl)-1,7-naphthyridine

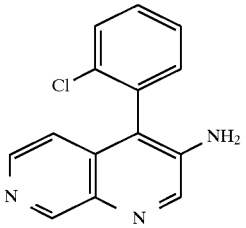

(a) Preparation of 2-hydroxy-N-[α-(3-amino-4-pyridyl)-2-chlorobenzylidine]-ethylamine A mixture of 3-amino-4-(2-chlorobenzoyl)pyridine (5.65 g, 24 mmol), 2-methylimidazole hydrochloride (4.7 g, 40 mmol) and ethanolamine (12.2 g, 200 mmol) was melted with heating at about 130° C. for 5 hours. After allowed to stand for cooling, to the mixture was added water. The precipitated crystals were collected by filtration, and recrystallized from ethyl acetate to give the title compound (6.28 g, 22 mmol) as a pale yellow crystal.

m.p. 175°–178° C. $^1$H-NMR δ (DMSO-$d_6$) 8.18 (1H, s), 7.47–7.65 (6H, m), 7.24–7.27 (1H, m), 6.32 (1H, d, J=5.3 Hz), 4.73 (1H, t, J=5.6 Hz, disappeared with $D_2O$-exchange), 3.62–3.68 (2H, m), 3.17–3.30 (2H, m); IR (KBr) 3387, 1614, 1434, 1308, 1239, 1055 $cm^{-1}$ (b) Preparation of 2,2-diethoxy-N-[α-(3-amino-4-pyridyl)-2-chloro-benzylidene]ethylamine A solution of 2-hydroxy-N-[α-(3-amino-4-pyridyl)-2-chlorobenzylidene]-ethylamine (6.28 g, 22 mmol), aminoacetaldehyde diethyl acetal (10 g, 75.1 mmol) and acetic acid (3 ml) in ethanol (150 ml) was refluxed for 30 hours. The mixture was concentrated under reduced pressure, and to the residue was added water, and the mixture was extracted with ethyl acetate. The extract was washed with water, washed with a saturated aqueous sodium chloride solution, dried over anhydrous sodium sulfate, and concentrated under reduced pressure. The residue was purified by column chromatography (silica gel; methanol: chloroform=1:9) to give the title compound (4.27 g, 11.9 mmol) as a pale yellow solid.

m.p. 94°–95° C. $^1$H-NMR δ ($CDCl_3$) 8.18 (1H, s), 7.74 (1H, d, J=5.28 Hz), 7.35–7.51 (3H, m), 7.07–7.13 (1H, m), 6.64 (2H, brs), 6.50 (1H, d, J=5.0 Hz), 4.88 (1H, dd, J=5.9 Hz, 5.3 Hz), 3.33–3.76 (6H, m), 1.21 (3H, t, J=7.0 Hz), 1.20 (3H, t, J=7.3 Hz); IR (KBr) 3393, 2978, 1608, 1594,1429, 1236 $cm^{-1}$ (c) Preparation of 3-amino-4-(2-chlorophenyl)-1,7-naphthyridine 2,2-Diethoxy-N-[α-(3-amino-4-pyridyl)-2-chlorobenzylidene]ethylamine (4.00 g, 11.17 mmol) was dissolved in 10% hydrogen chloride in ethanol (60 ml), and the mixture was refluxed for 5 hours. The mixture was concentrated under reduced pressure, and to the residue was added a saturated aqueous sodium hydrogen carbonate solution, and the mixture was extracted with ethyl acetate. The extract was washed with water, washed with a saturated aqueous sodium chloride solution, dried over anhydrous sodium sulfate, and concentrated under reduced pressure. The residue was purified by column chromatography (silica gel; methanol:chloroform=1:19) to give the title compound (0.99 g, 3.87 mmol) as a colorless solid.

$^1$H-NMR δ ($CDCl_3$) 8.30 (1H, s), 7.86 (1H, dd, J=5.3 Hz, 0.7 Hz), 7.27–7.50 (5H, m), 6.95 (1H, d, J=5.3 Hz), 6.28 (2H, br)

REFERENCE EXAMPLE 2

Preparation of 4-(2-chlorophenyl)-1,2-dihydro-1-methyl-2-oxo-1,8-naphthyridine-3-carboxylic acid

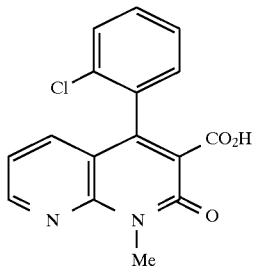

(a) Preparation of ethyl 4-(2-chlorophenyl)-1,2-dihydro-2-oxo-1,8-naphthyridine-3-carboxylate A mixture of 2-amino-3-(2-chlorobenzoyl)pyridine (3.91 g, 16.8 mmol), diethyl malonate (4.04 g, 25.2 mmol) and pyridine (0.33 g, 4.2 mmol) was heated with stirring at about 170° C. for five hours. After allowed to stand for cooling, the precipitated crystals were recrystallized from ethanol to give the title compound (4.73 g, 14.4 mmol) as a colorless crystal.

m.p. 218°–221° C. $^1$H-NMR δ (CDCl$_3$) 11.53 (1H, brs), 8.76 (1H, dd, J=5.0 Hz, 1.32 Hz), 7.26–7.57 (5H, m), 7.17 (1H, dd, J=7.9 Hz, 5.0 Hz), 4.04–4.17 (2H, m), 0.97 (3H, t, J=7.0 Hz); IR (KBr) 1739, 1667, 1613, 1568, 1466, 1425, 1375 cm$^{-1}$ (b) Preparation of ethyl 1-methyl-4-(2-chlorophenyl)-1,2-dihydro-2-oxo-1,8-naphthyridine-3-carboxylate To a solution of ethyl 4-(2-chlorophenyl)-1,2-dihydro-2-oxo-1,8-naphthyridine-3-carboxylate (4.50 g, 13.7 mmol) in N,N-dimethylformamide (50 ml) was added sodium hydride (60% oily, 547 mg, 13.7 mg) at room temperature, and the mixture was stirred for 0.5 hour. To the mixture was added methyl iodide (1.9 g, 13.7 mmol) at 0° C. to 5° C., and the mixture was stirred at the same temperature for 0.5 hour, and then stirred at room temperature for five hours. The mixture was poured into water, and extracted with ethyl acetate. The extract was washed with water, washed with a saturated aqueous sodium chloride solution, dried over anhydrous sodium sulfate, and concentrated under reduced pressure to give the title compound (4.60 g, 13.4 mmol), which was used without further isolation in the subsequent reaction.

$^1$H-NMR δ (CDCl$_3$) 8.65 (1H, dd, J=4.6 Hz, 1.7 Hz), 7.29–7.56 (5H, m), 7.10–7.15 (1H, m), 4.07–4.13 (2H, m), 3.92 (3H, s), 0.98 (3H, t, J=7.0 Hz)

(c) Preparation of 1-methyl-4-(2-chlorophenyl)-1,2-dihydro-2-oxo-1,8-naphthyridine-3-carboxylic acid To a solution of ethyl 1-methyl-4-(2-chlorophenyl)-1,2-dihydro-2-oxo-1,8-naphthyridine-3-carboxylate (4.6 g, 13.4 mmol) in ethanol (20 ml) was added sodium hydroxide (2.1 g, 52.5 mmol), and the mixture was refluxed for 0.5 hour. The mixture was diluted with water, and the pH value thereof was adjusted to pH 4 with 2N aqueous hydrochloric acid. The mixture was extracted with ethyl acetate, and the extract was washed with a saturated aqueous sodium chloride solution, dried over anhydrous sodium sulfate, and concentrated under reduced pressure. The precipitated crystals were recrystallized from ethyl acetate to give the title compound (3.52 g, 11.2 mmol) as a colorless crystal.

m.p. 178°–180° C. $^1$H-NMR δ (CDCl$_3$) 8.80 (1H, dd, J=4.6 Hz, 2.0 Hz), 7.39–7.57 (4H, m), 7.24–7.29 (1H, dd, J=7.9 Hz, 4.6 Hz), 7.11 (1H, dd, J=7.9 Hz, 2.0 Hz), 4.07 (3H, s); IR (KBr) 1747, 1612, 1576, 1472, 1446, 1342 cm$^{-1}$

REFERENCE EXAMPLE 3

Preparation of 1-methyl-4-(2-chlorophenyl)-1,2-dihydro-2-oxo-1,7-naphthyridine-3-carboxylic acid

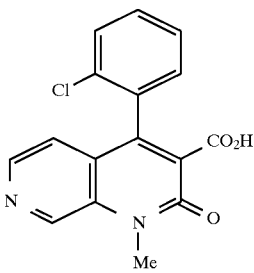

The title compound was obtained in the same manner as in Reference Example 2.

m.p.>250° C.; $^1$H-NMR δ (DMSO-d$_6$) 9.08 (1H, s), 8.41 (1H, d, J=5.3 Hz), 7.50–7.69 (3H, m), 7.40 (1H, dd, J=7.3 Hz, 1.7 Hz), 6.86 (1H, d, J=5.3 Hz), 3.82 (3H, s); IR (KBr) 1722, 1657, 1434,1295, 1251 cm$^{-1}$

REFERENCE EXAMPLE 4

Preparation of 1-methyl-4-(3-methoxyphenyl)-1,2-dihydro-2-oxo-1,8-naphthyridine-3-carboxylic acid

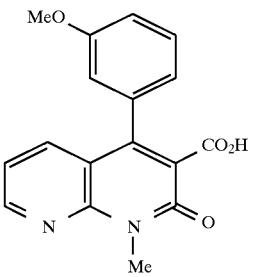

The title compound was obtained in the same manner as in Reference Example 2.

m.p. 196°–197° C.; $^1$H-NMR δ (CDCl$_3$) 8.77 (1H, dd, J=4.6 Hz, 2.0 Hz), 7.66 (1H, dd, J=8.3 Hz, 2.0 Hz), 7.44 (1H, t, J=8.3 Hz), 7.22–7.25 (1H, m), 7.01–7.05 (1H, m), 6.70–6.78 (2H, m), 4.04 (3H, s), 3.83 (3H, s); IR (KBr) 1734, 1624, 1604, 1573, 1462, 1249 cm$^{-1}$

REFERENCE EXAMPLE 5

Preparation of 4-(3-methoxyphenyl)-1,2-dihydro-2-oxo-1,8-naphthyridine-3-carboxylic acid The title compound was obtained in the same manner as in Reference Example 2.

$^1$H-NMR δ (CDCl$_3$) 8.84 (1H, d, J=3.0 Hz), 7.69 (1H, d, J=8.2 Hz), 7.46 (1H, dd, J=7.9 Hz, 7.9 Hz), 7.28–7.33 (1H, m), 7.05 (1H, dd, J=8.3 Hz, 1.7 Hz), 6.73–6.80 (2H, m), 3.84 (3H, s)

REFERENCE EXAMPLE 6

Preparation of 1-butyl-4-(3-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.76 (1H, dd, J=4.6 Hz, 2.0 Hz), 7.65 (1H, dd, J=7.9 Hz, 2.0 Hz), 7.43 (1H, dd, J=7.9 Hz, 7.9 Hz), 7.22 (1H, dd, J=7.9 Hz, 4.6 Hz), 7.02 (1H, dd, J=7.6 Hz, 1.6 Hz), 6.70–6.78 (2H, m), 4.68–4.74 (2H, m), 3.82 (3H, s), 1.77–1.88 (2H, m), 1.45–1.59 (2H, m), 1.03 (3H, t, J=7.3 Hz)

REFERENCE EXAMPLE 7

Preparation of 1-(2-methoxyethyl)-4-(3-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.76 (1H, dd, J=4.6 Hz, 2.0 Hz), 7.65 (1H, dd, J=7.9 Hz, 2.0 Hz), 7.43 (1H, dd, J=7.9 Hz, 7.9 Hz), 7.23 (1H, dd, J=8.3 Hz, 4.6 Hz), 7.03 (1H, dd, J=7.9 Hz, 2.6 Hz), 6.71–6.79 (2H, m), 4.99 (2H, t, J=6.0 Hz), 3.88 (2H, t, J=6.0 Hz), 3.83 (3H, s), 3.42 (3H, s)

REFERENCE EXAMPLE 8

Preparation of 1-isopropyl-4-(3-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.73 (1H, dd, J=4.6 Hz, 1.0 Hz), 7.64 (1H, dd, J=7.9 Hz, 2.0 Hz), 7.43 (1H, dd, J=7.9 Hz, 7.9 Hz), 7.21 (1H, dd, J=7.9 Hz), 6.99–7.04 (1H, m), 6.70–6.78 (2H, m), 6.27 (1H, br), 3.82 (3H, s), 1.73 (6H, d, J=6.9 Hz)

REFERENCE EXAMPLE 9

Preparation of 1-methyl-4-(4-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.76 (1H, dd, J=4.6 Hz, 1.7 Hz), 7.25 (1H, dd, J=7.9 Hz, 4.6 Hz), 7.11 (2H, d, J=8 Hz), 7.05 (2H, d, J=8.3 Hz), 4.04 (3H, s), 3.89 (3H, s)

REFERENCE EXAMPLE 10

Preparation of 1-(3-cyanopropyl)-4-(4-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.76 (1H, dd, J=4.6 Hz, 2.0 Hz), 7.69 (1H, dd, J=7.9 Hz, 2.0 Hz), 7.44 (1H, dd, J=7.9 Hz, 7.9 Hz), 7.25–7.29 (1H, m), 7.03 (1H, d, J=7.9 Hz), 6.76 (1H, d, J=7.9 Hz), 6.71 (1H, s), 4.86 (2H, t, J=6.9 Hz), 3.83 (3H, s), 2.56 (2H, t, J=6.9 Hz), 2.29 (2H, m)

REFERENCE EXAMPLE 11

Preparation of 1-methyl-4-(2-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.75 (1H, dd, J=4.6 Hz, 2.0 Hz), 7.63 (1H, dd, J=8.3 Hz, 2.0 Hz), 7.44–7.51 (1H, m), 7.23 (1H, dd, J=7.9 Hz, 4.6 Hz), 6.98–7.13 (3H, m), 4.04 (3H, s), 1.70 (3H, s)

REFERENCE EXAMPLE 12

Preparation of 1-pentyl-4-(3-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.76 (1H, dd, J=4.6 Hz, 1.7 Hz), 7.64 (1H, dd, J=8.3 Hz, 1.7 Hz), 7.42 (1H, dd, J=7.9 Hz, 7.9 Hz), 7.22 (1H, dd, J=8.3 Hz, 4.6 Hz), 7.02 (1H, dd, J=7.9 Hz, 2.3 Hz), 6.73 (1H, d, J=7.9 Hz), 6.71 (1H, s), 4.70 (2H, t, J=7.6 Hz), 1.84 (2H, br), 1.46 (4H, br), 0.95 (3H, t, J=6.9 Hz)

REFERENCE EXAMPLE 13

Preparation of 1-(3-methylbutyl)-4-(3-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.76 (1H, dd, J=4.6 Hz, 2.0 Hz), 7.64 (1H, dd, J=8.3 Hz, 2.0 Hz), 7.42 (1H, dd, J=7.9 Hz, 7.9 Hz), 7.22 (1H, dd, J=8.3 Hz, 4.6 Hz), 7.02 (1H, dd, J=8.3 Hz, 2.0 Hz), 6.76 (1H, d, J=7.6 Hz), 6.71 (1H, d, J=2.0 Hz), 4.73 (2H, t, J=7.9 Hz), 3.82 (3H, s), 1.67–1.84 (3H, m), 1.06 (6H, d, J=6.6 Hz)

REFERENCE EXAMPLE 14

Preparation of 1-butyl-4-(2-pyridyl)-1,2-dihydro-2-oxo-1,8-naphthyridine-3-carboxylic acid The title compound was obtained in the same manner as in Reference Example 2.

¹H-NMR δ (CDCl₃) 8.80 (1H, dd, J=4.6 Hz, 2.0 Hz), 8.76 (1H, dd, J=4.6 Hz, 2.0 Hz), 8.45 (1H, d, J=1.3 Hz), 7.55–7.59 (2H, m), 7.45–7.50 (1H, m), 7.26 (1H, dd, J=7.9 Hz, 4.6 Hz), 4.73 (2H, t, J=7.6 Hz), 1.78–1.89 (2H, m), 1.46–1.59 (2H, m), 1.07 (3H, t, J=7.3 Hz)

REFERENCE EXAMPLE 15

Preparation of 1-(3-benzyloxypropyl)-4-(3-methoxyphenyl)-1,2-dihydro-2-oxo-1,8-naphthyridine-3-carboxylic acid The title compound was obtained in the same manner as in Reference Example 2.

¹H-NMR δ (CDCl₃) 8.74 (1H, dd, J=4.6 Hz, 1.7 Hz), 7.62 (1H, dd, J=7.9 Hz, 1.7 Hz), 7.43 (1H, dd, J=7.9 Hz, 7.9 Hz), 7.20–7.37 (5H, m), 7.21 (1H, dd, J=7.9 Hz, 4.6 Hz), 7.02 (1H, dd, J=7.9 Hz, 2.6 Hz), 6.60–6.75 (2H, m), 4.87 (2H, t, J=7.3 Hz), 4.51 (2H, s), 3.82 (3H, s), 3.69 (2H, t, J=5.9 Hz), 2.19 (2H, dd, J=7.3 Hz, 5.9 Hz)

REFERENCE EXAMPLE 16

Preparation of 1-butyl-4-(3-bromophenyl)-1,2-dihydro-2-oxo-1,8-naphthyridine-3-carboxylic acid The title compound was obtained in the same manner as in Reference Example 2.

¹H-NMR δ (CD₃Cl₃) 8.78 (1H, dd, J=4.6 Hz, 1.7 Hz), 7.56–7.64 (2H, m), 7.39 (1H, dd, J=7.9 Hz, 7.9 Hz), 7.33 (1H, dd, J=2.0 Hz, 1.7 Hz), 7.23–7.28 (1 H, m), 7.13 (1H, d, J=7.69 Hz), 4.72 (2H, t, J=7.6 Hz), 1.77–1.88 (2H, m), 1.45–1.58 (2H, m), 1.03 (3H, t, J=7.3 Hz)

REFERENCE EXAMPLE 17

Preparation of 1-butyl-4-(3-methylphenyl)-1,2-dihydro-2-oxo-1,8-naphthyridine-3-carboxylic acid The title compound was obtained in the same manner as in Reference Example 2.

$^1$H-NMR δ (CD$_3$Cl$_3$) 8.75 (1H, dd, J=4.6 Hz, 2.0 Hz), 7.62 (1H, dd, J=8.3 Hz, 2.0 Hz), 7.40 (1H, dd, J=7.9 Hz, 7.6 Hz), 7.19–7.31 (2H, m), 6.98 (2H, brs), 4.72 (3H, t, J=7.6 Hz), 2.42 (3H, s), 1.77–1.86 (2H, m), 1.48–1.52 (2H, m), 1.03 (3H, t, J=7.3 Hz)

REFERENCE EXAMPLE 18

Preparation of 1-butyl-4-(3-fluorophenyl)-1,2-dihydro-2-oxo-1,8-naphthyridine-3-carboxylic acid The title compound was obtained in the same manner as in Reference Example 2.

$^1$H-NMR δ (DMSO-d$_6$) 13.28 (1H, brs), 8.71 (1H, dd, J=4.6 Hz, 1.7 Hz), 7.56–7.64 (2H, m), 7.21–7.40 (4H, m), 4.47 (2H, t, J=7.3 Hz), 1.69 (2H, m), 1.39 (2H, m), 0.96 (3H, t, J=7.3 Hz)

REFERENCE EXAMPLE 19

Preparation of 1-butyl-4-(4-bromophenyl)-1,2-dihydro-2-oxo-1,8-naphthyridine-3-carboxylic acid The title compound was obtained in the same manner as in Reference Example 2.

m.p. 158°–160° C.

EFFECTS OF INVENTION

The naphthyridine derivative of the present invention or an acid addition salt thereof strongly inhibits ACAT activity in a specimen of rabbit liver or in rat peritoneal-derived macrophage. Therefore, the present compound or an acid addition salt thereof is useful not only as an agent for treatment of hyperlipidemia, but also in the prophylaxis or therapeutic treatment of atherosclerosis per se or various diseases accompanied by atherosclerosis, for example, cerebral infarction, cerebral thrombosis, transient cerebral ischemia, angina pectoris, myocardial infarction, peripheral thrombus or occlusion.

The ACAT inhibitory activity of the present compounds were evaluated as follows.

Experiment
1. Assay of ACAT inhibitory activity in a specimen prepared from rabbit liver An enzyme specimen ACAT was prepared according to the method disclosed in the literature: J. Lipid. Research, 30, 681–690, 1989, from the liver of New Zealand white rabbit which had been fed with 1% cholesterol feed for one month. The ACAT activity was determined according to the method disclosed in the literature: J. Lipid Research. 24, 1127–1134, 1983, i.e., using radioactive [1-$^{14}$C]oleoyl-CoA and endogenous cholesterol contained in the liver microsome, and calculated from the radioactivity of the labeled cholesterol oleate. The results are shown in Table 1.

TABLE 1

| Test compound (Example No.) | ACAT inhibitory rate (%) 10$^{-6}$ M |
|---|---|
| 4 | 87 |
| 6 | 82 |

2. Assay of ACAT inhibitory activity in the macrophage derived from rat peritoneal The rat peritoneal-derived macrophage was prepared according to the method disclosed in the literature: Biochimica et Biophysica Acta, 1126, 73–80, 1992. The ACAT activity was determined by a modified method of the method disclosed in the above literature: Biochimica et Biophysica Acta, 1126, 73–80, 1992, i.e., using radioactive [9,10-H] oleic acid and exogenous cholesterol contained in the liposome which was re-constituted according to the method disclosed in the literature: Biochimica Biophysica Acta, 1213, 127–134, 1994, and calculated from the labeled cholesterolyl oleate. The results are shown in Table 2.

TABLE 2

| Test compound (Example No.) | ACAT inhibitory rate (%) 10$^{-6}$ M |
|---|---|
| 4 | 88 |
| 7 | 94 |

What is claimed is:

1. A naphthyridine derivative of the formula:

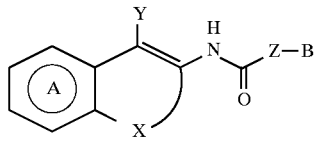
(1)

wherein Ring A is a substituted or unsubstituted pyridine ring,

X is a group of the formula:

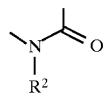

wherein R$^2$ is a hydrogen atom, an alkyl group, a substituted alkyl group, an alkenyl group, a substituted alkenyl group, an alkynyl group, a substituted alkynyl group, a cycloalkyl group, or a substituted cycloalkyl group, or a group of the formula:

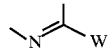

wherein W is a hydrogen atom or a group: —OR$^1$ (R$^1$ is an alkyl group, a substituted alkyl group, an alkenyl group, a substituted alkenyl group, an alkynyl group, or a substituted alkynyl group), Z is a direct bond, —NH—, an alkylene group having 1 to 2 carbon atoms, or —CH=CH—, Y is an alkyl group, a substituted alkyl group, a cycloalkyl group, a substituted cycloalkyl group, an aromatic group or a substituted aromatic group, B is an alkyl group, a substituted alkyl group, an alkenyl group, a substituted alkenyl group, a cycloalkyl group, a substituted cycloalkyl group, an aromatic group, or a substituted aromatic group, or an acid addition salt thereof.

2. The naphthyridine derivative according to claim 1, wherein Z is —NH—, or an acid addition salt thereof.

3. The naphthyridine derivative according to claim 1 or 2, wherein Ring A is a group selected from the following formulae (a), (b) and (c):

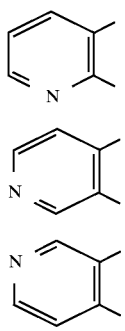

or an acid addition salt thereof.

4. The naphthyridine derivative according to claim 3, wherein X is a group of the formula:

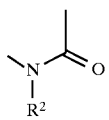

or an acid addition salt thereof.

5. The naphthyridine derivative according to claim 4, wherein B is an aromatic group or a substituted aromatic group, or an acid addition salt thereof.

6. The naphthyridine derivative according to claim 5, wherein Y is aromatic group or a substituted aromatic group, or an acid addition salt thereof.

7. The naphthyridine derivative according to claim 6, wherein $R^2$ is an alkyl group, a substituted alkyl group, an alkenyl group, or a substituted alkenyl group, or an acid addition salt thereof.

8. The naphthyridine derivative according to claim 7, wherein Y is a phenyl group substituted by a lower alkoxy group, or an acid addition salt thereof.

9. The naphthyridine derivative according to claim 7, wherein Y is a substituted phenyl group and said substituent is a group of the formula: —$D^1$—E—F ($D^1$ is a direct bond, an oxygen atom, a sulfur atom or a group of the formula: —$NR^3$—($R^3$ is a hydrogen atom or a lower alkyl group), E is a divalent hydrocarbon group having 1 to 8 carbon atoms and optionally containing an unsaturated bond, or a phenylene group, F is a hydrogen atom, a hydroxy group, a carboxyl group, a lower alkoxycarbonyl group, a benzyloxy-carbonyl group, a halogen atom, a cyano group, a benzyloxy group, a lower alkoxy group, a lower alkanoyloxy group, a lower alkylthio group, a lower alkylsulfinyl group, a lower alkylsulfonyl group, a benzenesulfonyloxy group optionally being substituted by an alkyl group, a lower alkanoylamino group, a lower alkoxycarbonylamino group, a lower alkylsulfonamido group, a phthalimido group, a cycloalkyl group, an aryl group, a substituted aryl group, a heteroaryl group, a substituted heteroaryl group, a group of the formula: —$NR^4R^5$ ($R^4$ and $R^5$ are independently a hydrogen atom, a lower alkyl group, a di-lower alkyl-amino-substituted lower alkyl group, a lower alkoxy-substituted lower alkyl group, a cycloalkyl group, a lower alkoxycarbonyl group, a heteroarylmethyl group, or an aralkyl group, or $R^4$ and $R^5$ may combine each other, and with the adjacent nitrogen atom to which they bond, form a saturated cyclic amino group having 4 to 8 carbon atoms as ones forming the said ring, and having one —$NR^8$—($R^8$ is a hydrogen atom, a lower alkyl group, a phenyl group, a lower alkoxycarbonyl group, or a benzyl group) or one oxygen atom in the cycle thereof), or a group of the formula: —C(=O)$NR^4R^5$ ($R^4$ and $R^5$ are the same as defined above)), or an acid addition salt thereof.

10. The naphthyridine derivative according to claim 9, wherein E is a divalent hydrocarbon group having 1 to 6 carbon atom and optionally containing an unsaturated bond, or a phenylene group, F is a hydroxy group, a carboxyl group, a lower alkoxycarbonyl group, a benzyloxycarbonyl group, a halogen atom, a cyano group, a benzyloxy group, a lower alkoxy group, a lower alkanoyloxy group, a lower alkylthio group, a lower alkylsulfinyl group, a lower alkylsulfonyl group, a lower alkanoylamino group, a lower alkoxycarbonylamino group, a lower alkylsulfonamido group, a phthalimido group, a cycloalkyl group, an aryl group, a substituted aryl group, a heteroaryl group, a substituted heteroaryl group, a group of the formula: —$NR^4R^5$ ($R^4$ and $R^5$ are independently a hydrogen atom, a lower alkyl group, a lower alkoxy-carbonyl group, or an aralkyl group, or $R^4$ and $R^5$ may combine each other, and with the adjacent nitrogen atom to which they bond, form a saturated 5- to 7-membered cyclic amino group having one —$NR^8$—($R^8$ is a hydrogen atom, a lower alkyl group, a phenyl group, a lower alkoxycarbonyl group, or a benzyl group) or one oxygen atom in the cycle thereof), or a group of the formula: —C(=O)$NR^4R^5$ ($R^4$ and $R^5$ are the same as defined above)), or an acid addition salt thereof.

11. The naphthyridine derivative according to claim 10, wherein F is a hydroxy group, a carboxyl group, a lower alkoxycarbonyl group, a benzyloxy-carbonyl group, a halogen atom, a cyano group, a benzyloxy group, a lower alkoxy group, a lower alkanoyloxy group, a lower alkylthio group, a lower alkyl-sulfinyl group, a lower alkylsulfonyl group, a lower alkanoylamino group, a lower alkylsulfonamido group, a phthalimido group, a heteroaryl group, a group of the formula: —$NR^4R^5$ ($R^4$ and $R^5$ are independently a hydrogen atom or a lower alkyl group, or $R^4$ and $R^5$ may combine each other, and with the adjacent nitrogen atom to which they bond, form a saturated 5- to 7-membered cyclic amino group having one —$NR^8$—($R^8$ is a hydrogen atom, a lower alkyl group, a phenyl group, or a benzyl group) or one oxygen atom in the cycle thereof), or a group of the formula: —C(=O)$NR^4R^5$ ($R^4$ and $R^5$ are the same as defined above)), or an acid addition salt thereof.

12. The naphthyridine derivative according to claim 9, wherein E is an alkylene group, or an acid addition salt thereof.

13. The naphthyridine derivative according to claim 9, wherein Y is a phenyl group substituted by a group of the formula: —$D^1$—E—F and F is a group of the formula:

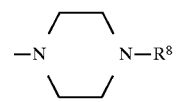

or an acid addition salt thereof.

14. The naphthyridine derivative according to claim 9, wherein $D^1$ is an oxygen atom, or an acid addition salt thereof.

15. The naphthyridine derivative according to claim 11, wherein F is a hydroxy group, a heteroaryl group, a substituted heteroaryl group, or a group of the formula: —$NR^4R^5$, or an acid addition salt thereof.

16. The naphthyridine derivative according to claim 11, wherein E is an alkylene group having 1 to 6 carbon atoms, F is a substituted or unsubstituted pyridyl group, or a 1,2,4-triazolyl group, or an acid addition salt thereof.

17. The naphthyridine derivative according to claim 12, wherein $R^2$ is an alkenyl group, or an acid addition salt thereof.

18. The naphthyridine derivative according to claim 9, wherein $D^1$ is a direct bond, or an acid addition salt thereof.

19. The naphthyridine derivative according to claim 7, wherein Ring A is an unsubstituted pyridine ring, or an acid addition salt thereof.

20. The naphthyridine derivative according to claim 1, which is selected from N-[1-(butyl-4-[3-{3-(1,2,4-triazol-1-yl)propoxy}phenyl]-1,2-dihydro-2-oxo-1,8-naphthyridin-3-yl]-N'-(2,6-diisopropylphenyl)urea and N-[1-(butyl-4-{3-(3-pyridylmethoxy)phenyl}-1,2-dihydro-2-oxo-1,8-naphthyridin-3-yl]-N'-(2,6-diisopropylphenyl)urea, or an acid addition salt thereof.

21. A pharmaceutical composition comprising a naphthyridine derivative of claim 1, or an acid addition salt thereof, in admixture with a pharmaceutically acceptable carrier or diluent.

22. A method for treatment of hyperlipidemia and atherosclerosis, which comprises administrating a naphthyridine derivative as set forth in claim 1, or an acid addition salt thereof, to human beings.

* * * * *

UNITED STATES PATENT AND TRADEMARK OFFICE
CERTIFICATE OF CORRECTION

PATENT NO. : 5,843,957
DATED : December 1, 1998
INVENTOR(S) : Masami MURAOKA et al.

It is certified that error appears in the above-identified patent and that said Letters Patent is hereby corrected as shown below:

On the Title Page:

Change the first line under [30] Foreign Application Priority Data to read as follows:

May 31, 1995 [JP] Japan .............................. 7-158475

Signed and Sealed this

Eighth Day of June, 1999

*Attest:*

Q. TODD DICKINSON

*Attesting Officer*   *Acting Commissioner of Patents and Trademarks*